(12) United States Patent
Dunning et al.

(10) Patent No.: US 7,220,856 B2
(45) Date of Patent: May 22, 2007

(54) SUBSTITUTED QUINOLINE CCR5 RECEPTOR ANTAGONISTS

(75) Inventors: Laura Dunning, Sonoma, CA (US); Stefan Jaroch, Berlin (DE); Monica J. Kochanny, Benicia, CA (US); Wheeseong Lee, Orinda, CA (US); Xiongdong Lian, Shanghai (CN); Meina Liang, Danville, CA (US); Shou-Fu Lu, Hercules, CA (US); James Onuffer, Alameda, CA (US); Gary Phillips, Pleasant Hill, CA (US); Guo-Ping Wei, San Ramon, CA (US); Bin Ye, Moraga, CA (US)

(73) Assignee: Schering Aktiengesellschaft, Berlin (DE)

( * ) Notice: Subject to any disclaimer, the term of this patent is extended or adjusted under 35 U.S.C. 154(b) by 250 days.

(21) Appl. No.: 10/607,530

(22) Filed: Jun. 26, 2003

(65) Prior Publication Data

US 2004/0072818 A1 Apr. 15, 2004

Related U.S. Application Data

(60) Provisional application No. 60/451,687, filed on Jun. 27, 2002.

(51) Int. Cl.
C07D 223/00 (2006.01)
C07D 453/02 (2006.01)
(52) U.S. Cl. ............... 540/484; 544/224; 544/242; 546/1; 546/26; 546/134; 514/211.01
(58) Field of Classification Search ............... 540/484; 544/224, 242; 546/1, 26, 134; 514/211.01
See application file for complete search history.

(56) References Cited

U.S. PATENT DOCUMENTS

| | | | | |
|---|---|---|---|---|
| 5,494,908 A | * | 2/1996 | O'Malley et al. | 514/228.2 |
| 6,169,088 B1 | * | 1/2001 | Matsuno et al. | 514/252.16 |
| 6,344,450 B1 | | 2/2002 | Bisacchi et al. | |

FOREIGN PATENT DOCUMENTS

| | | | |
|---|---|---|---|
| CN | 1234397 | * | 10/1999 |
| EP | 0882717 A1 | * | 4/1998 |
| EP | 0882717 | | 12/1998 |
| EP | 1013276 | | 6/2000 |
| EP | 1308439 | | 5/2003 |
| FR | 84902 | * | 6/1962 |
| FR | 84902 | | 5/1965 |
| WO | WO 98/27815 | | 7/1998 |
| WO | WO 99/31086 | | 6/1999 |
| WO | WO 02/22599 | | 3/2002 |
| WO | WO 02/072578 | | 9/2002 |
| WO | WO 02/094203 | | 11/2002 |

OTHER PUBLICATIONS

Agrawal et al., "Antiparasitic Agents . . . ", Indian journal of Chemistry, Vo. 26 B, Jun. 1987, pp. 550-555.*
Agrawal V K et al, "Antiparasitic Agents: Part VI—Synthesis of 7-Chloro-4-(4-substituted-phenylamino)- & 7-Chloro-4-(4-substituted-Piperazin-1-YL) Quinolines as Potential Antiparasitic Agents", *Indian Journal of Chemistry*, (1987) 26B:550-555.
Kireev D et al, "Molecular modeling and quantitative structure-activity studies of anti-HIV-1 2-heteroarylquinoline-4-amines" *European Journal of Medicinal Chemistry*, (1995) 30:395-402.
Tripathi, R.C. et al, *Indian J. Chemistry*, (1995) 34:164-166 (abstract).

* cited by examiner

*Primary Examiner*—James O. Wilson
*Assistant Examiner*—Paul V. Ward
(74) *Attorney, Agent, or Firm*—Millen, White, Zelano, Branigan, P.C.

(57) ABSTRACT

The present invention relates to CCR5 receptor antagonists of formulae (1a) or (1b):

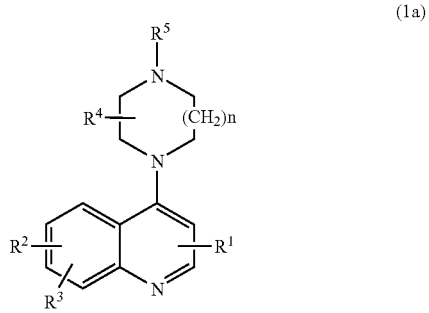

(1a)

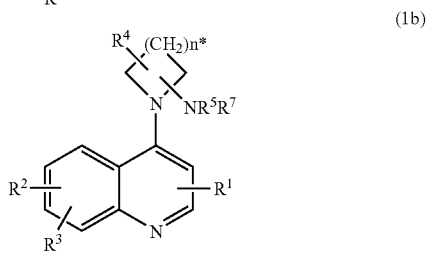

(1b)

enantiomers, diastereomers, salts and solvates thereof wherein $R^1$, $R^2$, $R^3$, $R^4$, $R^5$, and $R^7$ are as defined herein. The invention further includes a method of CCR5-mediated disorders employing such compounds.

8 Claims, No Drawings

SUBSTITUTED QUINOLINE CCR5 RECEPTOR ANTAGONISTS

This application claims priority to U.S. Provisional Application Ser. No. 60/451,687 filed Jun. 27, 2002 the entirety of which is incorporated herein by reference.

BACKGROUND OF THE INVENTION

Chemoattractant cytokines or chemokines are a family of proinflammatory mediators that promote recruitment and activation of leukocytes (e.g, monocytes, lymphocytes, and granulocytes) and also have additional effects on diverse cell types. They can be released by many kinds of tissue cells after activation. Continuous release of chemokines at sites of inflammation mediates the ongoing migration of effector cells in chronic inflammation. The chemokines characterized to date are related in primary structure. They share four conserved cysteines, which form disulfide bonds. Based upon this conserved cysteine motif, the family is divided into two main branches, designated as the C—X—C chemokines (α-chemokines), and the C—C chemokines (β-chemokines), in which the first two conserved cysteines are separated by an intervening residue, or adjacent respectively (Baggiolini, M. and Dahinden, C. A., Immunology Today, 15:127–133 (1994)).

RANTES (Regulated on Activation, Normal T Expressed and Secreted), the macrophage inflammatory proteins 1α. and 1β (MIP-1α. and MIP-1β), and human monocyte chemotactic proteins 1–3 (MCP-1, MCP-2, MCP-3) are members of the C—C chemokine family and have been characterized as chemoattractants and activators of monocytes or lymphocytes. Migration of leukocytes from blood vessels into diseased tissues is important to the initiation of normal disease-fighting inflammatory responses. This process, known as leukocyte recruitment, is also involved in the onset and progression of debilitating and life-threatening chronic inflammatory, allergic inflammatory and autoimmune diseases. Compounds which block leukocyte recruitment to target tissues in inflammatory and autoimmune disease would be a highly effective therapeutic intervention. Abnormal production of chemokines, such as RANTES and MIP-1α have been implicated in a wide range of human acute and chronic inflammatory diseases, including rheumatoid arthritis, multiple sclerosis, inflammatory bowel disease, endometriosis and respiratory diseases, such as asthma and allergic disorders. A review of the role of chemokines in allergic inflammation is provided by Kita, H., et al., J. Exp. Med. 183, 2421–2426 (1996). Chemokines and their receptors have been implicated in the pathogenesis of a number of neurological disorders including ischemic stroke, trauma, Alzheimer's disease, multiple sclerosis and cancer.

The chemokine receptors are members of a superfamily of G protein-coupled receptors (GPCR) which share structural features that reflect a common mechanism of action of signal transduction (Gerard, C. and Gerard, N. P., Annu Rev. Immunol., 12:775–808 (1994); Gerard, C. and Gerard, N. P., Curr. Opin. Immunol., 6:140–145 (1994)). The first receptor for the C—C chemokines that was cloned and expressed, binds the chemokines MIP-1α and RANTES. Accordingly, this MIP-1α/RANTES receptor was designated C—C chemokine receptor 1 (also referred to as CCR-1; Neote, K., et al., Cell, 72:415–425 (1993); Horuk, R. et al., WO 94/11504, May 26, 1994; Gao, J.-I. et al., J. Exp. Med., 177:1421–1427 (1993)). Two other receptors have been characterized which bind and/or signal in response to RANTES: CCR3 mediates binding and signaling of chemokines including eotaxin, RANTES, and MCP-3 (Ponath et al., J. Exp. Med., 183:2437 (1996)), and CCR5 binds chemokines including MIP-1α, RANTES, MIP-1β, and MCP-2. (Samson, et al., Biochem. 35: 3362–3367 (1996)).

The CCR5 ligand RANTES is chemotactic for a variety of cell types, including monocytes, eosinophils, and a subset of T-cells. The ability of RANTES to induce the directed migration of monocytes and a memory population of circulating T-cells (Schall, T. et al., Nature, 347:669–71 (1990)) suggests this chemokine and its receptor(s) plays an important role in chronic inflammatory diseases, since these diseases are characterized by destructive infiltrates of T cells and monocytes. Macrophages and microglia also express CCR5 and the expression is upregulated following activation, especially under conditions of tissue damage such as demyelination. Particular diseases or conditions in which RANTES/CCR5 have been implicated include: transplant rejection, multiple sclerosis, arteriosclerosis (the formation of atherosclerotic plaques that lead to heart attacks and stroke), arthritis (particularly osteo- and rheumatoid arthritis), stroke, atopic dermatitis, airway inflammatory disorders such as Rous Sarcoma Virus-induced bronchiolitis, delayed type hypersensitivity (DTH) reactions, glomerular nephritis, asthma, endometriosis (Am J Obstet Gyncol 169(6): 1545–1549), cancers such as breast, cervical, melanoma, lymphoma, myeloma, Hodgkin's disease, and Hairy cell leukemia. (Cancer Research 62; 1093–1102)(Cancer Research 59; 4681–4687)(Clin Can Res. 7:285–289). Small molecule antagonists of CCR5 would have potential therapeutic utility in treating a wide range of disease states.

It has recently been recognized that the human immunodeficiency viruses (HIV) requires a chemokine receptor, most probably CCR5 or CXCR4, as well as the primary receptor CD4 for efficient entry into target cells (Levy, N. Engl. J. Med., 335(20), 1528–1530 (Nov. 14, 1996). The principal cofactor for entry mediated by the envelope glycoproteins of macrophage tropic strains of HIV-1 is CCR-5, a receptor for the chemokines RANTES, MIP-1α, MIP-1β, and MCP-2 (Deng, et al., Nature, 381, 661–666 (1996)). Accordingly, agents which could antagonize the interaction of HIV with chemokine receptors in humans should prevent infection in healthy individuals and slow or halt viral progression in infected patients leading to a viable method for the prevention or treatment of infection by HIV and the prevention or treatment of AIDS and AIDS related syndromes such as HIV dementia.

SUMMARY OF THE INVENTION

The present invention relates to CCR5 receptor antagonists of formulae (1a) or (1 b):

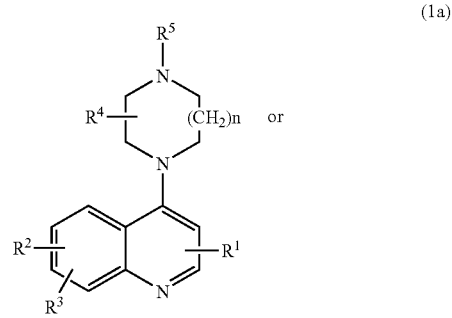

(1a)

-continued

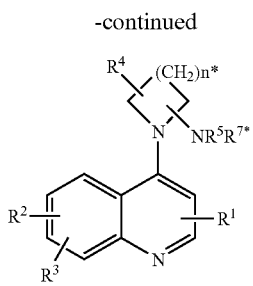

(1b)

enantiomers, diastereomers, salts and solvates thereof
wherein
R$^1$ and R$^{1*}$ are independnently hydrogen, a substituted or unsubstituted amino, alkyl, haloalkyl, hydroxy, alkoxy or —C(O)OR$^{9a}$;
R$^2$, R$^{2*}$, R$^3$ and R$^{3*}$ are independently hydrogen, alkyl, halogenated alkyl, halogen, substituted or unsubstituted amino, nitro, cyano, or alkoxy;
R$^4$ and R$^{4*}$ are independently hydrogen or one or more alkyl groups;
R$^5$ is
  (1) hydrogen, or
  (2) R$^9$, R$^9$-aminocycloalkyl, R$^9$-aminocycloalkenyl, (alkoxy)carbonyl, (aryloxy)carbonyl, —SO$_2$—R$^9$, —C(=O)—NR$^7$R$^9$, —C(=O)—NR$^7$—SO$_2$R$^9$, —C(=O)—R$^6$, —C(=O)—R$^9$, —C(=NR$^{10}$)—R$^9$, —C(=S)—R$^9$, —C(=NR$^{10}$)—NHR$^9$, —C(=)S—NHR$^9$, or —C(=S)—NR$^7$—SO$_2$R$^9$ any of which can be substituted or unsubstituted;
R$^6$ is a group of formula

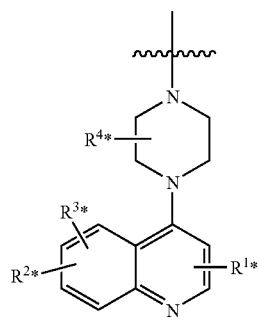

R$^7$ and R$^{7*}$ are independently hydrogen, substituted or unsubstituted C$_{1-6}$ alkyl, or substituted or unsubstituted aryl;
R$^9$ is arylalkyl, cycloalkyl, cycloalkenyl, cycloalkylalkyl, alkyl, heterocyclylalkyl, aryl or heterocyclyl any of which can be substituted or unsubstituted;
R$^{9a}$ is
  (1) hydrogen, or
  (2) arylalkyl, cycloalkyl, cycloalkenyl, cycloalkylalkyl, alkyl, heterocyclylalkyl, aryl or heterocyclyl any of which can be substituted or unsubstituted;
R$^{10}$ is
  (1) hydrogen, or cyano;
  (2) alkyl, or alkoxy, either of which optionally can be substituted;
n is 0, 1, 2 or 3; and
n* is 1, 2 or 3.

The compounds of the present invention are useful in the prevention and treatment of a wide variety of inflammatory and immunoregulatory disorders and diseases, allergic conditions, atopic conditions, as well as autoimmune, immunodeficiency, and demyelinating pathologies.

Also included in the invention are methods of using the compounds as agents for the treatment of CCR5 mediated disease states, in particular for the treatment of inflammatory diseases or conditions, autoimmune disorders, demyelinating pathologies, and immune deficiency disorders such as HIV infection.

In another aspect, the instant invention may be used to evaluate specific antagonists of CCR-5 receptors. Accordingly, the present invention is directed to the use of these compounds in the preparation and execution of screening assays for compounds which modulate the activity of CCR-5 receptors. For example, the compounds of this invention are useful for isolating receptor mutants, which are excellent screening tools for more potent compounds. Furthermore, the compounds of this invention are useful in establishing or determining the binding site of other compounds to CCR-5 receptors, e.g., by competitive inhibition.

The compounds of the invention can be used in the treatment of mammals, preferably humans, comprising administering to such mammal in need thereof, an effective amount of a compound of formula (I), or a pharmaceutically acceptable salt thereof, optionally in the form of a diastereomer and enantiomer.

Preferred compounds within the scope of the invention include compounds where
R$^5$ is alkoxycarbonyl (e.g., ethoxycarbonyl), —C(=O)NHR$^9$, —C(=O)—NR$^7$—SO$_2$R$^9$, —C(=S)NHR$^9$, or —C(=S)—NR$^7$—SO$_2$R$^9$; and
R$^7$ is hydrogen, substituted or unsubstituted C$_{1-6}$ alkyl, or substituted or unsubstituted aryl;
R$^9$ is alkyl, cycloalkyl, cycloalkylalkyl, aryl, arylalkyl, heterocyclyl, or heterocyclylalkyl any of which may be optionally substituted (especially preferred substituents are independently selected from alkyl and halo groups).

Preferred compounds within the scope of formulae (1a) and (1b) include compounds of the following formulae (2a) and (2b)

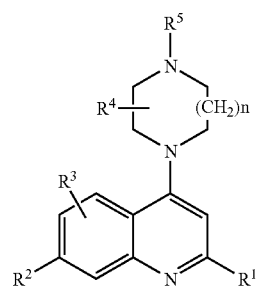

(2a)

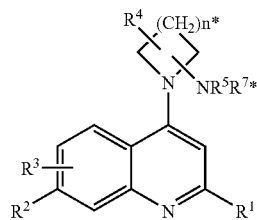

(2b)

enantiomers, diastereomers, salts and solvates thereof wherein

R¹ is hydrogen, amino or substituted amino;

R² is halo (especially chloro);

R³ is hydrogen, alkyl, halogenated alkyl, halogen, substituted or unsubstituted amino, nitro, cyano, or alkoxy;

R⁴ is hydrogen or one or more alkyl groups;

R⁵ is alkoxycarbonyl, —C(=O)NHR⁹, —C(=O)—NR⁷—SO$_2$R⁹, —C(=S)NHR⁹ or —C(=S)—N R⁷—SO$_2$R⁹;

R⁹ is cycloalkyl, cycloalkenyl, heterocyclyl, heterocyclylalkyl, aryl, or arylalkyl any of which may be optionally substituted.

Preferred compounds within the scope of formulae (2a) and (2b) include compounds wherein R¹ is hydrogen or amino;

R² is halo;

R³ is hydrogen;

R⁴ is hydrogen;

R⁵ is —C(=O)NHR⁹, or —C(=S)NHR⁹;

R⁹ is heterocyclo (especially pyrrolidinyl, hexahydrothiazepinyl, tetrahydrobenzazepinyl, or hexahydroazepinyl) optionally substituted with one to three hydroxy, oxo or thioxo groups and further optionally substitued with one or more (i) —(CR²⁰R²¹)$_m$—C(=O)R¹⁵, —(CR²⁰R²¹)$_m$—C(=O)OR¹⁵, —(CR²⁰R²¹)$_m$—SO$_2$R¹⁵ᵃ, —(CR²⁰R²¹)$_m$—C(=O)NR¹⁶R¹⁷, —(CR²⁰R²¹)$_m$—C(=S)NR¹⁶R¹⁷, —(CR²⁰R²¹)$_m$—C(=O)NR¹⁶—SO$_2$R¹⁵ᵇ;

(ii) aryl, arylalkyl, heterocyclyl, heterocyclylalkyl, cycloalkyl or cycloalkylalkyl any of which may be optionally independently substituted with one or more halo, alkoxy, hydroxy, or haloalkyl;

(iii) cyano;

R¹⁵ is hydrogen, alkyl, haloalkyl, alkenyl, cycloalkyl, cycloalkylalkyl, aryl, arylalkyl, aryloxyalkyl;

R¹⁵ᵃ is hydrogen, alkyl, haloalkyl, alkenyl, cycloalkyl, cycloalkylalkyl, aryl, arylalkyl, aryloxyalkyl provided that when m is zero R¹⁵ᵃ is not hydrogen;

R¹⁵ᵇ is alkyl, haloalkyl, alkenyl, cycloalkyl, cycloalkylalkyl, aryl, arylalkyl, aryloxyalkyl;

R¹⁶ and R¹⁷ are independently hydrogen, alkyl, alkenyl, cycloalkyl, haloalkyl, hydroxyalkyl, alkoxyalkyl, aryloxyalkyl, alkenyl, cycloalkylalkyl, heterocyclyl, heterocyclylalkyl, aryl, arylalkyl;

or R¹⁶ and R¹⁷ together with the nitrogen atom to which they are bonded may combine to form a heterocyclyl ring;

R²⁰ and R²¹ at each occurrence are the same or different and are independently selected from hydrogen or alkyl;

m is 0, 1, 2 or 3; and n is zero.

Preferred compounds within the scope of formula (2a) include compounds of formula (3a)

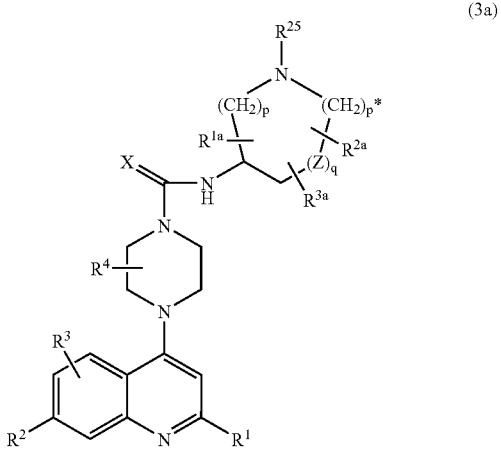

wherein

R¹ is hydrogen or amino;

R² is halo;

R³ is hydrogen, alkyl, halogenated alkyl, halogen, substituted or unsubstituted amino, nitro, cyano, or alkoxy;

R⁴ is hydrogen or one or more alkyl groups;

R¹ᵃ, R²ᵃ and R³ᵃ are independently selected from hydrogen, oxo, thioxo or when bonded to adjacent ring carbon atoms R²ᵃ and R³ᵃ may combine to form a fused aryl or heterocyclo ring;

R²⁵ is (i) hydrogen, or cyano (ii) alkyl, cycloalkyl, haloalkyl, hydroxyalkyl, alkoxyalkyl, aryloxyalkyl, alkenyl, cycloalkylalkyl, heterocyclylalkyl, aryl, or arylalkyl any of which may be optionally independently substituted with one to three halo, alkoxy, hydroxy, alkyl, or haloalkyl; or (iii) —(CR²⁰R²¹)$_m$—C(=O)R¹⁵, —(CR²⁰R²¹)$_m$—C(=O)OR¹⁵, —(CR²⁰R²¹)$_m$—SO$_2$R¹⁵ᵃ, —(CR²⁰R²¹)$_m$—C(=O)NR¹⁶R¹⁷, —(CR²⁰R²¹)$_m$—C(=S)NR¹⁶R¹⁷; or —(CR²⁰R²¹)$_m$—C(=O)N R¹⁶—SO$_2$R¹⁵ᵇ;

R¹⁵ is hydrogen, alkyl, haloalkyl, alkenyl, cycloalkyl, cycloalkylalkyl, aryl, arylalkyl, aryloxyalkyl;

R¹⁵ᵃ is hydrogen, alkyl, haloalkyl, alkenyl, cycloalkyl, cycloalkylalkyl, aryl, arylalkyl, aryloxyalkyl provided that when m is zero R¹⁵, is not hydrogen;

R¹⁵ᵇ is alkyl, haloalkyl, alkenyl, cycloalkyl, cycloalkylalkyl, aryl, arylalkyl, aryloxyalkyl;

R¹⁶ and R¹⁷ are independently hydrogen, alkyl, cycloalkyl, haloalkyl, hydroxyalkyl, alkoxyalkyl, aryloxyalkyl, alkenyl, cycloalkylalkyl, heterocyclylalkyl, aryl, or arylalkyl;

or R¹⁶ and R¹⁷ together with the nitrogen atom to which they are bonded may combine to form a heterocyclyl ring;

R²⁰ and R²¹ at each occurrence are the same or different and are independently selected from hydrogen or alkyl;

Z is —S—, —S(O)— or —S(O)$_2$—;
p is 1 or 2;
p* is 0, 1, 2, 3 or 4;
q is 0 or 1;
m is 0, 1 or 2.
Preferred compounds within the scope of formula (3a) include compounds of the following formulae:
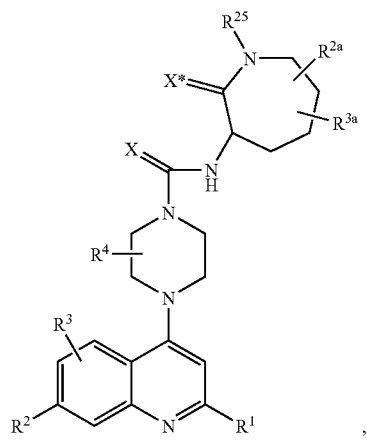
,
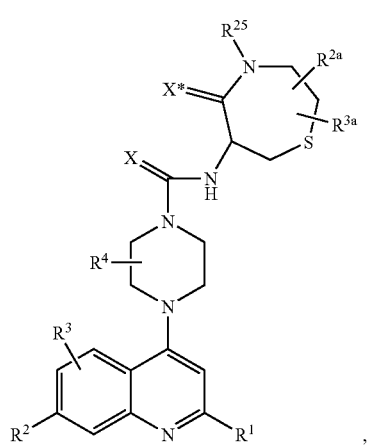
,
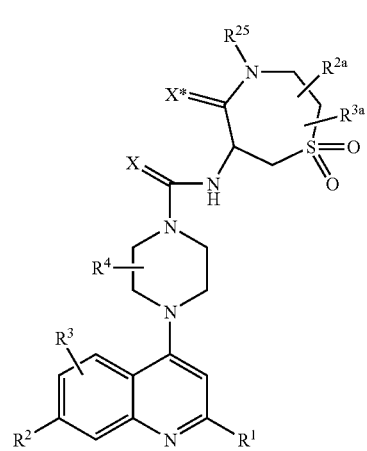
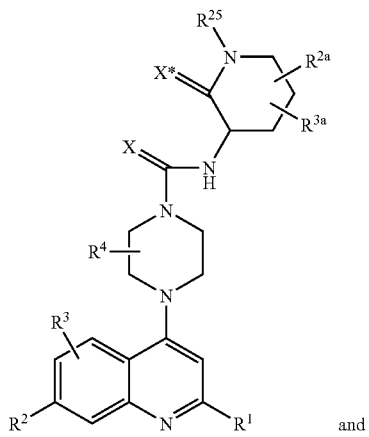
and
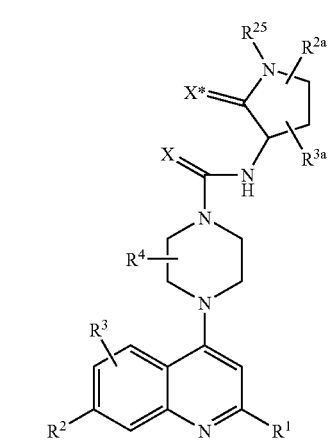
where X and X* are independently O or S.
Preferred compounds within the scope of formula (2a) include compounds of formula (4a)
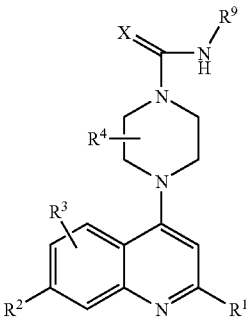
(4a)

wherein
R¹ is hydrogen or amino;
R² is halo;
R³ is hydrogen, alkyl, halogenated alkyl, halogen, substituted or unsubstituted amino, nitro, cyano, or alkoxy;
R⁴ is hydrogen or one or more alkyl groups;
R⁹ is
  (a) alkyl, haloalkyl, alkoxycarbonylalkyl, $-CH_2-C(=O)OR^{15}$, $-CH_2-C(=O)R^{15}$, or $-CH_2-C(=O)NR^{16}R^{17}$;
  (b) cycloalkyl (especially cyclohexyl, cycloheptyl, benzofused-cyclohexyl, or benzofused-cycloheptyl) optionally substituted with one to three groups independently selected from alkyl, haloalkyl, alkoxy, aryloxy, arylalkyloxy, heteroaryloxy, halo, hydroxy, oxo, thioxo, $=N-OR^{15}$, $-(CR^{20}R^{21})_m-C(=O)OR^{15}$, $-(CR^{20}R^{21})_m-C(=O)R^{15}$, $-(CR^{20}R^{21})_m-C(=O)NR^{16}R^{17}$;
  (c) aryl (especially phenyl or benzodioxinyl) optionally substituted with one to three groups independently selected from alkyl, alkoxy, heteroaryloxy, halo, hydroxy, oxo, thioxo, $=N-OR^{15}$, $-(CR^{20}R^{21})_m-C(=O)OR^{15}$, $-(CR^{20}R^{21})_m-C(=O)R^{15}$, $-(CR^{20}R^{21})_m-C(=O)NR^{16}R^{17}$; or
  (d) heteroaryl (especially pyridyl) optionally substituted with one to three groups independently selected from alkyl, alkoxy, aryloxy, heteroaryloxy, halo, hydroxy, oxo, thioxo, $=N-OR^{15}$, $-(CR^{20}R^{21})_m-C(=O)OR^{15}$, $-(CR^{20}R^{21})_m-C(=O)R^{15}$, $-(CR^{20}R^{21})_m-C(=O)NR^{16}R^{17}$.

Preferred compounds within the scope of formulae (1a) and (1b) include those wherein R⁵ is $-C(O)NHR^9$ wherein R⁹ is 2-oxopyrrolidinyl, 5-oxohexahydro-1,4-thiazepin-6-yl, 5-oxohexahydro-1,1-dioxido-1,4-thiazepin-6-yl, (2,3,4,5)-tetrahydro-2-oxo-1H-1-benzazepin-3-yl, hexahydro-1H-azepin-3-yl, 2-oxohexahydro-1H-azepin-3-yl, any of which may be optionally independently substituted by
  a) substituted or un-substituted alkyl, allyl, cyclopropylmethyl,
  b) substituted phenylmethyl;
  c) 2, 3, or 4-pyridinylmethyl
  d) substituted phenyl
  e) cyano;
  f) formyl, alkycarbonyl;
  g) cycloalkylcarbonyl, heterocyclocarbonyl (preferably pryolidinylcarbonyl), or arylcarbonyl;
  h) alkylsulfonyl, arylsulfonyl;
  i) alkoxycarbonyl, fluorinated alkoxycarbonyl, alloxycarbonyl;
  j) substituted phenoxycarbonyl, benzoxycarbonyl;
  k) aminocarbonyl, substituted or unsubstituted alkylaminocarbonyl, fluorinated alkylaminocarbonyl, allylaminocarbonyl, cycloalkylaminocarbonyl;
  l) N,N-alkylalkylaminocarbonyl;
  m) alkylaminocarbonothionyl;
  n) substituted or unsubstituted phenylaminocarbonyl;
  o) (aryllsulfonyl)aminocarbonyl;

Examples of specific preferred R⁵ groups include:
4-fluorophenylaminocarbonyl;
4-tert-butoxycarbonyl;
3,4-difluorophenylaminocarbonyl;
2,3,4-trifluorophenylaminocarbonyl;
4-phenylaminocarbonyl;
4-methylphenylaminocarbonyl;
3-methylphenylaminocarbonyl;
2-methylphenylaminocarbonyl;
(4-n-butylphenylaminocarbonyl);
4-methoxyphenylaminocarbonyl;
4-benzyloxyphenylaminocarbonyl;
benzylaminocarbonyl;
4-phenethylaminocarbonyl;
phenylpropylaminocarbonyl;
(1-methoxycarbonyl-1-phenylethyl)aminocarbonyl;
1-phenylethylaminocarbonyl;
2-chlorobenzylaminocarbonyl;
2-methylbenzylaminocarbonyl;
2-trifluoromethylbenzylaminocarbonyl;
1-indanylaminocarbonyl;
1,2,3,4-tetrahydronaphth-1-ylaminocarbonyl;
4-pyridinylaminocarbonyl;
3-pyridinylaminocarbonyl;
2-pyridinylaminocarbonyl;
4-trifluoromethylphenylaminocarbonyl;
4-ethoxyphenylaminocarbonyl;
4-isopropylphenylaminocarbonyl;
4-acetylphenylaminocarbonyl;
4-dimethylaminophenylaminocarbonyl;
cyclopentylaminocarbonyl;
3-piperonylaminocarbonyl;
(6-methylbenzothiazol-2-yl)phenylaminocarbonyl;
cyclobutylaminocarbonyl;
cyclohexylaminocarbonyl;
adamant-1-ylaminocarbonyl;
exo-norborn-2-ylaminocarbonyl;
benzimidazol-2-yl;
pyrimidin-2-yl;
cycloheptylaminocarbonyl;
cyclooctylaminocarbonyl;
(4-methylcyclohexyl)aminocarbonyl;
(2-methylcyclohexyl)aminocarbonyl;
fluorophenylaminocarbonyl;
2,3-dimethylcyclohexylaminocarbonyl;
4-(trifluoromethyl)cyclohexylaminocarbony;
cis-4-methylcyclohexylaminocarbony;
trans-4-methylcyclohexylaminocarbonyl
3,4-dimethoxyphenylaminocarbonyl;
2,3-dihydro-1,4-benzodioxin-6-ylaminocarbonyl;
4-fluoro-3-methoxyphenylaminocarbonyl;
3-fluoro-4-methoxyphenylaminocarbonyl;
3-chloro-4-methoxyphenylaminocarbonyl;
2-hydroxyphenylaminocarbonyl;
3-cyclohexen-1-ylaminocarbonyl;
3-fluoro-6,7,8,9-tetrahydro-5H-benzo[α]cyclohepten-5-ylaminocarbonyl;
6,7,8,9-tetrahydro-5H-benzo[α]cyclohepten-5-ylaminocarbonyl;
2-fluoro-6,7,8,9-tetrahydro-5H-benzo[α]cyclohepten-7-ylaminocarbonyl;
9-(acetyloxy)-2-fluoro-6,7,8,9-tetrahydro-5H-benzo[α]cyclohepten-7-yl-aminocarbonyl;
2-fluoro-6,7,8,9-tetrahydro-9-hydroxy-5H-benzo[α]cyclohepten-7-yl-aminocarbonyl;
4-tert-butoxycarbonyl-hexahydro-1H-azepin-4-ylaminocarbonyl;
4-methoxycarbonyl-hexahydro-1H-azepin-4-ylaminocarbonyl;
4-benzoxycarbonyl-hexahydro-1H-azepin-4-ylaminocarbonyl;
3-hydroxycycloheptylaminocarbonyl;
3-oxocycloheptylaminocarbonyl;
3-hydroxy-3-methylcycloheptylaminocarbonyl;
3-(ethoxyimino)cycloheptylamniocarbonyl;
3-methoxycycloheptylaminocarbonyl;
3-[(4-fluorophenyl)methoxy]cycloheptylaminocarbonyl;

2-pyridinyloxy)cycloheptylaminocarbonyl;
3-(2-pyrimidinyloxy)cycloheptylaminocarbonyl;
3-[(3-methyl-2-pyridinyl)oxy]cycloheptylaminocarbonyl;
3-[(4-methyl-2-pyridinyl)oxy]cycloheptylaminocarbonyl;
(3R)-hexahydro-2-oxo-1H-azepin-3-ylaminocarbonyl;
(3S)-hexahydro-2-oxo-1H-azepin-3-ylaminocarbonyl;
(3S)-hexahydro-2-oxo-1-methyl-1H-azepin-3-ylaminocarbonyl;
(3S)-hexahydro-2-oxo-1-(phenylmethyl)-1H-azepin-3-ylaminocarbonyl;
(3S)-hexahydro-2-oxo-1-[(4-fluorophenyl)methyl]-1H-azepin-3-ylaminocarbonyl;
(3S)-hexahydro-2-oxo-1-ethyl-1H-azepin-3-ylaminocarbonyl;
(3S)-hexahydro-2-oxo-1-(2-aminocarbonyl)ethyl]-1H-azepin-3-ylaminocarbonyl;
(3S)-hexahydro-2-oxo-1-(3-pyridinylmethyl)-1H-azepin-3-ylaminocarbonyl;
(3S)-hexahydro-2-oxo-1-(2-propenyl)-1H-azepin-3-ylaminocarbonyl;
(3S)-hexahydro-2-oxo-1-(cyclopropylmethyl)-1H-azepin-3-ylaminocarbonyl;
(3S)-hexahydro-2-oxo-1-(2-ethoxycarbonylethyl)-1H-azepin-3-ylaminocarbonyl;
(3S)-hexahydro-2-oxo-1-[(4-methoxyphenyl)methyl]-1H-azepin-3-ylaminocarbonyl;
4-fluorophenylmethylcarbonyl;
2,3,4,5,6-pentafluorophenylaminocarbonyl;
2-methoxyphenylaminocarbonyl;
1,2-dihydro-2-oxo-3-pyridinylaminocarbonyl;
cyclohexylaminocarbonothioyl;
2,2,2-trifluoroethylaminocarbonothioyl;
(2-ethoxycarbonyl)ethylaminocarbonothioyl;
(1S)-2-methoxy-1-methyl-2-oxoethylaminocarbonyl;
(1S)-2-(4-fluorophenylamino)-1-methyl-2-oxoethylaminocarbonyl;
2-[N-methyl(phenylmethyl)amino]-2-oxoethylaminocarbonyl;
2-[(4-fluorophenyl)amino]-2-oxoethylaminocarbonyl;
2-(dimethylamino)-2-oxoethylaminocarbonyl;
2-(methylphenylamino)-2-oxoethylaminocarbonyl;
4-nitrobenzoxycarbonyl;
2-[[(methoxycarbonyl)cycloheptyl]imino]oxycarbonyl;
2-(methoxycarbonyl)cycloheptylaminocarbonyl;
(6R)-hexahydro-5-oxo-1,4-thiazepin-6-ylaminocarbonothioyl;
(6R)-hexahydro-5-oxo-1,4-thiazepin-6-ylaminocarbonyl;
(6R)-hexahydro-1,1-dioxido-5-oxo-1,4-thiazepin-6-ylaminocarbonyl;
(3S)-2-oxopyrrolidinylaminocarbonyl;
(3S)-2,3,4,5-tetrahydro-2-oxo-1H-1-benzazepin-3-ylaminocarbonyl;
(3S)-2,3,4,5-tetrahydro-1-methyl-2-oxo-1H-1-benzazepin-3-ylaminocarbonyl;
(3S)-1,2,3,4-tetrahydro-2-oxoquinolinylaminocarbonyl;
2-methoxy-3-pyridinylaminocarbonyl;
1,2-dihydro-1-methyl-2-oxo-3-pyridinylaminocarbonyl;
(3R)-hexahydro-2-thioxo-1H-azepin-3-ylaminocarbonyl;
(9S)-6,7,8,9-tetrahydro-5H-[1,2,4]triazolo[4,3-α]azepin-9-ylaminocarbonyl;
(9S)-2,5,6,7,8,9-hexahydro-3-oxo-3H-[1,2,4]triazolo[4,3-α]azepin-9-ylaminocarbonyl;
N-[(3S)-1-acetylhexahydro-1H-azepin-3-ylaminocarbonyl;
2-(methoxycarbonyl)cyclohexylaminocarbonyl;
2-(hydroxycarbonyl)cyclohexylaminocarbonyl;
2-[(methylamino)carbonyl]cyclohexylaminocarbonyl;
4-(2-amino-7-chloro-4-quinolinyl)-N-[(3S)-hexahydro-2-oxo-1H-azepin-3-yl]-1-piperazinecarboxamide;
(3S)-1-[(2,6-dimethylphenyl)methyl]hexahydro-2-oxo-1H-azepin-3-ylaminocarbonyl;
(3S)-hexahydro-2-oxo-1-(2-pyridinylmethyl)-1H-azepin-3-ylaminocarbonyl;
(3S)-hexahydro-2-oxo-1-(4-pyridinylmethyl)-1H-azepin-3-ylaminocarbonyl;
(3S)-hexahydro-2-oxo-1-(2-hydroxy-3-phenoxypropyl)-1H-azepin-3-ylaminocarbonyl;
(3S)-hexahydro-1-(2-hydroxypropyl)-2-oxo-1H-azepin-3-ylaminocarbonyl;
(3S)-hexahydro-2-oxo-1-(2-methoxy-2-oxo-ethyl)-1H-azepin-3-ylaminocarbonyl;
(3S)-hexahydro-2-oxo-1-(2-hydroxy-2-oxo-ethyl)-1H-azepin-3-ylaminocarbonyl;
(3S)-hexahydro-2-oxo-1-(2-benzylamino-2-oxo-ethyl)-1H-azepin-3-ylaminocarbonyl;
(3S)-hexahydro-2-oxo-1-(2-methylamino-2-oxo-ethyl)-1H-azepin-3-ylaminocarbonyl;
(3S)-hexahydro-2-oxo-1-[2-(4-pyridinyl)amino-2-oxo-ethyl]-1H-azepin-3-ylaminocarbonyl;
(3R)-1-hexahydro-2-oxo-(4-fluorophenyl)-1H-azepin-3-ylaminocarbonyl;
(3S)-hexahydro-2-oxo-1-(2-phenoxyacetyl)-1H-azepin-3-ylaminocarbonyl;
(3S)-hexahydro-2-oxo-1-acetyl-1H-azepin-3-ylaminocarbonyl;
(3S)-hexahydro-2-oxo-1-cyclopropylcarbonyl-1H-azepin-3-ylaminocarbonyl;
(3S)-hexahydro-2-oxo-1-benzoyl-1H-azepin-3-ylaminocarbonyl (3S)-hexahydro-2-oxo-1-ethylsulfonyl-1H-azepin-3-ylaminocarbonyl;
(3S)-hexahydro-2-oxo-1-phenylsulfonyl-1H-azepin-3-ylaminocarbonyl;
(3S)-hexahydro-2-oxo-1-[[(phenylsulfonyl)amino]carbonyl]-1H-azepin-3-yl]aminocarbonyl;
(3S)-hexahydro-2-oxo-1-(2-phenylacetyl)-1H-azepin-3-ylaminocarbonyl;
4-(2-amino-7-chloro-4-quinolinyl)-1-piperazinylaminocarbonyl;
(3S)-hexahydro-2-oxo-1-formyl-1H-azepin-3-ylaminocarbonyl;
(3S)-hexahydro-2-oxo-1-(2,2-dimethyl-1-oxopropyl)-1H-azepin-3-ylaminocarbonyl;
(3S)-hexahydro-2-oxo-1-(methylsulfonyl)-1H-azepin-3-ylaminocarbonyl;
(3S)-hexahydro-2-oxo-1-(methoxycarbonyl)-1H-azepin-3-ylaminocarbonyl;
(3S)-hexahydro-2-oxo-1-(ethoxycarbonyl)-1H-azepin-3-ylaminocarbonyl;
(3S)-hexahydro-2-oxo-1-(2,2,2-trifluoroethoxycarbonyl)-1H-azepin-3-ylaminocarbonyl;
(3S)-hexahydro-2-oxo-1-(2-propenoxycarbonyl)-1H-azepin-3-ylaminocarbonyl;
(3S)-hexahydro-2-oxo-1-(phenoxycarbonyl)-1H-azepin-3-ylaminocarbonyl;
(3S)-hexahydro-2-oxo-1-(4-fluorophenoxycarbonyl)-1H-azepin-3-ylaminocarbonyl;
(3S)-hexahydro-2-oxo-1-(benzoxycarbonyl)-1H-azepin-3-ylaminocarbonyl;
(3S)-hexahydro-2-oxo-1-cyano-1H-azepin-3-ylaminocarbonyl;
(3S)-hexahydro-2-oxo-1-(phenoxycarbonyl)-1H-azepin-3-ylaminocarbonyl;
(3S)-hexahydro-2-oxo-1-(cyclohexylaminocarbonyl)-1H-azepin-3-ylaminocarbonyl;

(3S)-hexahydro-2-oxo-1-(aminocarbonyl)-1H-azepin-3-ylaminocarbonyl;
(2S)-6-[[[(trichloroacetyl)amino]carbonyl]amino]-1-methoxy-1-oxo-hexyl-2-aminocarbonyl;
(3S)-hexahydro-2-oxo-1-(2,2,2-trifluoroethylaminocarbonyl)-1H-azepin-3-ylaminocarbonyl;
(3S)-hexahydro-2-oxo-1-(cyclopropylaminocarbonyl)-1H-azepin-3-ylaminocarbonyl;
(3S)-hexahydro-2-oxo-1-(propylaminocarbonyl)-1H-azepin-3-ylaminocarbonyl;
(3S)-hexahydro-2-oxo-1-(pyrrolidinylcarbonyl)-1H-azepin-3-ylaminocarbonyl;
(3S)-hexahydro-2-oxo-1-(cyclopentylaminocarbonyl)-1H-azepin-3-ylaminocarbonyl;
(3S)-hexahydro-2-oxo-1-(cyclobutylaminocarbonyl)-1H-azepin-3-ylaminocarbonyl;
(3S)-hexahydro-2-oxo-1-(4-fluorophenylaminocarbonyl)-1H-azepin-3-ylaminocarbonyl;
(3S)-hexahydro-2-oxo-1-(phenylaminocarbonyl)-1H-azepin-3-ylaminocarbonyl;
(3S)-hexahydro-2-oxo-1-(isopropylaminocarbonyl)-1H-azepin-3-ylaminocarbonyl;
(3S)-hexahydro-2-oxo-1-(n-butylaminocarbonyl)-1H-azepin-3-ylaminocarbonyl;
(3S)-hexahydro-2-oxo-1-(2-methylpropylaminocarbonyl)-1H-azepin-3-ylaminocarbonyl;
(3S)-hexahydro-2-oxo-1-(t-butylaminocarbonyl)-1H-azepin-3-ylaminocarbonyl;
(3S)-hexahydro-2-oxo-1-(N,N-dimethylaminocarbonyl)-1H-azepin-3-ylaminocarbonyl;
(3S)-hexahydro-2-oxo-1-(4-trifluoromethylaminocarbonyl)-1H-azepin-3-ylaminocarbonyl;
(3S)-hexahydro-2-oxo-1-(3-fluorophenylaminocarbonyl)-1H-azepin-3-ylaminocarbonyl;
(3S)-hexahydro-2-oxo-1-(4-methylphenylaminocarbonyl)-1H-azepin-3-ylaminocarbonyl;
(3S)-hexahydro-2-oxo-1-(2-fluorophenylaminocarbonyl)-1H-azepin-3-ylaminocarbonyl;
(3S)-hexahydro-2-oxo-1-(N-2,6-diethylphenylaminocarbonyl)-1H-azepin-3-ylaminocarbonyl;
(3S)-hexahydro-2-oxo-1-(N-methylaminocarbonothioyl)-1H-azepin-3-ylaminocarbonyl;
(3S)-hexahydro-2-oxo-1-(N-ethylaminocarbonothioyl)-1H-azepin-3-ylaminocarbonyl;
(3S)-hexahydro-2-oxo-1-(N-isopropylaminocarbonothioyl)-1H-azepin-3-ylaminocarbonyl;
(3S)-hexahydro-2-oxo-1-(N-2-propenylaminocarbonothioyl)-1H-azepin-3-ylaminocarbonyl;
(3S)-hexahydro-2-oxo-1-(N-methylaminocarbonyl)-1H-azepin-3-ylaminocarbonyl;
(3S)-hexahydro-2-oxo-1-[N-(2-propenyl)aminocarbonyl]-1H-azepin-3-ylaminocarbonyl;
(3S)-hexahydro-2-oxo-1-[N-(2-chloroethyl)aminocarbonyl]-1H-azepin-3-ylaminocarbonyl;
(3R)-hexahydro-2-oxo-1-(N-methylaminocarbonyl)-1H-azepin-3-ylaminocarbonyl;

Also preferred are compounds of formula 1a wherein $R^5$ is
fluorophenylaminocarbonothionyl,
cyanimino(phenoxy)methyl,
cyanimino(ethoxy)methyl,
cyanimino(4-fluorophenylamino)methyl,
cyanimino(4-fluorobenzylamino)methyl,
tert-butylamino(cyanimino)methyl,
cyanimino(ethylamino)methyl,
4-fluorophenylamino-2,3-dioxocyclobut-1-enyl,
ethoxyimino(4-fluorophenylamino)methyl,
methoxyimino(4-fluorophenylamino)methyl;
fluorobenzylamino(imino)methyl, or
fluorophenylamino(imino)methyl.

Also preferred are compounds wherein $R^1$ is
a) —$CO_2H$
b) —$CONMe_2$,
c) methyl,
d) —COOethyl,
e) —H,
f) substituted or unsubstituted amino;
g) substituted (phenylamino)carbonylamino; or
h) [2-oxohexahydro-1-(t-butylcarbonyl)-1H-azepin-3-yl]carbonylamino;

Also preferred are compounds wherein $R^2$ and $R^3$ may be the same or different and are independently selected from
a) —Cl
b) —F
c) —Br
e) —$CF_3$
f) —$OCH_3$
g) -Me
h) $R^2$ and $R^3$ are on adjacent carbon atoms and combine to form —$OCH_2O$—
i) —$NO_2$
j) —$NH_2$
k) —NHAc
l) —NHMe or
m) —CN Other preferred embodiments of the present invention include:

a) A pharmaceutical composition comprising one or more compounds of formulae (1a) and/or (1b) in admixture with a pharmaceutically acceptable excipient, diluent, or carrier.

b) A method for modulation of chemokine receptor activity in a mammal which comprises the administration of an effective amount of at least one compound of formulae (1a) or (1b).

c) A method for the prevention or treatment of an inflammatory and immunoregulatory disorder or disease which comprises the administration to a patient of an effective amount of at least one compound of formulae (1a) or (1b).

d) A method for the prevention or treatment of asthma, allergic rhinitis, dermatitis, conjunctivitis, or atherosclerosis which comprises the administration to a patient an effective amount of at least one compound of formulae (1a) or (1b).

e) A method for the prevention or treatment of rheumatoid arthritis which comprises the administration to a patient of an effective amount of at least one compound of formulae (1a) or (1b).

f) A method for preventing infection by HIV, treating infection by HIV, delaying of the onset of AIDS, or treating AIDS or AIDS dementia complex comprising the administration to a patient of an effective amount of at least one compound of formulae (1a) or (1b).

g) A method for the prevention or treatment of demyelinating disorders such as multiple sclerosis or optic neuritis which comprises the administration to a patient of an effective amount of at least one compound of formulae (1a) or (1b).

h) A method for the prevention or treatment of endometriosis which comprises the administration to a patient of an effective amount of at least one compound of formulae (1a) or (1b).

i) A method for the prevention or treatment of ischemic stroke which comprises the administration to a patient of an effective amount of at least one compound of formulae (1a) or (1b).

j) A method for the prevention or treatment of cancer which comprises the administration to a patient of an effective amount of at least one compound of formulae (1a) or (1b).

k) A method for the prevention or treatment of psoriasis which comprises the administration to a patient of an effective amount of at least one compound of formulae (1a) or (1b).

Preferred compounds of the present invention include:
7-Chloro-4-[4-(4-fluorophenylaminocarbonyl)piperazin-1-yl]quinoline;
6-Chloro-4-[4-(4-fluorophenylaminocarbonyl)piperazin-1-yl]quinoline;
7-Chloro-4-[4-(4-fluorophenylaminocarbonyl)piperazin-1-yl]-2-methylquinoline;
5-Chloro-4-[4-(4-fluorophenylaminocarbonyl)piperazin-1-yl]-2-methylquinoline;
7-Chloro-4-[4-(4-fluorophenylaminocarbonyl)piperazin-1-yl]-8-methylquinoline;
7-Chloro-4-[4-(4-fluorophenylaminocarbonyl)piperazin-1-yl]-3-methylquinoline;
4-[4-(4-Fluorophenylaminocarbonyl)piperazin-1-yl]-7-methoxy-2-methylquinoline;
7-Chloro-6-fluoro-4-[4-(4-fluorophenylaminocarbonyl)piperazin-1-yl]quinoline;
7-Fluoro-4-[4-(4-fluorophenylaminocarbonyl)piperazin-1-yl]quinoline;
6,7-Difluoro-4-[4-(4-fluorophenylaminocarbonyl)piperazin-1-yl]quinoline;
7-Cyano-4-[4-(4-fluorophenylaminocarbonyl)piperazin-1-yl]quinoline;
4-[4-(4-Fluorophenylaminocarbonyl)piperazin-1-yl]-6,7-methylenedioxyquinoline;
4-[4-(4-Fluorophenylaminocarbonyl)piperazin-1-yl]-7-methylquinoline trifluoroacetate;
4-[4-(tert-Butoxycarbonyl)piperazin-1-yl]-7-nitroquinoline;
4-[4-(4-Fluorophenylaminocarbonyl)piperazin-1-yl]-7-nitroquinoline trifluoroacetate;
7-Amino-4-[4-(4-fluorophenylaminocarbonyl)piperazin-1-yl]quinoline;
7-Acetylamino-4-[4-(4-fluorophenylaminocarbonyl)piperazin-1-yl]quinoline, trifluoroacetate;
Ethyl 4-[4-(tert-butoxycarbonyl)piperazin-1-yl]-7-chloroquinoline-2-carboxylate;
Ethyl 7-chloro-4-[4-(4-fluorophenylaminocarbonyl)piperazin-1-yl]quinoline-2-carboxylate;
7-Chloro-4-[4-(4-fluorophenylaminocarbonyl)piperazin-1-yl]-2-(hydroxymethyl)quinoline, trifluoroacetate;
2-Azidomethyl-7-chloro-4-[4-(4-fluorophenylaminocarbonyl)piperazin-1-yl]quinoline;
7-Chloro-4-[4-(4-fluorophenylaminocarbonyl)piperazin-1-yl]-2-(methoxymethyl)quinoline, trifluoroacetate;
2-Aminomethyl-7-chloro-4-[4-(4-fluorophenylaminocarbonyl)piperazin-1-yl]quinoline, trifluoroacetate;
7-Chloro-4-[4-(4-fluorophenylaminocarbonyl)piperazin-1-yl]quinoline-2-carboxylic acid;
2-tert-Butoxycarbonylamino-7-chloro-4-[4-(4-fluorophenylaminocarbonyl)piperazin-1-yl]quinoline;
2-Amino-7-chloro-4-[4-(4-fluorophenylaminocarbonyl)piperazin-1-yl]quinoline, trifluoroacetate
2-Acetylamino-7-chloro-4-[4-(4-fluorophenylaminocarbonyl)piperazin-1-yl]quinoline;
N-[7-Chloro-4-[4-(4-fluorophenylaminocarbonyl)piperazin-1-yl]quinolin-2-yl]urea;
N-[7-Chloro-4-[4-(4-fluorophenylaminocarbonyl)piperazin-1-yl]quinolin-2-yl]-N'-phenylurea;
7-Chloro-4-[4-(4-fluorophenylaminocarbonyl)piperazin-1-yl]-2-(methylamino)quinoline, trifluoroacetate;
4-[4-(tert-Butoxycarbonyl)piperazin-1-yl]-7-chloro-2-quinolone;
7-Chloro-4-[4-(4-fluorophenylaminocarbonyl)piperazin-1-yl]-2-quinolone;
7-Chloro-2-dimethylamino-4-[4-(4-fluorophenylaminocarbonyl)piperazin-1-yl]quinoline;
7-Chloro-2-ethylamino-4-[4-(4-fluorophenylaminocarbonyl)piperazin-1-yl]quinoline;
7-Chloro-2-[2-(dimethylamino)ethylamino]-4-[4-(4-fluorophenylaminocarbonyl)piperazin-1-yl]quinoline;
7-Chloro-2-cyclohexylamino-4-[4-(4-fluorophenylaminocarbonyl)piperazin-1-yl]quinoline;
7-Chloro-2-cyclopropylamino-4-[4-(4-fluorophenylaminocarbonyl)piperazin-1-yl]quinoline;
7-Chloro-2-cyclopropylmethylamino-4-[4-(4-fluorophenylaminocarbonyl)piperazin-1-yl]quinoline;
4-[4-(tert-Butoxycarbonyl)piperazin-1-yl]-7-chloro-2-(2-hydroxyethylamino)quinoline;
7-Chloro-4-[4-(4-fluorophenylaminocarbonyl)piperazin-1-yl]-2-[2-(4-fluorophenylaminocarbonyloxy)ethylamino]quinoline;
7-Chloro-4-[4-(4-fluorophenylaminocarbonyl)piperazin-1-yl]-2-(2-hydroxyethylamino)quinoline trifluoroacetate;
7-Chloro-4-[4-(4-fluorophenylaminocarbonyl)piperazin-1-yl]-2-(2-methoxyethyl)aminoquinoline;
4-[4-(tert-Butoxycarbonyl)piperazin-1-yl]-7-chloro-2-(n-propylamino)quinoline;
7-Chloro-4-[4-(4-fluorophenylaminocarbonyl)piperazin-1-yl]-2-(n-propylamino)quinoline;
4-[4-(tert-Butoxycarbonyl)piperazin-1-yl]-7-chloro-2-(isopropylamino)quinoline
7-Chloro-4-[4-(4-fluorophenylaminocarbonyl)piperazin-1-yl]-2-(isopropylamino)quinoline;
4-[4-(tert-Butoxycarbonyl)piperazin-1-yl]-2-(n-butylamino)-7-chloroquinoline;
2-n-Butylamino-7-chloro-4-[4-(4-fluorophenylaminocarbonyl)piperazin-1-yl]quinoline;
4-[4-(tert-Butoxycarbonyl)piperazin-1-yl]-7-chloro-2-(n-pentylamino)-quinoline;
7-Chloro-4-[4-(4-fluorophenylaminocarbonyl)piperazin-1-yl]-2-(n-pentylamino)quinoline;
7-Chloro-4-[4-(4-fluorophenylaminocarbonyl)piperazin-1-yl]-2-[2-(4-fluorophenyl)ethylamino]quinoline;
7-Chloro-4-[4-(4-fluorophenylaminocarbonyl)-3-methylpiperazin-1-yl]quinoline;
4-[4-(tert-Butoxycarbonyl)-2-methylpiperazin-1-yl]-7-chloroquinoline;
7-Chloro-4-[4-(4-fluorophenylaminocarbonyl)-2-methylpiperazin-1-yl]quinoline;
7-Chloro-4-[3,5-dimethyl-4-(4-fluorophenylaminocarbonyl)piperazin-1-yl]quinoline;
7-Chloro-4-[3,6-dimethyl-4-(4-fluorophenylaminocarbonyl)piperazin-1-yl]quinoline, trifluoroacetate;
7-Chloro-4-[5-(4-fluorophenylaminocarbonyl)-2,5-diazanorbornan-2-yl]quinoline, trifluoroacetate;
7-Chloro-4-[4-(4-fluorophenylaminocarbonyl)-1,4-diazepin-1-yl]quinoline;
7-Chloro-4-[4-(3,4-difluorophenylaminocarbonyl)piperazin-1-yl]quinoline;
7-Chloro-4-[4-(2,3,4-trifluorophenylaminocarbonyl)piperazin-1-yl]quinoline;
7-Chloro-4-[phenylaminocarbonyl)piperazin-1-yl]quinoline;
7-Chloro-4-[4-(4-methylphenylaminocarbonyl)piperazin-1-yl]quinoline;

7-Chloro-4-[4-(3-methylphenylaminocarbonyl)piperazin-1-yl]quinoline;
7-Chloro-4-[4-(2-methylphenylaminocarbonyl)piperazin-1-yl]quinoline;
4-[4-(4-n-Butylphenylaminocarbonyl)piperazin-1-yl]-7-chloro-quinoline;
7-Chloro-4-[4-(4-methoxyphenylaminocarbonyl)piperazin-1-yl]quinoline;
4-[4-(4-Benzyloxyphenylaminocarbonyl)piperazin-1-yl]-7-chloroquinoline;
4-[4-(Benzylaminocarbonyl)piperazin-1-yl]-7-chloroquinoline;
7-Chloro-4-[4-(phenethylaminocarbonyl)piperazin-1-yl]quinoline;
7-Chloro-4-[4-(phenylpropylaminocarbonyl)piperazin-1-yl]quinoline;
7-Chloro-4-[4-[(1-methoxycarbonyl-1-phenylethyl)aminocarbonyl]piperazin-1-yl]quinoline;
7-Chloro-4-[4-(1-phenylethylaminocarbonyl)piperazin-1-yl]quinoline;
7-Chloro-4-[4-(2-chlorobenzylaminocarbonyl)piperazin-1-yl]quinoline;
7-Chloro-4-[4-(2-methylbenzylaminocarbonyl)piperazin-1-yl]quinoline;
7-Chloro-4-[4-(2-trifluoromethylbenzylaminocarbonyl)piperazin-1-yl]quinoline;
7-Chloro-4-[4-(1-indanylaminocarbonyl)piperazin-1-yl]quinoline;
7-Chloro-4-[4-(1,2,3,4-tetrahydronaphth-1-ylaminocarbonyl)piperazin-1-yl]quinoline;
7-Chloro-4-[4-(4-pyridinylaminocarbonyl)piperazin-1-yl]quinoline;
7-Chloro-4-[4-(3-pyridinylaminocarbonyl)piperazin-1-yl]quinoline;
7-Chloro-4-[4-(2-pyridinylaminocarbonyl)piperazin-1-yl]quinoline;
7-Chloro-4-[4-(4-trifluoromethylphenylaminocarbonyl)piperazin-1-yl]quinoline;
7-Chloro-4-[4-(4-ethoxyphenylaminocarbonyl)piperazin-1-yl]quinoline;
7-Chloro-4-[4-(4-isopropylphenylaminocarbonyl)piperazin-1-yl]quinoline;
4-[4-(4-Acetylphenylaminocarbonyl)piperazin-1-yl]-7-chloroquinoline;
7-Chloro-4-[4-(4-dimethylaminophenylaminocarbonyl)piperazin-1-yl]quinoline;
7-Chloro-4-[4-(cyclopentylaminocarbonyl)piperazin-1-yl]quinoline;
7-Chloro-4-[4-(3-piperonylaminocarbonyl)piperazin-1-yl]quinoline;
7-Chloro-4-[4-[4-(6-methylbenzothiazol-2-yl)phenylaminocarbonyl]piperazin-1-yl]quinoline;
7-Chloro-4-[4-(cyclobutylaminocarbonyl)piperazin-1-yl]quinoline;
7-Chloro-4-[4-(cyclohexylaminocarbonyl)piperazin-1-yl]quinoline;
4-[4-(Adamant-1-ylaminocarbonyl)piperazin-1-yl]-7-chloroquinoline;
7-Chloro-4-[4-(exo-norborn-2-ylaminocarbonyl)piperazin-1-yl]quinoline;
7-Chloro-4-[4-(4-fluorophenylsulfonyl)piperazin-1-yl]quinoline;
7-Chloro-4-[4-(4-fluorophenylaminothiocarbonyl)piperazin-1-yl]quinoline;
7-Chloro-4-[4-[cyanimino(phenoxy)methyl]piperazin-1-yl]quinoline;
7-Chloro-4-[4-[cyanimino(ethoxy)methyl]piperazin-1-yl]quinoline;
7-Chloro-4-[4-(cyanimino(4-fluorophenylamino)methyl)piperazin-1-yl]quinoline;
7-Chloro-4-[4-(cyanimino(4-fluorobenzylamino)methyl)piperazin-1-yl]quinoline;
4-[4-(tert-Butylamino(cyanimino)methyl)piperazin-1-yl]-7-chloroquinoline;
7-Chloro-4-[4-[cyanimino(ethylamino)methyl]piperazin-1-yl]quinoline;
7-Chloro-4-[4-[4-(4-fluorophenylamino]-2,3-dioxocyclobut-1-enyl]piperazin-1-yl]quinoline;
4-[4-(Benzimidazol-2-yl)piperazin-1-yl]-7-chloroquinoline;
7-Chloro-4-[4-(pyrimidin-2-yl)piperazin-1-yl]-7-chloroquinoline;
7-Chloro-4-[4-[ethoxyimino(4-fluorophenylamino)methyl]piperazin-1-yl]quinoline;
7-Chloro-4-[4-[methoxyimino(4-fluorophenylamino)methyl]piperazin-1-yl]quinoline;
7-Chloro-4-(piperazin-1-yl)quinoline;
7-Chloro-4-[4-(4-fluorobenzylamino(imino)methyl)piperazin-1-yl]quinoline;
7-Chloro-4-[4-(4-fluorophenylamino(imino)methyl)piperazin-1-yl]quinoline;
7-Chloro-4-[4-(cycloheptylaminocarbonyl)piperazin-1-yl]quinoline;
7-Chloro-4-[4-(cyclooctylaminocarbonyl)piperazin-1-yl]quinoline;
7-Chloro-4-[4-[(4-methylcyclohexyl)aminocarbonyl]piperazin-1-yl]quinoline;
-7-Chloro-4-[4-[(2-methylcyclohexyl)aminocarbonyl]piperazin-1-yl]quinoline;
2-(2-Aminoethylamino)-7-chloro-4-[4-(4-fluorphenylaminocarbonyl)piperazin-1-yl]quinoline;
7-Chloro-4-[4-(4-fluorphenylaminocarbonyl)piperazin-1-yl]-2-[2-(trifluoroacetamino)ethylamino]quinoline;
7-Chloro-4-[4-(4-fluorphenylaminocarbonyl)piperazin-1-yl]-2-methoxyquinoline;
4-(7-Chloro-4-quinolinyl)-N-(2,3-dimethylcyclohexyl)-1-piperazinecarboxamide;
4-(7-Chloro-4-quinolinyl)-N-[4-(trifluoromethyl)cyclohexyl]-1-piperazinecarboxamide;
4-(7-Chloro-4-quinolinyl)-N-(cis-4-methylcyclohexyl)-1-piperazinecarboxamide;
4-(7-Chloro-4-quinolinyl)-N-(trans-4-methylcyclohexyl)-1-piperazinecarboxamide
4-(7-Chloro-4-quinolinyl)-N-(3,4-dimethoxyphenyl)-1-piperazinecarboxamide;
4-(7-Chloro-4-quinolinyl)-N-(2,3-dihydro-1,4-benzodioxin-6-yl)-1-piperazinecarboxamide;
4-(7-Chloro-4-quinolinyl)-N-(4-fluoro-3-methoxyphenyl)-1-piperazinecarboxamide;
4-(7-Chloro-4-quinolinyl)-N-(3-fluoro-4-methoxyphenyl)-1-piperazinecarboxamide;
4-(7-Chloro-4-quinolinyl)-N-(3-chloro-4-methoxyphenyl)-1-piperazinecarboxamide;
4-(7-Chloro-4-quinolinyl)-N-(2-hydroxyphenyl)-1-piperazinecarboxamide;
4-(7-Chloro-4-quinolinyl)-N-(3-cyclohexen-1-yl)-1-piperazinecarboxamide;
4-(7-Chloro-4-quinolinyl)-N-(3-fluoro-6,7,8,9-tetrahydro-5H-benzo[α]cyclohepten-5-yl)-1-piperazinecarboxamide;
4-(7-Chloro-4-quinolinyl)-N-(6,7,8,9-tetrahydro-5H-benzo[α]cyclohepten-5-yl)-1-piperazinecarboxamide;

4-(7-Chloro-4-quinolinyl)-N-(2-fluoro-6,7,8,9-tetrahydro-5H-benzo[α]cyclohepten-7-yl)-1-piperazinecarboxamide;

4-(7-Chloro-4-quinolinyl)-N-[9-(acetyloxy)-2-fluoro-6,7,8,9-tetrahydro-5H-benzo[α]cyclohepten-7-yl]-1-piperazinecarboxamide;

4-(7-Chloro-4-quinolinyl)-N-(2-fluoro-6,7,8,9-tetrahydro-9-hydroxy-5H-benzo[α]cyclohepten-7-yl)-1-piperazinecarboxamide;

4-[[[4-(7-Chloro-4-quinolinyl)-1-piperazinyl]carbonyl]amino]hexahydro-1H-azepine-1-carboxylic acid, 1,1-dimethylethyl ester;

4-[[[4-(7-Chloro-4-quinolinyl)-1-piperazinyl]carbonyl]amino]hexahydro-1H-azepine-1-carboxylic acid, methyl ester;

4-[[[4-(7-Chloro-4-quinolinyl)-1-piperazinyl]carbonyl]amino]hexahydro-1H-azepine-1-carboxylic acid, phenylmethyl ester;

4-(7-Chloro-4-quinolinyl)-N-(3-hydroxycycloheptyl)-1-piperazinecarboxamide;

4-(7-Chloro-4-quinolinyl)-N-(3-oxocycloheptyl)-1-piperazinecarboxamide;

4-(7-Chloro-4-quinolinyl)-N-(3-hydroxy-3-methylcycloheptyl)-1-piperazinecarboxamide;

4-(7-Chloro-4-quinolinyl)-N-[(3E)-3-(ethoxyimino)cycloheptyl]-1-piperazinecarboxamide;

4-(7-Chloro-4-quinolinyl)-N-(3-methoxycycloheptyl)-1-piperazinecarboxamide;

4-(7-Chloro-4-quinolinyl)-N-[3-[(4-fluorophenyl)methoxy]cycloheptyl]-1-piperazinecarboxamide;

4-(7-Chloro-4-quinolinyl)-N-[3-(2-pyridinyloxy)cycloheptyl]-1-piperazinecarboxamide;

4-(7-Chloro-4-quinolinyl)-N-[3-(2-pyrimidinyloxy)cycloheptyl]-1-piperazinecarboxamide;

4-(7-Chloro-4-quinolinyl)-N-[3-[(3-methyl-2-pyridinyl)oxy]cycloheptyl]-1-piperazinecarboxamide;

4-(7-Chloro-4-quinolinyl)-N-[3-[(4-methyl-2-pyridinyl)oxy]cycloheptyl]-1-piperazinecarboxamide;

4-(7-Chloro-4-quinolinyl)-N-[(3R)-hexahydro-2-oxo-1H-azepin-3-yl]-1-piperazinecarboxamide;

4-(7-Chloro-4-quinolinyl)-N-[(3S)-hexahydro-2-oxo-1H-azepin-3-yl]-1-piperazinecarboxamide;

4-(7-Chloro-4-quinolinyl)-N-[(3S)-hexahydro-1-methyl-2-oxo-1H-azepin-3-yl]-1-piperazinecarboxamide;

4-(7-Chloro-4-quinolinyl)-N-[(3S)-hexahydro-2-oxo-1-(phenylmethyl)-1H-azepin-3-yl]-1-piperazinecarboxamide;

4-(7-Chloro-4-quinolinyl)-N-[(3S)-hexahydro-2-oxo-1-[(4-fluorophenyl)methyl]-1H-azepin-3-yl]-1-piperazinecarboxamide;

4-(7-Chloro-4-quinolinyl)-N-[(3S)-hexahydro-2-oxo-1-ethyl-1H-azepin-3-yl]-1-piperazinecarboxamide;

(3S)-[[[4-(7-Chloro-4-quinolinyl)-1-piperazinyl]carbonyl]amino]hexahydro-2-oxo-1H-azepin-1-acetamide;

4-(7-Chloro-4-quinolinyl)-N-[(3S)-hexahydro-2-oxo-1-(3-pyridinylmethyl)-1H-azepin-3-yl]-1-piperazinecarboxamide;

4-(7-Chloro-4-quinolinyl)-N-[(3S)-hexahydro-2-oxo-1-(2-propenyl)-1H-azepin-3-yl]-1-piperazinecarboxamide;

4-(7-Chloro-4-quinolinyl)-N-[(3S)-1-hexahydro-2-oxo-1-(cyclopropylmethyl)-1H-azepin-3-yl]-1-piperazinecarboxamide;

4-(7-Chloro-4-quinolinyl)-N-[(3S)-hexahydro-2-oxo-1-[(4-methoxyphenyl)methyl]-1H-azepin-3-yl]-1-piperazinecarboxamide;

(3S)-[[[4-(7-Chloro-4-quinolinyl)-1-piperazinyl]carbonyl]amino]hexahydro-2-oxo-1H-azepin-1-acetic acid, ethyl ester;

4-(7-Chloro-4-quinolinyl)-N-[(3S)-hexahydro-2-oxo-1-[3-(4-morpholinyl)propyl]-1-3-yl]-1-piperazinecarboxamide;

7-Chloro-4-(1-piperazinyl)-2-quinolinamine;

7-Chloro-4-[4-[(4-fluorophenyl)acetyl]-1-piperazinyl]-2-quinolinamine;

4-(2-Amino-7-chloro-4-quinolinyl)-N-(2,3,4,5,6-pentafluorophenyl)-1-piperazinecarboxamide;

4-(2-Amino-7-chloro-4-quinolinyl)-N-(2-methoxyphenyl)-1-piperazinecarboxamide;

4-(2-Amino-7-chloro-4-quinolinyl)-N-ethyl-1-piperazinecarboxamide;

4-(2-Amino-7-chloro-4-quinolinyl)-N-(4-methylphenyl)-1-piperazinecarboxamide;

4-[7-Chloro-2-[[[(4-methylphenyl)amino]carbonyl]amino]-4-quinolinyl]-N-(4-methylphenyl)-1-piperazinecarboxamide;

4-(2-Amino-7-chloro-4-quinolinyl)-N-tricyclo[3.3.1.1$^{3,7}$]dec-2-yl-1-piperazinecarboxamide;

4-(2-Amino-7-chloro-4-quinolinyl)-N-(1,2-dihydro-2-oxo-3-pyridinyl)-1-piperazinecarboxamide;

4-(2-Amino-7-chloro-4-quinolinyl)-N-cyclohexyl-1-piperazinecarbothioamide;

4-(2-Amino-7-chloro-4-quinolinyl)-N-(2,2,2-trifluoroethyl)-1-piperazinecarbothioamide;

4-(2-Amino-7-chloro-4-quinolinyl)-N-(4-fluorophenyl)-1-piperazinecarbothioamide;

[[[4-(2-Amino-7-chloro-4-quinolinyl)-1-piperazinyl]carbonothioyl]amino]-acetic acid, ethyl ester;

(2S)-2-[[[4-(2-Amino-7-chloro-4-quinolinyl)-1-piperazinyl]carbonyl]amino]-propanoic acid, methyl ester;

4-(2-Amino-7-chloro-4-quinolinyl)-N-[(1S)-2-[(4-fluorophenyl)amino]-1-methyl-2-oxoethyl]-1-piperazinecarboxamide;

4-(2-Amino-7-chloro-4-quinolinyl)-N-[2-[methyl(phenylmethyl)amino]-2-oxoethyl]-1-piperazinecarboxamide;

4-(2-Amino-7-chloro-4-quinolinyl)-N-[2-[(4-fluorophenyl)amino]-2-oxoethyl]-1-piperazinecarboxamide;

4-(2-Amino-7-chloro-4-quinolinyl)-N-[2-(dimethylamino)-2-oxoethyl]-1-piperazinecarboxamide;

4-(2-Amino-7-chloro-4-quinolinyl)-N-[2-(methylphenylamino)-2-oxoethyl]-1-piperazinecarboxamide;

4-(2-Amino-7-chloro-4-quinolinyl)-1-piperazinecarboxylic acid, 4-nitrophenyl ester;

2-[[[[4-(2-Amino-7-chloro-4-quinolinyl)-1-piperazinyl]carbonyl]oxy]imino]-cycloheptanecarboxylic acid, methyl ester;

2-[[[4-(2-Amino-7-chloro-4-quinolinyl)-1-piperazinyl]carbonyl]amino]-cycloheptanecarboxylic acid, methyl ester;

4-(2-Amino-7-chloro-4-quinolinyl)-N-[(6R)-hexahydro-5-oxo-1,4-thiazepin-6-yl]-1-piperazinecarbothioamide;

4-(2-Amino-7-chloro-4-quinolinyl)-N-[(6R)-hexahydro-5-oxo-1,4-thiazepin-6-yl]-1-piperazinecarboxamide;

4-(2-Amino-7-chloro-4-quinolinyl)-N-[(6R)-hexahydro-1,1-dioxido-5-oxo-1,4-thiazepin-6-yl]-1-piperazinecarboxamide;

4-(2-Amino-7-chloro-4-quinolinyl)-N-[(3S)-2-oxopyrrolidinyl]-1-piperazinecarboxamide;

4-(2-Amino-7-chloro-4-quinolinyl)-N-[(3S)-2,3,4,5-tetrahydro-2-oxo-1H-1-benzazepin-3-yl]-1-piperazinecarboxamide;

4-(2-Amino-7-chloro-4-quinolinyl)-N-[(3S)-2,3,4,5-tetrahydro-1-methyl-2-oxo-1H-1-benzazepin-3-yl]-1-piperazinecarboxamide;

4-(2-Amino-7-chloro-4-quinolinyl)-N-[(3S)-1,2,3,4-tetrahydro-2-oxoquinolinyl]-1-piperazinecarboxamide;
4-(2-Amino-7-chloro-4-quinolinyl)-N-cycloheptyl-1-piperazinecarboxamide;
4-(2-Amino-7-chloro-4-quinolinyl)-N-(4-fluoro-3-methoxyphenyl)-1-piperazinecarboxamide;
4-(2-Amino-7-chloro-4-quinolinyl)-N-(2-methoxy-3-pyridinyl)-1-piperazinecarboxamide;
4-(2-Amino-7-chloro-4-quinolinyl)-N-(1,2-dihydro-1-methyl-2-oxo-3-pyridinyl)-1-piperazinecarboxamide;
4-(2-Amino-7-chloro-4-quinolinyl)-N-[(3R)-hexahydro-2-thioxo-1H-azepin-3-yl]-1-piperazinecarboxamide;
4-(2-Amino-7-chloro-4-quinolinyl)-N-[(9S)-6,7,8,9-tetrahydro-5H-[1,2,4]triazolo[4,3-α]azepin-9-yl]-1-piperazinecarboxamide
4-(2-Amino-7-chloro-4-quinolinyl)-N-[(9S)-2,5,6,7,8,9-hexahydro-3-oxo-3H-[1,2,4]triazolo[4,3-α]azepin-9-yl]-1-piperazinecarboxamide
4-(2-Amino-7-chloro-4-quinolinyl)-N-[(3S)-hexahydro-1-acetyl-1H-azepin-3-yl]-1-piperazinecarboxamide;
3-[[[4-(2-Amino-7-chloro-4-quinolinyl)-1-piperazinyl]carbonyl]amino]-cyclohexanecarboxylic acid, methyl ester;
3-[[[4-(2-Amino-7-chloro-4-quinolinyl)-1-piperazinyl]carbonyl]amino]-cyclohexanecarboxylic acid;
4-(2-Amino-7-chloro-4-quinolinyl)-N-[3-[(methylamino)carbonyl]cyclohexyl]-1-piperazinecarboxamide;
4-(2-Amino-7-chloro-4-quinolinyl)-N-[(3S)-hexahydro-2-oxo-1H-azepin-3-yl]-1-piperazinecarboxamide;
4-(2-Amino-7-chloro-4-quinolinyl)-N-[(3S)-hexahydro-2-oxo-1-methyl-1H-azepin-3-yl]-1-piperazinecarboxamide;
4-(2-Amino-7-chloro-4-quinolinyl)-N-[(3S)-hexahydro-2-oxo-1-(cyclopropylmethyl)-1H-azepin-3-yl]-1-piperazinecarboxamide;
4-(2-Amino-7-chloro-4-quinolinyl)-N-[(3S)-hexahydro-2-oxo-1-(phenylmethyl)-1H-azepin-3-yl]-1-piperazinecarboxamide;
4-(2-Amino-7-chloro-4-quinolinyl)-N-[(3S)-hexahydro-2-oxo-1-[(2,6-dimethylphenyl)methyl]-1H-azepin-3-yl]-1-piperazinecarboxamide;
4-(2-Amino-7-chloro-4-quinolinyl)-N-[(3S)-hexahydro-2-oxo-1-(2-pyridinylmethyl)-1H-azepin-3-yl]-1-piperazinecarboxamide;
4-(2-Amino-7-chloro-4-quinolinyl)-N-[(3S)-hexahydro-2-oxo-1-(3-pyridinylmethyl)-1H-azepin-3-yl]-1-piperazinecarboxamide;
4-(2-amino-7-chloro-4-quinolinyl)-N-[(3S)-hexahydro-2-oxo-1-(4-pyridinylmethyl)-1H-azepin-3-yl]-1-piperazinecarboxamide;
4-(2-Amino-7-chloro-4-quinolinyl)-N-[(3S)-hexahydro-2-oxo-1-(2-hydroxy-3-phenoxypropyl)-1H-azepin-3-yl]-1-piperazinecarboxamide;
4-(2-Amino-7-chloro-4-quinolinyl)-N-[(3S)-hexahydro-2-oxo-1-(2-hydroxypropyl)-1H-azepin-3-yl]-1-piperazinecarboxamide;
(3S)-[[[4-(2-Amino-7-chloro-4-quinolinyl)-1-piperazinyl]carbonyl]amino]hexahydro-2-oxo-1H-azepine, 1-acetic acid, methyl ester;
(3S)-[[[4-(2-Amino-7-chloro-4-quinolinyl)-1-piperazinyl]carbonyl]amino]hexahydro-2-oxo-1H-azepine, 1-acetic acid;
(3S)-[[[4-(2-Amino-7-chloro-4-quinolinyl)-1-piperazinyl]carbonyl]amino]hexahydro-2-oxo-N-(1-phenylmethyl)-1H-azepine-1-acetamide;
(3S)-[[[4-(2-Amino-7-chloro-4-quinolinyl)-1-piperazinyl]carbonyl]amino]hexahydro-N-methyl-2-oxo-1H-azepine-1-acetamide;
(3S)-[[[4-(2-Amino-7-chloro-4-quinolinyl)-1-piperazinyl]carbonyl]amino]hexahydro-2-oxo-N-(4-pyridinyl)-1H-azepine-1-acetamide;
4-(2-Amino-7-chloro-4-quinolinyl)-N-[(3R)-1-(4-fluorophenyl)hexahydro-2-oxo-1H-azepin-3-yl]-1-piperazinecarboxamide;
4-[7-Chloro-2-(methylamino)-4-quinolinyl]-N-[(3S)-hexahydro-2-oxo-1H-azepin-3-yl]-1-piperazinecarboxamide;
4-(2-Amino-7-chloro-4-quinolinyl)-N-[(3S)-hexahydro-2-oxo-1-(2-phenoxyacetyl)-1H-azepin-3-yl]-1-piperazinecarboxamide;
4-(7-Chloro-4-quinolinyl)-N-[(3S)-hexahydro-2-oxo-1-acetyl-1H-azepin-3-yl]-1-piperazinecarboxamide;
4-(2-Amino-7-chloro-4-quinolinyl)-N-[(3S)-hexahydro-2-oxo-1-acetyl-1H-azepin-3-yl]-1-piperazinecarboxamide;
4-(2-Amino-7-chloro-4-quinolinyl)-N-[(3S)-hexahydro-2-oxo-1-(cyclopropylcarbonyl)-1H-azepin-3-yl]-1-piperazinecarboxamide;
4-(2-Amino-7-chloro-4-quinolinyl)-N-[(3S)-hexahydro-2-oxo-1-benzoyl-1H-azepin-3-yl]-1-piperazinecarboxamide;
4-(2-Amino-7-chloro-4-quinolinyl)-N-[(3S)-hexahydro-2-oxo-1-(ethylsulfonyl)-1H-azepin -3-yl]-1-piperazinecarboxamide;
4-(2-Amino-7-chloro-4-quinolinyl)-N-[(3S)-hexahydro-2-oxo-1-(phenylsulfonyl)-1H-azepin-3-yl]-1-piperazinecarboxamide;
4-(2-Amino-7-chloro-4-quinolinyl)-N-[(3S)-hexahydro-2-oxo-1-(cyclohexylcarbonyl)-1H-azepin-3-yl]-1-piperazinecarboxamide;
4-(2-Amino-7-chloro-4-quinolinyl)-N-[(3S)-hexahydro-2-oxo-1-[[(phenylsulfonyl)amino]carbonyl]-1H-azepin-3-yl]-1-piperazinecarboxamide;
4-(2-Amino-7-chloro-4-quinolinyl)-N-[(3S)-hexahydro-2-oxo-1-(2-phenylacetyl)-1H-azepin-3-yl]-1-piperazinecarboxamide;
4-[4-[[4-(2-Amino-7-chloro-4-quinolinyl)-1-piperazinyl]carbonyl]-1-piperazinyl]-2-quinolinamine;
4-(2-Amino-7-chloro-4-quinolinyl)-N-[(3S)-hexahydro-2-oxo-1-formyl-1H-azepin-3-yl]-1-piperazinecarboxamide;
4-(2-Amino-7-chloro-4-quinolinyl)-N-[(3S)-hexahydro-2-oxo-1-(2,2-dimethyl-1-oxopropyl)-1H-azepin-3-yl]-1-piperazinecarboxamide;
4-[7-Chloro-2-[[[[(3R)-1-(2,2-dimethyl-1-oxopropyl)hexahydro-2-oxo-1H-azepin-3-yl]amino]carbonyl]amino]-4-quinolinyl]-N-[(3S)-1-(2,2-dimethyl-1-oxopropyl)hexahydro-2-oxo-1H-azepin-3-yl]-1-piperazinecarboxamide;
4-(2-Amino-7-chloro-4-quinolinyl)-N-[(3S)-hexahydro-1-(methylsulfonyl)-2-oxo-1H-azepin-3-yl]-1-piperazinecarboxamide;
(3S)-3-[[[4-(2-Amino-7-chloro-4-quinolinyl)-1-piperazinyl]carbonyl]amino]hexahydro-2-oxo-1H-azepine-1-carboxylic acid, methyl ester;
(3S)-3-[[[4-(2-Amino-7-chloro-4-quinolinyl)-1-piperazinyl]carbonyl]amino]hexahydro-2-oxo-1H-azepine-1-carboxylic acid-ethyl ester;
(3S)-3-[[[4-(2-Amino-7-chloro-4-quinolinyl)-1-piperazinyl]carbonyl]amino]hexahydro-2-oxo-1H-azepine-1-carboxylic acid, 2,2,2-trifluoroethyl ester;
(3S)-[[[4-(2-Amino-7-chloro-4-quinolinyl)-1-piperazinyl]carbonyl]amino]hexahydro-2-oxo-1H-azepine-1-carboxylic acid, 2-propenyl ester;
(3S)-3-[[[4-(2-Amino-7-chloro-4-quinolinyl)-1-piperazinyl]carbonyl]amino]hexahydro-2-oxo-1H-azepine-1-carboxylic acid phenyl ester;

(3S)-3-[[[4-(2-Amino-7-chloro-4-quinolinyl)-1-piperazinyl]carbonyl]amino]hexahydro-2-oxo-1H-azepine-1-carboxylic acid-4-fluorophenyl ester;

(3S)-[[[4-(2-Amino-7-chloro-4-quinolinyl)-1-piperazinyl]carbonyl]amino]hexahydro-2-oxo-1H-azepine-1-carboxylic acid, phenylmethyl ester;

4-(2-Amino-7-chloro-4-quinolinyl)-N-[(3S)-1-cyanohexahydro-2-oxo-1H-azepin-3-yl]-1-piperazinecarboxamide;

(3S)-3-[[[4-(2-Amino-7-chloro-4-quinolinyl)-1-piperazinyl]carbonyl]amino]-N -cyclohexylhexahydro-2-oxo-1H-azepine-1-carboxamide;

(3S)-3-[[[4-(2-Amino-7-chloro-4-quinolinyl)-1-piperazinyl]carbonyl]amino]hexahydro-2-oxo-1H-azepine-1-carboxamide;

(2S)-2-[[[4-(2-Amino-7-chloro-4-quinolinyl)-1-piperazinyl]carbonyl]amino]-6-[[[(trichloroacetyl)amino]carbonyl]amino]-hexanoic acid, methyl ester;

(3S)-3-[[[4-(2-Amino-7-chloro-4-quinolinyl)-1-piperazinyl]carbonyl]amino]hexahydro-2-oxo-N-(2,2,2-trifluoroethyl)-1H-azepine-1-carboxamide;

(3S)-3-[[[4-(2-Amino-7-chloro-4-quinolinyl)-1-piperazinyl]carbonyl]amino]-N-cyclopropylhexahydro-2-oxo-1H-azepine-1-carboxamide;

(3S)-[[[4-(2-Amino-7-chloro-4-quinolinyl)-1-piperazinyl]carbonyl]amino]hexahydro-2-oxo-N-propyl-1H-azepine-1-carboxamide;

4-(2-Amino-7-chloro-4-quinolinyl)-N-[(3S)-hexahydro-2-oxo-1-(1-pyrrolidinylcarbonyl)-1H-azepin-3-yl]-1-piperazinecarboxamide;

(3S)-3-[[[4-(2-Amino-7-chloro-4-quinolinyl)-1-piperazinyl]carbonyl]amino]-N-cyclopentylhexahydro-2-oxo-1H-azepine-1-carboxamide;

(3S)-3-[[[4-(2-Amino-7-chloro-4-quinolinyl)-1-piperazinyl]carbonyl]amino]-N-cyclobutylhexahydro-2-oxo-1H-azepine-1-carboxamide;

(3R)-3-[[[4-(2-Amino-7-chloro-4-quinolinyl)-1-piperazinyl]carbonyl]amino]-N-(4-fluorophenyl)hexahydro-2-oxo-1H-azepine-1-carboxamide;

(3S)-3-[[[4-(2-Amino-7-chloro-4-quinolinyl)-1-piperazinyl]carbonyl]amino]-N-ethylhexahydro-2-oxo-1H-azepine-1-carboxamide;

(3S)-3-[[[4-(2-Amino-7-chloro-4-quinolinyl)-1-piperazinyl]carbonyl]amino]hexahydro-2-oxo-N-phenyl-1H-azepine-1-carboxamide;

(3S)-3-[[[4-(2-Amino-7-chloro-4-quinolinyl)-1-piperazinyl]carbonyl]amino]hexahydro-N-(1-methylethyl)-2-oxo-1H-azepine-1-carboxamide;

(3S)-3-[[[4-(2-Amino-7-chloro-4-quinolinyl)-1-piperazinyl]carbonyl]amino]-N-butylhexahydro-2-oxo-1H-azepine-1-carboxamide;

(3S)-3-[[[4-(2-Amino-7-chloro-4-quinolinyl)-1-piperazinyl]carbonyl]amino]hexahydro-N-(2-methylpropyl)-2-oxo-1H-azepine-1-carboxamide;

(3S)-3-[[[4-(2-Amino-7-chloro-4-quinolinyl)-1-piperazinyl]carbonyl]amino]-N-(1,1-dimethylethyl)hexahydro-2-oxo-1H-azepine-1-carboxamide;

(3S)-3-[[[4-(2-Amino-7-chloro-4-quinolinyl)-1-piperazinyl]carbonyl]amino]hexahydro-N,N-dimethyl-2-oxo-1H-azepine-1-carboxamide;

(3S)-3-[[[4-(2-Amino-7-chloro-4-quinolinyl)-1-piperazinyl]carbonyl]amino]hexahydro-2-oxo-N-[4-(trifluoromethyl)phenyl]-1H-azepine-1-carboxamide;

(3S)-3-[[[4-(2-Amino-7-chloro-4-quinolinyl)-1-piperazinyl]carbonyl]amino]-N-(3-fluorophenyl)hexahydro-2-oxo-1H-azepine-1-carboxamide;

(3S)-3-[[[4-(2-Amino-7-chloro-4-quinolinyl)-1-piperazinyl]carbonyl]amino]hexahydro-N-(4-methylphenyl)-2-oxo-1H-azepine-1-carboxamide;

(3S)-3-[[[4-(2-Amino-7-chloro-4-quinolinyl)-1-piperazinyl]carbonyl]amino]-N-(2-fluorophenyl)hexahydro-2-oxo-1H-azepine-1-carboxamide;

(3S)-3-[[[4-(2-Amino-7-chloro-4-quinolinyl)-1-piperazinyl]carbonyl]amino]-N-(2,6-diethylphenyl)hexahydro-2-oxo-1H-azepine-1-carboxamide;

4-(2-Amino-7-chloro-4-quinolinyl)-N-[(3S)-hexahydro-1-[(methylamino)carbonothioyl]-2-oxo-1H-azepin-3-yl]-1-piperazinecarboxamide;

4-(2-Amino-7-chloro-4-quinolinyl)-N-[(3S)-1-[(ethylamino)carbonothioyl]hexahydro-2-oxo-1H-azepin-3-yl]-1-piperazinecarboxamide;

4-(2-Amino-7-chloro-4-quinolinyl)-N-[(3S)-hexahydro-1-[[(1-methylethyl)amino]carbonothioyl]-2-oxo-1H-azepin-3-yl]-1-piperazinecarboxamide;

4-(2-Amino-7-chloro-4-quinolinyl)-N-[(3S)-hexahydro-2-oxo-1-[(2-propenylamino)carbonothioyl]-1H-azepin-3-yl]-1-piperazinecarboxamide;

(3S)-3-[[[4-(2-Amino-7-chloro-4-quinolinyl)-1-piperazinyl]carbonyl]amino]hexahydro-N-methyl-2-oxo-1H-azepine-1-carboxamide;

(3S)-3-[[[4-(2-Amino-7-chloro-4-quinolinyl)-1-piperazinyl]carbonyl]amino]hexahydro-2-oxo-N-(2-propenyl)-1H-azepine-1-carboxamide;

(3S)-3-[[[4-(2-Amino-7-chloro-4-quinolinyl)-1-piperazinyl]carbonyl]amino]-N-(2-chloroethyl)hexahydro-2-oxo-1H-azepine-1-carboxamide;

(3R)-3-[[[4-(2-Amino-7-chloro-4-quinolinyl)-1-piperazinyl]carbonyl]amino]hexahydro-N-methyl-2-oxo-1H-azepine-1-carboxamide;

4-[3-(tert-Butoxycarbonylamino)pyrrolidin 1-yl]-7-chloro-quinoline;

4-[3-(4-Fluorophenylaminocarbonylamino)pyrrolidin 1-yl]-7-chloroquinoline;

4-[3-[tert-Butoxycarbonyl(methyl)amino]pyrrolidin-yl]-7-chloroquinoline;

4-[3-[4-Fluorophenylaminocarbonyl(methyl)amino]pyrrolidin 1-yl]-7-chloroquinoline;

or enantiomers, diastereomers, salts and solvates thereof.

Other preferred embodiments of the present invention include:

a) A method of treating inflammation in a mammal in need thereof comprising administering to said mammal an effective anti-inflammatory amount of such compounds.

b) A pharmaceutical composition comprising a compound of the present invention in admixture with a pharmaceutically acceptable excipient, diluent, or carrier.

c) A method of inhibiting the binding of MIP-1α to its receptor comprising administering a therapeutically effective amount of such compound to a mammal in need thereof.

d) A method of inhibiting the binding of RANTES to its receptor comprising administering a therapeutically effective amount of such compounds to a mammal in need thereof.

e) A method of assaying compounds which modulate the activity of CCR-5 receptors comprising screening against compounds of formulae (1a) and/or (1b).

f) A method of inhibiting the binding of MIP-1β to its receptor comprising administering a therapeutically effective amount of such compound to a mammal in need thereof.

g) A method of inhibiting the binding of MCP-2 to its receptor comprising administering a therapeutically effective amount of such compound to a mammal in need thereof.

The selective inhibition of CCR5 receptor mechanisms by treatment with the receptor antagonists of the invention represents a novel therapeutic and preventative approach to the treatment of a broad spectrum of inflammatory and autoimmune diseases or conditions, in particular for the treatment of inflammatory diseases or conditions, atherosclerosis, restenosis, and autoimmune disorders such as arthritis, Graves disease and transplant rejection.

In a preferred embodiment, the disease or condition is one which is associated with lymphocyte and/or monocyte infiltration of tissues (including recruitment and/or accumulation in tissues), such as arthritis (e.g., rheumatoid arthritis, psoriatic arthitis, etc.), inflammatory bowel diseases (e.g., Crohn's disease, ulcerative colitis), multiple sclerosis, idiopathic pulmonary fibrosis, and graft rejection (e.g., in transplantation), including allograft rejection or graft-versus-host disease. In addition, diseases characterized by basophil activation and/or eosinophil recruitment, including allergic hypersensitivity disorders such as psoriasis, asthma and allergic rhinitis can be treated according to the present invention.

Other diseases and conditions that may be treated with the compounds of Formula 1 are: optic neuritis, uveitis, stroke, dermatitis, demyelinating disorders (e.g., Guillian-Barre etc.), Grave's disease, cancer (including myeloma, breast, cervical, lymphoma, Hodgkin's disease and Hairy Cell leukemia), endometriosis, stroke, chronic contact dermatitis, sarcoidosis, dermatomyositis, skin phemphigoid and related diseases (e.g., pemphigus vulgaris, p. foliacious, p. erythematosus), glomerulonephritides, vasculitides (e.g., necrotizing, cutaneous, and hypersensitivity vasculitis), hepatitis, diabetes, systemic lupus erythematosus and myasthenia gravis.

In addition to psoriasis, other inflammatory dermatoses such as dermatitis, eczema, atopic dermatitis, allergic contact dermatitis, urticaria and reperfusion injury can also be treated.

It will be understood that the substituent(s) $R^1$, $R^2$, $R^3$, $NR^9R^7$ and $R^4$ may be at any open position on the rings of formulae (Ia) and/or (1b) to which the substituent is attached. In addition, it will be understood that there may be more than one substituent $R^4$ in any given compound of formula (I), and that if there is more than one substituent $R^4$, that substituent may be the same or different.

The term "alkyl" is used herein at all occurrences (or a group per se or a part of a group) to mean a straight or branched chain radical of 1 to 6 carbon atoms, unless the chain length is otherwise limited, including, but not limited to methyl, ethyl, n-propyl, isopropyl, n-butyl, sec-butyl, isobutyl, tert-butyl, and the like. Substituted alkyl groups may be substituted one or more times by halogen, aryl, hydroxy, $R^9$—O—, amino, substituted amino, nitro, carboxy, alkoxycarbonyl, or cyano.

The term "cycloalkyl" is used herein at all occurrences to mean cyclic radicals, preferably of 3 to 8 carbons, including but not limited to cyclopropyl, cyclopentyl, cyclohexyl, cycloheptyl and the like. These groups can also contain one to three (as appropriate) double bonds to form the "cycloalkenyl" groups of the invention. Suitable substituents are halogen, $C_{1-6}$alkyl, aryl, arylalkyl, alkylcarbonyl, hydroxy, $R^9$—O—, amino, substituted amino, oxo, nitro, carboxy, or cyano.

Suitable substituents on the amino groups herein can be the same or different and include $R^9$, alkyl (optionally substituted), cycloalkyl (optionally substituted), $C_{1-6}$ acyl, ($C_{1-6}$ alkoxy)carbonyl, and ($C_{1-6}$ alkylamino)carbonyl. Typical substituents include OH, $C_{1-6}$ alkoxy, $C_{1-6}$ alkyl, and $R^9$ aminocarbonyloxy.

The terms "halo" or "halogen" are used interchangeably herein at all occurrences to mean radicals derived from the elements chlorine, fluorine, iodine and bromine. "Halogenated" is analogous and refers to a degree of halogen substitutions from single to full (per) substitution.

The terms "aryl" or "Ar—" are used herein at all occurrences to mean 5–10 membered (fused or connected) aromatic ring(s) or ring systems which may include bi- or tri-cyclic systems. Representative examples include, but are not limited to, phenyl and naphthyl. Substituted aryl groups may be substituted one or more times by halogen, $C_{1-6}$ alkyl, hydroxy, alkoxy, e.g, methoxy, amino, substituted amino, nitro, trifluoromethyl, carboxy, acyl, or cyano.

The term "heterocyclyl" (heterocyclic or heterocycle or heterocyclo) refers to a stable 3- to 15-membered ring radical which consists of carbon atoms and from one to five heteroatoms selected from the group consisting of nitrogen, oxygen and sulfur. For purposes of this invention, the heterocyclyl radical may be a monocyclic, bicyclic or tri-cyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated or aromatic (i.e., heteroaryl). The heterocyclyl radical may be attached to the main structure at any heteroatom or carbon atom which results in the creation of a stable compound. Examples of such heterocyclyl radicals include, but are not limited to Examples of heterocyclic groups include, e.g., piperidinyl, piperazinyl, oxopiperazinyl, oxopiperidinyl, oxopyrrolodinyl, oxoazepinyl, azepinyl, pyrrolyl, piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiophenyl, oxazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, benzimidazolyl, benzofuranyl, benzothiophenyl, benzoxazolyl, furyl, imidazolyl, indolyl, isoquinolyl, isothiazolyl, isoxazolyl, morpholinyl, oxadiazolyl, oxazolyl, piperidyl, pyrazolyl, pyrimidyl, pyrrolyl, quinolyl, tetrahydroisoquinoly, tetrahydroquinolyl, tetrahydrothienyl, tetrazolyl, thiadiazolyl, thiazolyl, triazolyl; pyrrolidine, piperidine, pyridine, tetrahydrofuran, thiophene, oxazole, thiazole, imidazole, benzothiazole, benzoxazole, benzimidazole, selenazole, benzoselenazole, tellurazole, triazole, benzotriazole, tetrazole, benzofuranyl, benzothienyl, oxadiazole, or thiadiazole rings. A prefered heterocyclic group is hexahydroazepinyl.

Heteroaryl refers to a fully unsaturated heterocycle having one or two rings and a total number of 5 to 10 ring atoms wherein at least one of the ring atoms is a heteroatom. Preferably, the heteroaryl group contains 1 to 3 hetero atoms which are selected from N, O and S. Suitable heteroaryl groups include but are not limited to furyl, thienyl, pyrrolyl, pyrazolyl, imidazolyl, triazolyl, dithialyl, oxathialyl, isoxazolyl, oxazolyl, thiazolyl, isothiazolyl, oxadiazolyl, oxatriazolyl, dioxazolyl, oxathiazolyl, thiadiazolyl, pyridyl, pyridazinyl, pyrimidinyl, pyrazinyl, triazinyl, oxazinyl, isoxazinyl, oxathiazinyl, oxadiazinyl, benzofuranyl, isobenzofuranyl, thionaphthenyl, isothionaphthenyl, indolyl, isoindolyl, indazolyl, benzisoxazolyl, benzoxazolyl, benzthiazolyl, benzisothiazolyl, purinyl, benzopyranyl, quinolinyl, isoquinolinyl, cinnolinyl, quinazolinyl, naphthyridinyl, and benzoxazinyl, e.g, 2-thienyl, 3-thienyl, 2-, 3- or 4-pyridyl, 2-, 3-, 4-, 5-, 6-, 7-, or 8-quinolinyl, and 1-, 3-, 4-, 5-, 6-, 7- or 8-isoquinolinyl.

Substituted heterocyclyl refers to the heterocyclyl groups described above which are substituted in one or more places by $R^9$, $COR^9$, —$SO_2$—$R^7$, halogen, aryl, alkyl, alkoxy, methylene, cyano, trifluoromethyl, carboxy, nitro, oxo, amino, alkoxycarbonyl, aminocarbonyl, substituted aminocarbonyl, or substituted amino.

Alkoxy groups means alkyl-O— groups in which the alkyl portion (substituted or unsubstituted) is in accordance with the previous discussion. Suitable alkoxy groups are methoxy, ethoxy, propoxy and butoxy.

The term "oxo" refers to the group =O, and the term "thioxo" refers to the group =S.

Acyl refers to alkanoyl radicals having 1 to 6 carbon atoms in which the alkyl portion can be substituted as defined above.

It will be understood throughout that the optional substituents are selected independently from one another.

The term "CCR5 mediated disease state" is used herein at all occurrences to mean any disease state which is affected or modulated by CCR5.

Some of the compounds of Formula 1a and 1b and related compounds are capable of forming both pharmaceutically acceptable acid addition and/or base salts. All of these forms are within the scope of the present invention, as are diastereomers and enantiomers.

The optical isomers can be obtained by resolution of the racemic mixtures according to conventional processes, for example, by the formation of diastereoisomeric salts using an optically active acid or base, or by formation of covalent diastereomers. Examples of appropriate acids are tartaric, diacetyltartaric, dibenzoyltartaric, ditoyluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves use of chiral chromatography (e.g., chiral HPLC columns), with or without conventional derivitization, optimally chosen to maximize the separation of the enantiomers. Suitable chiral HPLC columns are manufactured by Diacel, e.g., Chiracel OD and Chiracel OJ, among many others, all routinely selectable. Enzymatic separations, with or without derivitization, are also useful. The optically active compounds of formula I can likewise be obtained by utilizing optically active starting materials.

Compounds of the present invention can exist as salts (preferably pharmaceutically acceptable salts). Pharmaceutically acceptable acid addition salts of the compounds of Formulae (Ia) and (1 b) include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, 2-phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al., "Pharmaceutical Salts," J. Pharma. Sci., 1977;66:1). The acid addition salts of basic compounds can be prepared by contacting the free base form with a sufficient amount of the desired acid to produce the salt in the conventional manner. The free base form may be regenerated by contacting the salt form with a base and isolating the free base in the conventional manner. The free base forms can differ from their respective salt forms somewhat in certain physical properties such as solubility in polar solvents.

Pharmaceutically acceptable base addition salts can be formed with metals or amines, such as alkali and alkaline earth metals or organic amines. Examples of such metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see Berge, Supra, 1977).

The base addition salts of said acidic compounds can be prepared by contacting the free acid form with a sufficient amount of the desired base to produce the salt in the conventional manner. The free acid form may be regenerated by contacting the salt form with an acid and isolating the free acid in the conventional manner. The free acid forms can differ from their respective salt forms somewhat in certain physical properties such as solubility in polar solvents.

Certain of the compounds of the present invention can exist in unsolvated forms as well as solvated forms, including hydrated forms and are intended to be encompassed within the scope of the present invention.

Certain of the compounds of the present invention possess one or more chiral centers and each center may exist in the R(D) or S(L) configuration. The present invention includes all diastereomeric, enantiomeric and epimeric forms as well as all mixtures thereof.

The activity of compounds of the present invention can be assessed using suitable assays, such as receptor binding assays and chemotaxis assays. For example, as described in the Example Section, antagonist compounds of the present invention have been identified utilizing a CCR5 Receptor MIP1α SPA binding assay and have been found to exhibit $IC_{50}$ values ranging from 0.005 μM to 38 μM. Such values are indicative of the intrinsic activity of the compounds in use as modulators of chemokine receptor activity. There are numerous other such screening assays known to those skilled in the art which may be used to determine the CCR5 receptor antagonistic activity of the compounds of the present invention. One such screening technique is described in PCT WO 92/01810. Another assay, for example, may be employed for screening a receptor antagonist by contacting melanophore cells which encode the CC-CKR5 receptor with both a chemokine agonist and a compound to be screened. Inhibition of the signal generated by the ligand indicates that a compound is a potential antagonist for the receptor, i.e., inhibits activation of the receptor.

Other screening techniques include the use of cells which express the CC-CKR5 receptor (for example, transfected CHO cells, RBL-2 cells or other mammalian cells) in a system which measures extracellular pH changes caused by receptor activation, for example, as described in Science, volume 246, pages 181–296 (October 1989), herein incorporated by reference. For example, potential antagonists may be contacted with a cell which expresses the CC-CKR5 receptor and a second messenger response, e.g. signal transduction or pH changes, or making use of a reporter gene system, for example luciferase, may be measured to determine whether the potential antagonist is effective.

Another such screening technique involves introducing mRNA encoding the CC-CKR5 receptor into mammalian cells (Xenopus oocytes, RBL-2 or other mammalian cells) to transiently express the receptor. The cells with the expressed receptor may then be contacted in the case of antagonist screening with a chemokine agonist and a compound to be screened, followed by detection of inhibition of a calcium or cAMP signal.

Another screening technique involves expressing the CC-CKR5 receptor in which the receptor is linked to a phospholipase C or D. As representative examples of such cells, there may be mentioned endothelial cells, smooth muscle cells, embryonic kidney cells, etc. The screening for an antagonist may be accomplished as hereinabove described by detecting inhibition of activation of the receptor from the phospholipase second signal.

Another method involves screening for CC-CKR5 receptor inhibitors by determining inhibition of binding of labeled chemokine ligands to cells or membranes which have the receptor on the surface thereof. Such a method involves transfecting a eukaryotic cell, such as CHO or RBL-2 cell, with DNA encoding the CC-CKR5 receptor such that the cell expresses the receptor on its surface and contacting the cell with a potential antagonist in the presence of a labeled form of chemokine ligand. The chemokine ligand can be labeled, e.g., by radioactivity. The amount of labeled ligand bound to the receptors is measured, e.g., by measuring radioactivity associated with transfected cells or membrane from these cells. If the potential antagonist binds to the receptor, as determined by a reduction of labeled ligand which binds to the receptors, the binding of labeled ligand to the receptor is inhibited.

Another method involves screening for CC-CKR5 inhibitors by determining inhibition or stimulation of CC-CKR5-mediated cAMP and/or adenylate cyclase accumulation or diminution. Such a method involves transfecting a eukaryotic cell, such as CHO or RBL-2 cell, with CC-CKR5 receptor to express the receptor on the cell surface. The cell is then exposed to potential antagonists in the presence of chemokine agonist. The amount of cAMP accumulation is then measured. If the potential antagonist binds the receptor, and thus inhibits CC-CKR5 binding, the levels of CC-CKR5-mediated cAMP, or adenylate cyclase, activity will be reduced or increased.

Another such screening technique is described in U.S. Pat. No. 5,928,881, which provides a method for determining whether a ligand not known to be capable of binding to the CC-CKR5 receptor can bind to such receptor which comprises contacting a mammalian cell which expresses the CC-CKR5 receptor with a chemokine ligand such as RANTES under conditions permitting binding of ligands to the CC-CKR5 receptor, detecting the presence of a ligand which binds to the receptor and thereby determining whether the ligand binds to the CC-CKR5 receptor.

Another method involves screening of CCR5 expressed in yeast cells that have been modified to couple receptor activation by chemokine ligands to the yeast phermone response.

Another method involves screening of a CCR5 receptor that has been genetically modified so that it exhibits constitutive activity in either mammalian or yeast cells. In this case an activating chemokine ligand is not required and the nature of the receptor modulation (agonist, inverse agonism, antagonism, etc.) can be specifically addressed.

The antagonists of the present invention bind to the CC-CKR5 receptor, making it inaccessible to ligands such that normal biological activity is prevented. They may be administered to a mammal in need of treatment of CCR5 mediated disease states. Thus, the active ingredient may be administered in the mammal using conventional course of treatment determination tests.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism or inverse agonism of chemokine receptor activity, since the compounds of the invention are antagonists or inverse agonists.

Combined therapy to modulate chemokine receptor activity and thereby prevent and treat inflammatory and immunoregulatory disorders and diseases, including endometriosis, asthma and allergic diseases, as well as autoimmune pathologies such as rheumatoid arthritis, Graves' disease and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, epinephrine, naphazoline, xylometazoline, propylhexedrine, or levo-desoxy-ephedrine; an antiitussive such as codeine, hydrocodone, caramiphen, carbetapentane, or dextromethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred.

Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as beta 2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, caiprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, CCR1, CCR2, CCR3, CCR4, CCR8, CCR10, CXCR1, CXCR2, CXCR3, and CX3CR1; 0) cholesterol lowering agents such as HMG-COA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), .α.-glucosidase inhibitors (acarbose) and glitazones (troglitazone and pioglitazone); (l) preparations for multiple sclerosis such as interferon beta 1b (Betaseron), interferon-beta 1a (Avonex), glatiramer acetate (Copaxone), azathioprine (Imurek, Imuran), mitoxantrone (Novatrone), IgG, cyclophosphamide; (m) agents for dermatological conditions such as a lubricant, a keritolytic agent, vitamin D3 derivative, PUVA, anthralin; (n) other compounds such as 5-aminosalicylic acid and prodrugs thereof, antimetabolites such as azathioprine and 6-mercaptopurine, and cytotoxic cancer chemotherapeutic agents; (o) estrogen receptor agonists such as estriol, estradiol, or any synthetic ERα or ERβ agonist; (p) IL-2 receptor antagonists such as an anti-IL-2 receptor antibody (Zenapax); (q) IL-12 receptor antagonists; (r) T-helper cytokines such as IL-4 or IL-10; (s) anti-CD52 antibody (Campath).

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The compounds of the invention are effective for use in primates, such as humans, as well as for the treatment of warm-blooded animals such as mice, rats, horses, cattle, sheep, dogs, cats, monkeys, guinea pigs, other bovine, ovine, equine, canine, feline, rodent or murine species. However, the compounds of the invention are also effective for use in other species, such as avian species (e.g., chickens).

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxy-benzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.) The pharmaceutical composition and method of the present invention may further comprise other therapeutically active compounds as noted herein which are usually applied in the treatment of the above mentioned pathological conditions.

The compounds of the invention, or their pharmaceutically acceptable salts, are administered in a therapeutically effective amount which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disease-states; and the host undergoing therapy. Generally, a therapeutically effective daily dose is from about 0.14 mg to about 14.3 mg/kg of body weight per day of a compound of the invention, or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, or a pharmaceutically acceptable salt thereof, preferably from about 50 mg to about 700 mg per day, and most preferably from about 100 mg to about 500 mg per day.

The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Having described the invention, the following examples are given to illustrate specific applications of the invention including the best mode now known to perform the invention. These specific examples are not intended to limit the scope of the invention described in this application. Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above or below, is hereby incorporated by reference.

General Methods of Preparation

Specifically, the compounds of the invention are prepared according to the following general methods and schemes:

General Scheme for Preparing 4-(piperazin-1-yl)quinolines

General Scheme for Preparing 4-(pyrrolidin-1-yl)quinolines

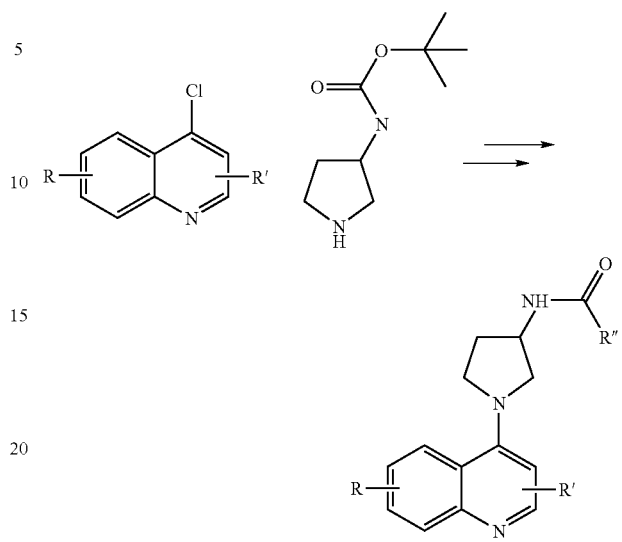

Method A.

A 4-chloroquinoline is heated with 1-tert-butoxycarbonylpiperazine at 150° C. for 2 h. The reaction mixture is diluted with EtOAc, washed with water, dried (MgSO$_4$), and concentrated. The residue is dissolved in CH$_2$Cl$_2$ and treated

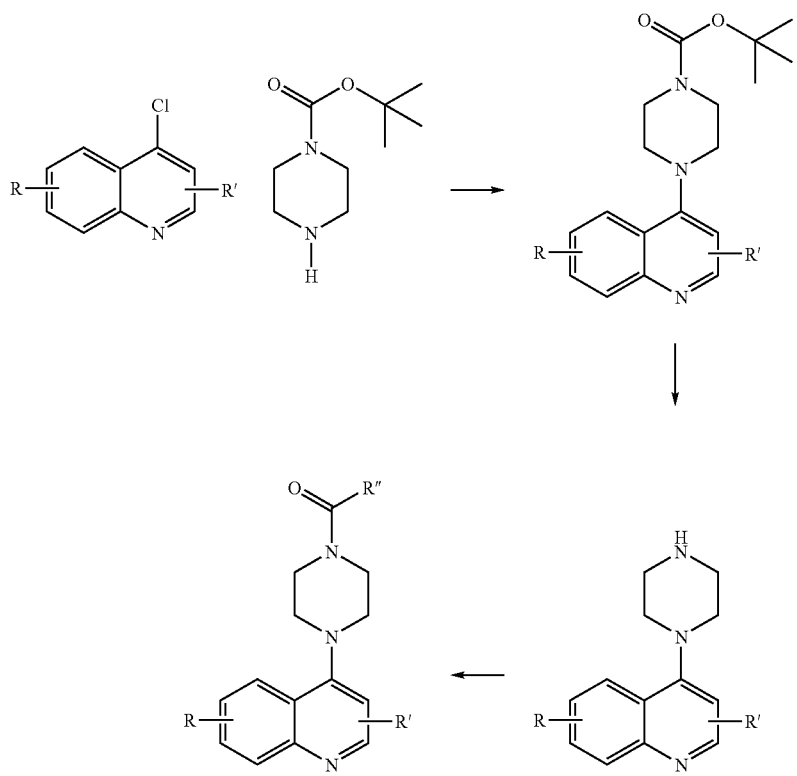

with trifluoroacetic acid for 1 h. The mixture is concentrated, diluted with EtOAc, washed with sat. NaHCO$_3$, dried (MgSO$_4$), and concentrated in vacuo.

Method B

A 4-chloroquinoline and piperazine are heated either in EtOH at reflux or in n-butanol at 150° C. in a sealed tube for 18 h. The reaction mixture is concentrated, and the residue dissolved in EtOAc. After washing with water, and drying (MgSO$_4$), the solvent was removed in vacuo.

General Method for Reacting 4-(Piperazin-1-yl)quinolin s with Isocyanates:

Method C

Iso(thio)cyanate is added to a suspension of a 4-(piperazin-1-yl)quinoline (and optionally triethylamine) in CH$_2$Cl$_2$ or THF. The reaction mixture is concentrated after 1 h, and the residue is purified either by recrystallization or column chromatography.

Method D

Amine, nitrophenyl chloroformate, and triethylamine are stirred either in EtOAc or CH$_2$Cl$_2$ for ½–1 h. In case of CH$_2$Cl$_2$ solutions the solvent is removed and the residue suspended in EtOAc. A 4-(piperazin-1-yl)quinoline is added, and the reaction mixture is heated at reflux for 1–2 h. After filtration the filtrate is concentrated and the residue purified by column chromatography.

General Method for Reacting 2-Quinolones with Amines:

Method E

Sodium hydride is added to a solution of a 2-quinolone in DMSO and stirred at 40° C. for 1 h, when N-phenyl (trifluoromethylsulfon)imide is added. After an hour amine is added, and the reaction mixture is heated in a sealed tube at 150° C. for 15 h. The mixture is diluted with EtOAc, washed with water and brine, dried (NaSO$_4$), and concentrated. The residue is purified by column chromatography with CH$_2$Cl$_2$-MeOH.

EXAMPLES

Example 1

Preparation of 7-Chloro-4-[4-(4-fluorophenylaminocarbonyl)piperazin-1-yl]quinoline Preparation of 7-Chloro-4-(piperazin-1-yl)quinoline. 4,7-Dichloroquinoline (9.9 g, 50 mmol) and piperazine (43.1 g, 500 mmol) in EtOH (200 mL) are reacted according to method B yielding 8.10 g of the product.
$^1$H NMR (CDCl$_3$) δ 3.17 (m, 8H), 6.82 (d, 1H), 7.40 (dd, 1H), 7.93 (d, 1H), 8.01 (d, 1H), 8.69 (d, 1H).

Preparation of 7-Chloro-4-[4-(4-fluorophenylaminocarbonyl)piperazin-1-yl]quinoline 7-Chloro-4-(piperazin-1-yl)quinoline (0.89 g, 3.6 mmol) and 4-fluorophenyl isocyanate (409 µL, 3.6 mmol) in THF (20 mL) are reacted according to method C yielding 0.71 g of the product as a colorless solid after column chromatography with hexane-EtOAc.
$^1$H NMR ([D]$_6$-DMSO), δ 3.18 (m, 4H), 3.71 (m, 4H), 7.04 (d, 1H), 7.06 (t, 2H), 7.46 (dd, 2H), 7.56 (dd, 1H), 7.98 (d, 1H), 8.09 (d, 1H), 8.68 (br. s, 1H), 8.72 (d, 1H).

Example 2

Preparation of 6-Chloro-4-[4-(4-fluorophenylaminocarbonyl)piperazin-1-yl]quinoline Preparation of 6-Chloro-4-(piperazin-1-yl)quinoline 4,6-Dichloroquinoline (De, D., Byers L. D., Krogstad, D. J. *J. Heterocyclic Chem.* 1997, 34, 315) (0.34 g, 1.7 mmol) and 1-tert-butoxycarbonylpiperazine (1.58 g, 8.5 mmol) are reacted according to method A. The Boc group is cleaved with trifluoroacetic acid (5 mL) in CH$_2$Cl$_2$ (5 mL) giving 0.25 g of the product.
$^1$H NMR (CDCl$_3$), δ 3.13 (s, 8H), 6.91 (d, 1H), 7.53 (dd, 1H), 7.92 (d, 1H), 7.94 (d, 1H), 8.66 (d, 1H).

Preparation of 6-Chloro-4-[4-(4-fluorophenylaminocarbonyl)piperazin-1-yl]quinoline 6-Chloro-4-(piperazin-1-yl)quinoline (0.25 g, 1.0 mmol), 4-fluorophenyl isocyanate (170 µL, 1.5 mmol), and DMAP (2 mg) in THF (10 mL) are reacted according to method C yielding the product as a colorless solid after column chromatography with hexane-EtOAc. $^1$H NMR ([D]$_6$-DMSO), δ 3.17 (m, 4H), 3.75 (m, 4H), 7.08 (t, 2H), 7.10 (d, 1H), 7.46 (dd, 2H), 7.72 (dd, 1H), 7.98 (d, 1H), 8.01 (d, 1H), 8.68 (br. s, 1H), 8.72 (d, 1H).

Example 3

Preparation of 7-Chloro-4-[4-(4-fluorophenylaminocarbonyl)piperazin-1-yl]-2-methylquinoline Preparation of 7-Chloro-2-methyl-4-(piperazin-1-yl)quinoline 4,7-Dichloro-2-methylquinoline (De, D., Byers L. D., Krogstad, D. J. *J. Heterocyclic Chem.* 1997, 34, 315) (453 mg, 2.1 mmol) and 1-tert-butoxycarbonylpiperazine (2.05 g, 11.0 mmol) are reacted according to method A. The Boc group is cleaved with trifluoroacetic acid (5 mL) in CH$_2$Cl$_2$ (5 mL) giving 0.26 g of the piperazine.
$^1$H NMR (CDCl$_3$), δ 2.62 (s, 3H), 3.12 (s, 8H), 6.67 (s, 1H), 7.30 (dd, 1H), 7.83 (d, 1H), 7.90 (d, 1H).

Preparation of 7-Chloro-4-[4-(4-fluorophenylaminocarbonyl)piperazin-1-yl]-2-methylquinoline 7-Chloro-2-methyl-4-(piperazin-1-yl)quinoline (0.26 g), 4-fluorophenyl isocyanate (114 µL, 1.0 mmol), and DMAP (2 mg) in THF (10 mL) are reacted according to method C yielding the product as a colorless solid after column chromatography with hexane-EtOAc. $^1$H NMR ([D]$_6$-DMSO), δ 2.58 (s, 3H), 3.17 (m, 4H), 3.71 (m, 4H), 6.94 (s, 1H), 7.06 (t, 2H), 7.46 (m, 3H), 7.87 (d, 1H), 8.01 (d, 1H), 8.68 (br. s, 1H).

Example 4

Preparation of 5-Chloro-4-[4-(4-fluorophenylaminocarbonyl)piperazin-1-yl]-2-methylquinoline Preparation of 5-Chloro-2-methyl-4-(piperazin-1-yl)quinoline 4,5-Dichloro-2-methylquinoline, obtained by treating 5-chloro-2-methyl-4-quinolone with POCl$_3$ (cf. De, D., Byers L. D., Krogstad, D. J. *J. Heterocyclic Chem.* 1997, 34, 315; $^1$H NMR (CDCl$_3$), δ 2.68 (s, 3H), 7.41 (s, 1H), 7.55 (t, 1H), 7.59 (dd, 1H), 7.95 (dd, 1H)), (125 mg, 0.59 mmol) and 1-tert-butoxycarbonylpiperazine (559 mg, 3.0 mmol) are reacted according to method A. The Boc group is cleaved with trifluoroacetic acid (3 mL) in CH$_2$Cl$_2$ (5 mL) giving 0.18 g of the piperazine.

$^1$H NMR (CDCl$_3$), δ 2.63 (s, 3H), 2.73 (t, 2H), 3.04 (d, 2H), 3.23 (t, 2H), 3.37 (d, 2H), 6.78 (s, 1H), 7.40 (dd, 1H), 7.44 (t, 1H), 7.84 (dd, 1H).

Preparation of 5-Chloro-4-[4-(4-fluorophenylaminocarbonyl)piperazin-1-yl]-2-methylquinoline 5-Chloro-2-methyl-4-(piperazin-1-yl)quinoline (0.18 g, 0.7 mmol), 4-fluorophenyl isocyanate (91 μL, 0.8 mmol), and DMAP (5 mg) in CH$_2$Cl$_2$ (10 mL) are reacted according to method C yielding the product as a colorless solid after column chromatography with hexane-EtOAc.

$^1$H NMR (CDCl$_3$), δ 2.66 (s, 3H), 2.80 (m, 2H), 3.50 (m, 4H), 4.05 (m, 2H), 6.45 (br. s, 1H), 6.80 (s, 1H), 6.98 (t, 2H), 7.30 (dd, 2H), 7.46 (dd, 1H), 7.49 (d, 1H), 7.90 (dd, 1H).

Example 5

Preparation of 7-Chloro-4-[4-(4-fluorophenylaminocarbonyl)piperazin-1-yl]-8-methylquinoline Preparation of 7-Chloro-8-methyl-4-(piperazin-1-yl)quinoline 4,7-Dichloro-8-methylquinoline [obtained from 3-chloro-2-methylaniline following the protocol of Krogstad et. al. (De, D., Byers L. D., Krogstad, D. J. *J. Heterocyclic Chem.* 1997, 34, 315; $^1$H NMR (CDCl$_3$), δ 2.88 (s, 3H), 7.47 (d, 1H), 7.60 (d, 1H), 8.03 (d, 1H), 8.79 (d, 1H))] (212 mg, 1.0 mmol) and 1-tert-butoxycarbonylpiperazine (931 mg, 5.0 mmol) are reacted according to method A. The Boc group is cleaved with trifluoroacetic acid (5 mL) in CH$_2$Cl$_2$ (5 mL) giving 80 mg of the piperazine.

Preparation of 7-Chloro-4-[4-(4-fluorophenylaminocarbonyl)piperazin-1-yl]-8-methylquinoline 7-Chloro-8-methyl-4-(piperazin-1-yl)quinoline (80 mg, 0.31 mmol), 4-fluorophenyl isocyanate (57 μL, 0.5 mmol), and DMAP (2 mg) in THF (10 mL) are reacted according to method C yielding the product as a yellow solid after column chromatography with hexane-EtOAc.

$^1$H NMR ([D]$_6$-DMSO), δ 2.71 (s, 3H), 3.65 (br., 4H), 3.75 (m, 4H), 7.07 (t, 2H), 7.15 (d, 1H), 7.46 (dd, 1H), 7.65 (d, 1H), 8.02 (d, 1H), 8.63 (d, 1H), 8.68 (br. s, 1H).

Example 6

Preparation of 7-Chloro-4-[4-(4-fluor phenylaminocarbonyl)piperazin-1-yl]-3-methylquinoline 4,7-Dichloro-3-methylquinoline (De, D., Byers L. D., Krogstad, D. J. *J. Heterocyclic Chem.* 1997, 34, 315) (0.30 g, 1.4 mmol) and 1-tert-butoxycarbonylpiperazine (0.78 g, 4.2 mmol) are reacted according to method A though the reaction time is extended to 24 h. The Boc group is cleaved with trifluoroacetic acid (3 mL) in CH$_2$Cl$_2$ (3 mL) giving 0.28 g of a yellow oil, which is treated with 4-fluorophenyl isocyanate (125 μL, 1.1 mmol) in THF (10 mL) according to method C yielding the product as a colorless solid after column chromatography with hexane-EtOAc.

$^1$H NMR ([D]$_6$-DMSO), δ 2.45 (s, 3H), 3.30 (m, 8H), 7.06 (t, 2H), 7.48 (dd, 2H), 7.55 (dd, 1H), 7.96 (d, 1H), 8.23 (d, 1H), 8.63 (s, 1H), 8.65 (br. s, 1H).

Example 7

Preparation of 4-[4-(4-Fluorophenylaminocarbonyl)piperazin-1-yl]-7-methoxy-2-methylquinoline Preparation of 7-Methoxy-8-methyl-4-(piperazin-1-yl)quinoline 4-Chloro-7-methoxy-8-methylquinoline [obtained from m-anisidine following the protocol of Krogstad et. al. (De, D., Byers L. D., Krogstad, D. J. *J. Heterocyclic Chem.* 1997, 34, 315; $^1$H NMR (CDCl$_3$), δ 2.70 (s, 3H), 3.93 (s, 3H), 7.20 (dd, 1H), 7.24 (s, 1H), 7.36 (d, 1H), 8.04 (d, 1H))] (0.31 g, 1.5 mmol) and 1-tert-butoxycarbonylpiperazine (1.49 g, 8.0 mmol) are reacted according to method A (reaction time: 3.5 h). The Boc group is cleaved with trifluoroacetic acid (5 mL) in CH$_2$Cl$_2$ (5 mL) giving 0.20 g of the piperazine as brown oil.

$^1$H NMR (CDCl$_3$), δ 2.61 (s, 3H), 3.13 (m, 4H), 3.17 (m, 4H), 3.87 (s, 3H), 6.59 (s, 1H), 7.02 (dd, 1H), 7.30 (d, 1H), 7.79 (d, 1H).

Preparation of 4-[4-(4-Fluorophenylaminocarbonyl)piperazin-1-yl]-7-methoxy-2-methylquinoline 7-Methoxy-8-methyl-4-(piperazin-1-yl)quinoline (0.20 g, 0.8 mmol) and 4-fluorophenyl isocyanate (102 μL, 0.9 mmol) in THF (10 mL) are reacted according to method C yielding the product as a yellow solid after column chromatography with hexane-EtOAc.

$^1$H NMR ([D]$_6$-DMSO), δ 2.53 (s, 3H), 3.11 (m, 4H), 3.71 (m, 4H), 3.85 (s, 3H), 6.80 (s, 1H), 7.06 (t, 2H), 7.09 (dd, 1H), 7.24 (d, 1H), 7.46 (m, 2H), 7.88 (d, 1H), 8.67 (br. s, 1H).

Example 8

Preparation of 7-Chloro-6-fluoro-4-[4-(4-fluorophenylaminocarbonyl)piperazin-1-yl]quinoline Preparation of 7-Chloro-6-fluoro-4-(piperazin-1-yl)quinoline 4,7-Dichloro-6-fluoroquinoline [obtained from 3-chloro-4-fluoroaniline following the protocol of Krogstad et. al. (De, D., Byers L. D., Krogstad, D. J. *J. Heterocyclic Chem.* 1997, 34, 315; $^1$H NMR (CDCl$_3$), δ 7.51 (d, 1H), 7.94 (d, 1H), 8.22 (d, 1H), 8.76 (d, 1H))] (0.32 g, 1.7 mmol) and 1-tert-butoxycarbonylpiperazine (1.40 g, 7.5 mmol) are reacted according to method A. The Boc group is cleaved with trifluoroacetic acid (5 mL) in CH$_2$Cl$_2$ (5 mL) giving 0.36 g of the piperazine as a pale yellow solid.

$^1$H NMR (CDCl$_3$), δ 3.15 (m, 8H), 6.86 (d, 1H), 7.70 (d, 1H), 8.11 (d, 1H), 8.69 (d, 1H).

Preparation of 7-Chloro-6-fluoro-4-[4-(4-fluorophenylaminocarbonyl)piperazin-1-yl]quinoline 7-Chloro-6-fluoro-4-(piperazin-1-yl)quinoline (0.36 g, 1.35 mmol) and 4-fluorophenyl isocyanate (171 μL, 1.5 mmol) in THF (10 mL) are reacted according to method C yielding the product as a colorless solid after column chromatography with hexane-EtOAc.

$^1$H NMR ([D]$_6$-DMSO) δ 3.17 (m, 4H), 3.71 (m, 4H), 7.07 (t, 2H), 7.10 (d, 1H), 7.46 (dd, 2H), 7.92 (d, 1H), 8.20 (d, 1H), 8.68 (br. s, 1H), 8.72 (d, 1H).

Example 9

Preparation of 7-Fluoro-4-[4-(4-fluorophenylaminocarbonyl)piperazin-1-yl]quinoline Preparation of 7-Fluoro-4-(piperazin-1-yl)quinoline 4-Chloro-7-fluoroquinoline [obtained from 3-fluoroaniline following the protocol of Krogstad et. al. (De, D., Byers L. D., Krogstad, D. J. *J. Heterocyclic Chem.* 1997, 34, 315; $^1$H NMR (CDCl$_3$), δ 7.43 (ddd, 1H), 7.46 (d, 1H), 7.75 (dd, 1H), 8.24 (dd, 1H), 8.77 (d, 1H))] (0.47 g, 2.6 mmol) and 1-tert-butoxycarbonylpiperazine (1.45 g, 7.8 mmol) are reacted according to method A. The Boc group is cleaved with trifluoroacetic acid (5 mL) in CH$_2$Cl$_2$ (5 mL) giving 0.30 g of the piperazine as yellow oil.

$^1$H NMR (CDCl$_3$) δ 3.14 (m, 4H), 3.19 (m, 4H), 6.80 (d, 1H), 7.24 (ddd, 1H), 7.64 (dd, 1H), 8.02 (dd, 1H), 8.71 (d, 1H).

Preparation of 7-Fluoro-4-[4-(4-fluorophenylaminocarbonyl)piperazin-1-yl]quinoline 7-Fluoro-4-(piperazin-1-yl)quinoline (0.29 g, 1.25 mmol) and 4-fluorophenyl isocyanate (142 µL, 1.25 mmol) in THF (10 mL) are reacted according to method C yielding the product as colorless crystals after column chromatography with hexane-EtOAc.

$^1$H NMR ([D]$_6$-DMSO) δ 3.18 (m, 4H), 3.71 (m, 4H), 7.01 (d, 1H), 7.07 (t, 2H), 7.46 (m, 3H), 7.66 (dd, 1H), 8.14 (dd, 1H), 8.68 (br. s, 1H), 8.70 (d, 1H).

Example 10

Preparation of 6,7-Difluoro-4-[4-(4-fluorophenylaminocarbonyl)piperazin-1-yl]quinoline 4-Chloro-6,7-difluoroquinoline [obtained from 3,4-difluoroaniline following the protocol of Krogstad et. al. (De, D., Byers L. D., Krogstad, D. J. *J. Heterocyclic Chem.* 1997, 34, 315; $^1$H NMR (CDCl$_3$) δ 7.50 (d, 1H), 7.88 (dd, 1H), 7.97 (dd, 1H), 8.75 (d, 1H))] (0.32 g, 1.6 mmol) and 1-tert-butoxycarbonylpiperazine (0.89 g, 4.8 mmol) are reacted according to method A. The Boc group is cleaved with trifluoroacetic acid (5 mL) in CH$_2$Cl$_2$ (5 mL) giving 0.16 g of a yellow solid, which is treated with 4-fluorophenyl isocyanate (74 µL, 0.65 mmol) in THF (10 mL) according to method C. The title product is obtained as colorless needles after column chromatography with hexane-EtOAc.

$^1$H NMR ([D]$_6$-DMSO) δ 3.17 (m, 4H), 3.71 (m, 4H), 7.06 (t, 2H), 7.08 (d, 1H), 7.46 (dd, 2H), 7.94 (m, 2H), 8.68 (br. s, 1H), 8.71 (d, 1H).

Example 11

Preparation of 7-Cyano-4-[4-(4-fluorophenylaminocarbonyl)piperazin-1-yl]quinoline 4-Chloro-7-cyanoquinoline [obtained from 3-aminobenzonitrile following the protocol of Krogstad et. al. (De, D., Byers L. D., Krogstad, D. J. *J. Heterocyclic Chem.* 1997, 34, 315; $^1$H NMR (CDCl$_3$), δ 7.63 (d, 1H), 7.79 (dd, 1H), 8.35 (d, 1H), 8.49 (d, 1H), 8.90 (d, 1H))] (0.29 g, 1.5 mmol) and 1-tert-butoxycarbonylpiperazine (0.56 g, 3.0 mmol) are reacted according to method A. The Boc group is cleaved with trifluoroacetic acid (3 mL) in CH$_2$Cl$_2$ (5 mL) giving 0.17 g an orange solid, which is treated with 4-fluorophenyl isocyanate (80 µL, 0.67 mmol) in THF (10 mL) according to method C. The title product is obtained as a yellow solid after column chromatography with hexane-EtOAc.

$^1$H NMR ([D]$_6$-DMSO) δ 3.20 (m, 4H), 3.73 (m, 4H), 7.06 (t, 2H), 7.16 (d, 1H), 7.46 (dd, 2H), 7.83 (dd, 1H), 8.22 (d, 1H), 8.49 (d, 1H), 8.69 (br. s, 1H), 8.82 (d, 1H).

Example 12

Preparation of 4-[4-(4-Fluorophenylaminocarbonyl)piperazin-1-yl]-6,7-methylenedioxyquinoline 4-Chloro-6,7-methylenedioxyquinoline [obtained from 3,4-methylendioxyaniline following the protocol of Krogstad et. al. (De, D., Byers L. D., Krogstad, D. J. *J. Heterocyclic Chem.* 1997, 34, 315; $^1$H NMR ([D]$_6$-DMSO), δ 6.28 (s, 2H), 7.45 (s, 1H), 7.50 (s, 1H), 7.65 (d, 1H), 8.62 (d, 1H)) (0.50 g, 2.4 mmol) and 1-tert-butoxycarbonylpiperazine (1.8 g, 9.6 mmol) are reacted according to method A yielding 391 mg of 4-[4-(tert-butoxycarbonyl)piperazin-1-yl]-6,7-methylenedioxy quinoline. After cleaving the Boc group with trifluoroacetic acid (1.5 mL) in CH$_2$Cl$_2$ (1.5 mL), the piperazine is treated with 4-fluorophenylisocyanate (86 µL) and triethylamine (0.245 mL) according to method C yielding the title product.

$^1$H NMR (CDCl$_3$) δ 3.20 (m, 4H), 3.80 (m, 4H), 6.10 (s, 2H), 6.45 (s, 1H), 680 (d, 1H), 7.05 (t, 2H), 7.35 (m, 3H), 7.40 (s, 1H), 8.60 (d, 1H).

Example 13

Preparation of 4-[4-(4-Fluorophenylaminocarbonyl)piperazin-1-yl]-7-methylquinoline trifluoroacetate 4-Chloro-7-methylquinoline [obtained from 3-toluidine following the protocol of Krogstad et. al. (De, D., Byers L. D., Krogstad, D. J. *J. Heterocyclic Chem.* 1997, 34, 315; $^1$H NMR ([D]$_6$-DMSO), δ 2.55 (s, 3H), 7.60 (m, 1H), 7.75 (d, 1H), 7.90 (s, 1H), 8.10 (d, 1H), 8.80 (d, 1H)) (0.80 g, 4.5 mmol) and 1-tert-butoxycarbonylpiperazine (3.35 g, 18 mmol) are reacted according to method A yielding 475 mg of 4-[4-(tert-butoxycarbonyl)piperazin-1-yl]-7-methylquinoline. After cleaving the Boc group with trifluoroacetic acid (1.8 mL) in CH$_2$Cl$_2$ (1.8 mL), the piperazine is treated with 4-fluorophenyl isocyanate and triethylamine (0.245 mL) according to method C yielding the title product.

$^1$H NMR ([D]$_6$-DMSO) δ 2.53 (s, 3H), 3.60–3.95 (m, 8H), 7.05–7.10 (m, 3(m, 3H), 7.70 (s, 1H), 8.12 (d, 1H), 8.60 (d, 1H), 8.65 (s, 1H).

Example 14

Preparation of 4-[4-(tert-Butoxycarbonyl)piperazin-1-yl]-7-nitroquinoline

4-Chloro-7-nitroquinoline (Ellis, J.; Gellert, E.; Robson, J. *Aust. J. Chem.* 1973, 26, 907) (1.8 g, 8.7 mmol) and 1-tert-butoxycarbonylpiperazine (5.0 g, 27 mmol) are reacted according to method A furnishing 0.36 g of the piperazine as brown oil after column chromatography with CH$_2$Cl$_2$-MeOH.

¹H NMR (CDCl₃) δ 1.5 (s, 9H), 3.2 (m, 4H), 3.8 (m, 4H), 7.0 (d, 1H), 8.2 (d, 1H), 8.25 (dd, 1H), 8.9 (d, 1H), 8.95 (d, 1H).

Example 15

Preparation of 4-[4-(4-Fluorophenylaminocarbonyl)piperazin-1-yl]-7-nitroquinolin trifluoroacetate To a solution of 4-[4-(tert-butoxycarbonyl)piperazin-1-yl]-7-nitroquinoline (360 mg, 1 mmol) in CH₂Cl₂ (1 mL) is added trifluoroacetic acid (1 mL). After 1½ h at room temp., the mixture is concentrated, and the residue is dissolved in CH₂Cl₂ (20 mL) and treated with triethylamine (0.56 mL, 4 mmol) and 4-fluorophenyl isocyanate (0.16 mL, 1.4 mmol). After 1½ h stirring at room temp., the reaction mixture is washed with water and brine, dried (Na₂SO₄), and concentrated. The residue is purified by reversed phase HPLC with water-MeCN-TFA yielding the title product.

¹H NMR ([D]₆-DMSO) δ 3.65 (m, 4H), 3.75 (m, 4H), 7.1 (m, 2H), 7.25 (d, 1H), 7.5 (m, 2H), 8.3 (m, 1H), 8.4 (d, 1H), 8.7 (s, 1H), 8.75 (m, 1H), 8.8 (d, 1H).

Example 16

Preparation of 7-Amino-4-[4-(4-fluorophenylaminocarbonyl)piperazin-1-yl]quinoline A suspension of 4-[4-(4-fluorophenylaminocarbonyl)piperazin-1-yl]-7-nitroquinoline trifluoroacetate (130 mg) and 10% Pd/C (20 mg) in MeOH is stirred in a hydrogen atmosphere for 30 min. The reaction mixture is filtered and concentrated giving the title product.

¹H NMR (CD₃OD) δ 3.8 (m, 8H), 6.8 (d, 1H), 6.85 (d, 1H), 7.0 (m, 3H), 7.4 (m, 2H), 7.9 (d, 1H), 8.2 (d, 1H).

Example 17

Preparation of 7-Acetylamino-4-[4-(4-fluorophenylaminocarbonyl)piperazin-1-yl]quinoline, trifluoroacetate A solution of 7-amino-4-[4-(4-fluorophenylaminocarbonyl)piperazin-1-yl]quinoline (85 mg, 0.23 mmol) and triethylamine (97 µL, 0.70 mmol) in CH₂Cl₂ (20 mL) is treated with acetyl chloride (0.022 mL, 0.28 mmol) and cat. DMAP and stirred at room temp. for 2 h. The reaction mixture is washed with water and brine, dried (Na₂SO₄), and concentrated. The residue is purified by reversed phase HPLC with water-MeCN-TFA yielding the title product.

¹H NMR (CD₃OD) δ 2.2 (s, 3H), 3.8 (m, 4H), 4.0 (m, 4H), 7.0 (m, 2H), 7.1 (d, 1H), 7.4 (m, 2H), 7.6 (m, 1H), 8.2 (d, 1H), 8.4 (d, 1H), 8.6 (s, 1H).

Example 18

Preparation of Ethyl 4-[4-(tert-butoxycarbonyl)piperazin-1-yl]-7-chloroquinoline-2-carboxylate Preparation of Ethyl 7-chloro-4-quinolone-2-carboxylate 3-Chloroaniline (28.5 g, 200 mmol) and diethyl acetylenedicarboxylate (37.4 g, 220 mmol) are heated in MeOH (300 mL) for 3 h at reflux. The reaction mixture is concentrated to yield a yellow residue, which is heated in phenyl ether (400 mL), for ¾ h. The mixture is cooled to room temp. and diluted with hexane whereupon a white solid precipitates which is filtered off: 34.4 g.

¹H NMR (CDCl₃) δ 1.4 (t, 3H), 4.4 (q, 2H), 6.6 (s, 1H), 7.4 (dd, 1H), 8.0 (d, 1H), 8.05 (d, 1H).

Preparation of Ethyl 4-[4-(tert-butoxycarbonyl)piperazin-1-yl]-7-chloroquinoline-2-carboxylate Ethyl 7-chloro-4-quinolone-2-carboxylate (1.0 g, 4 mmol) is stirred with sodium hydride (0.144 g, 6 mmol) in DMF (50 mL) for 1 h at 40° C. N-Phenyl (trifluoromethylsulfon)imide (2.0 g, 5.6 mmol) is added and, after an hour, 1-tert-butoxycarbonylpiperazine (3.0 g, 6 mmol). The reaction mixture is stirred at 50° C. for 15 h, concentrated, diluted with EtOAc, washed with water and brine, dried (Na₂SO₄), and concentrated. The residue is purified by column chromatography with CH₂Cl₂-MeOH yielding the title product as a colorless solid.

¹H NMR (CDCl₃) δ 1.5 (t, 3H), 1.55 (s, 9H), 3.2 (m, 4H), 3.8 (m, 4H), 4.6 (q, 2H), 7.5 (dd, 1H), 7.65 (s, 1H), 7.95 (d, 1H), 8.25 (d, 1H).

Example 19

Preparation of Ethyl 7-chloro-4-[4-(4-fluorophenylaminocarbonyl)piperazin-1-yl]quinoline-2-carboxylate To a solution of ethyl 4-[4-(tert-butoxycarbonyl)piperazin-1-yl]-7-chloroquinoline-2-carboxylate (1.0 g, 2.4 mmol) in CH₂Cl₂ (5 mL) is added trifluoroacetic acid (5 mL). After 1 h at room temp., the reaction mixture is adjusted to pH 10–11 with 10% aq. NaOH and extracted with EtOAc. The combined extracts are dried (Na₂SO₄) and concentrated. The residue is dissolved in CH₂Cl₂ (70 mL) and treated with 4-fluorophenyl isocyanate (0.32 mL, 2.8 mmol) for 15 h at room temp. The reaction mixture is washed with water and brine, dried (Na₂SO₄), and concentrated. The residue is purified by column chromatography with CH₂Cl₂-MeOH yielding the title product.

¹H NMR (CDCl₃) δ 1.5 (t, 3H), 3.4 (m, 4H), 3.8 (m, 4H), 4.6 (q, 2H), 6.4 (s, 1H), 7.0 (m, 2H), 7.35 (m, 2H), 7.55 (m, 1H), 7.7 (s, 1H), 8.0 (d, 1H), 8.3 (d, 1H).

Example 20

Preparation of 7-Chloro-4-[4-(4-fluorophenylaminocarbonyl)piperazin-1-yl]-2-(hydroxymethyl)quinoline, trifluoroacetate Ethyl 7-chloro-4-[4-(4-fluorophenylaminocarbonyl)piperazin-1-yl]quinoline-2-carboxylate (380 mg, 0.83 mmol) and a 1 M THF solution of super hydride (6.7 mL, 6.7 mmol) are stirred at room temp. for ⅔ h. Water (10 mL) and 10% aq. NaOH (10 mL) is added, and stirring is continued for ⅔ h. The mixture is acidified with 5 N HCl (pH 5) and extracted with EtOAc. The extracts are dried (Na₂SO₄) and concentrated. The residue is purified by reversed phase HPLC with water-MeCN-TFA yielding the title product.

¹H NMR ([D]₆-DMSO) δ 3.7 (m, 4H), 3.8 (m, 4H), 4.8 (s, 2H), 7.05 (m, 2H), 7.15 (s, 1H), 7.45 (m, 2H), 7.65 (m, 1H), 8.7 (m, 2H), 8.65 (s, 1H).

Example 21

Preparation of 2-Azidomethyl-7-chloro-4-[4-(4-fluorophenylaminocarbonyl)piperazin-1-yl]quinoline 7-Chloro-4-[4-(4-fluorophenylaminocarbonyl)piperazin-1-yl]-2-(hydroxymethyl)quinoline, trifluoroacetate (100 mg, 0.24 mmol) diphenylphosphoryl azide (DPPA, 0.052 mL, 0.24 mmol), and DBU (0.036 mL, 0.24 mmol) are stirred in THF (30 mL) for 2 h at room temp. The reaction mixture is diluted with EtOAc, washed with water and brine, dried ($Na_2SO_4$) and concentrated. The residue is purified by column chromatography with $CH_2Cl_2$-MeOH to give the title product as a yellow oil.

$^1$H NMR ($CDCl_3$) δ 3.3 (m, 4H), 3.8 (m, 4H), 4.6 (s, 2H), 6.4 (s, 1H), 7.0 (m, 2H), 7.3 (m, 2H), 7.5 (dd, 1H), 7.9 (d, 1H), 8.0 (s, 1H).

Example 22

Preparation of 7-Chloro-4-[4-(4-fluorophenylaminocarbonyl)piperazin-1-yl]-2-(methoxymethyl)quinoline, trifluoroacetate and

Example 23

Preparation of 2-Aminomethyl-7-chloro-4-[4-(4-fluorophenylaminocarbonyl)piperazin-1-yl]quinoline, trifluoroacetate A solution of 2-azidomethyl-7-chloro-4-[4-(4-fluorophenylaminocarbonyl)piperazin-1-yl]quinoline (24 mg, 0.055 mmol) in MeOH (5 mL) is added to a suspension of tin(II) chloride (32 mg, 0.055 mmol) in MeOH (10 mL). After stirring for 2 h at room temp. the reaction mixture is concentrated, and the residue is suspended in water. The mixture is adjusted with 10% aq. NaOH (pH 11–12) and extracted with EtOAc. The combined extracts are dried ($Na_2SO_4$) and concentrated. The residue is purified by reversed phase HPLC with water-MeCN-TFA yielding 7-chloro-4-[4-(4-fluorophenylaminocarbonyl)piperazin-1-yl]-2-(methoxymethyl)quinoline, trifluoroacetate and 2-aminomethyl-7-chloro-4-[4-(4-fluorophenylaminocarbonyl)piperazin-1-yl]quinoline, trifluoroacetate.

7-Chloro-4-[4-(4-fluorophenylaminocarbonyl)piperazin-1-yl]-2-(methoxymethyl)quinoline, trifluoroacetate $^1$H NMR ($CD_3OD$) δ 3.6 (s, 3H), 3.9 (m, 4H), 4.0 (m, 4H), 4.8 (s, 2H), 7.0 (m, 2H), 7.2 (s, 1H), 7.4 (m, 2H), 7.7 (m, 1H), 8.1 (d, 1H), 8.3 (d, 1H).

2-Aminomethyl-7-chloro-4-[4-(4-fluorophenylaminocarbonyl)piperazin-1-yl]quinoline, trifluoroacetate $^1$H NMR ($CD_3OD$) δ 3.6 (m, 4H), 3.8 (m, 4H), 4.4 (s, 2H), 7.0 (m, 2H), 7.1 (s, 1H), 7.3 (m, 2H), 7.6 (m, 1H), 8.0 (d, 1H), 8.2 (d, 1H).

Example 24

Preparation of 7-Chloro-4-[4-(4-fluorophenylaminocarbonyl)piperazin-1-yl]quinoline-2-carboxylic acid A solution of ethyl 7-chloro-4-[4-(4-fluorophenylaminocarbonyl)piperazin-1-yl]quinoline-2-carboxylate (389 mg, 0.85 mmol) in THF-water 3:1 (5 mL) is treated with LiOH x $H_2O$ (126 mg, 3 mmol) and stirred at room temp. for 4 h. The reaction mixture is concentrated and acidified with 1 N HCl (pH 4). The colorless precipitate is collected by filtration yielding the title product.

$^1$H NMR ($CD_3OD$) δ 3.50 (m, 4H), 3.75 (m, 4H), 7.00 (t, 2H), 7.40 (m, 2H), 7.55 (s, 1H), 7.60 (m, 1H), 8.20 (m, 2H).

Example 25

Preparation of 2-tert-Butoxycarbonylamino-7-chloro-4-[4-(4-fluorophenylaminocarbonyl)piperazin-1-yl]quinoline A solution of 7-chloro-4-[4-(4-fluorophenylaminocarbonyl)piperazin-1-yl]quinoline-2-carboxylic acid (215 mg, 0.5 mmol), diphenylphosphoryl azide (DPPA, 144 μL, 0.65 mmol), and triethylamine (92 μL, 0.65 mmol) in t-butanol (5 mL) is heated at 105° C. in an Ar atmosphere for 3 h. The solvent is removed, and the residue is dissolved in EtOAc, washed with water, dried ($MgSO_4$), and concentrated. Purification by column chromatography with $CH_2Cl_2$-MeOH affords the title product.

$^1$H NMR ($[D]_6$-DMSO) δ 1.35 (s, 9H), 3.05 (m, 4H), 3.60 (m, 4H), 6.95 (t, 2H), 7.10 (m, 1H), 7.20–7.40 (m, 3H), 7.55 (m, 2H), 7.85 (d, 1H), 8.60 (s, 1H).

Example 26

Preparation of 2-Amino-7-chloro-4-[4-(4-fluorophenylaminocarbonyl)piperazin-1-yl]quinoline, trifluoroacetate 2-tert-Butoxycarbonylamino-7-chloro-4-[4-(4-fluorophenylaminocarbonyl)piperazin-1-yl]quinoline (440 mg, 0.88 mmol) in $CH_2Cl_2$ (1.5 mL) is treated with trifluoroacetic acid (1.5 mL) for 2 h at room temp. The solvent is removed, and the residue purified by reversed phase HPLC with water-MeCN-TFA giving the title product.

$^1$H NMR ($CD_3OD$) δ 3.45 (m, 4H), 3.80 (m, 4H), 6.35 (s, 1H), 7.00 (t, 2H), 7.36 (m, 2H), 7.45 (d, 1H), 7.60 (s, 1H), 8.00 (d, 1H).

Example 27

Preparation of 2-Acetylamino-7-chloro-4-[4-(4-fluorophenylaminocarbonyl)piperazin-1-yl]quinoline 2-tert-Butoxycarbonylamino-7-chloro-4-[4-(4-fluorophenylaminocarbonyl)piperazin-1-yl]quinoline (110 mg, 0.22 mmol) in $CH_2Cl_2$ (1 mL) is treated with trifluoroacetic acid (1 mL) for 2 h at room temp. The reaction mixture is concentrated. The residue is dissolved in $CH_2Cl_2$ (9 mL). Triethylamine (154 μL, 1.1 mmol), acetyl chloride (26 μL, 0.24 mmol), and DMAP (10 mg) are added. The reaction mixture is stirred at room temp. for 3 h, washed with water, dried ($MgSO_4$), and concentrated. Purification of the residue by column chromatography with $CH_2Cl_2$-MeOH affords the title product.

$^1$H NMR ($CDCl_3$) δ 2.25 (s, 3H), 3.30 (m, 4H), 3.80 (m, 4H), 7.00 (t, 2H), 7.35 (m, 4H), 7.75 (s, 1H), 7.90 (d, 1H), 7.95 (s, 1H).

Example 28

Preparation of N-[7-Chloro-4-[4-(4-fluorophenylaminocarbonyl)piperazin-1-yl]quinolin-2-yl]urea, trifluoroacetate To a solution of 2-amino-7-chloro-4-[4-(4-fluorophenylaminocarbonyl)piperazin-1-yl]quinoline (42 mg, 0.11 mmol) in 1,4-dioxane-THF 3:1 (2 mL) is added trimethylsilyl isocyanate (0.1 mL). The reaction mixture is heated in a sealed tube for 18 h at 80° C. More isocyanate (0.2 mL) is added, and the mixture is heated for further 18 h. The solvent is removed, and the residue is purified by flash chromatography with $CH_2Cl_2$-MeOH followed by reversed phase HPLC with water-MeCN-TFA affording the title product. $^1$H NMR ($CD_3OD$) δ 3.65 (m, 4H), 3.80 (m, 4H), 6.55 (s, 1H), 7.00 (t, 2), 7.38 (m, 2H), 7.60 (d, 1H), 8.00 (s, 1H), 8.10 (d, 1H).

Exampl 29

Preparation of N-[7-Chloro-4-[4-(4-fluorophenylaminocarbonyl)piperazin-1-yl]quinolin-2-yl]-N'-phenylurea To a solution of 2-amino-7-chloro-4-[4-(4-fluorophenylaminocarbonyl)piperazin-1-yl]quinoline (20 mg, 0.05 mmol) in MeCN-1,2-dichloroethane 1:1 (12 mL) is added phenyl isocyanate (17 μL, 0.11 mmol). The reaction mixture is heated at reflux for 1 h. Upon cooling the title product precipitates and is collected by filtration.
$^1$H NMR ([D]$_6$-DMSO) δ 3.16 (m, 4H), 3.70 (m, 4H), 6.90 (s, 1H), 7.05 (m, 3H), 7.35 (t, 2H), 7.40 (m, 1H), 7.45 (m, 2H), 7.65 (d, 2H), 7.95 (m, 2H).

Example 30

Preparation of 7-Chloro-4-[4-(4-fluorophenylaminocarbonyl)piperazin-1-yl]-2-(methylamino)quinoline, trifluoroacetate To a solution of 2-tert-butoxycarbonylamino-4-[4-tert-butoxycarbonylpiperazin-1-yl]-7-chloroquinoline (150 mg, 0.35 mmol) in THF (2 mL) is added a suspension of sodium hydride (25 mg, 1.1 mmol) in THF (4 mL). After for ¾ h at room temp. iodomethane (33 μL, 0.53 mmol) is added, and stirring is continued for 7 h. The reaction mixture is diluted with EtOAc, washed with water, dried (MgSO$_4$), and concentrated. The residue is purified by column chromatography with $CH_2Cl_2$-MeOH giving 86 mg of 2-(N-t-butoxycarbonyl-N-methylamino)-4-[4-tert-butoxycarbonylpiperazin-1-yl]-7-chloroquinoline. This is treated with TFA-$CH_2Cl_2$ 1:1 (1 mL) to cleave the Boc groups and 4-fluorophenyl isocyanate (30 μL) and triethylamine (0.20 mL) according to method C affording the title product.
$^1$H NMR ($CD_3OD$) δ 3.10 (s, 3H), 3.40 (m, 4H), 3.80 (m, 4H), 6.35 (s, 1H), 7.00 (t, 2H), 7.35 (m, 2H), 7.45 (dd, 1H), 7.80 (m, 1H), 8.00 (d, 1H).

Example 31

Preparation of 4-[4-(tert-Butoxycarbonyl)piperazin-1-yl]-7-chloro-2-quinolone

Preparation of 4,7-Dichloro-2-quinolone 4,7-Dichloroquinoline (20.4 g) and peracetic acid (32 wt. % [from Aldrich], 24 mL) are heated at reflux for 8 h and kept at room temp. for 18 h. The precipitate is collected and washed with hexane to give 23 g of 4,7-dichloroquinoline-N-oxide. 1.0 g (4.7 mmol) thereof is heated in phosphoryl chloride (3.7 mL) for 1½ h at reflux. The reaction mixture is concentrated and the residue is treated with 10% aq. NaOH (pH 9). The precipitate is collected, washed with water, and dried yielding 1.0 g of 2,4,7-trichloroquinoline. 250 mg thereof is heated with 15% $H_2SO_4$ (20 mL) and 1,4-dioxane (10 mL) in a sealed tube at 140° C. for 8 h. The mixture is kept at room temp. for 18 h. The precipitate is collected, washed with water, and dried affording 195 mg of 4,7-dichloro-2-quinolone.
$^1$H NMR (CDCl$_3$) δ 7.55 (s, 1H), 7.60 (d, 1H), 8.03 (s, 1H), 8.16 (d, 1H).

Preparation of 4-[4-(tert-Butoxycarbonyl)piperazin-1-yl]-7-chloro-2-quinolone 4,7-Dichloro-2-quinolone (192 mg, 0.88 mmol) and 1-tert-butoxycarbonylpiperazine (580 mg, 3.1 mmol) in n-butanol (10 mL) are heated in a sealed tube for 2 h at 150° C., when additional piperazine (200 mg) is added and heating is continued for further 18 h. After removing the solvent, the residue is purified by column chromatography with $CH_2Cl_2$-MeOH—$NH_4OH$ yielding the title product as a colorless solid.
$^1$H NMR ([D]$_6$-DMSO) δ 1.4 (s, 9H), 3.0 (m, 4H), 3.5 (m, 4H), 5.9 (s, 1H), 7.15 (d, 1H), 7.3 (s, 1H), 7.7 (d, 1H).

Example 32

Preparation of 7-Chloro-4-[4-(4-fluorophenylaminocarbonyl)piperazin-1-yl]-2-quinolone 4-[4-(tert-Butoxycarbonyl)piperazin-1-yl]-7-chloro-2-quinolone (100 mg) is deprotected with TFA-$CH_2Cl_2$ 1:1 (0.5 mL) and transformed to the title product with 4-fluorophenyl isocyanate (50 μL) according to method C.
$^1$H NMR ([D]$_6$-DMSO) δ 3.15 (m, 4H), 3.65 (m, 4H), 5.90 (s, 1H), 7.05 (t, 2H), 7.18 (d, 1H), 7.30 (s, 1H), 7.45 (m, 2H), 7.70 (d, 1H), 8.65 (s, 1H), 11.40 (s, 1H).

Example 33

Preparation of 7-Chloro-2-dim thylamino-4-[4-(4-fluorophenylaminocarbonyl)piperazin-1-yl]quinoline 4-[4-(tert-Butoxycarbonyl)piperazin-1-yl]-7-chloroquinol-2-one (74 mg, 0.2 mmol), sodium hydride (8 mg, 0.3 mmol), N-phenyl(trifluoromethylsulfon)imide (101 mg, 0.28 mmol), and dimethylamine (2 M in THF, 2 mL, 4.0 mmol) are treated according to method E yielding 46 mg of the 4-[4-(tert-butoxycarbonyl)piperazin-1-yl]-7-chloro-2-dimethylaminoquinoline. This is treated with TFA-$CH_2Cl_2$ 1:1 (0.6 mL) for 1 h and concentrated. The residue is converted into the title product with 4-fluorophenyl isocyanate (19 μL) and triethylamine (0.11 mL).
$^1$H NMR (CDCl$_3$) δ 3.20 (m, 10H), 3.75 (m, 4H), 6.30 (s, 1H), 6.42 (s, 1H), 7.00 (t, 2H), 7.05 (d, 1H), 7.35 (m, 2H), 7.75 (m, 2H).

Example 34

Preparation of 7-Chloro-2-ethylamino-4-[4-(4-fluorophenylaminocarbonyl)piperazin-1-yl]quinoline To a solution of 2-tert-butoxycarbonylamino-4-[4-tert-butoxycarbonylpiperazin-1-yl]-7-chloroquinoline (135 mg, 0.29 mmol) in THF (2 mL) is added a suspension of sodium hydride (21 mg, 0.87 mmol) in THF (4 mL). After for ¾ h at room temp. iodoethane (0.45 mmol) in THF (1 mL) is added, and stirring is continued for 18 h. More iodoethane (0.42 mmol) is added, and stirring is continued at 45° C. for 18 h. The reaction mixture is diluted with EtOAc, washed with water, dried (MgSO$_4$), and concentrated. The residue is purified by column chromatography with CH$_2$Cl$_2$-MeOH giving 60 mg of 2-(N-tert-butoxycarbonyl-N-ethylamino)-4-[4-tert-butoxycarbonylpiperazin-1-yl]-7-chloroquinoline. This is treated with TFA-CH$_2$Cl$_2$ 1:1 (1 mL) to cleave the Boc groups. 4-Fluorophenyl isocyanate (24 μL) and triethylamine (0.14 mL) are added according to method C affording the title product.

$^1$H NMR (CD$_3$OD) δ 1.25 (t, 3H), 3.15 (m, 4H), 3.45 (q, 2H), 3.80 (m, 4H), 6.25 (s, 1H), 7.00 (t, 2H), 7.10 (m, 1H), 7.35 (m, 2H), 7.55 (s, 1H), 7.80 (d, 1H).

Example 35

Preparation of 7-Chloro-2-[2-(dimethylamino)ethylamino]-4-[4-(4-fluorophenylaminocarbonyl)piperazin-1-yl]quinoline 4-[4-(tert-Butoxycarbonyl)piperazin-1-yl]-7-chloroquinol-2-one (145 mg, 0.4 mmol), sodium hydride (15 mg, 0.6 mmol), N-phenyl(trifluoromethylsulfon)imide (202 mg, 0.56 mmol), and N,N-dimethylethylenediamine (276 μL, 2.4 mmol) are treated according to method E yielding 98 mg of 4-[4-(tert-butoxycarbonyl)piperazin-1-yl]-7-chloro-2-[2-(dimethylamino)ethylamino]quinoline. 38 mg thereof are treated with TFA-CH$_2$Cl$_2$ 1:1 (0.6 mL) for 1 h and concentrated. The residue is converted into the title product with 4-fluorophenyl isocyanate (16 μL) and triethylamine (120 μL).

$^1$H NMR ([D]$_6$-DMSO) δ 2.20 (s, 6H), 2.40 (t, 2H), 3.00 (m, 4H), 3.40 (m, 2H), 3.70 (m, 4H), 6.38 (s, 1H), 6.90 (m, 1H), 7.05 (m, 3H), 7.40 (s, 1H), 7.45 (m, 2H), 7.75 (d, 1H), 8.65 (s, 1H).

Example 36

Preparation of 7-Chloro-2-cyclohexylamino-4-[4-(4-fluorophenylaminocarbonyl)piperazin-1-yl]quinoline 4-[4-(tert-Butoxycarbonyl)piperazin-1-yl]-7-chloroquinol-2-one (150 mg, 0.4 mmol), sodium hydride (15 mg, 0.6 mmol), N-phenyl(trifluoromethylsulfon)imide (208 mg, 0.56 mmol), and cyclohexylamine (286 μL, 2.4 mmol) are treated according to method E yielding 21 mg of 4-[4-(tert-butoxycarbonyl)piperazin-1-yl]-7-chloro-2-(cyclohexylamino)quinoline which is treated with TFA-CH$_2$Cl$_2$ 1:1 (0.6 mL) for 1 h and concentrated. The residue is converted into the title product with 4-fluorophenyl isocyanate (8 μL) and triethylamine (60 μL).

$^1$H NMR (CD$_3$OD) δ 1.30 (m, 3H), 1.45 (m, 2H), 1.70 (m, 1H), 1.80 (m, 2H), 2.00 (m, 2H), 3.10 (m, 4H), 3.75 (m, 4H), 3.90 (m, 1H), 6.25 (s, 1H), 7.00 (t, 2H), 7.10 (d, 1H), 7.38 (m, 2H), 7.60 (s, 1H), 7.80 (d, 1H).

Example 37

Preparation of 7-Chloro-2-cyclopropylamino-4-[4-(4-fluorophenylaminocarbonyl)piperazin-1-yl]quinolin 4-[4-(tert-Butoxycarbonyl)piperazin-1-yl]-7-chloroquinol-2-one (150 mg, 0.4 mmol), sodium hydride (15 mg, 0.6 mmol), N-phenyl(trifluoromethylsulfon)imide (208 mg, 0.56 mmol), and cyclopropylamine (580 μL, 6.4 mmol) are treated according to method E yielding 75 mg of 4-[4-(tert-butoxycarbonyl)piperazin-1-yl]-7-chloro-2-(cyclopropylamino)quinoline. 62 mg thereof are treated with TFA-CH$_2$Cl$_2$ 1:1 (0.6 mL) for 1 h and concentrated. The residue is converted into the title product with 4-fluorophenyl isocyanate (26 μL) and triethylamine (193 μL).

$^1$H NMR (CD$_3$OD) δ 0.55 (m, 2H), 0.85 (m, 2H), 2.75 (m, 1H), 3.19 (m, 4H), 3.80 (m, 4H), 6.40 (s, 1H), 7.00 (t, 2H), 7.16 (d, 1H), 7.36 (m, 2H), 7.60 (s, 1H), 7.85 (d, 1H).

Example 38

Preparation of 7-Chloro-2-cyclopropylmethylamino-4-[4-(4-fluorophenylaminocarbonyl)piperazin-1-yl]quinoline 4-[4-(tert-Butoxycarbonyl)piperazin-1-yl]-7-chloroquinol-2-one (150 mg, 0.4 mmol), sodium hydride (15 mg, 0.6 mmol), N-phenyl(trifluoromethylsulfon)imide (208 mg, 0.56 mmol), and cyclopropylmethylamine (360 μL, 4.0 mmol) are treated according to method E yielding 53 mg of 4-[4-(tert-butoxycarbonyl)piperazin-1-yl]-7-chloro-2-(cyclopropylmethylamino)quinoline. 47 mg thereof are treated with TFA-CH$_2$Cl$_2$ 1:1 (0.6 mL) for 1 h and concentrated. The residue is converted into the title product with 4-fluorophenyl isocyanate (19 μL) and triethylamine (140 μL).

$^1$H NMR (CD$_3$OD), δ 0.30 (m, 2H), 0.55 (m, 2H), 1.10 (m, 1H), 3.10 (m, 4H), 3.20 (m, 2H), 3.80 (m, 4H), 6.30 (s, 1H), 7.00 (t, 2H), 7.15 (d, 1H), 7.40 (m, 2H), 7.55 (s, 1H), 7.80 (d, 1H).

Example 39

Preparation of 4-[4-(tert-Butoxycarbonyl)piperazin-1-yl]-7-chloro-2-(2-hydroxyethylamino)quinoline 4-[4-(tert-Butoxycarbonyl)piperazin-1-yl]-7-chloroquinol-2-one (150 mg, 0.4 mmol), sodium hydride (15 mg, 0.6 mmol), N-phenyl(trifluoromethylsulfon)imide (208 mg, 0.56 mmol), and ethanolamine (100 μL, 1.65 mmol) are treated according to method E yielding the title product.

$^1$H NMR (CDCl$_3$) δ 1.5 (s, 9H), 3.1 (m, 4H), 3.7 (m, 6H), 3.9 (m, 2H), 6.1 (s, 1H), 7.15 (dd, 1H), 7.65 (d, 1H), 7.7 (d, 1H).

Example 40

Preparation of 7-Chloro-4-[4-(4-fluorophenylaminocarbonyl)piperazin-1-yl]-2-[2-(4-fluorophenylaminocarbonyloxy)ethylamino]quinoline 4-[4-(tert-Butoxycarbonyl)piperazin-1-yl]-7-chloro-2-(2-hydroxyethylamino)quinoline (62 mg, 0.15 mmol) is deprotected with TFA followed by reaction with 4-fluorophenyl isocyanate (24 μL, 0.21 mmol) and triethylamine (150 μL, 1.1 mmol) according to method C yielding the title product as a colorless solid after column chromatography with CH$_2$Cl$_2$-MeOH.

$^1$H NMR (CDCl$_3$) δ 3.2 (m, 4H), 3.75 (m, 4H), 3.85 (m, 2H), 4.4 (m, 2H), 5.1 (s, 1H), 6.1 (s, 1H), 6.4 (s, 1H), 6.7 (s, 1H), 7.0 (m, 4H), 7.15 (dd, 1H), 7.3 (m, 4H), 7.7 (d, 1H).

Example 41

Preparation of 7-Chloro-4-[4-(4-fluorophenylaminocarbonyl)piperazin-1-yl]-2-(2-hydroxyethylamino)quinoline trifluoroacetate 7-Chloro-4-[4-(4-fluorophenylaminocarbonyl)piperazin-1-yl]-2-[2-(4-fluorophenylaminocarbonyloxy)ethylamino]quinoline (39 mg, 0.07 mmol) and 6 N KOH (1.1 mL, 6.6 mmol) in EtOH-THF 5:1 (6 mL) are heated at reflux for several hours until the starting material is consumed (TLC). The reaction mixture is diluted with water and extracted with EtOAc. The organic phase is dried ($MgSO_4$) and concentrated. The residue is purified by reversed phase HPLC with water-MeCN-TFA affording the title product.

$^1$H NMR ($CD_3OD$) δ 3.40 (m, 4H), 3.65 (m, 2H), 3.85 (m, 6H), 6.40 (s, 1H), 7.00 (t, 2H), 7.35 (m, 2H), 7.45 (d, 1H), 7.75 (s, 1H), 8.00 (d, 1H).

Example 42

Preparation of 7-Chloro-4-[4-(4-fluor phenylaminocarbonyl)piperazin-1-y]-2-(2-methoxyethyl)aminoquinoline 4-[4-(tert-Butoxycarbonyl)piperazin-1-yl]-7-chloroquinol-2-one (150 mg, 0.4 mmol), sodium hydride (15 mg, 0.6 mmol), N-phenyl(trifluoromethylsulfon)imide (208 mg, 0.56 mmol), and 2-methoxyethylamine (362 μL, 4.0 mmol) are treated according to method E yielding 85 mg of 4-[4-(tert-butoxycarbonyl)piperazin-1-yl]-7-chloro-2-(2-methoxyethylamino)quinoline. 74 mg thereof are treated with TFA-$CH_2Cl_2$ 1:1 (0.6 mL) for 1 h and concentrated. The residue is converted into the title product with 4-fluorophenyl isocyanate (30 μL) and triethylamine (230 μL).

$^1$H NMR ($CD_3OD$) δ 3.15 (m, 4H), 3.40 (s, 3H), 3.60 (m, 6H), 3.80 (m, 4H), 6.35 (s, 1H), 7.00 (t, 2H), 7.10 (d, 1H), 7.35 (m, 2H), 7.55 (s, 1H), 7.80 (d, 1H).

Example 43

Preparation of 4-[4-(tert-Butoxycarbonyl)piperazin-1-yl]-7-chloro-2-(n-propylamino)quinoline 4-[4-(tert-Butoxycarbonyl)piperazin-1-yl]-7-chloroquinol-2-one (150 mg, 0.41 mmol), sodium hydride (15 mg, 0.6 mmol), N-phenyl(trifluoromethylsulfon)imide (208 mg, 0.58 mmol), and propylamine (0.14 mL, 1.65 mmol) are treated according to method E yielding the title product.

$^1$H NMR ($CDCl_3$) δ 1.0 (t, 3H), 1.5 (s, 9H), 1.7 (m, 2H), 3.1 (m, 4H), 3.4 (q, 2H), 3.7 (m, 4H), 6.1 (s, 1H), 7.1 (dd, 1H), 7.6 (d, 1H), 7.7 (d, 1H).

Example 44

Preparation of 7-Chloro-4-[4-(4-fluorophenylaminocarbonyl)piperazin-1-yl]-2-(n-propylamino)quinoline 4-[4-(tert-Butoxycarbonyl)piperazin-1-yl]-7-chloro-2-(n-propylamino)quinoline (25 mg, 0.06 mmol) is deprotected with TFA in $CH_2Cl_2$ and transformed into the title product according to method C using 4-fluorophenyl isocyanate (10 μL, 0.09 mmol) and triethylamine (60 μL, 0.43 mmol) to give a colorless solid.

$^1$H NMR ($CDCl_3$) δ 1.0 (t, 3H), 1.8 (m, 2H), 3.2 (m, 4H), 3.4 (m, 2H), 3.8 (m, 4H), 6.1 (s, 1H), 6.4 (s, 1H), 7.0 (m, 2H), 7.1 (m, 1H), 7.3 (m, 2H), 7.65 (d, 1H),

Example 45

Preparation of 4-[4-(tert-Butoxycarbonyl)piperazin-1-yl]-7-chloro-2-(isopropylamino)-quinoline 4-[4-(tert-Butoxycarbonyl)piperazin-1-yl]-7-chloroquinol-2-one (150 mg, 0.41 mmol), sodium hydride (15 mg, 0.6 mmol), N-phenyl(trifluoromethylsulfon)imide (208 mg, 0.58 mmol), and isopropylamine (0.14 mL, 1.65 mmol) are treated according to method E yielding the title product.

$^1$H NMR ($CDCl_3$) δ 1.25 (d, 6H), 1.5 (s, 9H), 3.1 (m, 4H), 3.7 (m, 4H), 4.2 (m, 1H), 6.0 (s, 1H), 7.1 (dd, 1H), 7.6 (d, 1H), 7.7 (d, 1H).

Example 46

Preparation of 7-Chloro-4-[4-(4-fluorophenylaminocarbonyl)piperazin-1-yl]-2-(isopropylamino)quinoline 4-[4-(tert-Butoxycarbonyl)piperazin-1-yl]-7-chloro-2-(isopropylamino)quinoline (33 mg, 0.08 mmol) is deprotected with TFA in $CH_2Cl_2$ and transformed into the title product according to method C using 4-fluorophenyl isocyanate (13 μL, 0.11 mmol) and triethylamine (80 μL, 0.57 mmol) to give a colorless solid.

$^1$H NMR ($CDCl_3$) δ 1.2 (d, 6H), 3.2 (m, 4H), 3.8 (m, 4H), 4.2 (m, 1H), 4.6 (m, 1H), 6.0 (s, 1H), 6.4 (s, 1H), 7.0 (m, 2H), 7.1 (m, 1H), 7.3 (m, 2H), 7.6 (d, 1H), 7.7 (d, 1H).

Example 47

Preparation of 4-[4-(tert-Butoxycarbonyl)piperazin-1-yl]-2-(n-butylamino)-7-chloroquinoline 4-[4-(tert-Butoxycarbonyl)piperazin-1-yl]-7-chloroquinol-2-one (150 mg, 0.41 mmol), sodium hydride (15 mg, 0.6 mmol), N-phenyl(trifluoromethylsulfon)imide (208 mg, 0.58 mmol), and n-butylamine (0.16 mL, 1.65 mmol) are treated according to method E yielding the title product.

$^1$H NMR ($CDCl_3$) δ 1.0 (t, 3H), 1.45 (m, 2H), 1.5 (s, 9H), 3.1 (m, 4H), 3.4 (q, 2H), 3.7 (m, 4H), 6.0 (s, 1H), 7.1 (dd, 1H), 7.6 (d, 1H), 7.7 (d, 1H).

Example 48

Preparation of 2-n-Butylamino-7-chloro-4-[4-(4-fluorophenylaminocarbonyl)piperazin-1-yl]quinoline 4-[4-(tert-Butoxycarbonyl)piperazin-1-yl]-2-(n-butylamino)-7-chloroquinoline (47 mg, 0.11 mmol) is deprotected with TFA in $CH_2Cl_2$ and transformed into the title product according to method C using 4-fluorophenyl isocyanate (18 μL, 0.16 mmol) and triethylamine (110 μL, 0.79 mmol) to give a colorless solid.

$^1$H NMR ($CDCl_3$) δ 1.0 (t, 3H), 1.5 (m, 2H), 1.6 (m, 2H), 3.2 (m, 4H), 3.4 (m, 2H), 3.8 (m, 4H), 4.6 (m, 1H), 6.1 (s, 1H), 6.4 (s, 1H), 7.0 (m, 2H), 7.1 (m, 1H), 7.3 (m, 2H), 7.65 (d, 1H), 7.7 (d, 1H).

Example 49

Preparation of 4-[4-(tert-Butoxycarbonyl)piperazin-1-yl]-7-chloro-2-(n-pentylamino)quinoline 4-[4-(tert-Butoxycarbonyl)piperazin-1-yl]-7-chloroquinol-2-one (150 mg, 0.41 mmol), sodium hydride (15 mg, 0.6 mmol), N-phenyl(trifluoromethylsulfon)imide (208 mg, 0.58 mmol), and n-pentylamine (0.19 mL, 1.65 mmol) are treated according to method E yielding the title product.

$^1$H NMR (CDCl$_3$) δ 0.9 (t, 3H), 1.4 (m, 4H), 1.5 (s, 9H), 1.65 (m, 2H), 3.1 (m, 4H), 3.4 (q, 2H), 3.7 (m, 4H), 6.1 (s, 1H), 7.1 (dd, 1H), 7.6 (d, 1H), 7.7 (d, 1H).

Example 50

Preparation of 7-Chloro-4-[4-(4-fluorophenylaminocarbonyl)piperazin-1-yl]-2-(n-pentylamino)quinoline 4-[4-(tert-Butoxycarbonyl)piperazin-1-yl]-7-chloro-2-(n-pentylamino)quinoline (68 mg, 0.11 mmol) is deprotected with TFA in CH$_2$Cl$_2$ and transformed into the title product according to method C using 4-fluorophenyl isocyanate (18 μL, 0.16 mmol) and triethylamine (110 μL, 0.79 mmol) to give a colorless solid.

$^1$H NMR (CDCl$_3$) δ 0.9 (t, 3H), 1.4 (m, 4H), 1.7 (m, 2H), 3.2 (m, 4H), 3.4 (, 2H), 3.8 (m, 4H), 4.6 (m, 1H), 6.0 (s, 1H), 6.4 (s, 1H), 7.0 (m, 2H), 7.1 (m, 1H), 7.3 (m, 2H), 7.65 (d, 1H), 7.7 (d, 1H).

Example 51

Preparation of 7-Chloro-4-[4-(4-fluorophenylaminocarbonyl)piperazin-1-yl]-2-[2-(4-fluorophenyl)ethylamino]quinoline 4-[4-(tert-Butoxycarbonyl)piperazin-1-yl]-7-chloro-quinol-2-one (150 mg, 0.41 mmol), sodium hydride (15 mg, 0.6 mmol), N-phenyl(trifluoromethylsulfon)imide (208 mg, 0.58 mmol), and 4-fluorophenethylamine (0.22 mL, 1.65 mmol) are treated according to method E yielding 4-[4-(butoxycarbonyl)piperazin-1-yl]-7-chloro-2-[2-(4-fluorophenyl)ethylamino]quinoline, which is deprotected with TFA in CH$_2$Cl$_2$ and transformed into the title product according to method C using 4-fluorophenyl isocyanate (18 μL, 0.16 mmol) and triethylamine (110 μL, 0.79 mmol) to give a colorless solid.

$^1$H NMR (CDCl$_3$) δ 3.0 (t, 2H), 3.2 (m, 4H), 3.8 (m, 6H), 6.0 (s, 1H), 6.4 (s, 1H), 7.0 (m, 4H), 7.1 (m, 1H), 7.2 (m, 2H), 7.3 (m, 2H), 7.7 (m, 2H).

Example 52

Preparation of 7-Chloro-4-[4-(4-fluorophenylaminocarbonyl)-3-methylpiperazin-1-yl]quinoline Preparation of 7-Chloro-4-(3-methylpiperazin-1-yl)quinoline 4,7-Dichloroquinoline (0.5 g, 2.5 mmol) and 2-methylpiperazine (1.25 g, 12.5 mmol) are reacted according to method A yielding the product as a brown oil.

$^1$H NMR (CDCl$_3$) δ 1.55 (d, 3H), 2.52 (dd, 1H), 2.88 (td, 1H), 3.19 (m, 3H), 3.42 (m, 2H), 6.82 (d, 1H), 7.40 (dd, 1H), 7.93 (d, 1H), 8.02 (d, 1H), 8.69 (d, 1H).

Preparation of 7-Chloro-4-[4-(4-fluorophenylaminocarbonyl)-3-methylpiperazin-1-yl]quinoline 7-Chloro-4-(3-methylpiperazin-1-yl)quinoline (0.13 g, 0.5 mmol) and 4-fluorophenyl isocyanate (57 μL, 0.5 mmol) in CH$_2$Cl$_2$ (10 mL) are reacted according to method C yielding the title product after column chromatography with hexane-EtOAc.

$^1$H NMR ([D]$_6$-DMSO) δ 1.41 (d, 3H), 2.83 (m, 1H), 2.99 (m, 1H), 3.40 (m, 2H), 3.50 (m, 1H), 4.04 (m, 1H), 4.50 (m, 1H), 7.05 (m, 3H), 7.46 (m, 2H), 7.59 (dd, 1H), 7.98 (d, 1H), 8.11 (d, 1H), 8.60 (br. s, 1H), 8.71 (d, 1H).

Example 53

Preparation of 4-[4-(tert-Butoxycarbonyl)-2-methylpiperazin-1-yl]-7-chloroquinoline Sodium hydride (72 mg, 3 mmol) is added to a solution of 7-chloro-4-quinolone (359 mg, 2 mmol) in DMF. After 1 h at 40° C. N-phenyl(trifluoromethylsulfon)imide (1.0 g, 2.8 mmol) and, 1 h later, 1-tert-butoxycarbonyl-3-methylpiperazine (1.8 g, 8 mmol) is added. The reaction mixture is stirred at 80° C. for 2 days, concentrated, diluted with EtOAc, washed with water and brine, dried (Na$_2$SO$_4$), and concentrated. The residue is purified by reversed phase HPLC with water-MeCN-TFA to give the title product.

$^1$H NMR (CDCl$_3$) δ 1.0 (d, 3H), 1.5 (s, 9H), 2.9 (m, 1H), 3.3–3.8 (m, 6H), 6.9 (d, 1H), 7.5 (m, 1H), 8.1 (m, 2H), 8.8 (d, 1H).

Example 54

Preparation of 7-Chloro-4-[4-(4-fluorophenylaminocarbonyl)-2-methylpiperazin-1-yl]quinoline 4-[4-(tert-butoxycarbonyl)-2-methylpiperazin-1-yl]-7-chloroquinoline (0.30 g, 0.8 mmol) is deprotected with TFA in CH$_2$Cl$_2$ and transformed after being washed with base into the product according to method C using 4-fluorophenyl isocyanate (61 μL, 0.54 mmol) to give the title product a colorless solid.

$^1$H NMR (CDCl$_3$) δ 1.0 (d, 3H), 3.0 (m, 1H), 3.5 (m, 2H), 3.6–3.9 (m, 4H), 6.4 (s, 1H), 6.9 (d, 1H), 7.0 (m, 2H), 7.3 (m, 2H), 7.5 (m, 1H), 8.1 (m, 2H), 8.8 (d, 1

Example 55

Preparation of 7-Chloro-4-[3,5-dimethyl-4-(4-fluorophenylaminocarbonyl)piperazin-1-yl]quinoline Preparation of 7-Chloro-4-(3,5-dimethylpiperazin-1-yl)quinoline 4,7-Dichloroquinoline (0.40 g, 2.0 mmol) and. 2,6-dimethylpiperazine (0.57 g, 5.0 mmol) in n-butanol (20 mL) are reacted according to method B yielding the title product after column chromatography with CH$_2$Cl$_2$-MeOH.

$^1$H NMR (CDCl$_3$) δ 1.2 (d, 6H), 2.5 (t, 2H), 3.2 (m, 2H), 3.4 (d, 2H), 6.8 (d, 1H), 7.4 (d, 1H), 7.95 (d, 1H), 8.05 (s, 1H), 8.7 (d, 1H).

Preparation of 7-Chloro-4-[3,5-dimethyl-4-(4-fluorophenylaminocarbonyl)piperazin-1-yl]quinoline 7-Chloro-4-(3,5-dimethylpiperazin-1-yl)quinoline (100 mg, 0.36 mmol) and 4-fluorophenyl isocyanate (70 mg, 0.51 mmol) are reacted according to method C yielding the title product as colorless solid after column chromatography with CH$_2$Cl$_2$-MeOH.

$^1$H NMR ([D]$_6$-DMSO) δ 1.5 (d, 6H), 2.9 (m, 2H), 3.4 (m, 2H), 4.4 (m, 2H), 7.0 (m, 3H), 7.5 (m, 2H), 7.6 (dd, 1H), 8.0 (d, 1H), 8.2 (d, 1H), 8.4 (s, 1H), 8.7 (d, 1H).

Example 56

Preparation of 7-Chloro-4-[3,6-dimethyl-4-(4-fluorophenylaminocarbonyl)piperazin-1-yl]quinoline, trifluoroacetate Sodium hydride (72 mg, 3 mmol) is added to a solution of 7-chloro-4-quinolone (359 mg, 2 mmol) in DMF. After 1 h at 40° C. N-phenyl(trifluoromethylsulfon)imide (1.0 g, 2.8 mmol) and, 1 h later, 1-tert-butoxycarbonyl-2,5-dimethylpiperazine (1.8 g, 8 mmol) is added. The reaction mixture is stirred at 80° C. for 2 days, concentrated, diluted with EtOAc, washed with water and brine, dried (Na$_2$SO$_4$), and concentrated. The residue is purified by reversed phase HPLC with water-MeCN-TFA to give 4-[4-(tert-butoxycarbonyl)-2,5-dimethylpiperazin-1-yl]-7-chloroquinoline (188 mg, 0.5 mmol) which is deprotected with TFA in CH$_2$Cl$_2$ and transformed after being washed with base into the product with 4-fluorophenyl isocyanate (31 µL, 0.27 mmol) according to method C giving the title product as a colorless solid.
$^1$H NMR ([D]$_6$-DMSO) δ 1.1 (d, 3H), 1.3 (d, 3H), 3.6–3.8 (m, 3H), 4.1 (m, 1H), 4.5 (m, 2H), 7.0 (m, 2H), 7.3 (d, 1H), 7.4 (m, 2H), 7.7 (d, 1H), 8.0 (s, 1H), 8.2 (d, 1H), 8.6 (s, 1H), 8.7 (d, 1H).

Example 57

Preparation of 7-Chloro-4-[5-(4-fluorophenylaminocarbonyl)-2,5-diazanorbornan-2-yl]quinoline, trifluoroacetate Preparation of 7-Chloro-4-(2,5-diazanorborn-2-yl)quinoline 4,7-Dichloroquinoline (0.38 g, 1.9 mmol) and 2,5-diazanorbornane dihydrobromide (1.0 g, 3.8 mmol), and DABCO (1.3 g, 11.4 mmol) in n-butanol (20 mL) are reacted according to method B yielding the product after column chromatography with CH$_2$Cl$_2$-MeOH.
$^1$H NMR (CDCl$_3$) δ 2.0 (dd, 2H), 3.2 (dd, 1H), 3.4 (d, 2H), 3.9 (s, 1H), 4.1 (dd, 2H), 4.5 (s, 1H), 6.4 (d, 1H), 7.3 (d, 1H), 7.9 (s, 1H), 7.95 (d, 1H), 8.5 (d, 1H).

Preparation of 7-Chloro-4-[5-(4-fluorophenylaminocarbonyl)-2,5-diazanorbornan-2-yl]quinoline 7-Chloro-4-(2,5-diazanorborn-2-yl)quinoline (110 mg, 0.42 mmol) and 4-fluorophenyl isocyanate (67 µL, 0.59 mmol) are reacted according to method C yielding the title product as a colorless solid after column chromatography with CH$_2$Cl$_2$-MeOH.
$^1$H NMR (CD$_3$OD) δ 2.2 (m, 2H), 3.3 (s, 1H), 3.7–4.1 (m, 4H), 5.0 (s, 1H), 7.0 (m, 3H), 7.3 (m, 3H), 7.6 (d, 1H), 7.9 (s, 1H), 8.3 (d, 1H), 8.4 (m, 1H).

Example 58

Preparation of 7-Chloro-4-[4-(4-fluorophenylaminocarbonyl)-1,4-diazepin-1-yl]quinoline Synthesis analogous to example 1.
$^1$H NMR (CDCl$_3$) δ 2.25 (m, 2H), 3.45 (m, 2H), 3.50 (m, 2H), 3.80 (t, 2H), 3.90 (m, 2H), 6.30 (s, 1H), 6.85 (d, 1H), 7.00 (t, 2H), 7.35 (m, 2H), 7.42 (d, 1H), 8.00 (d, 1H), 8.05 (s, 1H), 8.70 (d, 1H).

Example 59

Preparation of 7-Chloro-4-[4-(3,4-difluorophenylaminocarbonyl)piperazin-1-yl]quinoline 7-Chloro-4-(piperazin-1-yl)quinoline (0.16 g, 0.65 mmol) and 3,4-difluorophenyl isocyanate (76 µL, 0.65 mmol) in THF (10 mL) are reacted according to method C yielding the title product as a colorless foam after column chromatography with hexane-EtOAc.
$^1$H NMR ([D]$_6$-DMSO) δ 3.18 (m, 4H), 3.72 (m, 4H), 7.04 (d, 1H), 7.22 (m, 1H), 7.29 (q, 1H), 7.56 (dd, 1H), 7.62 (ddd, 2H), 7.98 (d, 1H), 8.09 (d, 1H), 8.70 (d, 1H), 8.85 (br. s, 1H).

Example 60

Preparation of 7-Chloro-4-[4-(2,3,4-trifluorophenylaminocarbonyl)piperazin-1-yl]quinoline 7-Chloro-4-(piperazin-1-yl)quinoline (0.16 g, 0.65 mmol) and 2,3,4-difluorophenyl isocyanate (79 µL, 0.65 mmol) in THF (10 mL) are reacted according to method C yielding the title product as colorless solid after column chromatography with hexane-EtOAc.
$^1$H NMR ([D]$_6$-DMSO) δ 3.18 (m, 4H), 3.72 (m, 4H), 7.04 (d, 1H), 7.22 (m, 2H), 7.56 (dd, 1H), 7.98 (d, 1H), 8.09 (d, 1H), 8.68 (br. s, 1H), 8.72 (d, 1H).

Example 61

Preparation of 7-Chloro-4-[4-(phenylaminocarbonyl)piperazin-1-yl]quinoline

7-Chloro-4-(piperazin-1-yl)quinoline (62 mg, 0.25 mmol) and phenyl isocyanate (33 µL, 0.30 mmol) in THF (10 mL) are reacted according to method C yielding the title product as colorless needles after column chromatography with hexane-EtOAc.
$^1$H NMR ([D]$_6$-DMSO) δ 3.18 (m, 4H), 3.72 (m, 4H), 6.92 (t, 1H), 7.04 (d, 2H), 7.46 (d, 2H), 7.57 (dd, 1H), 7.98 (d, 1H), 8.10 (d, 1H), 8.64 (br. s, 1H 1H).

Example 62

Preparation of 7-Chloro-4-[4-(4-methylphenylaminocarbonyl)piperazin-1-yl]quinoline 7-Chloro-4-(piperazin-1-yl)quinoline (62 mg, 0.25 mmol) and p-tolyl isocyanate (32 µL, 0.25 mmol) in CH$_2$Cl$_2$ (5 mL) are reacted according to method C yielding the title product as a colorless solid.
$^1$H NMR ([D]$_6$-DMSO) δ 2.20 (s, 3H), 3.17 (m, 4H), 3.70 (m, 4H), 7.01 (d, 2H), 7.04 (d, 1H), 7.33 (d, 2H), 7.56 (dd, 1H), 7.98 (d, 1H), 8.08 (d, 1H), 8.53 (br. s, 1H), 8.7 (d, 1H).

Example 63

Preparation of 7-Chloro-4-[4-(3-methylphenylaminocarbonyl)piperazin-1-yl]quinoline 7-Chloro-4-(piperazin-1-yl)quinoline (62 mg, 0.25 mmol) and m-tolyl isocyanate (32 µL, 0.25 mmol) in CH$_2$Cl$_2$ (5 mL) are reacted according to method C yielding the title product as colorless solid.
$^1$H NMR ([D]$_6$-DMSO) δ 2.21 (s, 3H), 3.18 (m, 4H), 3.71 (m, 4H), 6.74 (d, 1H), 704 (d, 1H), 7.09 (t, 1H), 7.25 (d, 1H), 7.29 (d, 1H), 7.56 (dd, 1H), 7.98 (d, 1H), 8.09 (d, 1H), 8.56 (br. s, 1H), 8.71 (d, 1H).

Example 64

Preparation of 7-Chloro-4-[4-(2-methylphenylaminocarbonyl)piperazin-1-yl]quinoline 7-Chloro-4-(piperazin-1-yl)quinoline (62 mg, 0.25 mmol) and o-tolyl isocyanate (31 µL, 0.25 mmol) in CH$_2$Cl$_2$ (5 mL) are reacted according to method C yielding the title product as colorless solid.

$^1$H NMR ([D]$_6$-DMSO) δ 2.17 (s, 3H), 3.20 (m, 4H), 3.70 (m, 4H), 7.02 (td, 1H), 7.05 (d, 1H), 7.11 (td, 1H), 7.16 (dd, 1H), 7.18 (dd, 1H), 7.29 (d, 1H), 7.56 (dd, 1H), 7.98 (d, 1H), 8.09 (d, 1H), 8.18 (br. s, 1H), 8.71 (d, 1H).

Example 65

Preparation of 4-[4-(4-n-Butylphenylaminocarbonyl)piperazin-1-yl]-7-chloroquinoline 7-Chloro-4-(piperazin-1-yl)quinoline (62 mg, 0.25 mmol) and 4-(n-butyl)phenyl isocyanate (57 µL, 0.30 mmol) in THF (10 mL) are reacted according to method C yielding the title product as a colorless solid after column chromatography with hexane-EtOAc.

$^1$H NMR ([D]$_6$-DMSO) δ 0.88 (t, 3H), 1.25 (sext, 2H), 1.50 (pent, 2H), 2.50 (m, 2H), 3.17 (m, 4H), 3.71 (m, 4H), 7.03 (d, 2H), 7.04 (d, 1H), 7.34 (d, 2H), 7.56 (dd, 1H), 7.98 (d, 1H), 8.09 (d, 1H), 8.55 (br. s, 1H), 8.71 (d, 1H).

Example 66

Preparation of 7-Chloro-4-[4-(4-methoxyphenylaminocarbonyl)piperazin-1-yl]quinoline 7-Chloro-4-(piperazin-1-yl)quinoline (316 mg, 1.28 mmol) and 4-methoxyphenyl isocyanate (194 µL, 1.50 mmol) in THF (10 mL) are reacted according to method C yielding the title product as a colorless needles after column chromatography with hexane-EtOAc and recrystallization from ether.

$^1$H NMR ([D]$_6$-DMSO) δ 3.18 (m, 4H), 3.68 (s, 3H), 3.71 (m, 4H), 7.01 (d, 2H), 7.04 (d, 1H), 7.34 (d, 2H), 7.56 (dd, 1H), 7.98 (d, 1H), 8.09 (d, 1H), 8.48 (br. s, 1H), 8.71 (d, 1H).

Example 67

Preparation of 4-[4-(4-Benzyloxyphenylaminocarbonyl)piperazin-1-yl]-7-chloroquinoline 7-Chloro-4-(piperazin-1-yl)quinoline (62 mg, 0.25 mmol) and 4-benzyloxyphenyl isocyanate (68 mg, 0.30 mmol) in THF (10 mL) are reacted according to method C yielding the title product as a yellow solid after column chromatography with hexane-EtOAc.

$^1$H NMR ([D]$_6$-DMSO) δ 3.18 (m, 4H), 3.71 (m, 4H), 5.02 (s, 2H), 6.89 (d, 2H), 7.04 (d, 1H), 7.28–7.42 (m, 7H), 7.56 (dd, 1H), 7.98 (d, 1H), 8.08 (d, 1H), 8.49 (br. s, 1H), 8.71 (d, 1H).

Example 68

Preparation of 4-[4-(Benzylaminocarbonyl)piperazin-1-yl]-7-chloroquinoline

7-Chloro-4-(piperazin-1-yl)quinoline (62 mg, 0.25 mmol) and benzyl isocyanate (37 µL, 0.30 mmol) in THF (10 mL) are reacted according to method C yielding the title product as a colorless oil after column chromatography with hexane-EtOAc.

$^1$H NMR ([D]$_6$-DMSO) δ 3.12 (m, 4H), 3.60 (m, 4H), 4.26 (d, 2H), 7.02 (d, 1H), 7.16–7.32 (m, 6H), 7.55 (dd, 1H), 7.96 (d, 1H), 8.07 (d, 1H), 8.70 (d, 1H).

Example 69

Preparation of 7-Chloro-4-[4-(phenethylaminocarbonyl)piperazin-1-yl]quinoline

7-Chloro-4-(piperazin-1-yl)quinoline (62 mg, 0.25 mmol) and phenethyl isocyanate (45 µL, 0.30 mmol) in THF (10 mL) are reacted according to method C yielding the title product as a colorless oil after column chromatography with hexane-EtOAc.

$^1$H NMR ([D]$_6$-DMSO) δ 2.71 (t, 2H), 3.10 (m, 4H), 3.26 (q, 2H), 3.57 (m, 4H), 6.74 (t, 1H), 7.01 (d, 1H), 7.10–7.30 (m, 5H), 7.55 (dd, 1H), 7.97 (d, 1H), 8.06 (d, 1H), 8.70 (d, 1H).

Example 70

Preparation of 7-Chloro-4-[4-(phenylpropylaminocarbonyl)piperazin-1-yl]quinoline 3-Phenyl-1-propylamine (71 µL, 0.5 mmol), 4-nitrophenyl chloroformate (101 mg, 0.5 mmol), triethylamine (154 µL, 1.1 mmol), and 7-chloro-4-(piperazin-1-yl)quinoline (124 mg, 0.5 mmol) are treated according to method D delivering the title product as a colorless oil after column chromatography with hexane-EtOAc.

$^1$H NMR ([D]$_6$-DMSO) δ 1.72 (pent, 2H), 2.58 (t, 2H), 3.05 (q, 2H), 3.11 (m, 4H), 3.55 (m, 4H), 6.63 (t, 1H), 7.01 (d, 1H), 7.14 (t, 1H), 7.19 (d, 2H), 7.26 (t, 2H), 7.54 9dd, 1H), 7.97 (d, 1H), 8.06 (d, 1H), 8.70 (d, 1H).

Example 71

Preparation of 7-Chloro-4-[4-[[methoxycarbonyl(phenyl)methyl]aminocarbonyl]piperazin-1-yl]quinoline Phenylglycine methyl ester hydrochloride (606 mg, 3.0 mmol), 4-nitrophenyl chloroformate (606 mg, 3.0 mmol), triethylamine (1.84 mL, 13.2 mmol), and 7-chloro-4-(piperazin-1-yl)quinoline (743 mg, 3.0 mmol) are treated according to method D delivering the title product as a colorless solid after column chromatography with hexane-EtOAc.

$^1$H NMR ([D]$_6$-DMSO) δ 3.12 (m, 4H), 3.60 (s, 3H), 3.64 (m, 4H), 5.32 (d, 1H), 7.02 (d, 1H), 7.26 (d, 1H), 7.31–7.42 (m, 5H), 7.54 (dd, 1H), 7.96 (d, 1H), 8.06 (d, 1H), 8.69 (d, 1H).

Example 72

Preparation of 7-Chloro-4-[4-(1-phenylethylaminocarbonyl)piperazin-1-yl]quinoline 7-Chloro-4-(piperazin-1-yl)quinoline (62 mg, 0.25 mmol) and α-methylbenzyl isocyanate (42 µL, 0.30 mmol) in THF (10 mL) are reacted according to method C yielding the title product as a colorless solid after column chromatography with hexane-EtOAc.

¹H NMR ([D]₆-DMSO) δ 1.36 (d, 3H), 3.12 (m, 4H), 3.59 (m, 4H), 4.84 (pent, 1H), 6.92 (br. d, 1H), 7.02 (d, 1H), 7.16 (t, 1H), 7.28 (m, 4H), 7.54 (dd, 1H), 7.96 (d, 1H), 8.06 (d, 1H), 8.70 (d, 1H).

Example 73

Preparation of 7-Chloro-4-[4-(2-chlorobenzylaminocarbonyl)piperazin-1-yl]quinoline 2-Chlorobenzylamine (60 μL, 0.5 mmol), 4-nitrophenyl chloroformate (101 mg, 0.5 mmol), triethylamine (238 μL, 1.7 mmol), and 7-chloro-4-(piperazin-1-yl)quinoline (124 mg, 0.5 mmol) are treated according to method D delivering 147 mg of the product as a pale yellow solid after column chromatography with hexane-EtOAc.

¹H NMR (CDCl₃) δ 3.19 (m, 4H), 3.65 (m, 4H), 4.55 (d, 2H), 5.07 (t, 1H), 6.82 (d, 1H), 7.24 (m, 2H), 7.36 (m, 1H), 7.44 (m, 2H), 7.92 (d, 1H), 8.04 (d, 1H), 8.72 (d, 1H).

Example 74

Preparation of 7-Chloro-4-[4-(2-methylbenzylaminocarbonyl)piperazin-1-yl]quinoline 2-Methylbenzylamine (62 μL, 0.5 mmol), 4-nitrophenyl chloroformate (101 mg, 0.5 mmol), triethylamine (238 μL, 1.7 mmol), and 7-chloro-4-(piperazin-1-yl)quinoline (124 mg, 0.5 mmol) are treated according to method D delivering the title product as a pale yellow solid after column chromatography with hexane-EtOAc.

¹H NMR (CDCl₃), δ 3.20 (m, 4H), 3.66 (m, 4H), 4.46 (d, 2H), 4.60 (t, 1H), 6.83 (d, 1H), 7.19 (m, 3H), 7.28 (m, 1H), 7.44 (dd, 1H), 7.94 (d, 1H), 8.05 (d, 1H), 8.73 (d, 1H).

Example 75

Preparation of 7-Chloro-4-[4-(2-trifluoromethylbenzylaminocarbonyl)piperazin-1-yl]quinolin 2-Trifluoromethylbenzylamine (70 μL, 0.5 mmol), 4-nitrophenyl chloroformate (101 mg, 0.5 mmol), triethylamine (238 μL, 1.7 mmol), and 7-chloro-4-(piperazin-1-yl)quinoline (124 mg, 0.5 mmol) are treated according to method D delivering the title product as a pale yellow solid after column chromatography with hexane-EtOAc.

¹H NMR (CDCl₃) δ 3.20 (m, 4H), 3.66 (m, 4H), 4.64 (d, 2H), 4.86 (t, 1H), 6.92 (d, 1H) 7.38 (t, 1H), 7.43 (dd, 1H), 7.54 (t, 1H), 7.62 (d, 1H), 7.64 (d, 1H), 7.92 (d, 1H), 8.04 (d, 1H), 8.72 (d, 1H).

Example 76

Preparation of 7-Chloro-4-[4-(1-indanylaminocarbonyl)piperazin-1-yl]quinoline

2-Aminoindane (32 μL, 0.25 mmol), 4-nitrophenyl chloroformate (51 mg, 0.25 mmol), triethylamine (140 μL, 1.0 mmol), and 7-chloro-4-(piperazin-1-yl)quinoline (62 mg, 0.25 mmol) are treated according to method D delivering the title product as a colorless solid after column chromatography with hexane-EtOAc.

¹H NMR (CDCl₃) δ 1.85 (m, 1H), 2.67 (m, 1H), 2.90 (m, 1H), 3.00 (m, 1H), 3.22 (m, 4H), 3.67 (m, 4H), 4.72 (d, 1H), 5.45 (q, 1H), 6.84 (d, 1H), 7.23 (m, 3H), 7.34 (d, 1H), 7.44 (dd, 1H), 7.94 (d, 1H), 8.05 (d, 1H), 8.73 (d, 1H).

Example 77

Preparation of 7-Chloro-4-[4-(1,2,3,4-tetrahydronaphth-1-ylaminocarbonyl)piperazin-1-yl]quinoline 1,2,3,4-Tetrahydronaphthylamine (36 μL, 0.25 mmol), 4-nitrophenyl chloroformate (51 mg, 0.25 mmol), triethylamine (140 μL, 1.0 mmol), and 7-chloro-4-(piperazin-1-yl) quinoline (62 mg, 0.25 mmol) are treated according to method D delivering the title product as a colorless oil after column chromatography with hexane-EtOAc.

¹H NMR (CDCl₃) δ 1.88 (m, 3H), 2.08 (m, 1H), 2.80 (m, 2H), 3.20 (m, 4H), 3.66 (m, 4H), 4.72 (d, 1H), 5.12 (m, 1H), 6.84 (d, 1H), 7.10 (dd, 1H), 7.18 (d, 1H), 7.20 (d, 1H), 7.34 (dd, 1H), 7.44 (dd, 1H), 7.92 (d, 1H), 8.04 (d, 1H), 8.72 (d, 1H).

Example 78

Preparation of 7-Chloro-4-[4-(4-pyridinylaminocarbonyl)piperazin-1-yl]quinoline

At 0° C. under nitrogen, to a solution of 4-aminopyridine (114 mg, 1.21 mmol) and 4-nitrophenyl chloroformate (244 mg, 1.21 mmol) in dichloromethane (5 mL) is added diisopropyl(ethyl)amine dropwise (391 mg, 3.03 mmol). After 10 min, the ice bath is removed, and the reaction mixture is stirred at rt. for an additional hour. After removal of solvent under vacuum, EtOAc (5 mL), diisopropyl(ethyl)amine (261 mg, 2.02 mmol) and 7-chloro-4-(piperazin-1-yl)quinoline (250 mg, 1.01 mmol) are added. The resulting mixture is kept at reflux for about 5 hr, then cooled to rt, diluted with EtOAc (10 mL), and quenched with saturated sodium bicarbonate (5 mL). The aqueous solution is extracted with EtOAc (2×10 mL), and the combined organic phase is washed with brine (10 mL) and dried over sodium sulfate. Removal of solvent followed by purification through flash chromatography with CH₂Cl₂-MeOH affords the title product.

¹H NMR (CDCl₃) δ 8.61 (d, 2H), 8.32 (d, 2H), 7.98 (s, 1H), 7.86 (d, 1H), 7.8 (d, 2H), 7.74 (d, 1H), 3.79 (br. s, 4H), 3.12 (br. s, 4H).

Example 79

Preparation of 7-Chloro-4-[4-(3-pyridinylaminocarbonyl)piperazin-1-yl]quinoline

As described for example 78, 3-aminopyridine (114 mg, 1.21 mmol), 4-nitrophenyl chloroformate (244 mg, 1.21 mmol), diisopropyl(ethyl)amine (650 mg, 5.05 mmol), and 7-chloro-4-(piperazin-1-yl)quinoline (250 mg, 1.01 mmol) are reacted affording the title product after flash chromatography with CH₂Cl₂-MeOH.

¹H NMR (DSMO-d₆/TFA) δ 9.64 (s, 1H), 9.13 (s, 1H), 8.69 (d, 1H), 8.46–8.53 (m, 2H), 8.25 (d, 1H), 8.07 (d, 1H), 7.95 (dd, 1H), 7.68 (dd, 1H), 7.19 (d, 1H), 4.02 (m, 4H), 3.81 (m, 4H).

Example 80

Preparation of 7-Chloro-4-[4-(2-pyridinylaminocarbonyl)piperazin-1-yl]quinoline

As described for example 78, 2-aminopyridine (142 mg, 1.51 mmol), 4-nitrophenyl chloroformate (304 mg, 1.51 mmol), diisopropyl(ethyl)amine (650 mg, 5.05 mmol), and 7-chloro-4-(piperazin-1-yl)quinoline (250 mg, 1.01 mmol) are reacted affording the title product after flash chromatography with CH$_2$Cl$_2$-MeOH.

$^1$H NMR (DSMO-d$_6$/TFA) δ 8.62 (d, 1H), 8.18 (m, 2H), 7.96 (s, 1H), 7.83 (d, 1H), 7.38 (d, 1H), 7.22 (d, 1H), 6.78 (d, 1H), 3.91 (m, 2H), 3.82 (m, 2H), 3.2 (m, 4H).

Example 81

Preparation of 7-Chloro-4-[4-(4-trifluoromethylphenylaminocarbonyl)piperazin-1-yl]quinoline At room temp. under nitrogen, to a solution of 7-chloro-4-(piperazin-1-yl)quinoline (200 mg, 0.81 mmol) and diisopropyl(ethyl)amine (209 mg, 1.62 mmol) in acetonitrile (5 mL) is added 4-trifluoromethylphenyl isocyanate (197 mg, 0.97 mmol). The reaction mixture is stirred at room temp. for 2 h, concentrated, and the residue is purified by flash chromatography with CH$_2$Cl$_2$-MeOH to afford the title product.

$^1$H NMR (DSMO-d$_6$/TFA) δ 9.65 (s, 1H), 8.83 (d, 1H), 8.32 (d, 1H), 8.01 (d, 1H), 7.53–7.74 (m, 4H), 7.07 (d, 1H), 4.16 (m, 8H).

Example 82

Preparation of 7-Chloro-4-[4-(4-ethoxyphenylaminocarbonyl)piperazin-1-yl]quinoline As described for 7-chloro-4-[4-(4-trifluoromethylphenylaminocarbonyl)piperazin-1-yl]quinoline, 7-chloro-4-(piperazin-1-yl)quinoline (150 mg, 0.61 mmol), diisopropyl(ethyl)amine (158 mg, 1.22 mmol), and 4-ethoxyphenyl isocyanate (119 mg, 0.73 mmol) are reacted to give the title product after flash chromatography with CH$_2$Cl$_2$-MeOH.

$^1$H NMR (DSMO-d$_6$/TFA) δ 8.65 (d, 1H), 8.46 (s, 1H), 8.42 (d, 1H), 7.98 (d, 1H), 7.67 (dd, 1H), 7.26–7.35 (m, 3H), 7.16 (d, 1H), 6.81 (m, 3H), 3.97 (m, 6H), 3.76 (m, 4H), 1.24 (t, 3H);

Example 83

Preparation of 7-Chloro-4-[4-(4-isopropylphenylaminocarbonyl)piperazin-1-yl]quinoline As described for 7-chloro-4-[4-(4-trifluoromethylphenylaminocarbonyl)piperazin-1-yl]quinoline, 7-chloro-4-(piperazin-1-yl)quinoline (150 mg, 0.61 mmol), diisopropyl(ethyl)amine (158 mg, 1.22 mmol), and 4-isopropylphenyl isocyanate (117 mg, 0.73 mmol) are reacted to give the title product after flash chromatography with CH$_2$Cl$_2$-MeOH.

$^1$H NMR (DSMO-d$_6$/TFA) δ 8.65 (d, 1H), 8.58 (s, 1H), 8.23 (d, 1H), 7.66 (d, 1H), 7.37 (d, 2H), 7.18 (d, 1H), 7.06 (d, 2H), 3.92 (m, 4H), 3.76 (m, 4H), 2.77 (m, 1H), 1.18 (d, 6H).

Example 84

Preparation of 4-[4-(4-Acetylphenylaminocarbonyl)piperazin-1-yl]-7-chloroquinoline As described for 7-chloro-4-[4-(4-trifluoromethylphenylaminocarbonyl)piperazin-1-yl]quinoline, 7-chloro-4-(piperazin-1-yl)quinoline (250 mg, 1.01 mmol), diisopropyl(ethyl)amine (261 mg, 2.02 mmol), and 4-acetylphenyl isocyanate (195 mg, 1.21 mmol) are reacted to give the title product after flash chromatography with CH$_2$Cl$_2$-MeOH.

$^1$H NMR (DSMO-d$_6$/TFA), δ 9.07 (s, 1H), 8.69 (d, 1H), 8.23 (d, 1H), 8.02 (s, 1H), 7.83 (d, 2H), 7.65 (d, 1H), 7.61 (m, 2H), 7.19 (d, 1H), 3.99 (m, 4H), 3.78 (m, 4H), 2.5 (s, 3H).

Example 85

Preparation of 7-Chloro-4-[4-(4-dimethylaminophenylaminocarbonyl)piperazin-1-yl]quinoline As described for 7-chloro-4-[4-(4-trifluoromethylphenylaminocarbonyl)piperazin-1-yl]quinoline, 7-chloro-4-(piperazin-1-yl)quinoline (200 mg, 0.81 mmol), diisopropyl(ethyl)amine (209 mg, 1.62 mmol), and 4-(dimethylamino)phenyl isocyanate (157 mg, 0.97 mmol) are reacted to give the title product after flash chromatography with CH$_2$Cl$_2$-MeOH.

$^1$H NMR (DSMO-d$_6$/TFA) δ 9.64 (s, 1H), 9.12 (s, 1H), 8.68 (d, 1H), 8.52 (m, 2H), 8.24 (d, 1H), 8.03 (d, 1H), 7.94 (dd, 1H), 7.69 (dd, 1H), 7.18 (d, 1H), 4.02 (m, 4H), 3.82 (m, 4H) 2.42 (s, 6H).

Example 86

Preparation of 7-Chloro-4-[4-(cyclopentylaminocarbonyl)piperazin-1-yl]quinoline

As described for 7-chloro-4-[4-(4-trifluoromethylphenylaminocarbonyl)piperazin-1-yl]quinoline, 7-chloro-4-(piperazin-1-yl)quinoline (180 mg, 0.73 mmol), diisopropyl(ethyl)amine (189 mg, 1.46 mmol), and cyclopentyl isocyanate (97 mg, 0.88 mmol) are reacted to give the title product after flash chromatography with CH$_2$Cl$_2$-MeOH.

$^1$H NMR (DSMO-d$_6$/TFA) 68.62 (d, 1H), 8.21 (d, 1H), 7.98 (s, 1H), 7.64 (d, 1H), 7.17 (d, 1H), 3.86 (m, 5H), 3.58 (m, 4H), 1.78 (m, 2H), 1.62 (m, 2H), 1.32–1.56 (m, 4H).

Example 87

Preparation of 7-Chloro-4-[4-(3-piperonylaminocarbonyl)piperazin-1-yl]quinoline

As described for 7-chloro-4-[4-(4-trifluoromethylphenylaminocarbonyl)piperazin-1-yl]quinoline, 7-chloro-4-(piperazin-1-yl)quinoline (180 mg, 0.73 mmol), diisopropyl(ethyl)amine (189 mg, 1.46 mmol), and 3,4-(methylenedioxy)phenyl isocyanate (143 mg, 0.88 mmol) are reacted to give the product after flash chromatography with CH$_2$Cl$_2$-MeOH.

$^1$H NMR (DSMO-d$_6$/TFA) δ 8.64 (d, 1H), 8.42 (s, 1H), 8.21 (d, 1H), 7.95 (d, 1H), 7.66 (dd, 1H), 7.15 (dd, 1H), 7.07 (d, 1H), 6.74 (d, 1H), 5.83 (S, 2H), 4.41 (m, 4), 4.2 (m, 4H).

Example 88

Preparation of 7-Chloro-4-[4-[4-(6-methylbenzothiazol-2-yl)phenylaminocarbonyl]piperazin-1-yl]quinoline As described for 7-chloro-4-[4-(4-trifluoromethylphenylaminocarbonyl)piperazin-1-yl]quinoline, 7-chloro-4-(piperazin-1-yl)quinoline (120 mg, 0.49 mmol), diisopropyl(ethyl)amine (127 mg, 0.98 mmol), and 4-(6-methyl-2- benzothiazolyl)phenyl isocyanate (100 mg, 0.38 mmol) are reacted to give the title product after flash chromatography with CH$_2$Cl$_2$-MeOH.

$^1$H NMR (DSMO-d$_6$/TFA) δ 8.97 (s, 1H), 8.62 (d, 1H), 8.23 (d, 1H), 7.96 (d, 1H), 7.92 (d, 2H), 7.8 (m, 2H), 7.64–7.71 (m, 3H), 7.25 (dd, 1H), 7.16 (d, 1H), 3.96 (m, 4H), 3.79 (m, 4H), 2.38 (s, 3H).

Example 89

Preparation of 7-Chloro-4-[4-(cyclobutylaminocarbonyl)piperazin-1-yl]quinoline

As described for example 78, cyclobutylamine (87 mg, 1.21 mmol), 4-nitrophenyl chloroformate (244 mg, 1.21 mmol), diisopropyl(ethyl)amine (2×261 mg, 2×2.02 mmol), and 7-chloro-4-(piperazin-1-yl)quinoline (250 mg, 1.01 mmol) are reacted affording the title product after flash chromatography with CH$_2$Cl$_2$-MeOH.

$^1$H NMR (DSMO-d$_6$/TFA) δ 8.65 (d, 1H), 8.04 (d, 1H), 7.94 (s, 1H), 7.57 (d, 1H), 7.0 (d, 1H), 6.77 (d, 1H), 4.12 (m, 1H), 3.58 (m, 4H), 3.09 (m, 4H), 2.11 (m, 2H), 1.95 (m, 2H), 1.52 (m, 2H).

Example 90

Preparation of 7-Chloro-4-[4-(cyclohexylaminocarbonyl)piperazin-1-yl]quinoline

As described for 7-chloro-4-[4-(4-trifluoromethylphenylaminocarbonyl)piperazin-1-yl]quinoline, 7-chloro-4-(piperazin-1-yl)quinoline (200 mg, 0.81 mmol), diisopropyl(ethyl)amine (125 mg, 0.97 mmol), and cyclohexyl isocyanate (121 mg, 0.97 mmol) are reacted to give the title product after flash chromatography with CH$_2$Cl$_2$-MeOH.

$^1$H NMR (DSMO-d$_6$/TFA) 68.62 (d, 1H), 8.21 (d, 1H), 7.96 (s, 1H), 7.63 (d, 1H), 7.16 (d, 1H), 3.92 (m, 4H), 3.61 (m, 4H), 3.41 (m, 1H), 1.4–1.8 (m, 4H), 1.0–1.3 (m, 6H).

Example 91

Preparation of 4-[4-(Adamant-1-ylaminocarbonyl)piperazin-1-yl]-7-chloroquinoline 7-Chloro-4-(piperazin-1-yl)quinoline (124 mg, 0.5 mmol) and 1-adamantyl isocyanate (89 mg, 0.5 mmol) in CH$_2$Cl$_2$ (5 mL) are reacted according to method C yielding the title product as a colorless solid after column chromatography with hexane-EtOAc.

$^1$H NMR ([D]$_6$-DMSO) δ 1.59 (m, 6H), 1.91 (m, 6H), 1.97 (m, 3H), 3.08 (m, 4H), 3.50 (m, 4H), 5.78 (br. s, 1H), 7.00 (d, 1H), 7.53 (dd, 1H), 7.96 (d, 1H), 8.04 (d, 1H), 8.68 (d, 1H).

Example 92

Preparation of 7-Chloro-4-[4-(exo-norborn-2-ylaminocarbonyl)piperazin-1-yl]quinoline exo-2-Aminonorbornane (59 μL, 0.5 mmol), 4-nitrophenyl chloroformate (101 mg, 0.5 mmol), triethylamine (140 μL, 1.0 mmol), and 7-chloro-4-(piperazin-1-yl)quinoline (124 mg, 0.5 mmol) are treated according to method D delivering the title product as a colorless foam after column chromatography with hexane-EtOAc.

$^1$H NMR ([D]$_6$-DMSO) δ 1.05 (m, 3H), 1.37 (m, 3H), 1.50 (m, 2H), 2.07 (m, 1H), 2.15 (m, 1H), 3.10 (m, 4H), 3.42 (m, 1H), 3.57 (m, 4H), 6.33 (d, 1H), 7.00 (d, 1H), 7.54 dd, 1H), 7.96 (d, 1H), 8.05 (d, 1H), 8.68 (d, 1H).

Example 93

Preparation of 7-Chloro-4-[4-(4-fluorophenylsulfonyl)piperazin-1-yl]quinoline

7-Chloro-4-(piperazin-1-yl)quinoline (0.25 g, 1.0 mmol), 4-fluorobenzenesulfonyl chloride (0.23 g, 1.2 mmol), and triethylamine (349 μL, 2.5 mmol) are stirred at room temp. for 15 h. The reaction mixture is diluted with EtOAc, washed with water, dried (MgSO$_4$), and concentrated. The residue is purified by column chromatography with hexane-EtOAc yielding the title product as a colorless solid.

$^1$H NMR (CDCl$_3$) δ 3.31 (m, 8H), 6.84 (d, 1H), 7.28 (dd, 2H), 7.37 (dd, 1H), 7.75 (d, 1H), 7.85 (dd, 2H), 8.03 (d, 1H), 8.73 (d, 1H).

Example 94

7-Chloro-4-[4-(4-fluorophenylaminothiocarbonyl)piperazin-1-yl]quinoline

7-Chloro-4-(piperazin-1-yl)quinoline (0.20 g, 0.8 mmol) and 4-fluorophenyl isothiocyanate (0.14 g, 0.9 mmol) in THF (10 mL) are reacted according to method C yielding the title product as a solid after column chromatography with hexane-EtOAc.

$^1$H NMR ([D]$_6$-DMSO) δ 3.29 (m, 4H), 4.18 (m, 4H), 7.04 (d, 1H), 7.12 (t, 2H), 7.30 (m, 2H), 7.56 (dd, 1H), 7.98 (d, 1H), 8.13 (d, 1H), 8.72 (d, 1H), 9.44 (s, 1H).

Example 95

7-Chloro-4-[4-[cyanimino(phenoxy)methyl]piperazin-1-yl]quinoline

7-Chloro-4-(piperazin-1-yl)quinoline (798 mg, 3.22 mmol) and diphenyl cyanocarbonimidate (853 mg, 3.58 mmol) in THF (10 mL) are stirred at room temp. for 15 h. The reaction mixture is diluted with ether, and the precipitate is filtered off to yield the title product as a colorless solid.

$^1$H NMR (CDCl$_3$), δ 3.29 (m, 4H), 4.02 (m, 4H), 6.87 (d, 1H), 7.12 (d, 2H), 7.12 (t, 1H), 7.42 (t, 2H), 7.46 (dd, 1H), 7.91 (d, 1H), 8.06 (d, 1H), 8.76 (d, 1H).

Example 96

Preparation of 7-Chloro-4-[4-[cyanimino(ethoxy)methyl]piperazin-1-yl]quinoline

7-Chloro-4-[4-(cyanimino(phenoxy)methyl)piperazin-1-yl]quinoline (196 mg, 0.5 mmol) and potassium tert-butoxide (62 mg, 0.55 mmol) in EtOH (5 mL) are stirred at room temp. for 4 h. The reaction mixture is concentrated, and the residue purified by column chromatography delivering the title product.

$^1$H NMR (CDCl$_3$) δ 1.38 (t, 3H), 3.23 (m, 4H), 3.98 (m, 4H), 4.50 (q, 2H), 6.83 (d, 1H), 7.45 (dd, 2H), 7.89 (d, 1H), 8.05 (d, 1H), 8.74 (d, 1H).

Example 97

Preparation of 7-Chloro-4-[4-(cyanimino(4-fluorophenylamino)methyl)piperazin-1-yl]quinoline Diphenyl cyanocarbonimidate (0.24 g, 1.0 mmol) and 4-fluoroaniline (104 4μL, 1.1 mmol) are stirred in isopropanol (10 mL) for 15 h. The reaction mixture is concentrated, and the residue dissolved in EtOAc. Washing with sat NaHCO$_3$, drying (MgSO$_4$) and removing the solvent delivers 0.34 g of N-cyano-N'-(4-fluorophenyl)-O-phenylisourea as a colorless solid. It is dissolved in pyridine (15 mL) and 7-chloro-4-(piperazin-1-yl)quinoline (0.25 g, 1.0 mmol) is added. The reaction mixture is heated at reflux for 4 h and afterwards concentrated. Column chromatography of the residue with hexane-EtOAc gives the title product as a colorless solid.

$^1$H NMR ([D]$_6$-DMSO) δ 3.23 (m, 4H), 3.76 (m, 4H), 7.02 (d, 1H), 7.16 (m, 4H), 7.56 (dd, 1H), 7.98 (d, 1H), 8.07 (d, 1H), 8.72 (d, 1H), 9.45 (br. s, 1H).

Example 98

Preparation of 7-Chloro-4-[4-(cyanimino(4-fluorobenzylamino)methyl)piperazin-1-yl]quinoline 7-Chloro-4-[4-(cyanimino(phenoxy)methyl)piperazin-1-yl]quinoline (107 mg, 0.27 mmol) and 4-fluorobenzylamine (62 μL, 0.54 mmol) are heated in pyridine (10 mL) for 3 h at reflux. The solvent is removed, and the residue purified by column chromatography with CH$_2$Cl$_2$-MeOH giving the title product as a colorless solid.

$^1$H NMR (CDCl$_3$) δ 3.25 (m, 4H), 3.77 (m, 4H), 4.57 (d, 2H), 5.31 (t, 1H), 6.83 (d, 1H), 7.04 (t, 2H), 7.30 (dd, 2H), 7.44 (dd, 1H), 7.88 (d, 1H), 8.05 (d, 1H), 8.73 (d, 1H).

Example 99

Preparation of 4-[4-(tert-Butylamino(cyanimino)methyl)piperazin-1-yl]-7-chloroquinoline 7-Chloro-4-[4-(cyanimino(phenoxy)methyl)piperazin-1-yl]quinoline (53 mg, 0.14 mmol) and tert-butylamine (2.0 mL, 19 mmol) are heated in pyridine (10 mL) for 6 h at reflux. The solvent is removed, and the residue purified by column chromatography with CH$_2$Cl$_2$-MeOH giving the title product as a colorless solid.

$^1$H NMR (CDCl$_3$) δ 1.25 (s, 9H), 2.78 (m, 4H), 4.02 (m, 4H), 6.23 (d, 1H), 7.27 (dd, 2H), 7.80 (d, 1H), 8.53 (d, 1H), 8.69 (d, 1H).

Example 100

Preparation of 7-Chloro-4-[4-[cyanimino(ethylamino)methyl]piperazin-1-yl]quinoline 7-Chloro-4-[4-(cyanimino(phenoxy)methyl)piperazin-1-yl]quinoline (0.39 g, 1.0 mmol), ethylamine hydrochloride (1.68 g, 20.6 mmol), and diaza[2.2.2]bicyclooctane (2.24 g, 20.0 mmol) in isopropanol (20 mL) are heated in a sealed tube for 4 h at 110° C. The reaction mixture is concentrated, and the residue is suspended in EtOAc. Washing with water, drying (MgSO$_4$), and removing the solvent leads to a colorless solid, which is washed with hot ether to yield the title product.

$^1$H NMR ([D]$_6$-DMSO) δ 1.13 (t, 3H), 3.20 (m, 4H), 3.35 (m, 2H), 3.68 (m, 4H), 7.01 (d, 1H), 7.39 (br. t, 1H), 7.55 (dd, 1H), 7.97 (d, 1H), 8.06 (d, 1H), 8.70 (d, 1H).

Example 101

Preparation of 7-Chloro-4-[4-[4-(4-fluorophenylamino]-2,3-dioxocyclobut-1-enyl]piperazin-1-yl]quinoline 4-(4-Fluorophenylamino)-1-methoxy-2,3-dioxocyclobut-1-ene Dimethyl squarate (142 mg, 1.0 mmol) and 4-fluoroaniline (104 μL, 1.1 mmol) in isopropanol (10 mL) are stirred for 60 h at room temp. The reaction mixture is diluted with EtOAc, washed with water, dried (MgSO$_4$), and concentrated giving the desired product.

$^1$H NMR ([D]$_6$-DMSO) δ 4.36 (s, 3H), 7.18 (t, 2H), 7.28 (br. m, 1H).

7-Chloro-4-[4-[4-(4-fluorophenylamino)-2,3-dioxocyclobut-1-enyl]piperazin-1-yl]quinoline 7-Chloro-4-(piperazin-1-yl)quinoline (247 mg, 1.0 mmol) and 4-(4-fluorophenylamino)-1-methoxy-2,3-dioxocyclobut-1-ene (218 mg, 1.0 mmol) in pyridine (20 mL) are heated at reflux for 4 h. The reaction mixture is concentrated, and the residue purified by column chromatography with CH$_2$Cl$_2$-MeOH and recrystallization from ether yielding the title product as a yellow solid.

$^1$H NMR ([D]$_6$-DMSO) δ 3.31 (m, 4H), 4.03 (m, 4H), 7.06 (d, 1H), 7.15 (t, 2H), 7.24 (dd, 2H), 7.57 (dd, 1H), 7.99 (d, 1H), 8.10 (d, 1H), 8.73 (d, 1H).

Example 102

Preparation of 4-[4-(Benzimidazol-2-yl)piperazin-1-yl]-7-chloroquinoline

7-Chloro-4-(piperazin-1-yl)quinoline (247 mg, 1.0 mmol) and 2-chlorobenzimidazole (46 mg, 0.3 mmol) are heated at 150° C. for 1 h. The mixture is dissolved in EtOAc-water. The organic layer is separated, dried (MgSO$_4$), and concentrated. Column chromatography of the residue with hexane-EtOAc furnishes the title product as colorless solid.

$^1$H NMR ([D]$_6$-DMSO) δ 3.30 (m, 4H), 3.78 (m, 4H), 6.88 (t, 1H), 6.94 (t, 1H), 7.07 (d, 1H), 7.17 (d, 1H), 7.22 (d, 1H), 7.58 (dd, 1H), 7.98 (d, 1H), 8.12 (d, 1H), 8.71 (d, 1H).

Example 103

Preparation of 7-Chloro-4-[4-(pyrimidin-2-yl)piperazin-1-yl]-7-chloroquinoline 4,7-Dichloroquinoline (0.10 g, 0.5 mmol) and 1-(pyrimidin-2-yl)piperazine (0.33 g, 2.0 mmol) are heated at 150° C. for 2.5 h. The mixture is dissolved in EtOAc-water. The organic layer is separated, dried (MgSO$_4$), and concentrated. Column chromatography of the residue with hexane-EtOAc furnishes the title product as a colorless solid.

$^1$H NMR ([D]$_6$-DMSO) δ 3.23 (m, 4H), 4.00 (m, 4H), 6.66 (t, 1H), 7.03 (d, 1H), 7.57 (dd, 1H), 7.98 (d, 1H), 8.12 (d, 1H), 8.38 (d, 2H), 8.70 (d, 1H).

Example 104

Preparation of 7-Chloro-4-[4-[ethoxyimino(4-fluorophenylamino)methyl]piperazin-1-yl]quinoline Preparation of N-Ethoxy-N'-(4-fluorophenyl)thiourea 4-Fluorophenyl isothiocyanate (306 mg, 2.0 mmol), O-ethyl hydroxylamine hydrochloride (585 mg, 6.0 mmol), and triethylamine (1.5 mL, 11.0 mmol) are stirred in $CH_2Cl_2$ (50 mL) for 2 h. The reaction mixture is diluted with ether, washed with water and 1 M HCl, dried ($MgSO_4$), and concentrated. The residue is purified by column chromatography with hexane-EtOAc yielding a colorless solid.

$^1$H NMR ($CDCl_3$) δ 1.15 (t, 3H), 4.05 (q, 2H), 7.06 (dd, 2H), 7.51 (dd, 2H), 8.41 (br. s, 1H).

Preparation of 7-Chloro-4-[4-(ethoxyimino(4-fluorophenylamino)methyl)piperazin-1-yl]quinoline 7-Chloro-4-(piperazin-1-yl)quinoline (124 mg, 0.5 mmol), N-ethoxy-N'-(4-fluorophenyl)thiourea (105 mg, 0.49 mmol), and sodium periodate (118 mg, 0.55 mmol) in DMF-water 1:1 (20 mL) are heated at 85° C. for 1 h. The reaction mixture is diluted with water and extracted with ether. The organic phase is dried ($MgSO_4$) and concentrated. The residue is purified by column chromatography with hexane-EtOAc yielding the title product as pale yellow crystals.

$^1$H NMR ($CDCl_3$) δ 1.29 (t, 3H), 3.17 (m, 4H), 3.31 (m, 4H), 4.03 (q, 2H), 6.58 (br. s, 1H), 6.79 (d, 1H), 6.96 (t, 2H), 7.15 (dd, 2H), 7.39 (dd, 1H), 7.89 (d, 1H), 8.01 (d, 1H), 8.69 (d, 1H).

Example 105

Preparation of 7-Chloro-4-[4-[methoxyimino(4-fluorophenylamino)methyl]piperazin-1-yl]quinoline Preparation of N-(4-Fluorophenyl)-N'-methoxythiourea 4-Fluorophenyl isothiocyanate (306 mg, 2.0 mmol), O-methyl hydroxylamine hydrochloride (835 mg, 10.0 mmol), and triethylamine (1.5 mL, 11.0 mmol) are stirred in THF-water (6 mL) for 2 h. The reaction mixture is diluted with ether, washed with water, dried ($MgSO_4$), and concentrated yielding 240 mg of pale yellow crystals.

$^1$H NMR ($CDCl_3$) δ 3.85 (s, 3H), 7.06 (dd, 2H), 7.52 (dd, 2H, 8.41 (br. s, 1H).

7-Chloro-4-[4-(methoxyimino(4-fluorophenylamino)methyl)piperazin-1-yl]quinoline

7-Chloro-4-(piperazin-1-yl)quinoline (297 mg, 1.2 mmol), N-(4-Fluorophenyl)-N'-methoxythiourea (240 mg, 1.2 mmol), and sodium periodate (278 mg, 1.3 mmol) in DMF-water 1:1 (40 mL) are heated at 85° C. for 1 h. The reaction mixture is diluted with water and extracted with ether. The organic phase is dried ($MgSO_4$) and concentrated. The residue is purified by column chromatography with hexane-EtOAc yielding the title product.

$^1$H NMR ($CDCl_3$) δ 3.14 (m, 4H), 3.30 (m, 4H), 3.79 (s, 3H), 6.54 (br. s, 1H), 6.80 (d, 1H), 6.96 (t, 2H), 7.14 (dd, 2H), 7.38 (dd, 1H), 7.88 (d, 1H), 8.01 (d, 1H), 8.69 (d, 1H).

Example 106

Preparation of 7-Chloro-4-[4-(4-fluorobenzylamino(imino)methyl)piperazin-1-yl]quinoline 7-Chloro-4-(4-cyanopiperazin-1-yl)quinoline A suspension of 7-Chloro-4-(piperazin-1-yl)quinoline (496 mg, 2.0 mmol) and $NaHCO_3$ (504 mg, 6.0 mmol) in EtOH is treated with cyanogen bromide (5 M in MeCN, 440 μL, 2.2 mmol) and stirred at room temp. for 2 h. The solvent is removed, and the residue suspended in $CH_2Cl_2$ and filtered. The filtrate is concentrated, and the residue is purified by column chromatography with hexane-EtOAc giving 221 mg of the product as a colorless solid.

$^1$H NMR ($[D]_6$-DMSO) δ 3.27 (m, 4H), 3.52 (m, 4H), 6.86 (d, 1H), 7.45 (dd, 1H), 7.86 (d, 1H), 8.06 (d, 1H), 8.76 (d, 1H).

7-Chloro-4-[4-(4-fluorobenzylamino(imino)methyl)piperazin-1-yl]quinoline

7-Chloro-4-(4-cyanopiperazin-1-yl)quinoline (219 mg, 0.8 mmol) and 4-fluorobenzylamine (114 μL, 1.0 mmol) in 1,1,1,3,3,3-hexafluoro-2-propanol (5 mL) are heated at 130° C. in a sealed tube for 44 h. The reaction mixture is concentrated, and the residue is purified by column chromatography with $CH_2Cl_2$—$NH_3$-MeOH to give the title product as a yellow foam.

$^1$H NMR ($[D]_6$-DMSO) δ 3.17 (m, 4H), 3.49 (m, 4H), 4.17 (s, 2H), 5.80 (br., 2H), 7.01 (d, 1H), 7.09 (t, 2H), 7.35 (dd, 2H), 7.53 (dd, 1H), 7.96 (d, 1H), 8.05 (d, 1H), 8.68 (d, 1H);

MS, m/e=398 ($M^+$).

Example 107

Preparation of 7-Chloro-4-[4-(4-fluorophenylamino(imino)methyl)piperazin-1-yl]quinoline 7-Chloro-4-(4-cyanopiperazin-1-yl)quinoline (150 mg, 0.55 mmol) and 4-fluoroaniline (66 μL, 0.7 mmol) in 1,1,1,3,3,3-hexafluoro-2-propanol (5 mL) are heated at 150° C. in a sealed tube for 66 h. The reaction mixture is concentrated, and the residue is purified by column chromatography with $CH_2Cl_2$—$NH_3$-MeOH to give the title product as a colorless foam.

$^1$H NMR ($[D]_6$-DMSO) δ 3.19 (m, 4H), 3.59 (m, 4H), 5.39 (br. s, 2H), 6.70 (dd, 2H), 6.98 (t, 2H), 7.03 (d, 1H), 7.54 (dd, 1H), 7.96 (d, 1H), 8.08 (d, 1H), 8.70 (d, 1H);

MS, m/e=384 ($M^+$).

Example 108

Preparation of 7-Chloro-4-[4-(cycloheptylaminocarbonyl)piperazin-1-yl]quinoline

As described for example 78, cycloheptylamine (206 mg, 1.82 mmol), 4-nitrophenyl chloroformate (366 mg, 1.82 mmol), diisopropyl(ethyl)amine (554 mg, 4.3 mmol), and 7-chloro-4-(piperazin-1-yl)quinoline (300 mg, 1.21 mmol) are reacted affording the title product after flash chromatography with $CH_2Cl_2$-MeOH.

$^1$H NMR (DSMO-$d_6$/TFA) δ 8.62 (d, 1), 8.21 (d, 1), 7.94 (s, 1), 7.63 (d, 1), 6.37 (br, 1), 3.85 (m, 4), 3.61 (m, 1), 3.54 (m, 4), 1.72 (m, 2), 1.24–1.6 (m, 10);

Example 109

Preparation of 7-Chloro-4-[4-(cyclooctylaminocarbonyl)piperazin-1-yl]quinoline

As described for example 78, cyclooctylamine (234.1 mg, 1.82 mmol), 4-nitrophenyl chloroformate (366 mg, 1.82 mmol), diisopropyl(ethyl)amine (554 mg, 4.3 mmol), and 7-chloro-4-(piperazin-1-yl)quinoline (300 mg, 1.21 mmol) are reacted affording the title product after flash chromatography with $CH_2Cl_2$-MeOH.

$^1$H NMR (DSMO-$d_6$/TFA) δ 8.62 (d, 1), 8.2 (d, 1), 7.97 (s, 1), 7.63 (d, 1), 7.18 (d, 1), 6.32 (br, 1), 3.85 (m, 4), 3.64 (m, 1), 3.57 (m, 4), 1.38–1.65 (m, 14);

Example 110

Preparation of 7-Chloro-4-[4-[(4-methylcyclohexyl)aminocarbonyl]piperazin-1-yl]quinoline As described for example 78, 4-methylcyclohexylamine (206.1 mg, 1.82 mmol), 4-nitrophenyl chloroformate (366 mg, 1.82 mmol), diisopropyl(ethyl)amine (554 mg, 4.3 mmol), and 7-chloro-4-(piperazin-1-yl)quinoline (300 mg, 1.21 mmol) are reacted affording the title product after flash chromatography with $CH_2Cl_2$-MeOH.

$^1$H NMR (DSMO-$d_6$/TFA) δ 8.61 (d, 1), 8.2 (d, 1), 7.97 (s, 1), 7.61 (d, 1), 7.19 (d, 1), 3.85 (m, 4), 3.64 (m, 1), 3.37 (m, 4), 1.71 (m, 1), 1.1–1.67 (m, 9), 0.75–0.9 (m, 3);

Example 111

Preparation of 7-Chloro-4-[4-[(2-methylcyclohexyl)aminocarbonyl]piperazin-1-yl]quinoline As described for example 78, 2-methylcyclohexylamine (170 mg, 1.5 mmol), 4-nitrophenyl chloroformate (302 mg, 1.5 mmol), diisopropyl(ethyl)amine (469 mg, 3.7 mmol), and 7-chloro-4-(piperazin-1-yl)quinoline (248 mg, 1.0 mmol) are reacted affording the title product after flash chromatography with $CH_2Cl_2$-MeOH.

$^1$H NMR (DSMO-$d_6$/TFA) δ 8.61 (d, 1), 8.2 (d, 1), 8.0 (s, 1), 7.62 (d, 1), 7.17 (d, 1), 3.91 (m, 4), 3.75 (m, 1), 3.58 (m, 4), 0.9–1.8 (m, 9), 0.86 (m, 3);

Example 112

Preparation of 2-(2-Aminoethylamino)-7-chloro-4-[4-(4-fluorphenylaminocarbonyl)piperazin-1-yl]quinoline To 7-Chloro-4-[4-(4-fluorphenylaminocarbonyl)piperazin-1-yl]-2-[2-(trifluoroacetamino)ethylamino]quinoline (13 mg, 0.024 mmol) was added THF (0.5 mL) and 0.5 N KOH (2.0 eq, 0.14 mL), the mixture was stirred at rt. for 2 h, additional 0.5 N KOH (0.5 mL, 10 eq.) was added and the reaction mixture was heated at 50° C. for 30 min, MeOH (0.2 ml) was added and heated at the same temperature for 30 min. Evaporation and dilution with AcOEt, washing with brine, usual workup gave the residue, which was purified by preparative TLC with 20% MeOH in DCM with 0.5% hydroxylamine by twice developing the plate to afford the title compound.

$^1$H NMR (CD$_3$OD) δ 3.10 (m, 4H), 3.25 (m, 2H), 3.50 (m, 2H), 3.75 (m, 4H), 6.5 (s., 1H), 6.95 (m, 2H), 7.10 (m, 1H), 7.30 (m, 2H), 7.50 (s, 1H), 7.80 (m, 1H).

Example 113

Preparation of 7-Chloro-4-[4-(4-fluorphenylaminocarbonyl)piperazin-1-yl]-2-[2-(trifluoroacetylamino)ethylamino]quinoline 2-[[(Trifluoroacetylamino)ethyl]amino]-7-chloro-4-[4-(t-butoxycarbonyl)piperazin-1-yl]quinoline (31 mg, 0.062 mmol) was treated with TFA:DCM (1:1, 0.2 mL) at r.t. for 40 min. Evaporation of the solvents, dilution with DCM and evaporation afford the corresponding unsubstituted piperazine as the TFA salt which was dissolved in DCM (15 mL) cooled in an ice bath. NEt$_3$ (79 μl, 9 eq.) and 4-fluorophenyl isocyanate (8 μl, 1.5 eq.) was added. After stirring at rt. for 1 h, the mixture was diluted with DCM and washed with water followed by the usual work up. Flash chromatography on silica gel with MeOH in DCM afforded the title compound.

$^1$H NMR (CD$_3$OD) δ 3.0 (m, 4H), 3.4 (m, 2H), 3.55 (m, 2H), 3.70 (m, 4H), 6.2 (s., 1H), 6.95 (m, 2H), 7.05 (d, 1H), 7.30 (m, 2H), 7.50 (s, 1H), 7.75 (d, 1H).

Example 114

Preparation of 7-Chloro-4-[4-(4-fluorphenylaminocarbonyl)piperazin-1-yl]-2-methoxyquinoline To a solution of 2,4,7-trichloroquinoline (150 mg, 0.685 mmol) in toluene (3 mL) was added a suspension of NaOMe (136 mg, 3.4 eq.) in toluene (3 mL). The mixture was refluxed at 130° C. for 24 h. After cooling to r.t. the solid was filtered and the filtrate was evaporated. The residue was dissolved in MeOH and evaporated to afford 2-methoxy-4,7-dichloroquinoline (139 mg) as an off-white solid. To it was added 1-N-Boc piperazine (455 mg, 4.0 eq.). The mixture was heated in a sealed tube at 150° C. for 3 h, additional piperazine (6 eq.) was added and treated with n-BuOH (2 mL). The reaction mixture was heated at the same temperature overnight. Evaporation of solvent under vacuum and flash chromatography on silica gel with AcOEt in hexane affords the corresponding t-butoxy-carbonylpiperazinylquinoline (20 mg), which was treated with TFA:DCM(1:1, 0.4 mL) at rt. for 1 h. Evaporation of the solvents and dilution with DCM and evaporation affords the corresponding unsubstituted piperazine as the TFA salt, which was dissolved in DCM (15 mL), in an ice bath. NEt$_3$ (7 eq.) and 4-fluorophenylisocyanate (9 μl, 1.5 eq.) was added. After stirring at rt. for 3 h, the mixture was diluted with DCM and washed with water, followed by the usual work up. Flash chromatography on silica gel with MeOH in DCM afforded the title compound.

$^1$H NMR (CDCl$_3$) δ 3.20 (m, 4H), 3.75 (m, 4H), 4.05 (s., 3H), 6.35 (s, 1H), 6.45 (s, 1H), 7.00 (t, 2H), 7.30- (m, 3H), 7.80 (s, 1H), 7.85 (d, 1H).

Exampl 115

Preparation of 4-(7-Chloro-4-quinolinyl)-N-(2,3-dimethylcyclohexyl)-1-piperazinecarboxamide

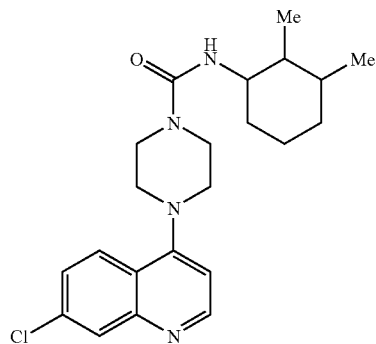

As described for example 78, 2,3-dimethyl-cyclohexanamine (154 mg, 1.21 mmol), 4-nitrophenyl chloroformate (244 mg, 1.21 mmol), diisopropyl(ethyl)amine (209 mg, 1.62 mmol), and 7-chloro-4-(piperazin-1-yl)quinoline (200 mg, 0.81 mmol) are reacted affording the title product after flash chromatography with $CH_2Cl_2$-MeOH. $^1$H NMR (DSMO-$d_6$) δ 0.7–0.9 (m, 7H), 1.13–1.92 (m, 8H), 3.2 (m, 1H), 3.6 (br. s, 4H), 3.9 (br. s, 4H), 7.2 (m, 1H), 7.7 (m, 1H), 8.0 (s, 1H), 8.2 (m, 1H), 8.6 (m, 1H).

Example 116

Preparation of 4-(7-Chloro-4-quinolinyl)-N-[4-(trifluoromethyl)cyclohexyl]-1-piperazinecarboxamide

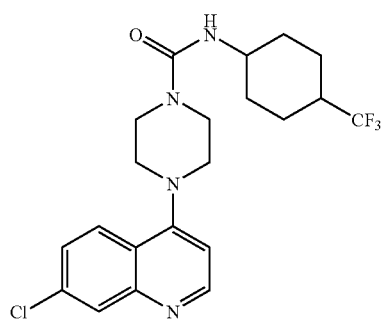

As described for example 78, 4-trifluoromethyl cyclohexyl amine, 4-nitrophenyl chloroformate, diisopropyl (ethyl)amine, and 7-chloro-4-(piperazin-1-yl)quinoline are reacted to afford the product after flash chromatography with $CH_2Cl_2$-MeOH. LC-MS: 441 ($M^+$+1). $^1$H NMR (CDCl$_3$) δ 8.78 (d, 1H), 8.05 (s, 1H), 7.95 (d, 1H), 7.46 (d, 1H), 6.85 (d, 1H), 4.60 (d, 1H), 4.03 (m, 1H), 3.65 (m, 4H), 3.20 (m, 4H), 2.10 (m, 1H), 1.85 (m, 4H), 1.50–1.70 (m, 4H).

Example 117

Preparation of 4-(7-Chloro-4-quinolinyl)-N-(cis-4-methylcyclohexyl)-1-piperazinecarboxamide

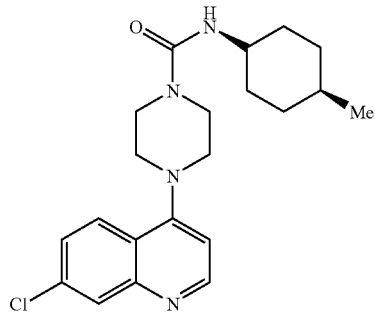

Preparation of cis-4-methyl-1-cyclohexanamine: To a solution of trans-4-methyl-1-cyclohexanol (5 g, 44 mmol) and Et$_3$N (8.9 g, 88 mmol) in CH$_2$Cl$_2$ at 0° C. was added MsCl (6.03 g, 53 mmol). After 2 h at 0° C., the reaction was quenched with NaHCO$_3$ (sat.), extracted with EtOAc, and dried over Na$_2$SO$_4$. Concentration in vacuo afforded 8.9 g of trans-4-methyl-1-methanesulfonatecyclohexanol. The mixture of trans-4-methyl-1-methanesulfonatecyclohexanol (8.9 g) with NaN$_3$ (28.5 g, 0.44 mol) in DMSO (300 mL) was kept at 95° C. for 6 h, then cooled to rt, and poured into ice-water (300 mL). The reaction mixture was extracted with EtOAc (3×200 mL), washed with brine, and dried over Na$_2$SO$_4$. Concentration in vacuo afforded crude cis-1-(4-methylcyclohexyl)azide. To a suspension of LiAlH$_4$ (2.5 g, 66 mmol) in THF (100 mL) was added cis-1-(4-methylcyclohexyl)azide in THF (15 mL) at 0° C. After 12 h at rt, the reaction was quenched with 6 N NaOH (20 mL), and the solid was filtered off. The resulting filtrate was concentrated in vacuo to give 7.2 g of cis-4-methyl-1-cyclohexanamine.

Preparation of 4-(7-chloro-4-quinolinyl)-N-(cis-4-methylcyclohexyl)-1-piperazinecarboxamide: As described for example 78, cis-4-methyl-1-cyclohexanamine (170 mg, 1.5 mmol), 4-nitrophenyl chloroformate (302 mg, 1.5 mmol), diisopropyl(ethyl)amine (258 mg, 2 mmol), and 7-chloro-4-(piperazin-1-yl)quinoline (248 mg, 1 mmol) are reacted affording the title product after flash chromatography with CH$_2$Cl$_2$-MeOH. $^1$H NMR (DSMO-$d_6$) δ 0.92 (d, 3H), 1.2 (m, 2H), 1.55–1.7 (m, 8H), 3.22 (m, 4H), 3.65 (m, 4H), 4.02 (br. s, 1H), 4.6 (m, 1H), 6.82 (d, 1H), 7.44 (d, 1H), 7.98 (d, 1H), 8.06 (s, 1), 8.78 (d, 1H).

Example 118

Preparation of 4-(7-Chloro-4-quinolinyl)-N-(trans-4-methylcyclohexyl)-1-piperazin carboxamid

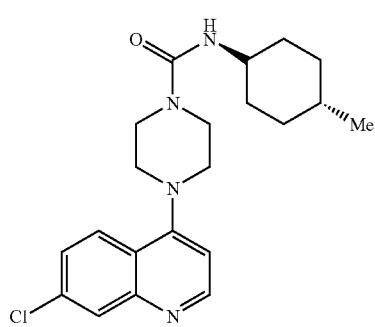

As described for example 78, trans-4-methyl-1-cyclohexanamine (170 mg, 1.5 mmol) prepared in a similar manner as for cis-4-methyl-1-cyclohexanamine, 4-nitrophenyl chloroformate (302 mg, 1.5 mmol), diisopropyl(ethyl)amine (258 mg, 2 mmol), and 7-chloro-4-(piperazin-1-yl)quinoline (248 mg, 1 mmol) are reacted affording the title product after flash chromatography with CH$_2$Cl$_2$-MeOH. $^1$H NMR (DSMO-d$_6$) δ 0.9 (d, 3H), 1.0–1.2 (m, 3H), 1.23–1.4 (m, 2H), 1.7 (m, 2H), 2.02 (m, 2H), 3.2 (m, 4H), 3.61 (m, 4H), 4.38 (m, 1H), 6.83 (d, 1H), 7.43 (d, 1H), 7.94 (d, 1H), 8.05 (s, 1H), 8.77 (d, 1H).

Example 119

Preparation of 4-(7-chloro-4-quinolinyl)-N-(3,4-dimethoxyphenyl)-1-piperazinecarboxamide

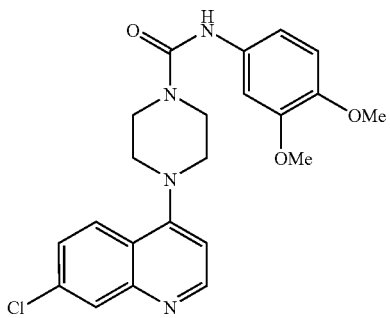

As described for example 78, 3,4-dimethoxyaniline, p-nitrophenyl chloroformate, diisopropylethyl amine, and 7-chloro-4-piperazinylquinoline are reacted to afford the product. LC-MS: 427 (M$^+$+1). $^1$H NMR (CDCl$_3$) δ 8.80 (d, 1H), 8.05 (s, 1H), 7.95 (d, 1H), 7.50 (d, 1H), 7.20 (s, 1H), 6.85 (d, 1H), 6.80 (d, 1H), 6.75 (m, 1H), 6.40 (s, 1H), 3.90 (s, 3H), 3.85 (s, 3H), 380 (m, 4H), 3.25 (m, 4H).

Example 120

Preparation of 4-(7-Chloro-4-quinolinyl)-N-(2,3-dihydro-1,4-benzodioxin-6-yl)-1-piperazinecarboxamide

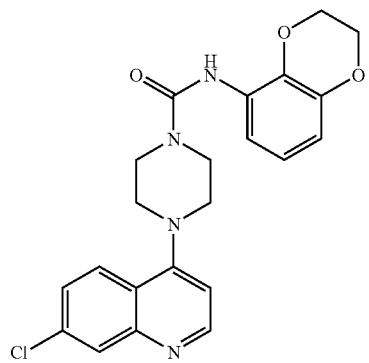

As described for example 78, 5-amino-1,4-benzodioxane, p-nitrophenyl chloroformate, diisopropylethyl amine, and 7-chloro-4-piperazinylquinoline are reacted to afford the product. LC-MS: 425 (M$^+$+1). $^1$H NMR (DMSO-d$_6$) δ 8.70 (d, 1H), 8.50 (s, 1H), 8.05 (d, 1H), 7.95 (s, 1H), 7.55 (d, 1H), 7.00 (m, 2H), 6.85 (d, 1H), 6.70 (d, 1H), 4.15 (m, 4H), 3.65 (m, 4H), 3.20 (m, 4H).

Example 121

Preparation of 4-(7-Chloro-4-quinolinyl)-N-(4-fluoro-3-methoxyphenyl)-1-piperazinecarboxamide

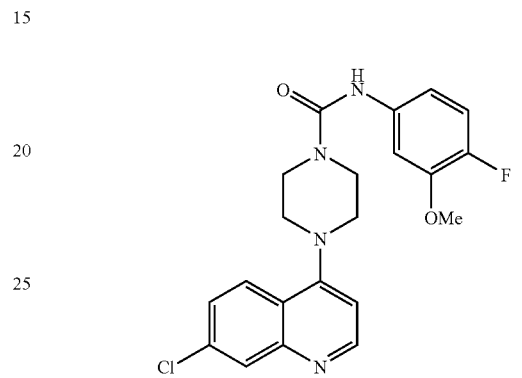

As described for example 78, 3-methoxy-4-fluoro-aniline, p-nitrophenyl chloroformate, diisopropylethyl amine, and 7-chloro-4-piperazinylquinoline are reacted to afford the product. LC-MS: 415 (M$^+$+1). $^1$H NMR (CDCl$_3$) δ 8.78 (d, 1H), 8.05 (s, 1H), 7.95 (d, 1H), 7.50 (d, 1H), 7.35 (d, 1H), 7.00 (m, 1H), 6.85 (d, 1H), 6.70 (m, 1H), 6.65 (s, 1H), 3.85 (s, 3H), 3.75 (m, 4H), 3.25 (m, 4H).

Example 122

Preparation of 4-(7-Chloro-4-quinolinyl)-N-(3-fluoro-4-methoxyphenyl)-1-piperazinecarboxamide

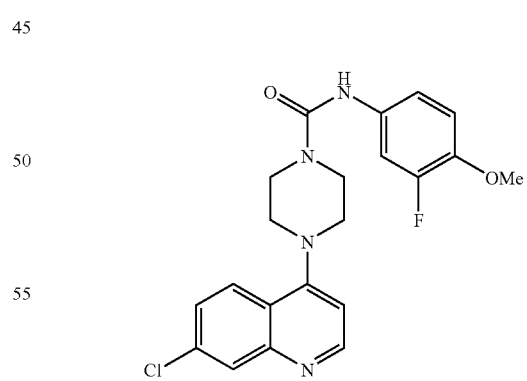

As described for example 78, 4-methoxy-3-fluoro-aniline, p-nitrophenyl chloroformate, diisopropylethyl amine, and 7-chloro-4-piperazinylquinoline are reacted to afford the product. LC-MS: 415 (M$^+$+1). $^1$H NMR (CDCl$_3$) δ 8.78 (d, 1H), 8.05 (s, 1H), 7.95 (d, 1H), 7.50 (d, 1H), 7.35 (d, 1H), 7.00 (m, 1H), 6.85 (d, 1H), 6.70 (m, 1H), 6.60 (s, 1H), 3.85 (s, 3H), 3.78 (m, 4H), 3.25 (m, 4H).

Example 123

Preparation of N-(3-Chloro-4-methoxyphenyl)-4-(7-chloro-4-quinolinyl)-1-piperazinecarboxamide

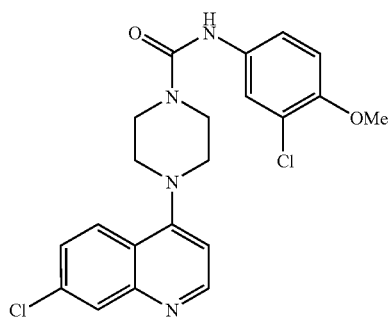

As described for example 78, 4-methoxy-3-chloroaniline, p-nitrophenyl chloroformate, diisopropylethyl amine, and 7-chloro-4-piperazinylquinoline are reacted to afford the product. LC-MS: 431 (M$^+$+1). $^1$H NMR (CDCl$_3$) δ 8.78 (d, 1H), 8.05 (s, 1H), 7.95 (d, 1H), 7.50 (d, 1H), 7.45 (s, 1H), 7.22 (d, 1H), 6.90 (m, 2H), 6.38 (s, 1H), 3.85 (s, 3H), 3.80 (m, 4H), 3.25 (m, 4H).

Example 124

Preparation of 4-(7-Chloro-4-quinolinyl)-N-(2-hydroxyphenyl)-1-piperazinecarboxamide

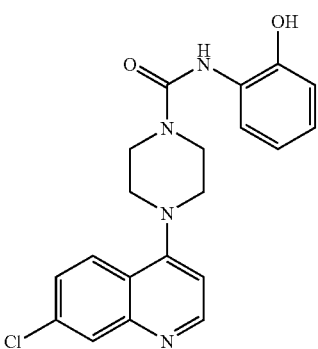

Preparation of 4-(7-chloro-4-quinolinyl)-N-(2-methoxyphenyl)-1-piperazinecarboxamide: As described for example 78, 2-methoxyaniline, 4-nitrophenyl chloroformate, diisopropyl(ethyl)amine, and 7-chloro-4-(piperazin-1-yl)quinoline are reacted to afford the product after flash chromatography with CH$_2$Cl$_2$-MeOH.

Preparation of 4-(7-chloro-4-quinolinyl)-N-(2-hydroxyphenyl)-1-piperazinecarboxamide To a stirred solution of 4-(7-chloro-4-quinolinyl)-N-(2-methoxyphenyl)-1-piperazine carboxamide (40 mg, 0.1 mmol) in CH$_2$Cl$_2$ (6 mL) was added a solution of BBr$_3$ (0.2 mL, 1.0 M) at rt. The reaction mixture was stirred at rt overnight, then quenched with 1 N NaOH solution. The reaction mixture was extracted with CH$_2$Cl$_2$, washed with brine, and dried over Na$_2$SO$_4$. Concentration in vacuo followed by flash chromatography afforded the title product. LC-MS 383 (M$^+$+1). $^1$H NMR (CDCl$_3$) δ 8.75 (d, 1H), 8.05 (s, 1H), 7.95 (d, 1H), 7.45 (d, 1H), 7.05 (m, 3H), 6.85 (m, 2H), 6.70 (s, 1H), 3.85 (m, 4H), 3.30 (m, 4H).

Example 125

Preparation of 4-(7-Chloro-4-quinolinyl)-N-(3-cyclohexen-1-yl)-1-piperazinecarboxamide

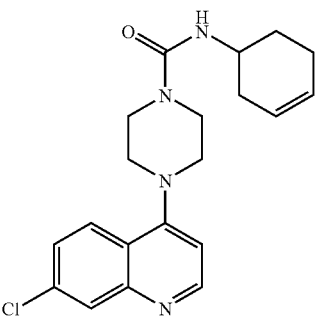

Preparation of 4-(7-chloro-4-quinolinyl)-N-(4-hydroxycyclohexyl)-1-piperazinecarboxamide: As described for example 78, 4-aminocyclohexanol (84 mg, 0.73 mmol), 4-nitrophenyl chloroformate (146 mg, 0.73 mmol), diisopropyl(ethyl)amine (320 mg, 2.4 mmol), and 7-chloro-4-(piperazin-1-yl)quinoline (150 mg, 0.81 mmol) are reacted affording 80 mg of the product after flash chromatography with CH$_2$Cl$_2$-MeOH. $^1$H NMR (DSMO-d$_6$) 61.17 (m,-4H), 1.74 (m, 4H), 3.38 (m, 2H), 3.56 (br. s, 4H), 3.82 (br., s, 4H), 7.16 (d, 1H), 7.64 (dd, 1H), 1.97 (d, 1H), 8.2 (d, 1H), 8.62 (d, 1H).

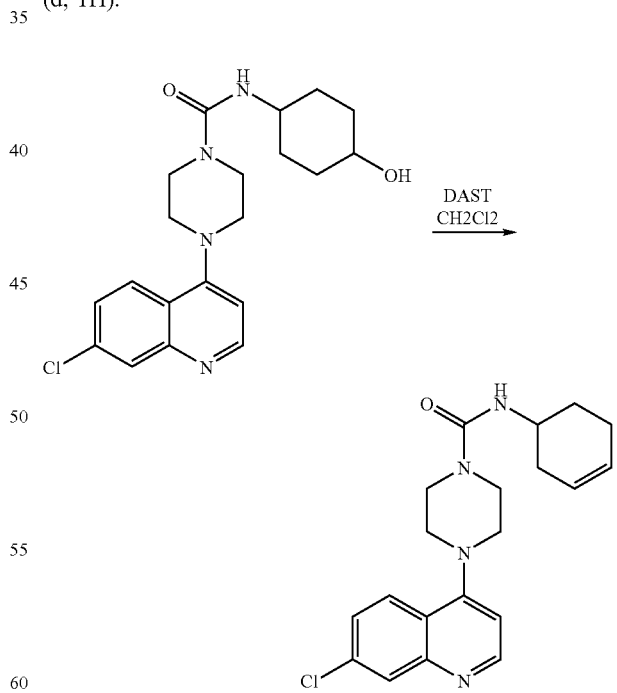

Preparation of 4-(7-chloro-4-quinolinyl)-N-(3-cyclohexen-1-yl)-1-piperazinecarboxamide: To a stirred solution of 4-(7-chloro-4-quinolinyl)-N-(4-hydroxycyclohexyl)-1-piperazinecarboxamide (100 mg) in CH$_2$Cl$_2$ at −78° C. was added DAST (100 mg). The reaction was warmed to rt overnight, and quenched with NaOH (sat.). The reaction mixture was extracted with EtOAc, and dried. Concentration in vacuo followed by flash chromatography with CH$_2$Cl$_2$-MeOH afforded the title product. $^1$H NMR (DSMO-d$_6$) δ1.03 (m, 1H), 1.4 (m, 1H), 1.7 (m, 1H), 1.9 (m, 1H), 2.05 (m, 1H), 2.1 (m, 1H), 3.1 (br. s, 4H), 3.6 (br. s, 4H), 3.65 (m, 1H), 5.6 (m, 2H), 6.4 (d, 1H), 7.0 (d, 1H), 7.6 (m, 1H), 8.0 (s, 1H), 8.1 (d, 1H), 8.7 (d, 1H).

Example 126

Preparation of 4-(7-Chloro-4-quinolinyl)-N-(3-fluoro-6,7,8,9-tetrahydro-5H-benzo[α]cyclohepten-5-yl)-1-piperazinecarboxamide

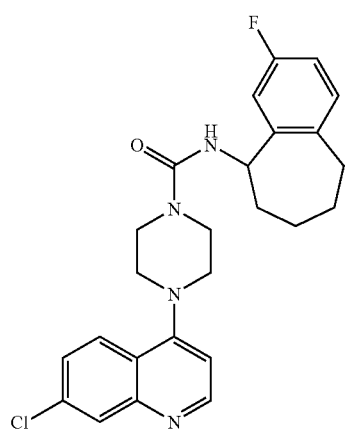

As described for example 78, 8-fluoro-benzocyloheptyl-1-amine hydrochloride, p-nitrophenyl chloroformate, diisopropylethyl amine, and 7-chloro-4-piperazinylquinoline are reacted to afford the product after flash chromatography with CH$_2$Cl$_2$-MeOH. LC-MS: 453 (M$^+$+1). $^1$H NMR (CDCl$_3$) δ 8.76 (d, 1H), 8.05 (s, 1H), 7.96 (d, 1H), 7.45 (d, 1H), 7.05 (m, 1H), 6.95 (m, 1H), 6.85 (d, 1H), 6.80 (m, 1H), 5.12 (m, 1H), 4.85 (m, 1H), 3.70 (m, 4H), 3.25 (m, 4H), 2.85 (m, 2H), 1.95 (m, 2H), 1.80 (m, 2H), 1.67 (m, 1H), 1.50 (m, 1H).

Example 127

Preparation of 4-(7-Chloro-4-quinolinyl)-N-(6,7,8,9-tetrahydro-5H-benzo[α]cyclohepten-5-yl)-1-piperazinecarboxamide

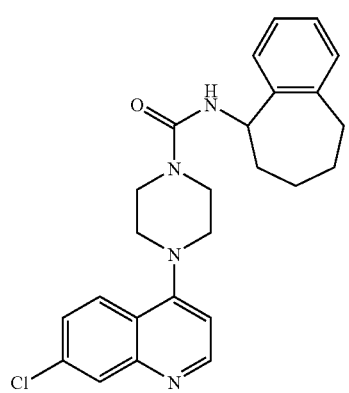

As described for example 78, benzocyloheptyl-1-amine hydrochloride, p-nitrophenyl chloroformate, diisopropylethyl amine, and 7-chloro-4-piperazinylquinoline are reacted to afford the product. LC-MS: 435 (M$^+$+1). $^1$H NMR (DMSO-d$_6$) δ 8.60 (s, 1H), 8.05 (d, 1H), 7.90 (s, 1H), 7.50 (d, 1H), 7.15 (m, 1H), 7.00 (m, 4H), 4.95 (m, 1H), 3.65 (m, 4H), 3.18 (m, 4H), 2.85 (m, 2H), 1.85 (m, 3H), 1.70 (m, 1H), 1.58 (m, 1H), 1.20 (m, 1H).

Example 128

Preparation of 4-(7-Chloro-4-quinolinyl)-N-(2-fluoro-6,7,8,9-tetrahydro-5H-benzo[α]cyclohepten-7-yl)-1-piperazinecarboxamide

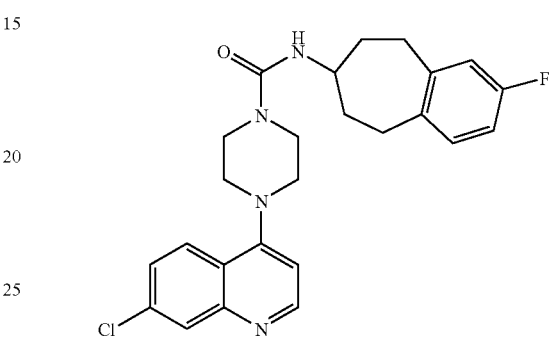

As described for example 78, 8-fluoro-benzocyloheptyl-3-amine, p-nitrophenyl chloroformate, diisopropylethyl amine, and 7-chloro-4-piperazinylquinoline are reacted to afford the product. LC-MS: 453 (M$^+$+1). $^1$H NMR (CD$_3$OD) δ 8.50 (d, 1H), 8.25 (d, 1H), 7.90 (s, 1H), 7.65 (d, 1H), 7.15 (d, 1H), 7.05 (m, 1H), 6.85 (m, 1H), 6.78 (m, 1H), 3.95 (m, 4H), 3.90 (m, 1H), 3.70 (m, 4H), 2.78 (m, 4H), 2.10 (m, 2H), 1.35 (m, 2H).

Example 129

Preparation of 4-(7-Chloro-4-quinolinyl)-N-[9-(acetyloxy)-2-fluoro-6,7,8,9-tetrahydro-5H-benzo[α]cyclohepten-7-yl]-1-piperazinecarboxamide

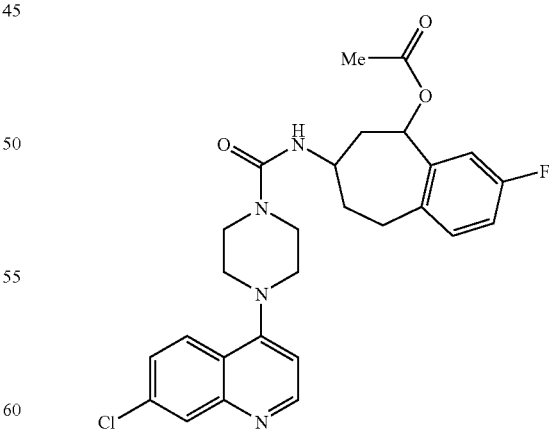

As described for example 78, 8-fluoro-benzocyloheptyl-1-acetyloxy-3-amine, p-nitrophenyl chloroformate, diisopropylethyl amine and 7-chloro-4-piperazinylquinoline are reacted to afford the product. LC-MS: 512 (M$^+$+1). $^1$H NMR (CD$_3$OD) δ 8.50 (d, 1H), 8.25 (d, 1H), 7.90 (s, 1H), 7.65 (d, 1H), 7.15 (d, 2H), 7.05 (m, 1H), 6.85 (m, 1H), 5.90 (m, 1H), 4.10 (m, 1H), 3.95 (m, 4H), 3.75 (m, 4H), 2.80 (m, 2H), 2.26 (m, 1H), 2.20 (s, 3H), 2.15 (m, 1H), 1.65 (m, 1H), 1.30 (m, 1H).

Example 130

Preparation of 4-(7-Chloro-4-quinolinyl)-N-(2-fluoro-6,7,8,9-tetrahydro-9-hydroxy-5H-benzo[α]cyclohepten-7-yl)-1-piperazinecarboxamide

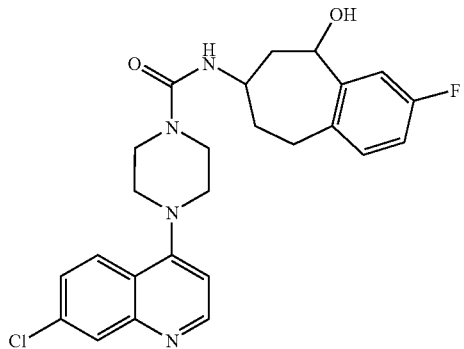

To a stirred solution of N-[9-(acetyloxy)-2-fluoro-6,7,8,9-tetrahydro-5H-benzo[α]cyclohepten-7-yl]-4-(7-chloro-4-quinolinyl)-1-piperazinecarboxamide (30.0 mg, 0.0588 mmol) in THF:H$_2$O (3:1, 2 mL) was added LiOH (8 mg). The reaction mixture was stirred at rt for 3 h, then THF was evaporated in vacuo. The reaction mixture was diluted with AcOEt (100 mL), washed with brine, and dried. Concentration followed by flash chromatography afforded the title product. LC-MS: 469 (M$^+$+1). δ $^1$H NMR (CDCl$_3$) δ 8.70 (d, 1H), 8.05 (s, 1H), 7.95 (d, 1H), 7.45 (d, 1H), 7.05 (m, 2H), 6.85 (m, 2H), 4.95 (m, 1H), 4.35 (m, 1H), 3.65 (m, 4H), 3.20 (m, 4H), 3.15 (m, 1H), 2.60 (m, 1H), 2.20 (m, 2H), 1.8 (m, 3H).

Example 131

Preparation of 4-[[[4-(7-Chloro-4-quinolinyl)-1-piperazinyl]carbonyl]amino]hexahydro-1H-azepine-1-carboxylic Acid, 1,1-dimethylethyl Ester

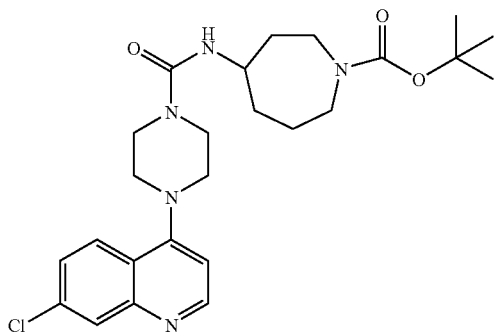

As described for example 78, 4-amino-N-1-Boc-azepine, p-nitrophenyl chloroformate, diisopropylethyl amine and 7-chloro-4-piperazinylquinoline are reacted to afford the title product. LC-MS: 488 (M$^+$+1). $^1$H NMR (CDCl$_3$) δ 8.75 (d, 1H), 8.05 (s, 1H), 7.96 (d, 1H), 7.45 (d, 1H), 6.85 (d, 1H), 4.55 (m, 1H), 4.05 (m, 1H), 3.90 (m, 1H), 3.60 (m, 4H), 3.30 (m, 1H), 3.20 (m, 4H), 3.10 (m, 2H), 2.10 (m, 1H), 1.60–1.90 (m, 3H), 1.50 (s, 9H).

Example 132

Preparation of 4-[[[4-(7-Chloro-4-quinolinyl)-1-piperazinyl]carbonyl]amino]hexahydro-1H-azepine-1-carboxylic Acid, Methyl Ester

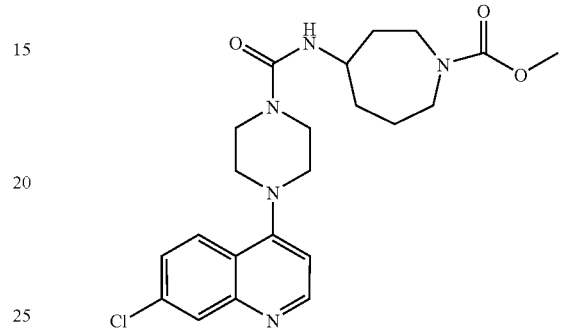

To a mixture of 4-(7-chloro-4-quinolinyl)-N-(hexahydro-1H-azepin-4-yl)-1-piperazine carboxamide (40 mg, 0.082 mmol) obtained by the de-protection of 4-[[[4-(7-chloro-4-quinolinyl)-1-piperazinyl]carbonyl]amino]hexahydro-1H-azepine-1-carboxylic acid 1,1-dimethylethyl ester with TFA and Cs$_2$CO$_3$ (40 mg) in DMF (3 mL), MeI (11.6 mg) was introduced. The reaction mixture was stirred at 50° C. for 30 min, then MeI (30 mg.) was added. After 1 h at rt, the reaction mixture was diluted with water and extracted with AcOEt, washed with water and brine, and dried. Concentration in vacuo followed by flash chromatography afforded the title product. LC-MS: 446 (M$^+$+1). $^1$H NMR (CDCl$_3$) δ 8.78 (d, 1H), 8.05 (s, 1H), 7.95 (d, 1H), 7.45 (d, 1H), 6.85 (d, 1H), 4.45 (m, 1H), 3.90 (m, 1H), 3.70 (s, 3H), 3.65 (m, 4H), 3.20 (m, 5H), 2.10 (m, 1H), 1.95 (m, 2H), 1.60–1.70 (m, 3H), 1.27 (m, 2H).

Example 133

Preparation of 4-[[[4-(7-Chloro-4-quinolinyl)-1-piperazinyl]carbonyl]amino]hexahydro-1H-azepine-1-carboxylic Acid, Phenylmethyl Ester

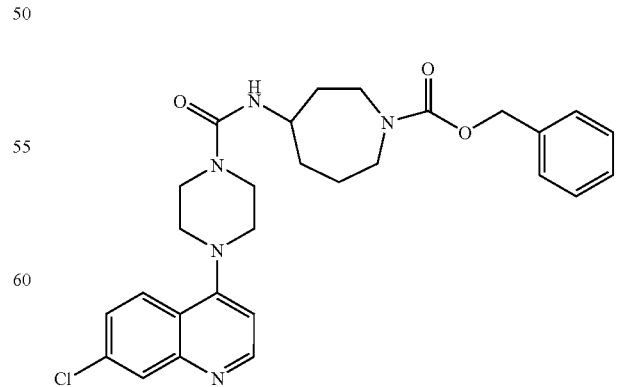

As described for example 132, 4-(7-chloro-4-quinolinyl)-N-(hexahydro-1H-azepin-4-yl)-1-piperazinecarboxamide obtained from the de-protection of 4-[[[4-(7-chloro-4-quinolinyl)-1-piperazinyl]carbonyl]amino]hexahydro-1H-azepine-1-carboxylic acid 1,1-dimethylethyl ester with TFA, Cs₂CO₃, and CbzCl are reacted to afford the title product. LC-MS: 522 (M⁺+1), ¹H NMR (CDCl₃) δ 8.75 (d, 1H), 8.05 (s, 1H), 7.95 (d, 1H), 7.45 (d, 1H), 7.30 (m, 5H), 6.80 (d, 1H), 5.15 (m, 2H), 4.50 (m, 1H), 3.65–3.95 (m, 3H), 3.58 (m, 4H), 3.30 (m, 1H), 3.18 (m, 4H), 2.10 (m, 1H), 1.65–1.95 (m, 3H), 1.60 (m, 2H).

Example 134

Preparation of 4-(7-Chloro-4-quinolinyl)-N-(3-hydroxycycloheptyl)-1-piperazinecarboxamide

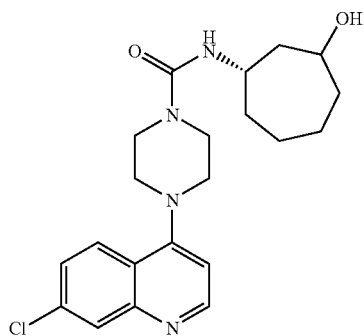

As described for example 78, 3-hydroxycycloheptylamine, p-nitrophenyl chloroformate, diisopropylethyl amine and 7-chloro-4-piperazinylquinoline are reacted to afford the product. LC-MS: 403 (M⁺+1). ¹H NMR (CDCl₃) δ 8.75 (d, 1H), 8.05 (s, 1H), 7.96 (d, 1H), 7.45 (d, 1H), 6.84 (d, 1H), 4.50 (d, 1H), 4.10 (m, 2H), 3.65 (m, 4H), 3.20 (m, 4H), 2.38 (m, 1H), 2.0 (m, 3H), 1.80 (m, 4H), 1.40 (m, 2H).

Example 135

Preparation of 4-(7-Chloro-4-quinolinyl)-N-(3-oxocycloheptyl)-1-piperazinecarboxamide

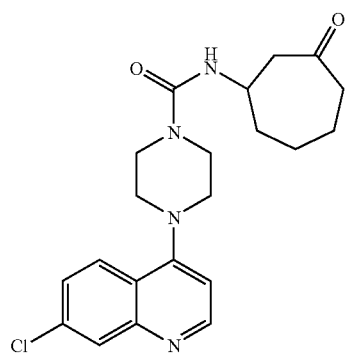

To a stirred solution of 4-(7-chloro-4-quinolinyl)-N-(3-hydroxycycloheptyl)-1-piperazinecarboxamide (300 mg, 0.744 mmol) in CH₂Cl₂ (20 mL), the Dess-Martin reagent (348 mg, 0.82 mmol) was added at rt. After 3 h, the reaction mixture was quenched with 1 g of Na₂S₂O₃ and 5 mL of NaHCO₃ (sat.). The reaction mixture was extracted with CH₂Cl₂, washed with brine, and dried over Na₂SO₄. Concentration in vacuo followed by flash chromatography afforded the title product. LC-MS: 401 (M⁺+1). ¹H NMR (CDCl₃) δ 8.78 (d, 1H), 8.05 (s, 1H), 7.95 (d, 1H), 7.45 (d, 1H), 6.85 (d, 1H), 4.70 (m, 1H), 4.25 (m, 1H), 3.60 (m, 4H), 3.25 (m, 4H), 3.00 (m, 1H), 2.45–2.65 (m, 3H), 1.70–1.90 (m, 6H).

Example 136

Preparation of 4-(7-Chloro-4-quinolinyl)-N-(3-hydroxy-3-methylcycloheptyl)-1-piperazinecarboxamide

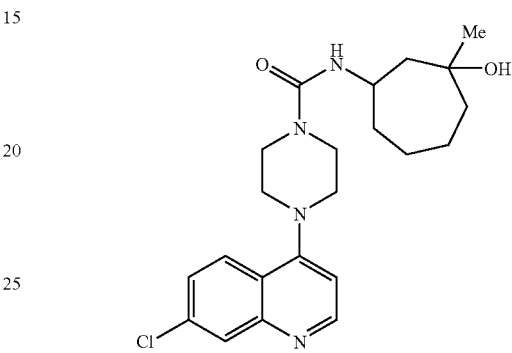

To a stirred solution of 4-(7-chloro-4-quinolinyl)-N-(3-oxocycloheptyl)-1-piperazinecarboxamide (8 mg, 0.02 mmol) in THF (3 mL) was added a solution of MeMgBr (3M, 0.1 mL) at 0° C. After 5 h at 0° C., the reaction mixture was quenched with MeOH and Na₂CO₃ (sat. 50 mL). The reaction mixture was extracted with CH₂Cl₂, washed with brine, and dried over Na₂SO₄. Concentration in vacuo followed by preparative TLC gave the title product. LC-MS: 401 (M⁺+1). ¹H NMR (CDCl₃) δ 8.78 (d, 1H), 8.05 (s, 1H), 7.95 (d, 1H), 7.45 (m, 1H), 6.85 (d, 1H), 5.75 (d, 1H), 4.45 (d, 1H), 4.05 (m, 1H), 3.65 (m, 4H), 3.20 (m, 4H), 1.55–1.95 (m, 10H), 1.35 (s, 3H).

Example 137

Preparation of 4-(7-Chloro-4-quinolinyl)-N-[(3E)-3-(thoxyimino)cycloheptyl]-1-piperazinecarboxamid

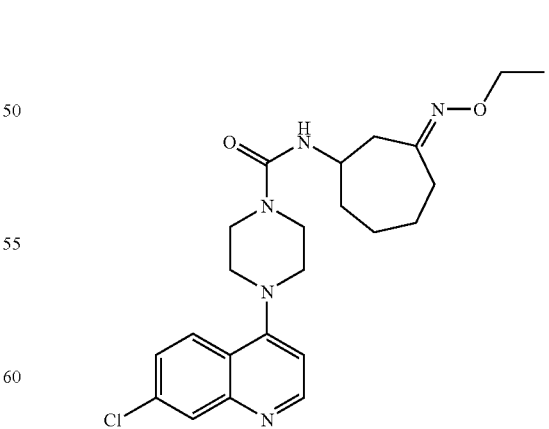

To a stirred solution of 4-(7-chloro-4-quinolinyl)-N-(3-oxocycloheptyl)-1-piperazinecarboxamide (30 mg, 0.075 mmol) in EtOH (3 mL) was added ethoxyamine hydrochloride (36 mg, 0.225 mmol), followed by NaOAc (31 mg, 0.225 mmol). The mixture was heated at reflux for 2 h. After cooling to rt, the reaction mixture was poured into water (100 mL), extracted with AcOEt, washed with brine, and dried over Na₂SO₄. Concentration in vacuo followed by flash chromatography afforded the title product. LC-MS: 444 (M⁺+1). ¹H NMR (CDCl₃) δ 8.78 (d, 1H), 8.05 (s, 1H), 7.95 (d, 1H), 7.45 (m, 1H), 6.85 (d, 1H), 4.80 (d, 1H), 4.10 (m, 3H), 3.6 (m, 4H), 4H), 3.20 (m, 4H), 2.30–2.90 (m, 4H), 1.50–1.95 (m, 6H), 1.25 (t, 3H).

Example 138

Preparation of 4-(7-Chloro-4-quinolinyl)-N-(3-methoxycycloheptyl)-1-piperazinecarboxamide

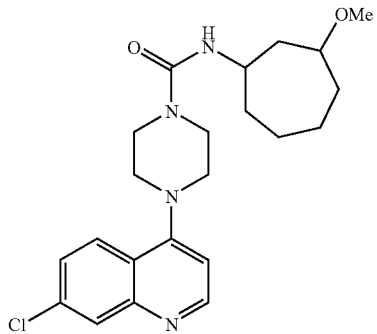

To a stirred solution of 4-(7-chloro-4-quinolinyl)-N-(3-hydroxycycloheptyl)-1-piperazinecarboxamide (30 mg, 0.074 mmol) in DMF (3 mL) was added NaH (8.9 gm, 0.37 mmol) at rt. After 30 min, MeI (11.5 mg, 0.09 mmol) was added, and the reaction mixture was heated at rt for 2 h. After cooling to rt, the reaction mixture was quenched with MeOH, then poured into water (100 mL). The reaction mixture was extracted with EtOAc, washed with brine, and dried over Na₂SO₄. Concentration in vacuo followed by flash chromatography afforded the title product. LC-MS: 416 (M⁺+1). ¹H NMR (CDCl₃) δ 8.75 (d, 1H), 8.05 (s, 1H), 7.95 (d, 1H), 7.45 (d, 1H), 6.85 (d, 1H), 4.40 (d, 1H), 4.10 (m, 1H), 3.65 (m, 4H), 3.45 (m, 1H), 3.36 (s, 3H), 3.20 (m, 4H), 2.15 (m, 1H) 2.05 (m, 1H), 1.50–1.90 (m, 6H), 1.40 (m, 2H).

Example 139

Preparation of 4-(7-Chloro-4-quinolinyl)-N-[3-[(4-fluorophenyl)methoxy]cycloheptyl]-1-piperazinecarboxamide

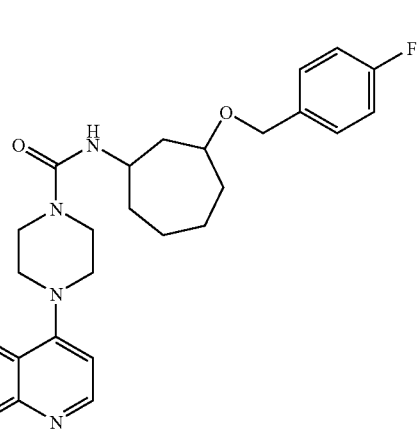

As described for example 138, 4-(7-chloro-4-quinolinyl)-N-(3-hydroxycycloheptyl)-1-piperazinecarboxamide (50 mg, 0.124 mmol), NaH (8.9 mg, 0.37 mmol), and 4-fluorobenzyl bromide (28.2 mg, 0.15 mmol) are reacted to give the title product after flash chromatography with CH₂Cl₂-MeOH. LC-MS: 511 (M⁺+1). ¹H NMR (CDCl₃) δ 8.75 (d, 1H), 8.05 (s, 1H), 7.95 (d, 1H), 7.45 (d, 1H), 7.35 (m, 2H), 7.00 (m, 2H), 6.85 (d, 1H), 4.50 (m, 2H), 4.40 (m, 1H), 4.10 (m, 1H), 3.65 (m, 4H), 3.20 (m, 4H), 2.20 (m, 1H), 2.10 (m, 1H), 1.50–1.90 (m, 6H), 1.40 (m, 2H).

Example 140

Preparation of 4-(7-Chloro-4-quinolinyl)-N-[3-(2-pyridinyloxy)cycloheptyl]-1-piperazinecarboxamide

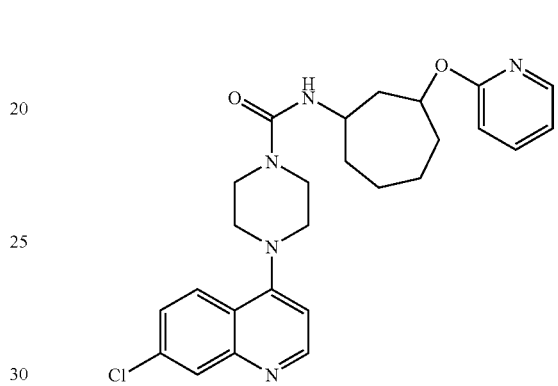

As described for example 138, 4-(7-chloro-4-quinolinyl)-N-(3-hydroxycycloheptyl)-1-piperazinecarboxamide, NaH, and 2-fluoropyridine are reacted to give the product after flash chromatography with CH₂Cl₂-MeOH. LC-MS: 480 (M⁺+1). ¹H NMR (CDCl₃) δ 8.75 (d, 1H), 8.05 (s, 1H), 8.0 (m, 2H), 7.60 (m, 1H), 7.45 (d, 1H), 6.85 (m, 2H), 6.75 (d, 1H), 6.05 (d, 1H), 5.20 (m, 1H), 4.10 (m, 1H), 3.75 (m, 4H), 3.25 (m, 4H), 2.28 (m, 1H), 2.10 (m, 3H), 1.85 (m, 2H), 1.70 (m, 1H), 1.40–1.60 (m, 3H).

Example 141

Preparation of 4-(7-Chloro-4-quinolinyl)-N-[3-(2-pyrimidinyloxy)cycloheptyl]-1-piperazinecarboxamide

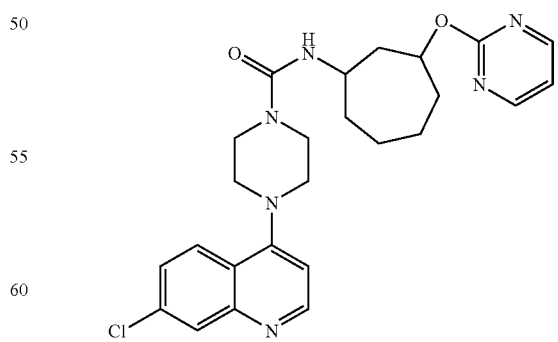

As described for example 138, 4-(7-chloro-4-quinolinyl)-N-(3-hydroxycycloheptyl)-1-piperazinecarboxamide, NaH, and 2-chloropyrimidine are reacted to give the product after flash chromatography with CH₂Cl₂-MeOH. LC-MS: 481

(M⁺+1). ¹H NMR (CDCl₃) δ 8.75 (d, 1H), 8.50 (d, 2H), 8.05 (s, 1H), 7.95 (d, 1H), 7.45 (d, 1H), 6.92 (t, 1H), 6.85 (d, 1H), 5.55 (m, 1H), 5.15 (m, 1H), 4.10 (m, 1H), 3.70 (m, 4H), 3.23 (m, 4H), 1.80–2.25 (m, 7H), 1.50–1.70 (m, 3H).

Example 142

Preparation of 4-(7-Chloro-4-quinolinyl)-N-[3-[(3-methyl-2-pyridinyl)oxy]cycloheptyl]-1-piperazinecarboxamide

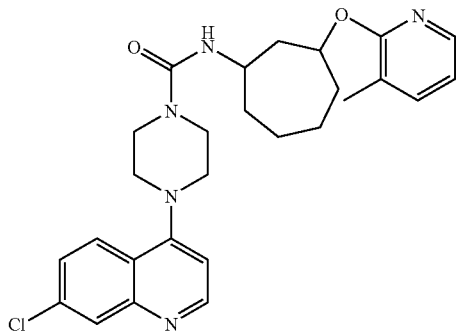

As described for example 138, 4-(7-chloro-4-quinolinyl)-N-(3-hydroxycycloheptyl)-1-piperazinecarboxamide, NaH, and 2-bromo-3-picoline are reacted to give the product. LC-MS: 494 (M⁺+1). ¹H NMR (CDCl₃) δ 8.75 (d, 1H), 8.05 (s, 1H), 7.98 (d, 1H), 7.85 (m, 1H), 7.45 (d, 1H), 7.40 (m, 1H), 6.85 (d, 1H), 6.78 (m, 1H), 6.10 (d, 1H), 5.20 (m, 1H), 4.10 (m, 1H), 3.76 (m, 4H), 3.25 (m, 4H), 2.26 (m, 1H), 2.18 (s, 3H), 2.12 (m, 2H), 1.45–1.90 (m, 7H).

Example 143

Preparation of 4-(7-Chloro-4-quinolinyl)-N-[3-[(4-methyl-2pyridinyl)oxy]cycloheptyl]-1-piperazinecarboxamide

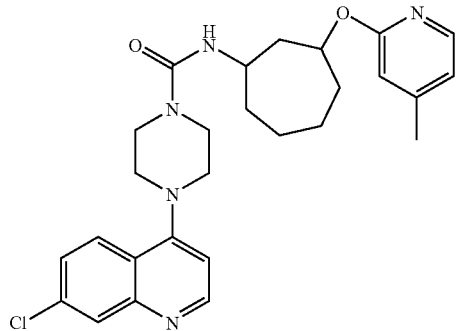

As described for example 138, 4-(7-chloro-4-quinolinyl)-N-(3-hydroxycycloheptyl)-1-piperazinecarboxamide, NaH, and 2-bromo-4-picoline are reacted to give the product. LC-MS 494 (M⁺+1). ¹H NMR (CDCl₃) δ 8.75 (d, 1H), 8.05 (s, 1H), 7.98 (d, 1H), 7.85 (d, 1H), 7.45 (d, 1H), 6.85 (d, 1H), 6.68 (d, 1H), 6.56 (s, 1H), 6.20 (d, 1H), 5.16 (m, 1H), 4.10 (m, 1H), 3.78 (m, 4H), 3.25 (m, 4H), 2.25 (s, 3H), 2.10 (m, 3H), 1.85 (m, 2H), 1.30–1.73 (m, 5H).

Example 144

Preparation of 4-(7-Chl r -4-quinolinyl)-N-[(3R)-hexahydro-2-oxo-1H-azepin-3-yl]-1-piperazinecarboxamid

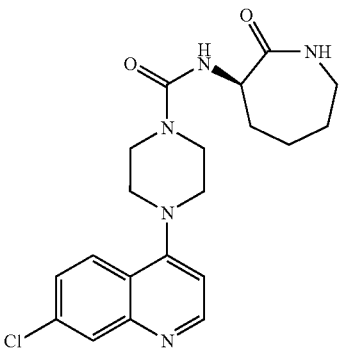

As described for example 78, (3S)-amino-azepin-2-one, p-nitrophenyl chloroformate, diisopropylethyl amine, and 7-chloro-4-piperazinylquinoline are reacted to afford the product. LC-MS: 402 (M⁺+1). ¹H NMR (CDCl₃) δ 8.76 (d, 1H), 8.05 (s, 1H), 7.96 (d, 1H), 7.45 (d, 1H), 6.85 (d, 1H), 6.15 (d, 1H), 6.00 (m, 1H), 4.50 (m, 1H), 3.70 (m, 4H), 3.30 (m, 2H), 3.20 (m, 4H), 2.16 (m, 1H), 2.05 (m, 1H), 1.85 (m, 2H), 1.50 (m, 2H).

Example 145

Preparation of 4-(7-Chloro-4-quinolinyl)-N-[(3S)-hexahydro-2-oxo-1H-azepin-3-yl]-1-piperazinecarboxamide

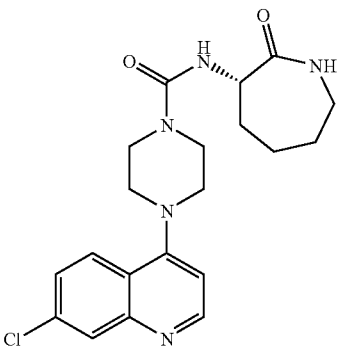

As described for example 78, (3R)-3-aminohexahydro-2H-azepin-2-one obtained by de-protection of [(3R)-hexahydro-2-oxo-1H-azepin-3-yl]-carbamic acid, 1,1-dimethylethyl ester with TFA, p-nitrophenyl chloroformate, diisopropylethyl amine and 7-chloro-4-piperazinylquinoline are reacted to afford the product. LC-MS 402 (M⁺+1). ¹H NMR (CDCl₃) δ 8.75 (d, 1H), 8.05 (s, 1H), 7.96 (d, 1H), 7.45 (d, 1H), 6.84 (d, 1H), 6.15 (d, 1H), 6.0 (m, 1H), 4.50 (m, 1H), 3.70 (m, 4H), 3.30 (m, 2H), 3.24 (m, 4H), 2.18 (m, 1H), 2.06 (m, 1H), 1.85 (m, 2H), 1.4–1.6 (m, 2H).

Example 146

Preparation of 4-(7-Chloro-4-quinolinyl)-N-[(3S)-hexahydro-1-methyl-2-oxo-1H-azepin-3-yl]-1-piperazinecarboxamide

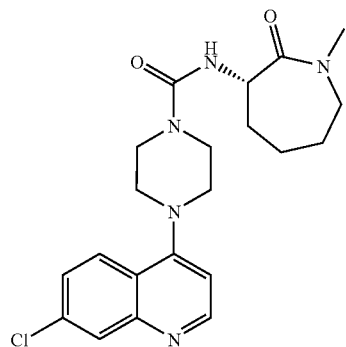

Preparation of [(3R)-hexahydro-1-methyl-2-oxo-1H-azepin-3-yl]-carbamic acid, 1,1-dimethylethyl ester: To a stirred solution of [(3R)-hexahydro-2-oxo-1H-azepin-3-yl]-carbamic acid, 1,1-dimethylethyl ester (500 mg) in THF (5 mL) at rt, KHDMS (5.26 mL, 1.0 M in THF) was added. After 30 min, $CH_3I$ (0.26 mL) was introduced. The reaction was kept at rt overnight, and then quenched with brine. The reaction mixture was extracted with EtOAc, washed with brine, and dried over $Na_2SO_4$. Concentration in vacuo afforded the crude product which was used directly for the next step reaction without further purification.

In a similar way, the following intermediates were prepared:
[(3S)-hexahydro-2-oxo-1-(phenylmethyl)-1H-azepin-3-yl]-carbamic acid, 1,1-dimethylethyl ester
[(3S)-1-[(4-fluorophenyl)methyl]hexahydro-2-oxo-1H-azepin-3-yl]-carbamic acid, 1,1-dimethylethyl ester
[(3S)-1-ethylhexahydro-2-oxo-1H-azepin-3-yl]-carbamic acid, 1,1-dimethylethyl ester
[(3S)-1-(2-amino-2-oxoethyl)hexahydro-2-oxo-1H-azepin-3-yl]-carbamic acid, 1,1-dimethylethyl ester
[(3S)-hexahydro-2-oxo-1-(3-pyridinylmethyl)-1H-azepin-3-yl]-carbamic acid, 1,1-dimethylethyl ester
[(3S)-hexahydro-2-oxo-1-(2-propenyl)-1H-azepin-3-yl]-carbamic acid, 1,1-dimethylethyl ester
[(3S)-1-(cyclopropylmethyl)hexahydro-2-oxo-1H-azepin-3-yl]-carbamic acid, 1,1-dimethylethyl ester
[(3S)-hexahydro-1-[(4-methoxyphenyl)methyl]-2-oxo-1H-azepin-3-yl]-carbamic acid, 1,1-dimethylethyl ester
(3S)-3-[[(1,1-dimethylethoxy)carbonyl]amino]hexahydro-2-oxo-1H-azepine-1-acetic acid, ethyl ester
(3S)-3-[[(1,1-dimethylethoxy)carbonyl]amino]hexahydro-2-oxo-1H-azepine-1-acetic acid, methyl ester
[(3S)-hexahydro-1-[3-(4-morpholinyl)propyl]-2-oxo-1H-azepin-3-yl]-carbamic acid, 1,1-dimethylethyl ester
[(3S)-1-[(2,6-dimethylphenyl)methyl]hexahydro-2-oxo-1H-azepin-3-yl]-carbamic acid-1,1-dimethylethyl ester
[(3S)-hexahydro-2-oxo-1-(2-pyridinylmethyl)-1H-azepin-3-yl]-carbamic acid, 1,1-dimethylethyl ester
[(3S)-hexahydro-2-oxo-1-(4-pyridinylmethyl)-1H-azepin-3-yl]-carbamic acid, 1,1-dimethylethyl ester Preparation of 4-(7-chloro-4-quinolinyl)-N-[(3S)-hexahydro-1-methyl-2-oxo-1H-azepin-3-yl]-1-piperazinecarboxamide: As described for example 78, (3R)-3-aminohexahydro-1-methyl-2H-azepin-2-one obtained by de-protection of [(3R)-hexahydro-1-methyl-2-oxo-1H-azepin-3-yl]-carbamic acid-1,1-dimethylethyl ester with TFA, p-nitrophenyl chloroformate, diisopropylethyl amine and 7-chloro-4-piperazinylquinoline are reacted to afford the product. LC-MS 416 ($M^+$+1). $^1H$ NMR ($CDCl_3$) δ 8.78 (d, 1H), 8.05 (s, 1H), 7.95 (d, 1H), 7.46 (d, 1H), 6.85 (d, 1H), 6.25 (m, 1H), 4.60 (m, 1H), 3.68 (m, 4H), 3.20 (m, 4H), 1.80–2.10 (m, 5H), 1.45 (m, 3H).

Example 147

Preparation of 4-(7-Chloro-4-quinolinyl)-N-[(3S)-hexahydro-2-oxo-1-(phenylmethyl)-1H-azepin-3-yl]-1-piperazinecarboxamide

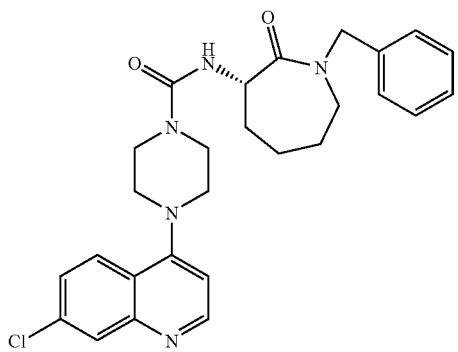

As described for example 78, (3R)-3-aminohexahydro-1-benzyl-2H-azepin-2-one obtained by de-protection of [(3S)-hexahydro-2-oxo-1-(phenylmethyl)-1H-azepin-3-yl]-carbamic acid, 1,1-dimethylethyl ester with TFA, p-nitrophenyl chloroformate, diisopropylethyl amine and 7-chloro-4-piperazinylquinoline are reacted to afford the product. LC-MS 492 ($M^+$+1). $^1H$ NMR ($CDCl_3$) δ 8.78 (d, 1H), 8.05 (s, 1H), 7.95 (d, 1H), 7.46 (d, 1H), 7.35 (m, 3H), 7.22 (m, 2H), 6.85 (d, 1H), 6.35 (m, 1H), 4.65 (m, 1H), 4.50 (m, 2H), 3.72 (m, 4H), 3.50 (m, 1H), 3.25 (m, 1H), 3.20 (m, 4H), 2.20 (m, 1H), 1.70–1.90 (m, 3H), 1.50 (m, 1H), 1.26 (m, 1H).

Example 148

Preparation of 4-(7-Chloro-4-quinolinyl)-N-[(3S)-1-[(4-fluorophenyl)methyl]hexahydro-2-oxo-1H-azepin-3-yl]-1-piperazinecarboxamide

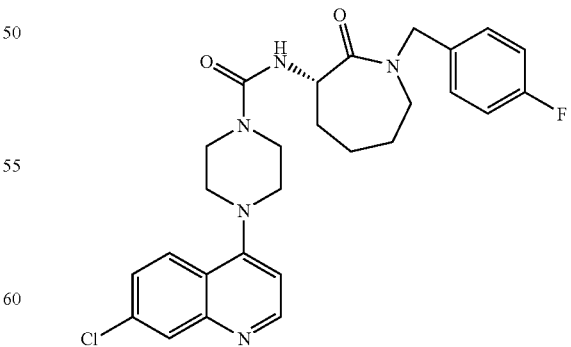

As described for example 78, (3R)-3-amino-1-[(4-fluorophenyl)methyl]hexahydro-2H-azepin-2-one obtained by de-protection of [(3S)-1-[(4 fluorophenyl)methyl]hexahydro-2-oxo-1H-azepin-3-yl]-carbamic acid, 1,1-dimethylethyl ester with TFA, p-nitrophenyl chloroformate, diisopropylethyl amine, and 7-chloro-4-piperazinylquinoline are reacted to afford the product. LC-MS: 510 (M⁺+1). ¹H NMR (CDCl$_3$) δ 8.78 (d, 1H), 8.05 (s, 1H), 7.95 (d, 1H), 7.46 (d, 3H), 7.22 (m, 2H), 7.03 (t, 2H), 6.85 (d, 1H), 6.30 (m, 1H), 4.65 (m, 1H), 4.50 (m, 2H), 3.70 (m, 4H), 3.50 (m, 1H), 3.22 (m, 5H), 2.10 (m, 1H), 1.70–1.95 (m, 3H), 1.50 (m, 1H), 1.20 (m, 1H).

Example 149

Preparation of 4-(7-Chloro-4-quinolinyl)-N-[(3S)-1-ethylhexahydro-2-oxo-1H-azepin-3-yl]-1-piperazinecarboxamide

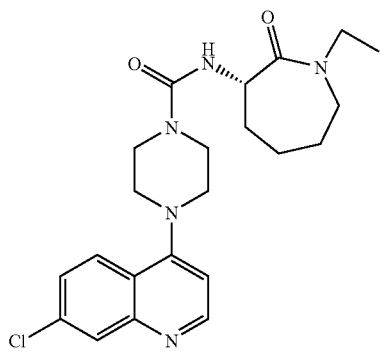

As described for example 78, (3R)-3-amino-1-ethylhexahydro-2H-azepin-2-one obtained by de-protection of [(3S)-1-ethylhexahydro-2-oxo-1H-azepin-3-yl]-carbamic acid, 1,1-dimethylethyl ester with TFA, p-nitrophenyl chloroformate, diisopropylethyl amine, and 7-chloro-4-piperazinylquinoline are reacted to afford the product. LC-MS: 430 (M⁺+1). ¹H NMR (CDCl$_3$) δ 8.78 (d, 1H), 8.05 (s, 1H), 7.95 (d, 1H), 7.46 (d, 1H), 6.85 (d, 1H), 6.30 (m, 1H), 4.58 (m, 1H), 3.70 (m, 4H), 3.50 (m, 2H), 3.42 (m, 1H), 3.22 (m, 5H), 2.10 (m, 1H), 1.85–1.98 (m, 3H), 1.46 (m, 2H), 1.17 (t, 3H).

Example 150

Preparation of (3S)-[[[4-(7-Chloro-4-quinolinyl)-1-piperazinyl]carbonyl]amino]hexahydro-2-oxo-1H-azepine-1-acetamide

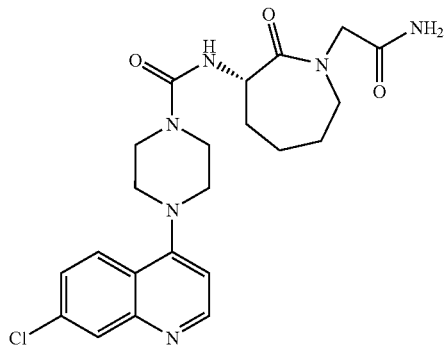

As described for example 78, (3R)-3-aminohexahydro-2-oxo-1H-azepine-1-acetamide obtained by de-protection of [(3S)-1-(2-amino-2-oxoethyl)hexahydro-2-oxo-1H-azepin-3-yl]-carbamic acid, 1,1-dimethylethyl ester with TFA, p-nitrophenyl chloroformate, diisopropylethyl amine, and 7-chloro-4-piperazinylquinoline are reacted to afford the product. LC-MS: 459 (M⁺+1). ¹H NMR (CDCl$_3$) δ 8.68 (d, 1H), 8.0 (s, 1H), 7.90 (d, 1H), 7.40 (d, 1H), 6.78 (d, 1H), 5.98 (m, 2H), 5.25 (m, 1H), 4.65 (m, 1H), 4.0 (m, 2H), 3.65 (m, 5H), 3.30 (m, 1H), 3.18 (m, 4H), 2.0 (m, 2H), 1.80 (m, 2H), 1.50 (m, 2H).

Example 151

Preparation of 4-(7-Chloro-4-quinolinyl)-N-[(3S)-hexahydro-2-oxo-1-(3-pyridinylmethyl)-1H-azepin-3-yl]-1-piperazinecarboxamide

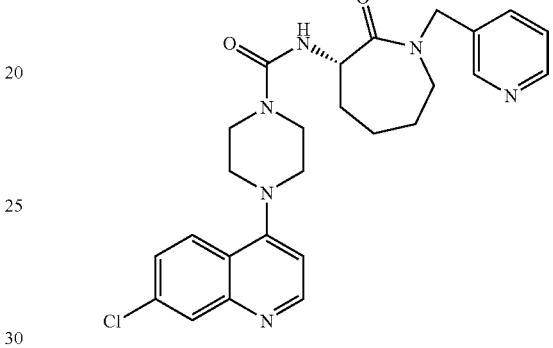

As described for example 78, (3R)-3-aminohexahydro-1-(3-pyridinylmethyl)-2H-azepin-2-one obtained by de-protection of [(3S)-hexahydro-2-oxo-1-(3-pyridinylmethyl)-1H-azepin-3-yl]-carbamic acid, 1,1-dimethylethyl ester with TFA, p-nitrophenyl chloroformate, diisopropylethyl amine, and 7-chloro-4-piperazinylquinoline are reacted to afford the product. LC-MS: 493 (M⁺+1). ¹H NMR (CDCl$_3$) δ 8.70 (d, 1H), 8.50 (m, 2H), 8.05 (s, 1H), 7.92 (d, 1H), 7.60 (d, 1H), 7.40 (d, 1H), 7.22 (m, 1H), 6.80 (m, 1H), 6.20 (m, 1H), 4.65 (m, 1H), 4.56 (m, 2H), 3.70 (m, 4H), 3.50 (m, 1H), 3.20 (m, 5H), 2.10 (m, 1H), 1.70–1.95 (m, 3H), 1.50 (m, 1H), 1.20 (m, 1H).

Example 152

Preparation of 4-(7-Chloro-4-quinolinyl)-N-[(3S)-hexahydro-2-oxo-1-(2-propenyl)-1H-azepin-3-yl]-1-piperazinecarboxamide

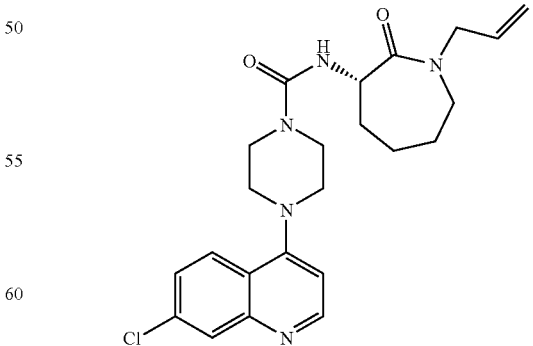

As described for example 78, (3R)-3-aminohexahydro-1-(2-propenyl)-2H-azepin-2-one obtained by de-protection of [(3S)-hexahydro-2-oxo-1-(2-propenyl)-1H-azepin-3-yl]-carbamic acid, 1,1-dimethylethyl ester with TFA, p-nitrophenyl chloroformate, diisopropylethyl amine, and 7-chloro-4-piperazinylquinoline are reacted to afford the product. LC-MS: 442 (M⁺+1). ¹H NMR (CDCl₃) δ 8.78 (d, 1H), 8.05 (s, 1H), 7.95 (d, 1H), 7.46 (d, 1H), 6.85 (d, 1H), 6.30 (m, 1H), 5.80 (m, 1H), 5.20 (m, 2H), 4.62 (m, 1H), 4.20 (m, 1H), 3.90 (m, 1H), 3.70 (m, 4H), 3.50 (m, 2H), 3.22 (m, 5H), 2.10 (m, 1H), 1.80–1.98 (m, 3H), 1.35–1.53 (m, 2H).

Example 153

Preparation of 4-(7-Chloro-4-quinolinyl)-N-[(3S)-1-(cyclopropylmethyl)hexahydro-2-oxo-1H-azepin-3-yl]-1-piperazinecarboxamide

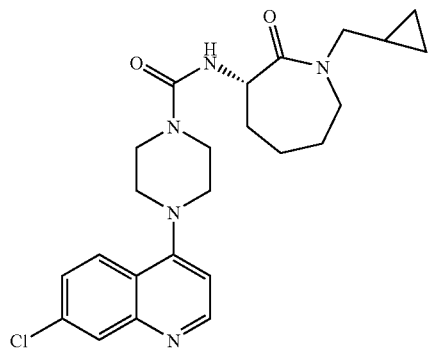

As described for example 78, (3R)-3-amino-1-(cyclopropylmethyl)hexahydro-2H-azepin-2-one obtained by de-protection of [(3S)-1-(cyclopropylmethyl)hexahydro-2-oxo-1H-azepin-3-yl]-carbamic acid, 1,1-dimethylethyl ester with TFA, p-nitrophenyl chloroformate, diisopropylethyl amine, and 7-chloro-4-piperazinylquinoline are reacted to afford the product. LC-MS: 456 (M⁺+1). ¹H NMR (CDCl₃) δ 8.78 (d, 1H), 8.05 (s, 1H), 7.95 (d, 1H), 7.46 (d, 1H), 6.85 (d, 1H), 6.30 (m, 1H), 4.62 (m, 1H), 3.70 (m, 4H), 3.61 (m, 1H), 3.46 (m, 2H), 3.26 (m, 5H), 2.10 (m, 1H), 1.80–2.00 (m, 3H), 1.56 (m, 2H), 0.96 (m, 1H).

Example 154

Preparation of 4-(7-Chloro-4-quinolinyl)-N-[(3S)-hexahydro-1-[(4-methoxyphenyl)methyl]-2-oxo-1H-azepin-3-yl]-1-piperazinecarboxamide

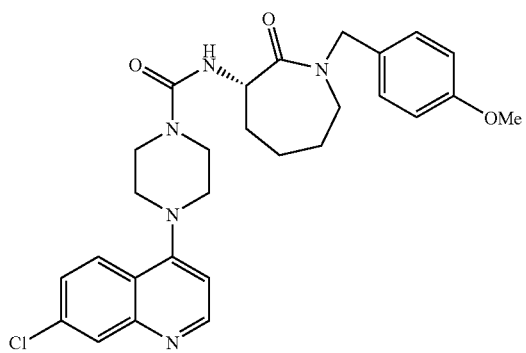

As described for example 78, (3R)-3-aminohexahydro-1-[(4-methoxyphenyl)methyl]-2H-azepin-2-one obtained by de-protection of [(3S)-hexahydro-1-[(4-methoxyphenyl)methyl]-2-oxo-1H-azepin-3-yl]-carbamic acid, 1,1-dimethylethyl ester with TFA, p-nitrophenyl chloroformate, diisopropylethyl amine, and 7-chloro-4-piperazinylquinoline are reacted to afford the product. LC-MS: 552 (M⁺+1). ¹H NMR (CDCl₃) δ 8.70 (d, 1H), 8.05 (s, 1H), 7.90 (d, 1H), 7.40 (d, 1H), 7.15 (d, 2H), 6.80 (m, 2H), 6.30 (m, 1H), 4.60 (m, 1H), 4.50 (m, 2H), 3.76 (s, 3H), 3.65 (m, 4H), 3.40 (m, 1H), 3.20 (m, 5H), 2.10 (m, 1H), 1.60–1.90 (m, 3H), 1.50 (m, 1H), 1.20 (m, 1H).

Example 155

Preparation of (3S)-[[[4-(7-Chloro-4-quinolinyl)-1-piperazinyl]carbonyl]amino]hexahydro-2-oxo-1H-azepine-1-acetic Acid, Ethyl Ester

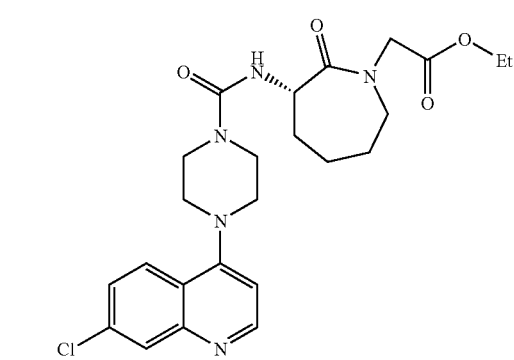

As described for example 78, (3R)-3-aminohexahydro-2-oxo-1H-azepine-1-acetic acid, ethyl ester obtained by de-protection of (3S)-3-[[(1,1-dimethylethoxy)carbonyl]amino]hexahydro-2-oxo-1H-azepine-1-acetic acid, ethyl ester with TFA, p-nitrophenyl chloroformate, diisopropylethyl amine, and 7-chloro-4-piperazinylquinoline are reacted to afford the product. LC-MS: 488 (M⁺+1). ¹H NMR (CDCl₃) δ 8.68 (d, 1H), 8.0 (s, 1H), 7.90 (d, 1H), 7.40 (d, 1H), 6.70 (d, 1H), 6.15 (d, 1H), 4.60 (m, 1H), 4.20 (m, 4H), 3.65 (m, 5H), 3.20 (m, 5H), 2.10 (m, 1H), 1.96 (m, 1H), 1.80 (m, 2H), 1.60 (m, 2H), 1.25 (t, 3H).

Example 156

Preparation of 4-(7-Chloro-4-quinolinyl)-N-[(3S)-hexahydro-1-[3-(4-morpholinyl)propyl]-2-oxo-1H-azepin-3-yl]-1-piperazinecarboxamide

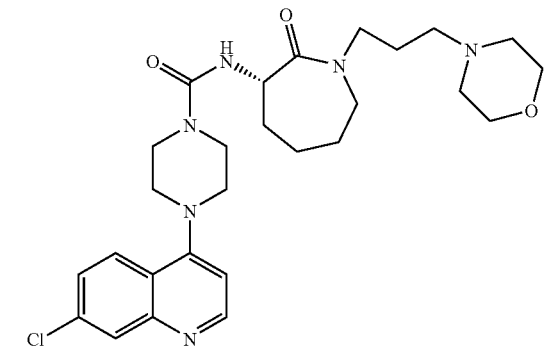

As described for example 78, (3R)-3-aminohexahydro-1-[3-(4-morpholinyl)propyl]-2H-azepin-2-one obtained by de-protection of [(3S)-hexahydro-1-[3-(4-morpholinyl)propyl]-2-oxo-1H-azepin-3-yl]-carbamic acid, 1,1-dimethylethyl ester with TFA, p-nitrophenyl chloroformate, diisopropylethyl amine, and 7-chloro-4-piperazinylquinoline are reacted to afford the product. LC-MS: 529 (M++1). $^1$H NMR (CDCl$_3$) δ 8.68 (d, 1H), 8.0 (s, 1H), 7.90 (d, 1H), 7.40 (d, 1H), 6.78 (d, 1H), 6.20 (d, 1H), 4.50 (m, 1H), 3.60 (m, 7H), 3.50 (m, 3H), 3.30 (m, 1H), 3.10 (m, 5H), 2.30–2.50 (m, 6H), 2.05 (m, 1H), 1.90 (m, 1H), 1.60–1.80 (m, 4H), 1.25–1.40 (m, 2H).

Example 157

Preparation of 7-Chloro-4-(1-piperazinyl)-2-quinolinamine

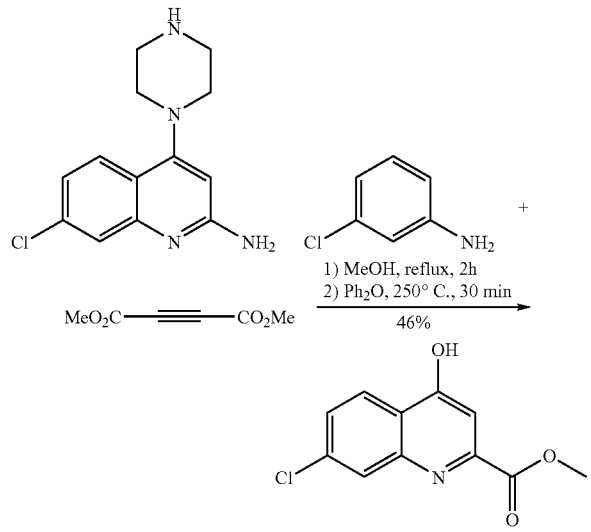

Preparation of 7-chloro-4-hydroxy-2-quinolinecarboxylic Acid Methyl Ester [1. Juan C. Jaen, et al, *J. Med. Chem.*, 1995, 38, 4439–4445. 2. WO 91/01973]:

To a stirred solution of 3-chloroaniline (40.8 g, 320 mmol) in MeOH (500 mL) at rt was added dimethyl acetylene dicarboxylate (50 g, 352 mmol). After addition, the reaction was kept at reflux for 2 h, then cooled to rt. After evaporating methanol in vacuo, the resulting crude adduct was dissolved in Ph$_2$O (160 mL), and was added dropwise to a hot solution of Ph$_2$O (800 mL) in a three-neck flask at 250° C. The reaction mixture was kept at 250° C. for an additional 30 min, and was cooled to rt. The reaction mixture was diluted with hexane, and the product precipitated. The crude mixture was collected by filtration (washed with hexane and ether). This mixture (78 g) was re-dissolved in pyridine (468 mL) (Note: the other solvent for re-crystallization is acetic acid, and the ratio of crude product to acetic acid is 1:6 based on weight), and kept at reflux for about 30 min. After cooling to rt, the desired product was collected by filtration (washed with ether). The solid was air dried overnight to give 35 g (46%) of 7-chloro-4-hydroxy-2-quinolinecarboxylic acid methyl ester. LC-MS: 237 (M++1). $^1$H NMR (DMSO-d$_6$): δ 3.98 (s, 3H), 6.6 (s, 1), 7.38 (d, 1H), 7.96 (s, 1H), 8.04 (d, 1), 12.1 (s, 1).

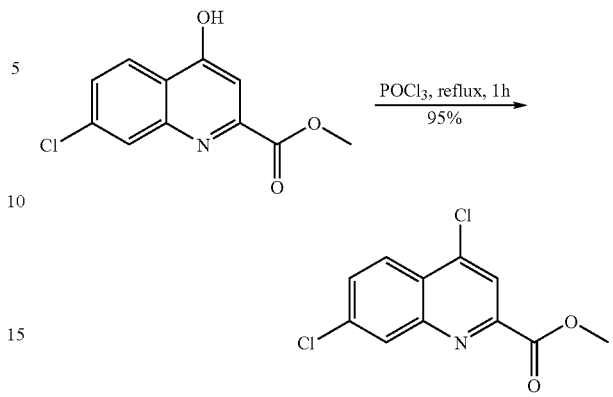

Preparation of 4,7-dichloro-2-quinolinecarboxylic acid methyl ester (D. J. Krogstad et al, *J. Hetero. Chem.*, 1997, 34, 315–320): 7-Chloro-4-hydroxy-2-quinolinecarboxylic acid methyl ester (76 g) was added to POCl$_3$ (100 mL) at rt, and heated at 140 degrees C. for 1 h, then cooled to rt. After the removal of excess POCl$_3$ in vacuo, cold 1 N NaOH solution was added to pH 8, and precipitated solid was triturated, washed with water and dried under vacuum to afford 78 g (95.2%) of 4,7-dichloro-2-quinolinecarboxylic acid methyl ester as an off-white powder. LC-MS, 255 (M++1). $^1$H NMR (DMSO-d$_6$): δ 3.95 (s, 3H), 7.91 (d, 1H), 8.22 (s, 1H), 8.26 (d, 1H), 8.33 (s, 1H).

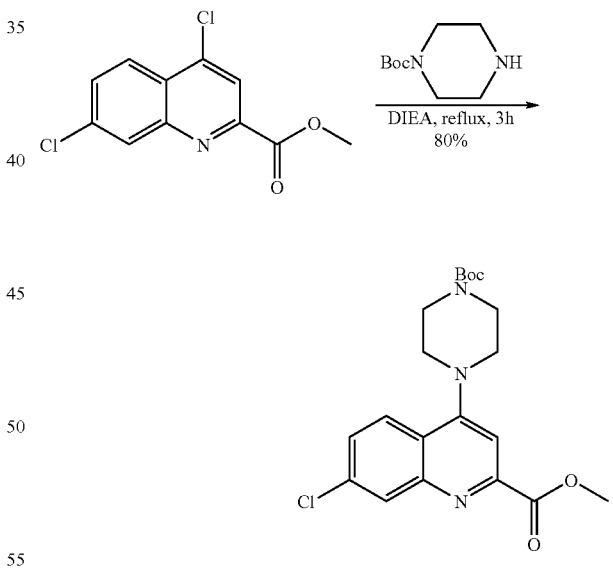

Preparation of 7-chloro-4-[4-[(1,1-dimethylethoxy)carbonyl]-1-piperazinyl]-2-quinolinecarboxylic acid methyl ester (D. J. Krogstad et al, *J. Hetero. Chem.*, 1997, 34, 315–320): The mixture of 4,7-dichloro-2-quinolinecarboxylic acid methyl ester (90.2 g, 379 mmol) and N-boc-piperazine (60.1 g, 387 mmol) in dry diisopropylethyl amine (300 mL) was kept at 140 degrees C. for 3 h. After the removal of diisopropylethyl amine in vacuo, ethyl ether was added to precipitate the product. The crude solid was collected by filtration and was purified by re-crystallization from EtOAc (500 mL) to afford 123 g (80%) of 7-chloro-4-[4-[(1,1-dimethylethoxy)carbonyl]-1-piperazinyl]-2-quinolinecarboxylic acid methyl ester as an off-white solid. $^1$H NMR (DMSO-d$_6$): δ 1.42 (s, 18H), 3.18 (m, 4H), 3.61 (m, 4H), 3.92 (s, 3H), 7.47 (s, 1H), 7.63 (d, 1H), 8.04 (d, 1H), 8.1 (s, 1H).

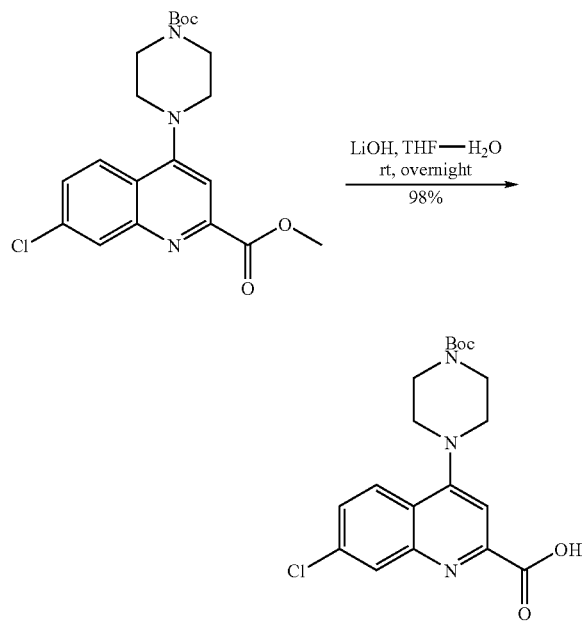

Preparation of 7-chloro-4-[4-[(1,1-dimethylethoxy)carbonyl]-1-piperazinyl]-2-quinolinecarboxylic acid To a stirred solution of 7-chloro-4-[4-[(1,1-dimethylethoxy)carbonyl]-1-piperazinyl]-2-quinolinecarboxylic acid methyl ester (100.4 g, 247 mmol) in THF (400 mL) was added LiOH.H$_2$O (15.6 g, 371 mmol) in water (400 mL) at rt. After stirring overnight, THF was removed in vacuo, and the resulting mixture was treated with 1 N HCl to pH 4. The solid precipitated, and was collected by filtration, washed with water and cold ether. The solid was dried under vacuum overnight to afford 94.7 g (98%) of the product as a pale yellow solid. $^1$H NMR (400 MHz, DMSO): δ 1.39 (s, 9H), 3.28 (m, 4H), 3.59 (m, 4H), 7.51 (s, 1H), 7.63 (d, 1H), 8.07 (d, 1H), 8.14 (s, 1H).

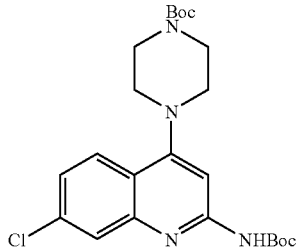

Preparation of 4-[7-chloro-2-[[(1,1-dimethylethoxy)carbonyl]amino]-4-quinolinyl]-1-piperazinecarboxylic acid-1,1-dimethylethyl ester [1) J. W. Gilman, et al, *Syn. Comm.*, 1993, 23, 335–341; 2) G. M. Coppola et al, *Bioorg. Med. Chem. Lett.*, 2000, 10, 1555-1558]: A mixture of 7-chloro-4-[4-[(1,1-dimethylethoxy)carbonyl]-1-piperazinyl]-2-quinolinecarboxylic acid (41 g, 105 mmol) proton-sponge (45 g, 210 mmol), diphenylphosphoryl azide (DPPA) (37.7 g, 137 mmol), dry diisopropylethyl amine (DIEA) (17.7 g, 137 mmol) in t-BuOH (250 mL) was kept at reflux for 3 h, then cooled to rt. After the removal of the solvents in vacuo, the crude product was loaded onto silica-gel column, and washed with hexane-EtOAc (9:1) to afford 46.2 g (95%) of the product as an off-white solid. $^1$H NMR (400 MHz, CDCl$_3$): δ 1.44 (s, 9H), 1.51 (s, 9H), is 3.19 (m, 4H), 3.66 (m, 4H), 7.27 (d, 1H), 7.51 (s, 1H), 7.72 (s, 1H), 7.83 (d, 1H).

Preparation of 7-chloro-4-(1-piperazinyl)-2-quinolinamine: To a stirred sloution of 4-[7-chloro-2-[[(1,1-dimethylethoxy)carbonyl]amino]-4-quinolinyl]-1-piperazinecarboxylic acid, 1,1-dimethylethyl ester (2 g, 4.33 mmol) in CH$_2$Cl$_2$ (30 mL) was added TFA (4 mL) at rt. The reaction mixture was kept at reflux for 4 h, then cooled to rt. After removal of the solvent and excess TFA, the mixture was diluted with CH$_2$Cl$_2$, and treated with NaOH (10%) to pH 12. The mixture was extracted with CH$_2$Cl$_2$, washed with brine, and dried over Na$_2$SO$_4$. Concentration in vacuo afforded the product as a free base (1.13 g, 98%). LC-MS: 262 (M$^+$+1). $^1$H NMR (DMSO-d$_6$): 62.90 (s, 8H), 6.20 (s, 1H), 6.4 (s, 2H) 7.08 (d, 1H), 7.35 (s, 1H), 7.68 (d, 1H).

Example 158

Preparation of 7-Chloro-4-[4-[(4-fluorophenyl)acetyl]-1-piperazinyl]-2-quinolinamine

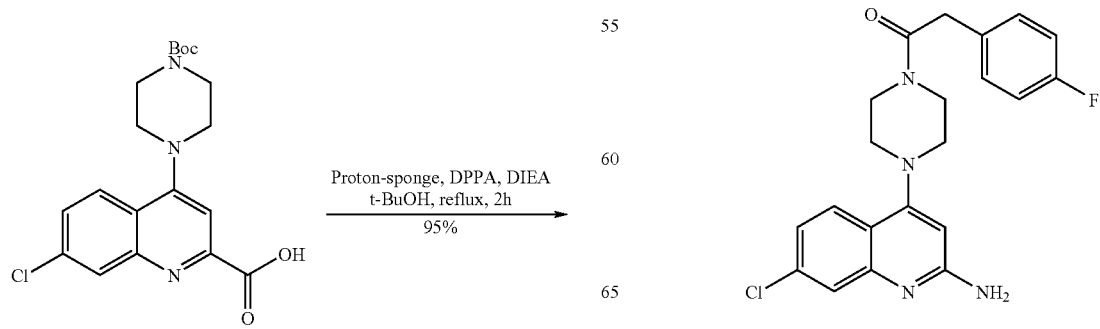

To a stirred solution of 4,7-dichloro-2-quinolinamine (50 mg, 0.19 mmol) in DSMO (10 mL) was added 4-fluorobenzeneacetic acid (32 mg, 0.2 mmol) followed by HATU (94 mg, 0.25 mmol) and triethylamine (0.053 ml, 0.38 mmol) at rt. After stirring overnight, the reaction mixture was poured into ice-water (10 mL), extracted with EtOAc, washed with brine, and dried over $Na_2SO_4$. Concentration in vacuo followed by preemptive TLC afforded the product. LC-MS: 398 ($M^+$+1)). $^1$H NMR (DMSO-$d_6$): 62.9–3.05 (m, 4H), 3.68–3.85 (m, 6H), 6.22 (s, 1H), 6.45 (s, 2H), 7.05–7.2 (m, 3H), 7.22–7.33 (m, 2H), 7.35–7.4 (m, 1H), 7.7–7.8 (d, 1H).

Example 159

Preparation of 4-(2-Amino-7-chloro-4-quinolinyl)-N-(2,3,4,5,6-pentafluorophenyl)-1-piperazinecarboxamide

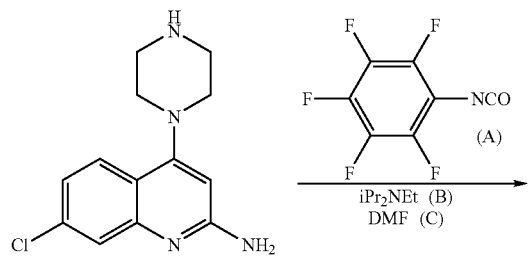

To a mixture of pentafluorophenyl isocyanate (0.03 mL, 0.23 mmol) and $iPr_2NEt$ (0.05 mL, 0.29 mmol) in DMF (1 mL), a hot solution of 7-chloro-4-(1-piperazinyl)-2-quinolinamine (50 mg, 0.19 mmol) in DMF (2 mL) was added. After stirring at rt overnight, the mixture was poured into ice-water. The solid was collected by filtration and re-dissolved in $CH_2Cl_2$-MeOH, then purified by preparative TLC ($CH_2Cl_2$-MeOH, 9:1) affording the product as a light yellow solid. LC-MS: 472 ($M^+$+1). $^1$HNMR (DMSO-$d_6$) δ 3.02 (br.s, 4H), 3.70 (br.s, 4H), 6.28 (s, 1H), 6.50 (s, 2H), 7.10 (d, 1H), 7.39 (s, 1H), 7.78 (d, 1H), 8.80 (s, 1H).

Example 160

Preparation of 4-(2-Amino-7-chloro-4-quinolinyl)-N-(2-methoxyphenyl)-1-piperazinecarboxamide

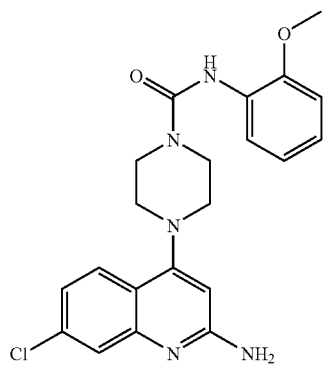

As described for example 159, 7-chloro-4-(1-piperazinyl)-2-quinolinamine, 1-isocyanato-2-methoxy-benzene, and diisopropylethyl amine, are reacted to give the title product. LC-MS: 411 ($M^+$+1). $^1$H NMR (CDCl$_3$) δ 3.15–3.25 (m, 4H), 3.7–3.85 (m, 4H), 3.9 (s, 3H), 4.6–4.8 (s, 2H), 6.2 (s, 1H), 6.86–6.9 (m, 1H), 6.94–7.02 (m, 2H), 7.16–7.21 (m, 2H), 7.62–7.65 (d, 1H), 7.74–7.78 (d, 1H), 8.14–8.19 (m, 1H).

Example 161

Preparation of 4-(2-Amino-7-chloro-4-quinolinyl)-N-ethyl-1-piperazinecarboxamide

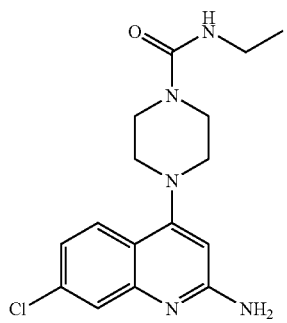

As described for example 159, 7-chloro-4-(1-piperazinyl)-2-quinolinamine, ethylisocyanate, and diisopropylethyl amine, are reacted to give the product. LC-MS: 333 ($M^+$+1). $^1$H NMR (DMSO-$d_6$): 61.0 (t, 3H), 2.8–3.0 (m, 4H), 3.0–3.14 (q, 2H), 3.45–3.6 (m, 4H), 6.25 (s, 1H), 6.4–6.55 (s, 2H), 6.55–6.65 (m, 1H), 7.1–7.2 (m, 1H), 7.35–7.4 (m, 1H), 7.7–7.8 (d, 1H).

Example 162

Preparation of 4-(2-Amino-7-chloro-4-quinolinyl)-N-(4-methylphenyl)-1-piperazinecarboxamide

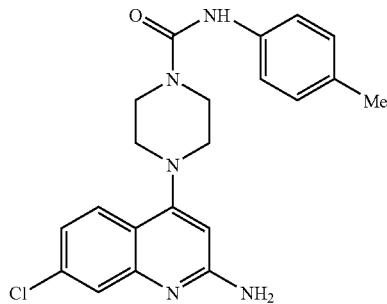

As described for example 159, 7-chloro-4-(1-piperazinyl)-2-quinolinamine, 4-methylphenyl isocyanate, and diisopropylethyl amine, are reacted to give the product as a white solid. LC-MS: 395 (M$^+$+1). $^1$H NMR (DMSO-d$_6$) δ 2.25 (s, 3H), 3.0–3.1 (m, 4H), 3.64–3.75 (m, 4H), 6.3 (s, 1H), 6.5 (s, 2H), 7.0–7.1 (d, 2H), 7.1–7.2 (m, 1H), 7.3–7.45 (m, 3H), 7.75–7.85 (d, 1H), 8.5–8.6 (s, 1H).

4-[7-Chloro-2-[[[(4-methylphenyl)amino]carbonyl]amino]-4-quinolinyl]-N-(4-methylphenyl)-1-piperazinecarboxamide

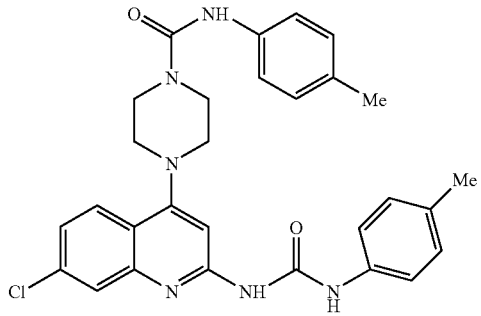

The title compound was obtained as product during the preparation of example 162. LC-MS: 529 (M+1). $^1$H NMR (DMSO-d$_6$) δ 2.18–2.35 (d, 6H), 3.1–3.3 (m, 4H), 3.6–3.8 (m, 4H), 6.8–6.9 (s, 1H), 7.0–7.1 (d, 2H), 7.1–7.2 (d, 2H), 7.3–7.48 (m, 3H), 7.55–7.64 (d, 2H), 7.9–8.0 (m, 2H), 8.5–8.6 (s, 1H), 9.8–9.9 (s, H), 11.62–11.69 (s, 1H).

Example 163

Preparation of 4-(2-Amino-7-chloro-4-quinolinyl)-N-tricyclo[3.3.1.1$^{3,7}$]dec-2-yl-1-piperazinecarboxamide

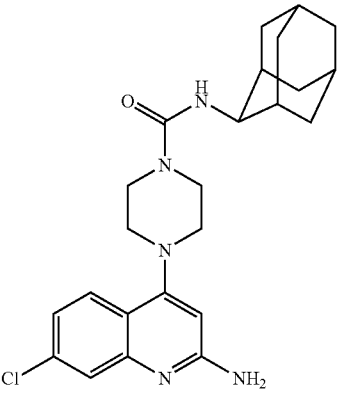

As described for example 159, 7-chloro-4-(1-piperazinyl)-2-quinolinamine, 1-admantyl isocyanate, and diisopropylethyl amine, are reacted to give the product. LC-MS: 440 (M+1). $^1$H NMR (DMSO-d$_6$) δ 1.60, 1.95 and 2.11 (each s, 14H), 2.95 (br.s, 4H), 3.49 (m, 4H), 5.25 (m, 2H), 6.25 (s, 1H), 6.45 (br.s, 2H), 7.10 (dd, 1H), 7.38 (d, 1H), 7.74 (d, 1H).

Example 164

Preparation of 4-(2-amino-7-chloro-4-quinolinyl)-N-(1,2-dihydro-2-oxo-3-pyridinyl)-1-piperazinecarboxamide

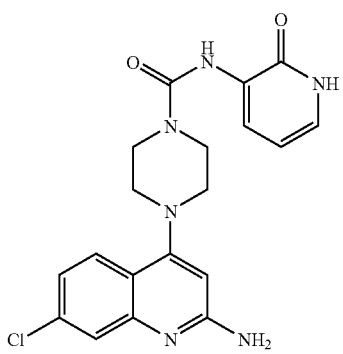

Preparation of 3-isocyanato-2(1H)-pyridinone: To a solution of 3-amino-pyridone (220 mg, 2 mmol) in 1,4-dioxane (20 mL) was added diphosgene (0.363 mL) at 0° C. After addition, the reaction mixture was stirred at rt for 2.5 h, and the precipitate was formed. The solid was filtered, washed with Et$_2$O, dried in vacuo to afford the isocyanate (192 mg).

Preparation of 4-(2-amino-7-chloro-4-quinolinyl)-N-(1,2-dihydro-2-oxo-3-pyridinyl) 1-piperazinecarboxamide: As described example 159, 7-chloro-4-(1-piperazinyl)-2-quinolinamine, 3-isocyanato-2(1H)-pyridinone, and diisopropylethyl amine, are reacted to give the title product as a white solid. LC-MS: 399 (M⁺+1). ¹H NMR (DMSO-d₆) δ 7.95 (m, 2H), 7.76 (d, 1H), 7.40 (s, 1H), 7.12 (m, 1H), 7.0 (d, 1H), 6.45 (m, 2H), 6.25 (s, 1H), 6.22 (m, 1H), 3.75 (m, 4H), 3.10 (m, 4H).

Example 165

Preparation of 4-(2-Amino-7-chloro-4-quinolinyl)-N-cyclohexyl-1-piperazinecarbothioamide

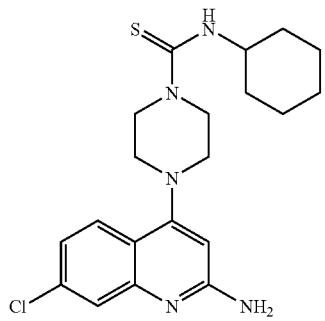

As described for example 159, 7-chloro-4-(1-piperazinyl)-2-quinolinamine, hexyl thioisocyanate, and diisopropylethyl amine, are reacted to give the product. LC-MS: 403 (M+1). ¹H NMR (DMSO-d₆) δ 1.0–1.4 (m, 5H), 1.5–1.8 (m, 3H), 1.8–2.0 (m, 2H), 2.9–3.1 (m, 4H), 3.85–4.05 (m, 4H), 4.1–4.25 (m, 1H), 6.2–6.26 (s, 1H), 6.36–6.52 (s, 2H), 7.04–7.14 (m, 1H), 7.32–7.44 (m, 2H), 7.7–7.78 (d, 1H).

Example 166

Preparation of 4-(2-Amino-7-chloro-4-quinolinyl)-N-(2,2,2-trifluoroethyl)-1-piperazinecarbothioamide

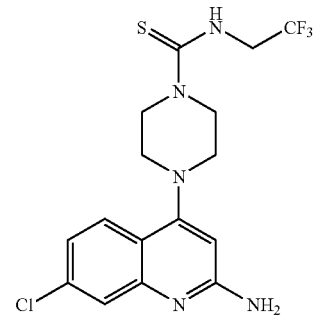

As described for example 159, 7-chloro-4-(1-piperazinyl)-2-quinolinamine, 1,1,1-trifluoro-2-isothiocyanato-ethane, and diisopropylethyl amine, are reacted to give the product. LC-MS: 466 (M⁺+1). ¹H NMR (DMSO-TFA-d₆) δ 1.0–1.3 (m, 1H), 3.0–3.14 (d, 1H), 3.18–3.38 (m, 6), 3.38–3.7 (m, 7H), 4.6–4.8 (m, 1H), 6.2–6.4 (s, 1H), 6.7–7.0 (m, 1H), 7.28–7.44 (m, 1H), 7.6–7.7 (s, 1H), 7.8–8.0 (m, 1H), 8.1–8.2 (m, 1H).

Example 167

Preparation of 4-(2-Amino-7-chloro-4-quinolinyl)-N-(4-fluorophenyl)-1-piperazinecarbothioamide

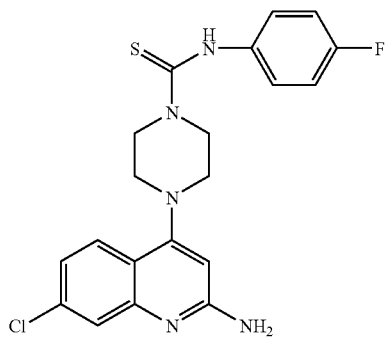

As described for example 159, 7-chloro-4-(1-piperazinyl)-2-quinolinamine, 4-fluorophenyl isothiocyanate, and diisopropylethyl amine, are reacted to give the product as a white solid. LC-MS: 416 (M⁺+1). ¹H NMR (DMSO-d₆) δ 3.10 (br.s, 4H), 4.15 (br.s, 4H), 6.20 (s, 1H), 6.45 (br.s, 2H), 7.10 (m, 3H), 7.30 (m, 2H), 7.40 (s, 1H), 7.80 (d, 1H), 9.42 (br.s, 1H).

Example 168

Preparation of [[[4-(2-Amino-7-chloro-4-quinolinyl)-1-piperazinyl]carbonothioyl]amino]-acetic acid-ethyl ester

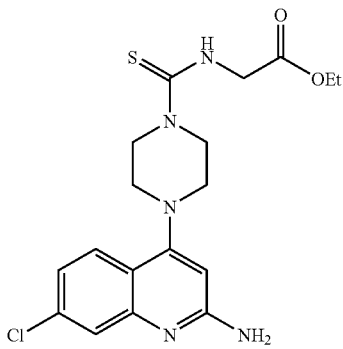

As described for example 159, 7-chloro-4-(1-piperazinyl)-2-quinolinamine, isothiocyanato-acetic acid-ethy ester, and diisopropylethyl amine, are reacted to give the product as a white solid. LC-MS: 407 (M⁺+1). ¹H NMR (DMSO-d₆): δ 1.16 (t, 3H), 3.05 (br.s, 4H), 4.01 (br.s, 4H), 4.06 (q, 2H), 4.20 (d, 2H), 6.24 (s, 1H), 6.47 (br.s, 2H), 7.08 (dd, 1H), 7.36 (d, 1H), 7.76 (d, 1H), 8.23 (dd, 1H).

Example 169

Preparation of (2S)-2-[[[4-(2-Amino-7-chloro-4-quinolinyl)-1-piperazinyl]carbonyl]amino]-propanoic acid-methyl Ester

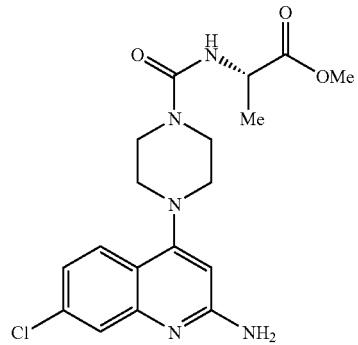

As described example 159, 7-chloro-4-(1-piperazinyl)-2-quinolinamine, 2-isocyanato-propanic acid-methyl ester, and diisopropylethyl amine, are reacted to give the product as a white solid. LC-MS: 392 (M$^+$+1). $^1$H NMR (DMSO-d$_6$) δ 1.30 (d, 3H), 2.96 (br.s, 4H), 3.55 (m, 4H), 3.61 (s, 3H), 4.16 (m, 1H), 6.26 (s, 1H), 6.45 (br.s, 2H), 6.90 (d, 1H), 7.10 (dd, 1H), 7.38 (d, 1H), 7.75 (d, 1H).

Example 170

Preparation of 4-(2-Amino-7-chloro-4-quinolinyl)-N-[(1S)-2-[(4-fluorophenyl)amino]-1-methyl-2-oxoethyl]-1-piperazinecarboxamide

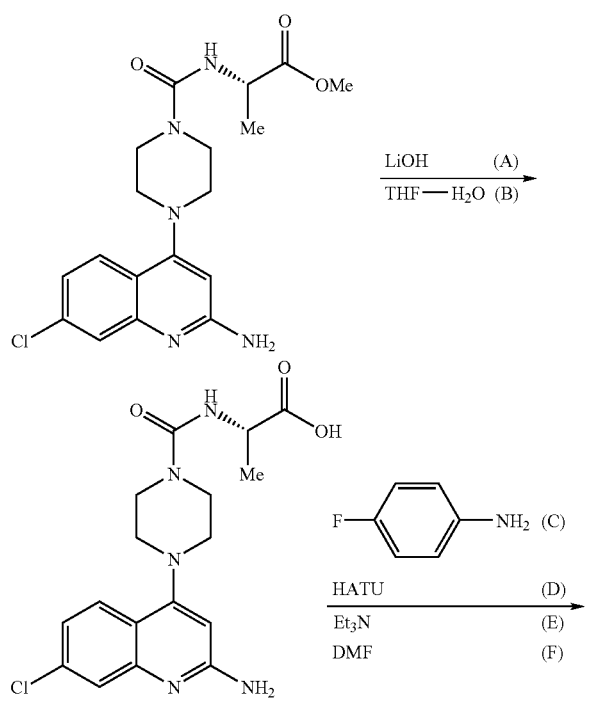

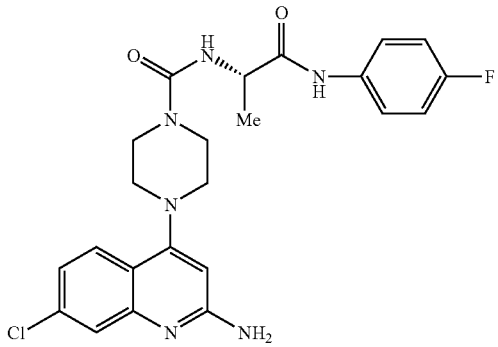

Preparation of (2S)-2-[[[4-(2-amino-7-chloro-4-quinolinyl)-1-piperazinyl]carbonyl]amino]propanoic acid: A mixture of (2S)-2-[[[4-(2-amino-7-chloro-4-quinolinyl)-1-piperazinyl]carbonyl]amino]-propanoic acid-methyl ester (~50 mg, 0.13 mmol), LiOH (100 mg) in THF-H$_2$O (5 mL, 5:1) was stirred at rt for 3 h. The mixture was diluted with H$_2$O, and acidified with 1.0 N HCl to pH~5. The crude acid was obtained as a white solid by filtration.

Preparation of 4-(2-amino-7-chloro-4-quinolinyl)-N-[(1S)-2-[(4-fluorophenyl)amino]-1-methyl-2-oxoethyl]-1-piperazinecarboxamide: To a solution of (2S)-2-[[[4-(2-amino-7-chloro-4-quinolinyl)-1-piperazinyl]carbonyl]amino]-propanoic acid (~30 mg), 4-fluoroanaline (0.03 mL, 0.32 mmol), Et$_3$N (0.14 mL, 0.35 mmol) in DMF (2 mL) was added HATU (133 mg, 0.35 mmol) at rt. After stirring at rt overnight, the reaction mixture was poured into ice-water. The crude solid was obtained by filtration and re-dissolved in CH$_2$Cl$_2$-MeOH, dried over Na$_2$SO$_4$. Concentration in vacuo followed by preparative TLC(CH$_2$Cl$_2$-MeOH-Et$_3$N, 9:1:1%) afforded the title product as a light yellow powder. LC-MS: 471 (M$^+$+1). $^1$H NMR (DMSO-d$_6$): δ 1.30 (d, 3H), 3.00 (br.s, 4H), 3.58 (m, 4H), 4.28 (m, 1H), 6.26 (s, 1H), 6.60 (br.s, 2H), 6.30 (d, 1H), 7.16 (m, 3H), 7.40 (d, 1H), 7.63 (dd, 2H), 7.75 (d, 1H).

Example 171

Preparation of 4-(2-Amino-7-chloro-4-quinolinyl)-N-[2-[methyl(phenylmethyl)amino]-2-oxoethyl]-1-piperazinecarboxamide

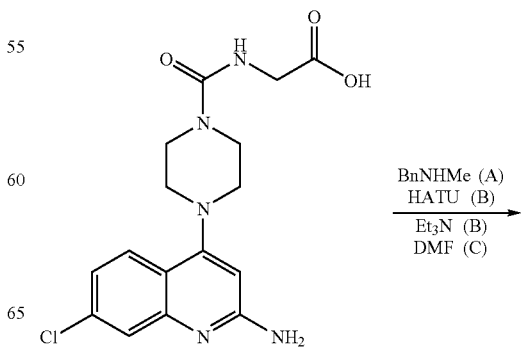

-continued

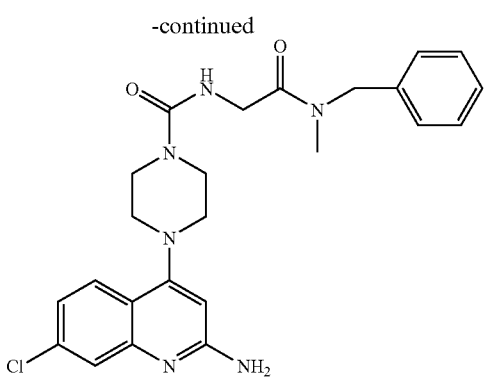

Preparation of [[[4-(2-amino-7-chloro-4-quinolinyl)-1-piperazinyl]carbonyl]amino]-acetic acid: As described example 159, 7-chloro-4-(1-piperazinyl)-2-quinolinamine (1.5 g, 5.7 mmol), isocyanato-acetic acid-ethy ester (0.7 mL, 6.3 mmol) and diisopropylethyl amine (1.5 mL, 8.6 mmol) are reacted to give [[[4-(2-amino-7-chloro-4-quinolinyl)-1-piperazinyl]carbonyl]amino]-acetic acid-ethyl ester the product as a white solid (990 mg, 40%). A mixture of the ester (990 mg), LiOH.H$_2$O (1 g) in THF-H$_2$O (5:1, 45 mL) was stirred at rt overnight, then acidified with 1.0 N HC (aq.) to pH to 4–5. After the removal of THF in vacuo, crude product precipitated. 760 mg (76%) of the acid was obtained after drying under vacuum for 3 h. LC-MS: 363 (M$^+$+1).

Preparation of 4-(2-amino-7-chloro-4-quinolinyl)-N-[2-[methyl(phenylmethyl)amino]-2-oxoethyl]-1-piperazinecarboxamide: To a mixture of [[[4-(2-amino-7-chloro-4-quinolinyl)-1-piperazinyl]carbonyl]amino]-acetic acid (50 mg, 0.14 mmol), N-methylbenzylamine (0.022 mL, 0.17 mmol), iPr$_2$NEt (0.07 mL, 0.50 mmol) in DMF (3 mL) was added HATU (68 mg, 0.18 mmol) and stirred at rt overnight. The reaction mixture was poured into ice-water, and the solid was collected by filtration. The solid was re-dissolved in CH$_2$Cl$_2$ and purified by preparative TLC (CH$_2$Cl$_2$-MeOH-Hexane, 8:2:2) affording the product as a light yellow powder. LC-MS: 467 (M$^+$+1). $^1$H NMR (CDCl$_3$): δ 2.92 and 3.00 (each s, 3H), 3.05~3.12 (m, 4H), 3.62~3.72 (m, 4H), 4.12~4.20 (m, 2H), 4.52 and 4.62 (each s, 2H), 5.08 (br.s, 2H), 5.94 (m, 1H), 6.15 (m, 1H), 7.14~7.24 (m, 3H), 7.26~7.40 (m, 3H), 7.58~7.62 (m, 1H), 7.68~7.72 (m, 1H).

Exampl 172

Preparation of 4-(2-Amino-7-chloro-4-quinolinyl)-N-[2-[(4-fluorophenyl)amino]-2-oxoethyl]-1-piperazinecarboxamide

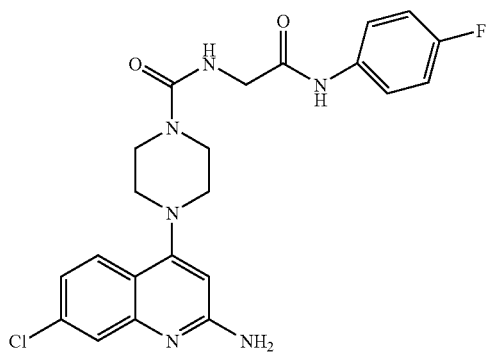

As described for example 171, [[[4-(2-amino-7-chloro-4-quinolinyl)-1-piperazinyl]carbonyl]amino]-acetic acid, 4-fluorophenylaniline, iPr$_2$NE, HATU, are reacted to afford the product. LC-MS: 456 (M$^+$+1). $^1$H NMR (CDCl$_3$): δ 3.05–3.3 (m, 4H), 3.6–3.8 (m, 4H), 4.0–4.2 (m, 2H), 4.65–4.9 (s, 2H), 6.1–6.2 (s, 1H), 7.0–7.1 (m, 2H), 7.2 (m, 1H), 7.3 (m, 2H), 7.6–7.7 (s, 1H), 7.7–7.8 (m, 1H), 8.6–8.7 (s, 1H).

Example 173

Preparation of 4-(2-Amino-7-chloro-4-quinolinyl)-N-[2-(dimethylamino)-2-oxoethyl]-1-piperazinecarboxamide

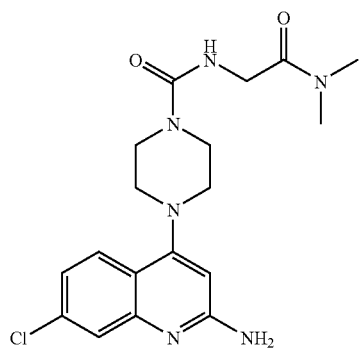

As described for example 171, [[[4-(2-amino-7-chloro-4-quinolinyl)-1-piperazinyl]carbonyl]amino]-acetic acid, di-methylamine, iPr$_2$NEt, and HATU are reacted to afford the product. LC-MS: 390 (M$^+$+1). $^1$H NMR (CDCl$_3$): δ 3.05 (s, 6H), 3.1–3.2 (m, 4H), 3.6–3.8 (m, 4H), 4.05–4.15 (d, 2H), 4.9–5.0 (s, H), 5.8 (m, 1H), 6.1–6.2 (s, 1H), 7.1–7.2 (m, 1H), 7.6 (m, 1H), 7.7–7.8 (m, 1H).

Example 174

Preparation of 4-(2-Amino-7-chloro-4-quinolinyl)-N-[2-(methylphenylamino)-2-oxoethyl]-1-piperazinecarboxamide

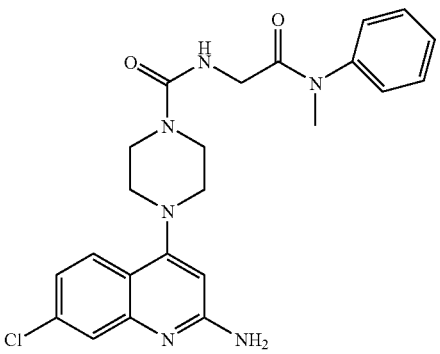

As described for example 171, [[[4-(2-amino-7-chloro-4-quinolinyl)-1-piperazinyl]carbonyl]amino]-acetic acid, N-methyl-benzenamine, iPr$_2$NEt, and HATU are reacted to afford the product. LC-MS: 452 (M$^+$+1). $^1$H NMR (CDCl$_3$):

δ 3.0–3.2 (m, 4H), 3.3 (s, 3H), 3.6–3.76 (m, 4H), 3.76–3.9 (d, 2H), 4.8–5.0 (s, 2H), 5.6–5.8 m, 1H), 6.1–6.2 (s, 1H), 7.13–7.18 (m, 1H), 7.2–7.25 (m, 2H), 7.36–7.48 (m, 3H), 7.6 (d, 1H), 7.68–7.72 (d, 1H).

Example 175

4-(2-Amino-7-chloro-4-quinolinyl)-1-piperazinecarboxylic Acid, 4-nitrophenyl Ester

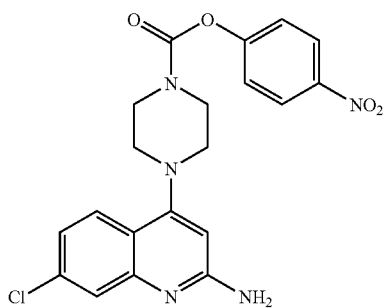

As described for example 78, 7-chloro-4-aminoqunoline, p-nitrophenyl chloroformate, diisopropylethyl amine, and 7-chloro-4-(1-piperazinyl)-2-quinolinamine are reacted to afford the product. LC-MS: 427 (M$^+$+1). $^1$H NMR (DMSO-d$_6$) δ 3.0–3.2 (m, 4H), 3.6–3.9 (m, 4H), 6.2–6.3 (s, 1H), 6.4–6.6 (s, H), 7.05–7.2 (m, 1H), 7.35–7.4 (m, 1H), 7.4–7.5 (d, 2H), 7.7–7.8 (d, 1H), 8.2–8.35 (d, 2H).

Example 176

Preparation of 2-[[[[4-(2-Amino-7-chloro-4-quinolinyl)-1-piperazinyl]carbonyl]oxy]imino]-cycloheptanecarboxylic acid, methyl ester

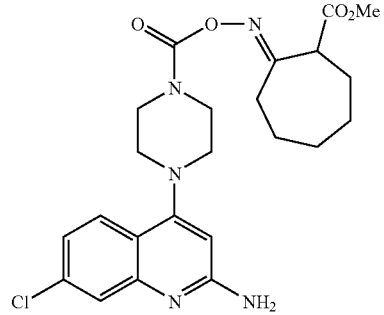

As described for 78, 2-methoxycarbonyl-cycloheptanone-oxime, 4-nitrophenyl chloroformate, diisopropyl(ethyl) amine, and 7-chloro-4-(1-piperazinyl)-2-quinolinamine are reacted to afford the product. LC-MS: 474 (M$^+$+1). $^1$H NMR (CDCl$_3$) δ 7.75 (d, 1H), 7.60 (s, 1H), 7.18 (d, 1H), 6.15 (s, 1H), 4.80 (s, 2H), 3.80 (m, 5H), 3.75 (s, 3H), 3.15 (m, 4H), 2.90 (m, 1H), 2.40 (m, 1H), 2.05 (m, 2H), 1.72 (m, 2H), 1.60 (m, 3H), 1.45 (m, 1H).

Example 177

Preparation of 2-[[[4-(2-Amino-7-chloro-4-quinolinyl)-1-piperazinyl]carbonyl]amino]-cycloheptanecarboxylic Acid, Methyl Ester

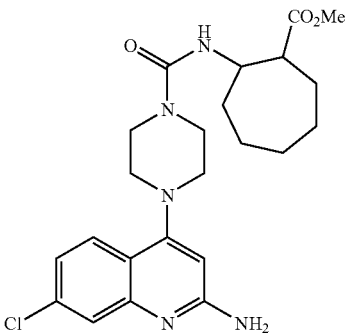

As described for 78, 2-methoxycarbonyl cycloheptyl amine, 4-nitrophenyl chloroformate, diisopropyl(ethyl) amine, and 7-chloro-4-(1-piperazinyl)-2-quinolinamine are reacted to afford the product. LC-MS: 460 (M$^+$+1). $^1$H NMR (CDCl$_3$) δ 7.72 (d, 1H), 7.60 (s, 1H), 7.18 (d, 1H), 6.15 (s, 1H), 5.50 (d, 1H), 4.70 (s, 2H), 4.15 (m, 1H), 3.70 (s, 3H), 3.60 (m, 4H), 3.10 (m, 4H), 2.95 (m, 1H), 2.00 (m, 1H), 1.85 (m, 3H), 1.65 (m, 5H), 1.45 (m, 1H).

Example 178

Preparation of 4-(2-Amino-7-chloro-4-quinolinyl)-N-[(6R)-hexahydro-5-oxo-1,4-thiazepin-6-yl]-1-piperazinecarbothioamide

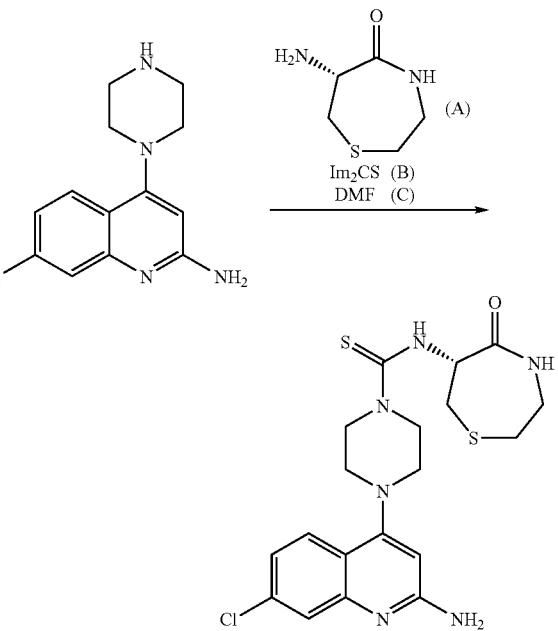

Preparation of (6R)-6-aminotetrahydro-1,4-thioazepin-5 (2H)-one (According to K. Soda, et al, *FEBS Letters*, 1984, 174, 76–79): To a mixture of L-cysteine methyl ester hydrochloride (5 g) in MeOH (30 mL) and Et₃N (7 mL) was added 2-chloroethylamine hydrochloride (5 g) in MeOH (10 mL) slowly at rt. After addition, the reaction mixture was kept at reflux for 16 h, then cooled to rt, and concentrated to give the crude product which was used for next step reaction without further purification.

Preparation of 4-(2-amino-7-chloro-4-quinolinyl)-N-[(6R)-hexahydro-5-oxo-1,4-thiazepin-6-yl]-1-piperazinecarbothioamide: To a solution of Im₂CS (41 mg, 0.29 mmol) in DMF (2 mL) was added slowly a suspension of (6R)-6-aminotetrahydro-1,4-thiazepin-5(2H)-one (34 mg, 0.23 mmol) in DMF (5 mL) at 0° C. After 3 h at rt, the mixture was added to a solution of 7-chloro-4-(1-piperazinyl)-2-quinolinamine (50 mg, 0.19 mmol) in DMF (2 mL). After stirring at rt overnight, the reaction mixture was concentrated in vacuo, and the product precipitated. The title product was collected by filtration, and washed with chilly DMF and CH₂Cl₂. LC-MS: 451 (M⁺+1). ¹H NMR (DMSO-d₆): δ 2.50~2.56 (m, 1H), 2.62~2.74 (m, 2H), 2.80~2.86 (m, 1H), 3.40~3.52 (m, 6H), 4.02 (br.s, 4H), 5.30 (m, 1H), 6.25 (s, 1H), 7.40 (dd, 1H), 7.65~7.70 (m, 2H), 7.95 (d, 1H), 8.15 (m, 1H).

Exampl 179

Preparation of 4-(2-Amino-7-chloro-4-quinolinyl)-N-[(6R)-hexahydro-5-oxo-1,4-thiazepin-6-yl]-1-piperazinecarboxamide

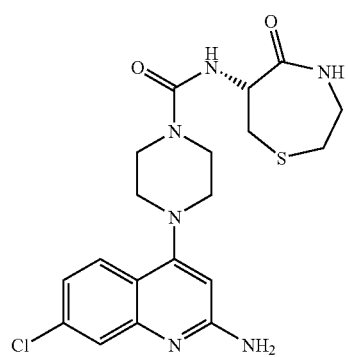

As described for example 78, (6S)-6-aminotetrahydro-1,4-thiazepin-5(2H)-one, p-nitrophenyl chloroformate, diisopropylethyl amine, and 7-chloro-4-(1-piperazinyl)-2-quinolinamine are reacted to afford the product. LC-MS: 434 (M⁺+1). ¹H NMR (CDCl₃) δ 2.55–2.95 (m, 4), 3.0–3.25 (m, 4H), 3.6–3.9 (m, 6H), 4.8–5.0 (m, 3H), 6.1–6.2 (s, 1H), 6.2–6.4 (m, 2H), 7.1–7.24 (m, 1H), 7.6 (s, 1H), 7.7–7.8 (m, 1H).

Example 180

Preparation of 4-(2-Amino-7-chloro-4-quinolinyl)-N-[(6R)-hexahydro-1,1-dioxido-5-oxo-1,4-thiazepin-6-yl]-1-piperazinecarboxamide

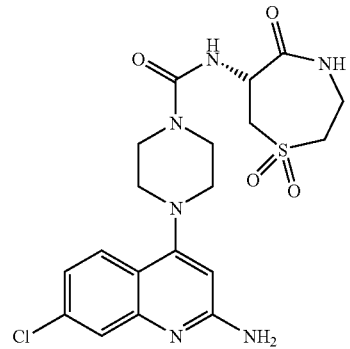

Preparation of [(6R)-hexahydro-1,1-dioxido-5-oxo-1,4-thioazepin-6-yl]-carbamic acid, 1,1-dimethylethyl ester To a solution of (6R)-6-aminotetrahydro-1,4-thiazepin-5(2H)-one (400 mg) in THF (50 mL) and brine (50 mL) was added (Boc)₂O (589 mg) at rt. After 12 h, the reaction mixture was extracted with EtOAc, washed with water, and dried over Na₂SO₄. Concentration in vacuo afforded the crude [(6S)-hexahydro-5-oxo-1,4-thioazepin-6-yl]-carbamic acid, 1,1-dimethylethyl ester. This crude product was re-dissolved in MeOH, and treated with Oxone (3.71 g) for 24 h. After the removal of most MeOH, the reaction mixture was diluted with water, and extracted with EtOAc, dried over Na₂SO₄. Concentration in vacuo gave the crude product which was used directly for next step reaction without further purification.

Preparation of 4-(2-amino-7-chloro-4-quinolinyl)-N-[(6R)-hexahydro-1,1-dioxido-5-oxo-1,4-thiazepin-6-yl]-1-piperazinecarboxamide: As described for example 78, (6R)-6-aminotetrahydro-1,4-thioazepin-5(2H)-one, 1,1-dioxide obtained by de-protection of [(6R)-hexahydro-1,1-dioxido-5-oxo-1,4-thiazepin-6-yl]-carbamic acid, 1,1-dimethylethyl ester with TFA, p-nitrophenyl chloroformate, diisopropylethyl amine, and 7-chloro-4-(1-piperazinyl)-2-quinolinamine are reacted to afford the product. LC-MS: 466 (M⁺+1). ¹H NMR (DMSO-TFA-d₃) δ 1.0–1.3 (m, 1H), 3.0–3.14 (d, 1H), 3.18–3.38 (m, 6), 3.38–3.7 (m, 7H), 4.6–4.8 (m, 1H), 6.2–6.4 (s, 1H), 6.7–7.0 (m, 1H), 7.28–7.44 (m, 1H), 7.6–7.7 (s, 1H), 7.8–8.0 (m, 1H), 8.1–8.2 (m, 1H).

Example 181

Preparation of 4-(2-Amino-7-chloro-4-quinolinyl)-N-[(3S)-2-oxopyrrolidinyl]-1-piperazinecarboxamide

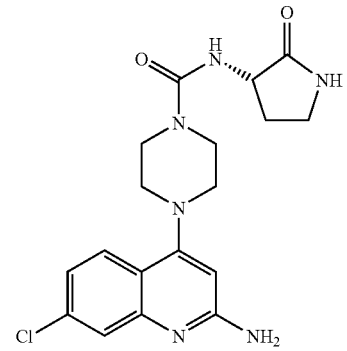

As described for example 78, (3S)-3-amino-2-pyrrolidinone, p-nitrophenyl chloroformate, diisopropylethyl amine, and 7-chloro-4-(1-piperazinyl)-2-quinolinamine are reacted to afford the product. LC-MS: 388 (M$^+$+1). $^1$H NMR (CDCl$_3$) δ 1.9–2.1 (m, 1), 2.8–2.9 (m, 1H), 3.0–3.2 (m, 4H), 3.35–3.5 (m, 2H), 3.6–3.8 (m, 4H), 4.2–4.4 (m, 1H), 4.7–5.0 (s, 2H), 5.3–5.4 (m, 1H), 5.7–5.85 (s, 1H), 6.1–6.2 (s, 1H), 7.1–7.2 (m, 1H), 7.6 (m, 1H), 7.7–7.8 (d, 1H).

Example 182

Preparation of 4-(2-Amino-7-chloro-4-quinolinyl)-N-[(3S)-2,3,4,5-tetrahydro-2-oxo-1H-1-benzazepin-3-yl]-1-piperazinecarboxamide

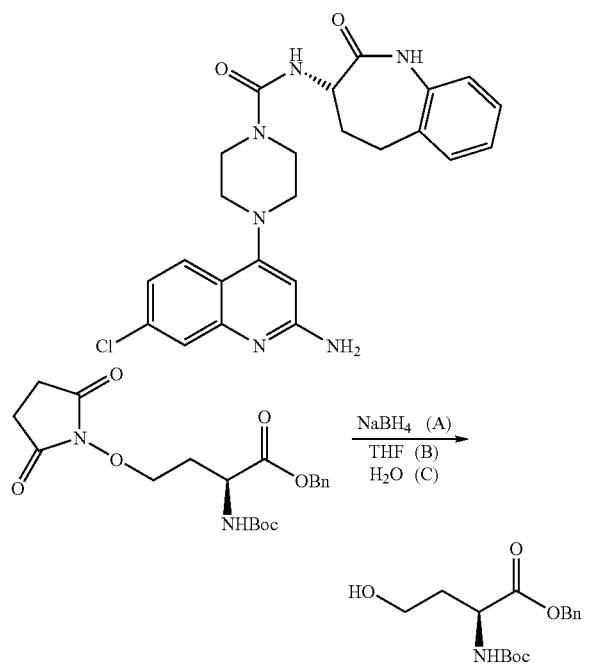

Preparation of (2S)-2-[[(1,1-dimethylethoxy)carbonyl]amino]-4-hydroxy-butanoic acid phenylmethyl ester (Richard F. W. Jackson, Rebecca J. Moore, and Charles S. Dexter, Jason Elliott and Charles E Mowbray, *J. Org. Chem.*, 63, 7875–7884(1998)): To a mixture of NaBH$_4$ (1.4 g, 37 mmol) in THF (80 mL) and H$_2$O (20 mL) was added a solution of (2S)-2-[[(1,1-dimethylethoxy)carbonyl]amino]-4-[(2,5-dioxo-1-pyrrolidinyl)oxy]-butanoic acid phenylmethyl ester (10 g, 24 mmol) in THF at 0° C. After 15 min, the reaction mixture was quenched with NH$_4$Cl (sat.), and extracted with EtOAc, dried over Na$_2$SO$_4$. Concentration in vacuo followed by flash chromatography (hexane-EtOAc, 7:3 to 6:4) afforded the product as colorless oil. LC-MS: 310 (M$^+$+1).

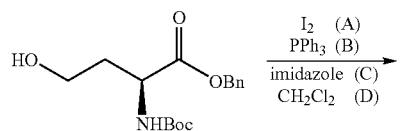

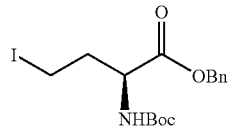

Preparation of (2S)-2-[[(1,1-dimethylethoxy)carbonyl]amino]-4-iodo-butanoic acid phenylmethyl ester: To a mixture of PPh$_3$ (4.19 g, 16 mmol) and imidazole (1.09 g, 16 mmol) in anhydrous CH$_2$Cl$_2$ (40 mL) was added slowly iodine (4.07 g, 16 mmol) at rt. After 5 min, a solution of (2S)-2-[[(1,1-dimethylethoxy)carbonyl]amino]-4-hydroxy-butanoic acid phenylmethyl ester (4.12 g, 13.3 mmol) in CH$_2$Cl$_2$ (20 mL) was added at 0° C. After 2 h at rt, the reaction mixture was filtered through a short silica gel column. The filtrate was concentrated in vacuo, and the resulting residue was purified by flash chromatography (hexane-EtOAc, 95:5 to 9:1) to afford the product as light yellow oil (3.22 g, 58%). $^1$H NMR (CDCl$_3$) δ 1.43 (s, 9H), 2.20 (m, 1H), 2.40 (m, 1H), 3.13 (m, 2H), 4.35 (br.s, 1H), 5.10 (br.s, 1H), 5.20 (AB, 2H), 7.30–7.40 (m, 5H). LC-MS: 420 (M$^+$+1).

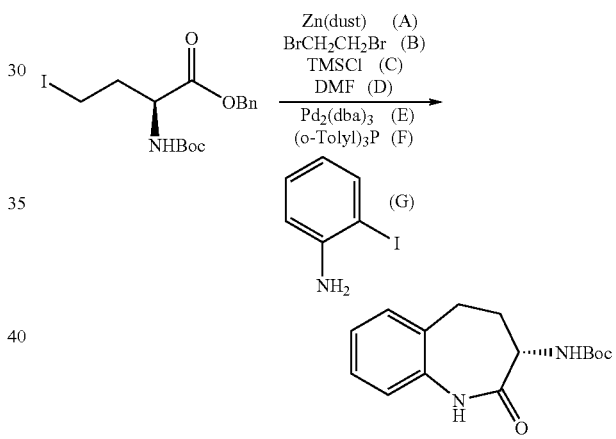

Preparation of [(3S)-2,3,4,5-tetrahydro-2-oxo-1H-1-benzazepin-3-yl]-carbamic acid-1,1-dimethylethyl ester: To a nitrogen-purged flask with Zinc dust (2.5 g, 37.08 mmol) was added dry DMF (3 mL) and 1,2-dibromoethane (0.16 mL, 1.85 mmol). The reaction mixture was heated at 60° C. for 30 min, then cooled to rt, and treated with trimethylsilyl chloride (0.05 mL, 0.39 mmol). After additional 30 min at rt, a solution of (2S)-2-[[(1,1-dimethylethoxy)carbonyl]amino]-4-iodo-butanoic acid phenylmethyl ester (2.62 g, 6.25 mmol) in DMF (3 mL) was added. The reaction mixture was heated to 35° C. for 30 min, then cooled to rt. To this reaction mixture, Pd$_2$(dba)$_3$ (110 mg, 0.12 mmol,), (o-Tolyl)$_3$P (144 mg, 0.47 mmol), and 2-iodoanaline (1.04 g, 4.74 mmol), were added sequentially. After 2 days at rt, the reaction mixture was quenched with brine, extracted with EtOAc, and dried over Na$_2$SO$_4$. Concentration in vacuo followed by flash chromatography (hexane-EtOAc, 9:1 to 8:2 to 7.5:2.5) afforded the product as a light yellow solid (260 mg, 15%). LC-MS: 277 (M$^+$+1). $^1$H NMR (DMSO-d$_6$) δ 1.40 (s, 9H), 2.00 (m, 1H), 2.70 (m, 2H), 2.90 (m, 2H), 4.30 (m, 1H), 5.50 (m, 1H), 7.00 (d, 1H), 7.15 (m, 1H), 7.25 (m, 2H), 8.00 (br.s, 1H).

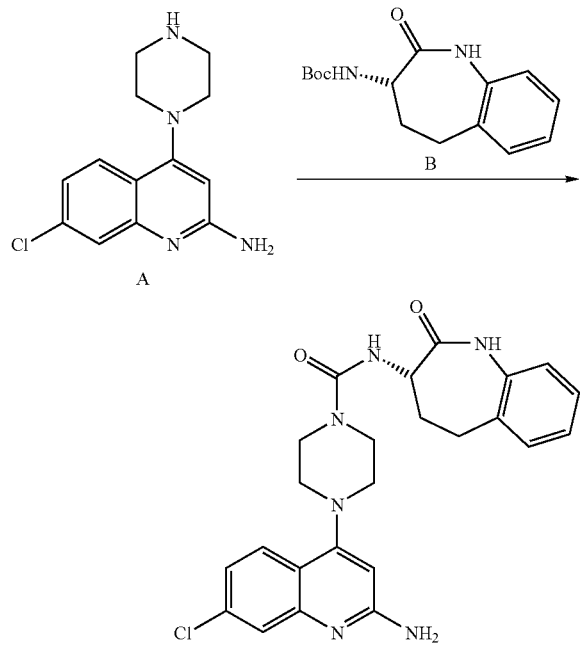

Preparation of 4-(2-amino-7-chloro-4-quinolinyl)-N-[(3S)-2,3,4,5-tetrahydro-2-oxo-1H-1-benzazepin-3-yl]-1-piperazinecarboxamide: As described for example 78, (3R)-3-amino-1,3,4,5-tetrahydro-2H-1-benzazepin-2-one obtained by the de-protection of [(3S)-2,3,4,5-tetrahydro-2-oxo-1H-1-benzazepin-3-yl]-carbamic acid-1,1-dimethylethyl ester with TFA, p-nitrophenyl chloroformate, diisopropylethyl amine, and 7-chloro-4-(1-piperazinyl)-2-quinolinamine are reacted to afford the product. $^1$H NMR (CDCl$_3$) δ 2.02 (m, 1H), 2.67 (m, 1H), 2.81 (m, 1H), 2.98 (m, 1H), 3.12 (m, 4H), 3.64 (m, 4H), 4.52 (m, 1H), 4.96 (br. s, 2H), 5.69 (d, 1H), 6.17 (s, 1H), 6.98 (d, 1H), 7.17–7.3 (m, 5H), 7.58 (br. s, 1H), 7.6 (s, 1H), 7.72 (d, 1H).

Example 183

Preparation of 4-(2-Amino-7-chloro-4-quinolinyl)-N-[(3S)-2,3,4,5-tetrahydro-1-methyl-2-oxo-1H-1-benzazepin-3-yl]-1-piperazinecarboxamide

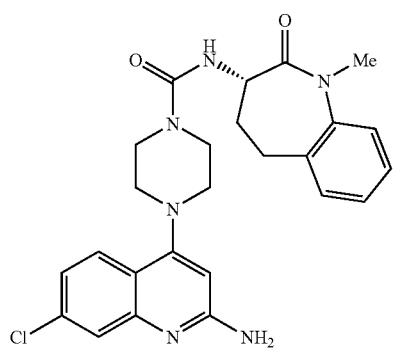

Preparation of [(3R)-2,3,4,5-tetrahydro-1-methyl-2-oxo-1H-1-benzazepin-3-yl]-carbamic acid-1,1-dimethylethyl ester As described for Example 146, [(3S)-2,3,4,5-tetrahydro-2-oxo-1H-1-benzazepin-3-yl]-carbamic acid-1,1-dimethylethyl ester, LiHDMS, MeI are reacted to afford the product.

Preparation of 4-(2-amino-7-chloro-4-quinolinyl)-N-[(3S)-2,3,4,5-tetrahydro-1-methyl-2-oxo-1H-1-benzazepin-3-yl]-1-piperazinecarboxamide: As described for example 78, (3R)-3-amino-1,3,4,5-tetrahydro-1-methyl-2H-1-benzazepin-2-one obtained by de-protection of [(3R)-2,3,4,5-tetrahydro-1-methyl-2-oxo-1H-1-benzazepin-3-yl]-carbamic acid-1,1-dimethylethyl ester with TFA, p-nitrophenyl chloroformate, diisopropylethyl amine, and 7-chloro-4-(1-piperazinyl)-2-quinolinamine are reacted to afford the product. LC-MS: 479 (M$^+$+1). $^1$H NMR (CDCl$_3$): δ 1.90–2.00 (m, 1H), 2.60~2.74 (m, 2H), 2.80~2.90 (m, 1H), 3.10 (dd, 4H), 3.42 (s, 3H), 3.62 (dd, 4H), 4.40~4.48 (br.s, 2H), 5.72 (d, 1H), 6.13 (s, 1H), 7.14~7.26 (m, 4H), 7.30 (m, 1H), 7.61 (d, 1H), 7.71 (d, 1H).

Example 184

Preparation of 4-(2-Amino-7-chloro-4-quinolinyl)-N-[(3S)-1,2,3,4-tetrahydro-2-oxoquinolinyl]-1-piperazinecarboxamide

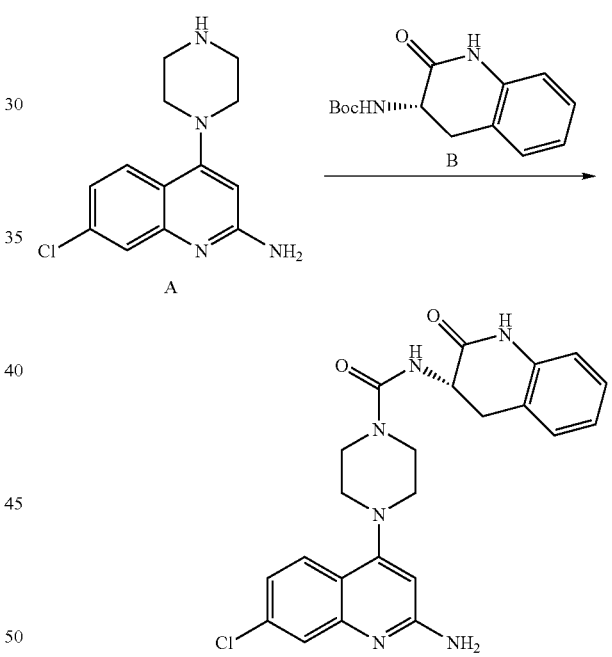

Preparation of [(3S)-1,2,3,4-tetrahydro-2-oxoquinolinyl]-carbamic acid-1,1-dimethylethyl ester: The intermediate was prepared in a similar manner as for [(3S)-2,3,4,5-tetrahydro-2-oxo-1H-1-benzazepin-3-yl]-carbamic acid-1,1-dimethylethyl ester in Example 182. LC-MS: 263 (M$^+$+1). $^1$H NMR (DMSO-d$_6$): δ 1.40 (s, 9H), 2.80~3.00 (m, 2H), 4.10 (m, 1H), 6.80 (m, 1H) 6.90 (m, 1H), 6.95 (m, 1H), 10.20 (s, 1H)

Preparation of 4-(2-amino-7-chloro-4-quinolinyl)-N-[(3S)-1,2,3,4-tetrahydro-2-oxoquinolinyl]-1-piperazinecarboxamide: As described for example 78, (3R)-3-amino-3,4-dihydro-2(1H)-quinolinone obtained by de-protection of (3R)-1,2,3,4-tetrahydro-2-oxoquinolinyl]-carbamic acid, 1,1-dimethylethyl ester with TFA, p-nitrophenyl chloroformate, diisopropylethyl amine, and 7-chloro-4-piperazinylquinoline are reacted to afford the product. $^1$H NMR (CDCl$_3$) δ 2.82 (t, 1H), 3.17 (m, 4H), 3.58 (dd, 1H), 3.67 (m, 4H), 4.53 (m, 1H), 4.92 (br. s, 2H), 5.84 (br. s, 1H), 6.19 (s, 1H), 6.8 (d, 2H), 7.05 (t, 1H), 7.2 (m, 2H), 7.61 (s, 1H), 7.77 (d, 1H), 7.83 (br. s, 1H).

Example 185

Preparation of 4-(2-Amino-7-chloro-4-quinolinyl)-N-cycloheptyl-1-piperazinecarboxamide

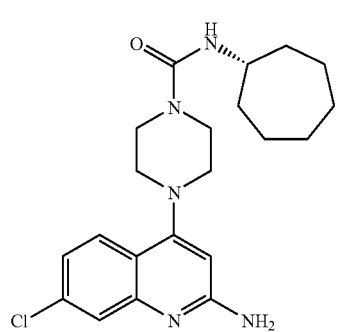

As described for example 78, cycloheptylamine, 4-nitrophenyl chloroformate, diisopropyl(ethyl)amine, and 7-chloro-4-(1-piperazinyl)-2-quinolinamine are reacted to afford the product as a light yellow solid. LC-MS: 402 (M$^+$+1). $^1$H NMR (CDCl$_3$) δ 7.75 (d, 1H), 7.62 (s, 1H), 7.15 (d, 1H), 6.15 (s, 1H), 4.78 (s, 2H), 4.40 (d, 1H), 3.90 (m, 1H), 3.60 (m, 4H), 3.10 (m, 4H), 1.95 (m, 2H) 1.40–1.65 (m, 10H).

Example 186

Preparation of 4-(2-Amino-7-chloro-4-quinolinyl)-N-(4-fluoro-3-methoxyphenyl)-1-piperazinecarboxamide

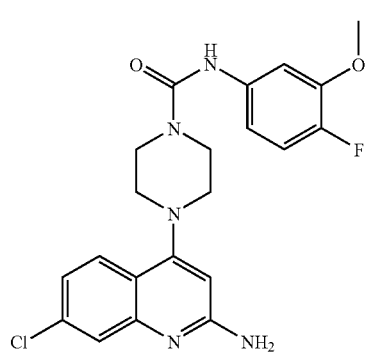

As described for example 78, 4-fluoro-3-methoxy-aniline, 4-nitrophenyl chloroformate, diisopropyl(ethyl)amine, and 7-chloro-4-(1-piperazinyl)-2-quinolinamine are reacted to afford the product as a light yellow solid. LC-MS: 430 (M$^+$+1). $^1$H NMR (CD$_3$OD) δ 8.25 (m, 2H), 7.82 (m, 1H), 7.45 (s, 1H), 7.40 (d, 2H), 7.20 (d, 1H), 6.40 (s, 1H), 3.95 (s, 3H), 3.80 (m, 4H), 3.25 (m, 4H).

Example 187

Preparation of 4-(2-Amino-7-chloro-4-quinolinyl)-N-(2-methoxy-3-pyridinyl)-1-piperazinecarboxamide

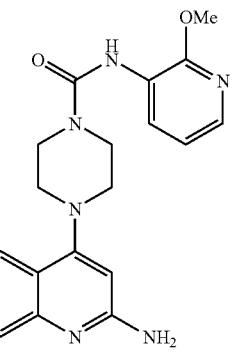

As described for example 78, 3-amino-2-methoxypyridine, 4-nitrophenyl chloroformate, diisopropyl(ethyl)amine, and 7-chloro-4-(1-piperazinyl)-2-quinolinamine are reacted to afford the product as a light yellow solid. LC-MS: 413 (M$^+$+1). $^1$H NMR (CDCl$_3$) δ 8.40 (d, 1H), 7.80 (m, 1H), 7.75 (d, 1H), 7.64 (d, 1H), 7.20 (dd, 1H), 7.05 (s, 1H), 6.90 (m, 1H), 6.20 (s, 1H), 4.80 (s, 1H), 4.00 (s, 3H), 3.80 (m, 4H), 3.25 (m, 4H).

Example 188

Preparation of 4-(2-Amino-7-chloro-4-quinolinyl)-N-(1,2-dihydro-1-methyl-2-oxo-3-pyridinyl)-1-piperazinecarboxamide

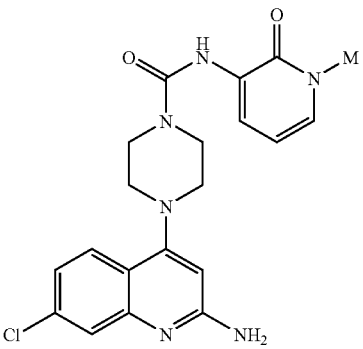

As described for example 78, 3-amino-1-methyl-2-pyridone, 4-nitrophenyl chloroformate, diisopropyl(ethyl)amine, and 7-chloro-4-(1-piperazinyl)-2-quinolinamine are reacted to afford the product. LC-MS: 413 (M$^+$+1). $^1$H NMR (CDCl$_3$) δ 8.15 (dd, 1H), 8.02 (s, 1H), 7.74 (d, 1H), 7.65 (s, 1H), 7.20 (dd, 1H), 6.95 (dd, 1H), 6.25 (m, 1H), 6.16 (s, 1H), 5.00 (s, 2H), 3.80 (m, 4H), 3.62 (s, 3H), 3.20 (m, 4H).

Example 189

Preparation of 4-(2-Amino-7-chloro-4-quinolinyl)-N-[(3R)-hexahydro-2-thioxo-1H-azepin-3-yl]-1-piperazinecarboxamide

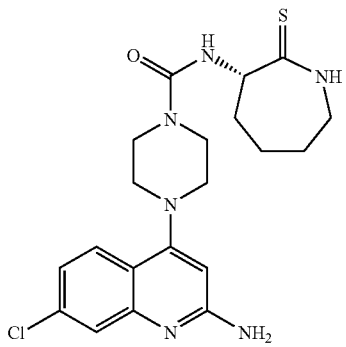

Preparation of [(3R)-hexahydro-2-thioxo-1H-azepin-3-yl]-carbamic acid, 1,1-dimethylethyl ester (3S)-Hxahydro-2-oxo-1H-azepin-3-yl]-carbamic acid, 1,1-dimethylethyl ester (1 g, 4.24 mmol) and Lawesson's reagent (2.3 g) were mixed with toluene (10 mL) at reflux for 1 h under nitrogen. After cooling to rt, the solvents was concentrated in vacuo and the resulting residue was purified by flash chromatography to yield the product.

Preparation of 4-(2-amino-7-chloro-4-quinolinyl)-N-[(3R)-hexahydro-2-thioxo-1H-azepin-3-yl]-1-piperazinecarboxamide: As described for example 78, (3R)-3-aminohexahydro-2H-azepine-2-thione obtained by de-protection of [(3R)-hexahydro-2-thioxo-1H-azepin-3-yl]-carbamic acid, 1,1-dimethylethyl ester with TFA, 4-nitrophenyl chloroformate, diisopropyl(ethyl)amine, and 7-chloro-4-(1-piperazinyl)-2-quinolinamine are reacted to afford the product as a light yellow solid. LC-MS: 432 (M$^+$+1). $^1$H NMR (CDCl$_3$) δ 1.2–1.65 (m, 2H), 1.8–2.2 (m, 4H), 3.05–3.3 (m, 4H), 3.35–3.9 (m, 5H), 4.6–4.8 (m, 1H), 4.8–5.1 (s, 2H), 6.1 (s, 1H), 6.8–7.0 (d, 1H), 7.14–7.22 (m, 1H), 7.6–7.65 (d, 1H), 7.7–7.78 (d, 1H), 8.56–8.74 (m, 1H).

Example 190

Preparation of 4-(2-Amino-7-chloro-4-quinolinyl)-N-[(9S)-6,7,8,9-tetrahydro-5H-[1,2,4]triazolo[4,3-α]azepin-9-yl]-1-piperazinecarboxamide

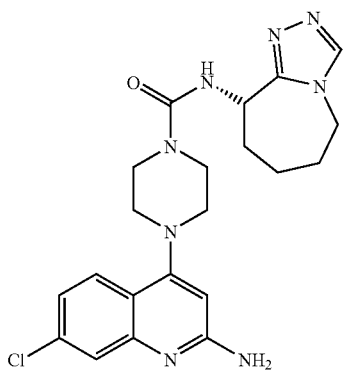

Preparation of [(9S)-6,7,8,9-tetrahydro-5H-[1,2,4]triazolo[4,3-α]azepin-9-yl]-carbamic acid, 1,1-dimethylethyl ester To a mixture [(3S)-hexahydro-2-thioxo-1H-azepin-3-yl]-carbamic acid, 1,1-dimethylethyl ester and formic hydrazine (60 mg) in MeCN (6 mL) was added Hg(OAc)$_2$ (318 mg) at rt. After 2 h, the reaction mixture was diluted with brine, extracted with EtOAc, and dried. Concentration in vacuo followed by flash chromatography gave the product.

Preparation of 4-(2-amino-7-chloro-4-quinolinyl)-N-[(9S)-6,7,8,9-tetrahydro-5H-[1,2,4]triazolo[4,3-α]azepin-9-yl]-1-piperazinecarboxamide: As described for example 78, (9R)-6,7,8,9-tetrahydro-5H-[1,2,4]triazolo[4,3-α]azepin-9-amine obtained by de-protect of [(9S)-6,7,8,9-tetrahydro-5H-[1,2,4]triazolo[4,3-α]azepin-9-yl]-carbamic acid, 1,1-dimethylethyl ester with TFA, 4-nitrophenyl chloroformate, diisopropyl(ethyl)amine, and 7-chloro-4-(1-piperazinyl)-2-quinolinamine are reacted to afford the product. LC-MS: 441 (M$^+$+1). $^1$H NMR (CD$_3$OD) δ 1.20 (m, 2H), 1.50 (m, 1H), 1.70 (m, 1H), 1.80 (m, 1H), 2.00 (m, 3H), 3.10 (m, 4H), 3.70 (m, 4H), 3.90 (m, 1H), 4.35 (m, 1H), 5.05 (d, 1H), 6.30 (s, 1H), 7.10 (d, 1H), 7.40 (s, 1H), 7.80 (d, 1H), 8.35 (s, 1H).

Example 191

Preparation of 4-(2-Amino-7-chloro-4-quinolinyl)-N-[(9S)-2,5,6,7,8,9-hexahydro-3-oxo-3H-[1,2,4]triazolo[4,3-α]azepin-9-yl]-1-piperazinecarboxamide

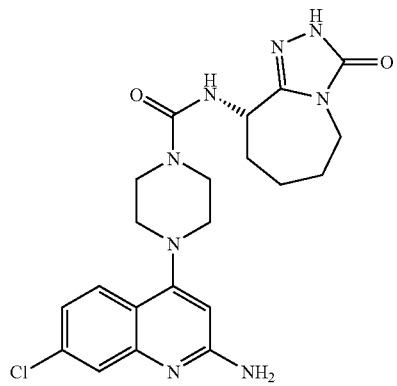

Preparation of [(9S)-Z 5,6,7,8,9-hexahydro-3-oxo-3H-[1,2,4]triazolo[4,3-α]azepin-9-yl -carbamic acid, 1,1-dimethylethyl ester: To a mixture of [(3S)-hexahydro-2-thioxo-1H-azepin-3-yl]-carbamic acid, 1,1-dimethylethyl ester (300 mg, 1.22 mmol) and methyl hydrazinocarboxylate (130 mg, 1.75 mmol) in MeCN (5 mL) was added Hg(OAc)$_2$ (510 mg), and the reaction mixture was stirred at rt for 2 h. The solid was filtered off, and the filtrate was diluted with MeCN (10 mL), then K$_2$CO$_3$ was added. The reaction mixture was kept 80° C. for 30 min. After cooling to rt, the reaction mixture was diluted with AcOEt (250 mL), washed with water (100 mL×2), and dried. Concentration in vacuo afforded the product.

Preparation of 4-(2-amino-7-chloro-4-quinolinyl)-N-[(9S)-2,5,6,7,8,9-hexahydro-3-oxo-3H-[1,2,4]triazolo[4,3-α]azepin-9-yl]-1-piperazinecarboxamide: As described for example 78, (9R)-9-amino-2,5,6,7,8,9-hexahydro-3H-[1,2,4]triazolo[4,3-α]azepin-3-one obtained by de-protection of [(9S)-2,5,6,7,8,9-hexahydro-3-oxo-3H-[1,2,4]triazolo[4,3-α]azepin-9-yl]-carbamic acid, 1,1-dimethylethyl ester with TFA, 4-nitrophenyl chloroformate, diisopropyl(ethyl)amine, and 7-chloro-4-(1-piperazinyl)-2-quinolinamine are reacted to afford the product. LC-MS: 457 (M$^+$+1). $^1$H NMR (CD$_3$OD) δ 1.75 (m, 3H), 2.0 (m, 3H), 3.20 (m, 1H), 3.40

(m, 5H), 3.75 (m, 4H), 4.10 (m, 1H), 6.37 (s, 1H), 7.30 (s, 1H), 7.40 (d, 1H), 7.60 (s, 1H), 7.95 (d, 1H).

Example 192

Preparation of 4-(2-Amino-7-chloro-4-quinolinyl)-N-[(3S)-1-acetylhexahydro-1H-azepin-3-yl]-1-piperazinecarboxamide

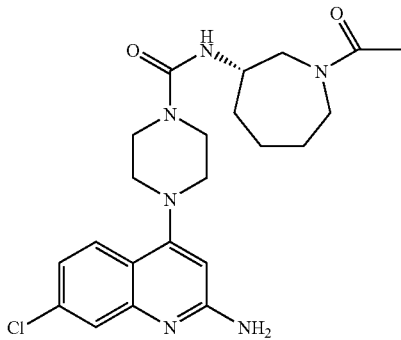

As described for example 78, (3R)-1-acetylhexahydro-1H-azepin-3-amine, 4-nitrophenyl chloroformate, diisopropyl(ethyl)amine, and 7-chloro-4-(1-piperazinyl)-2-quinolinamine are reacted to afford the product as a light yellow solid. LC-MS: 445 (M$^+$+1). $^1$H NMR (CDCl$_3$) δ 7.70 (d, 1H), 7.60 (s, 1H), 7.15 (d, 1H), 6.02 (s, 1H), 4.70 (s, 2H), 4.22 (d, 1H), 4.10 (m, 1H), 3.92 (m, 1H), 3.60 (m, 4H), 3.10 (m, 6H), 2.25 (m, 1H), 2.15 (s, 3H), 1.60–1.90 (m, 3H), 1.30–1.40 (m, 2H).

Example 193

Preparation of 3-[[[4-(2-Amino-7-chloro-4-quinolinyl)-1-piperazinyl]carbonyl]amino]-cyclohexanecarboxylic Acid, Methyl Ester

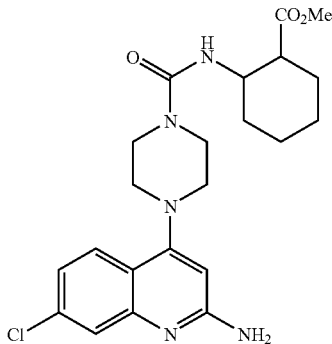

As described for example 78, 2-amino-cyclohexanecarboxylic acid-methyl ester, 4-nitrophenyl chloroformate, diisopropyl(ethyl)amine, and 7-chloro-4-(1-piperazinyl)-2-quinolinamine are reacted to afford the product as a light yellow solid. LC-MS: 446 (M$^+$+1). $^1$H NMR (CD$_3$OD) δ 1.20–1.40 (m, 4H), 1.90 (m, 3H), 2.10 (m, 1H), 2.45 (m, 1H), 3.30 (m, 4H), 3.70 (m, 8H), 6.35 (s, 1H), 7.38 (d, 1H), 7.60 (s, 1H), 790 (d, 1H).

Example 194

Preparation of 3-[[[4-(2-Amino-7-chloro-4-quinolinyl)-1-piperazinyl]carbonyl]amino]-cyclohexanecarboxylic Acid

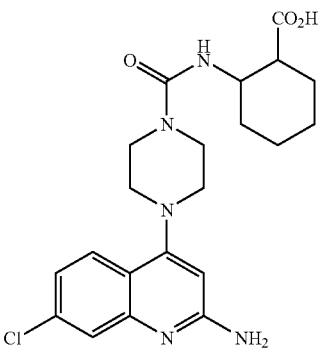

To a solution of 3-[[[4-(2-amino-7-chloro-4-quinolinyl)-1-piperazinyl]carbonyl]amino]-cyclohexanecarboxylic acid, methyl ester (150 mg, 0.33 mmol) in THF (20 mL) and water (6 mL) was added LiOH.H$_2$O (28.0 mg). The reaction mixture was stirred at rt overnight, and then solvent was evaporated in vacuo. The resulting residue was acidified to pH 4, the precipitate was collected by filtration and dried to afford the title product. LC-MS: 432 (M$^+$+1). $^1$H NMR (DMSO-d$_6$) δ 1.10 (m, 2H), 1.25 (m, 2H), 1.75 (m, 3H), 1.95 (m, 1H), 2.25 (m, 1H), 3.10 (m, 4H), 3.50 (m, 5H), 6.25 (s, 1H), 6.40 (d, 1H), 7.25 (m, 1H), 7.50 (s, 1H), 780 (d, 1H).

Example 195

Preparation of 4-(2-Amino-7-chloro-4-quinolinyl)-N-[3-[(methylamino)carbonyl]cyclohexyl]-1-piperazinecarboxamide

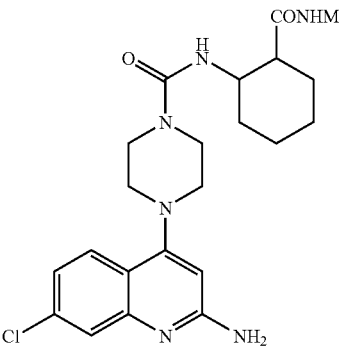

The mixture of 3-[[[4-(2-amino-7-chloro-4-quinolinyl)-1-piperazinyl]carbonyl]amino]cyclohexanecarboxylic acid (30 mg, 0.069 mmol), HATU (100 mg), methylamine (1.0M in THF, 3 mL) and diisopropylethylamine (0.5 mL) in DMF (3 mL) was stirred at rt for 3 h. The reaction mixture was diluted with ethyl acetate (100 mL), washed with sat. NaHCO$_3$ solution and water, and dried over Na$_2$SO$_4$. Concentration in vacuo followed by flash chromatography afforded the title product. LC-MS: 445 (M$^+$+1). $^1$H NMR (CD$_3$OD) δ 1.10–1.35 (m, 4H), 1.65–1.90 (m, 4H), 2.20 (m, 1H), 2.65 (s, 3H), 3.08 (m, 4H), 3.60 (m, 5H), 5.80 (d, 1H), 6.15 (s, 1H), 7.10 (d, 2H), 7.45 (s, 1H), 7.65 (a, 1H).

Example 196

Preparation of 4-(2-Amino-7-chloro-4-quinolinyl)-N-[(3S)-hexahydro-2-oxo-1H-azepin-3-yl]-1-piperazinecarboxamide

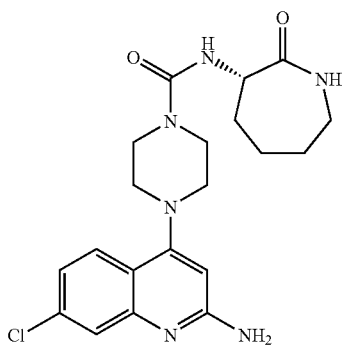

As described for example 78, (s)-3-amino-azepan-2-one, 4-nitrophenyl chloroformate, diisopropyl(ethyl)amine, and 7-chloro-4-(1-piperazinyl)-2-quinolinamine are reacted to afford the product as a light yellow solid. LC-MS: 417 (M$^+$+1). $^1$H NMR (CD$_3$OD) δ 7.80 (d, 1H), 7.45 (s, 1H), 7.15 (d, 1H), 6.35 (s, 1H), 4.45 (d, 1H), 3.68 (m, 4H), 3.25 (m, 2H), 3.10 (m, 4H), 2.00 (m, 2H), 1.80 (m, 2H), 1.60 (m, 1H), 1.38 (m, 1H).

Example 197

Preparation of 4-(2-Amino-7-chloro-4-quinolinyl)-N-[(3S)-hexahydro-1-methyl-2-oxo-1H-azepin-3-yl]-1-piperazin carboxamide

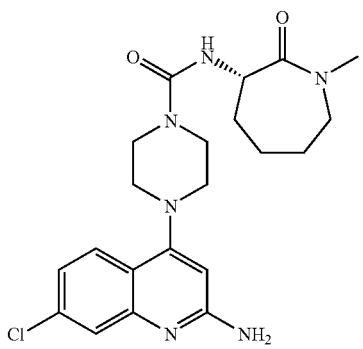

As described for example 78, (3R)-3-aminohexahydro-1-methyl-2H-azepin-2-one obtained by de-protection of [(3R)-hexahydro-1-methyl-2-oxo-1H-azepin-3-yl]-carbamic acid, 1,1-dimethylethyl ester with TFA, 4-nitrophenyl chloroformate, diisopropyl(ethyl)amine, and 7-chloro-4-(1-piperazinyl)-2-quinolinamine are reacted to afford the product as a light yellow solid. LC-MS: 431 (M$^+$+1). $^1$H NMR (CDCl$_3$) δ 7.70 (d, 1H), 7.60 (s, 1H), 7.15 (d, 1H), 6.25 (d, 1H), 6.15 (s, 1H), 4.95 (s, 2H), 4.60 (m, 1H), 3.68 (m, 5H), 3.20 (m, 1H), 3.10 (m, 4H), 3.05 (s, 3H), 2.10 (m, 1H), 1.95 (m, 1H), 1.85 (m, 2H), 1.46 (m, 2H).

Example 198

Preparation of 4-(2-Amino-7-chloro-4-quinolinyl)-N-[(3S)-1-(cyclopropylmethyl)hexahydro-2-oxo-1H-azepin-3-yl]-1-piperazinecarboxamide

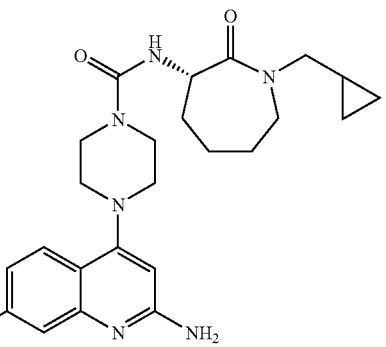

As described for example 78, (3R)-3-amino-1-(cyclopropylmethyl)hexahydro-2H-azepin-2-one by de-protection of [(3S)-1-(cyclopropylmethyl)hexahydro-2-oxo-1H-azepin-3-yl]-carbamic acid, 1,1-dimethylethyl ester with TFA, p-nitrophenyl chloroformate, diisopropylethyl amine, and 7-chloro-4-(1-piperazinyl)-2-quinolinamine are reacted to afford the product. LC-MS: 471 (M$^+$+1). $^1$H NMR (CDCl$_3$) δ 7.65 (d, 1H), 7.55 (s, 1H), 7.10 (d, 1H), 6.22 (d, 1H), 6.05 (s, 1H), 4.85 (s, 2H), 4.50 (m, 1H), 3.60 (m, 4H), 3.50 (m, 1H), 3.40 (m, 1H), 3.30 (m, 1H), 3.20 (m, 1H), 3.06 (m, 4H), 2.05 (m, 1H), 1.70–1.90 (m, 3H), 1.40 (m, 2H), 0.90 (m, 1H), 0.45 (m, 2H), 0.20 (m, 2H).

Example 199

Preparation of 4-(2-Amino-7-chloro-4-quinolinyl)-N-[(3S)-hexahydro-2-oxo-1-(phenylmethyl)-1H-azepin-3-yl]-1-piperazinecarboxamide

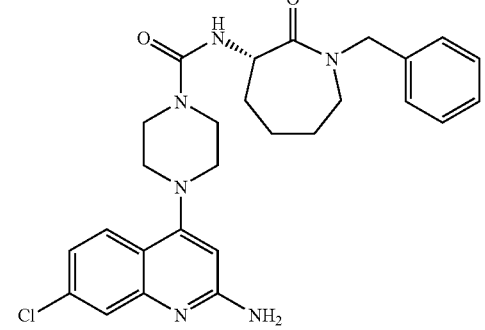

As described for example 78, (3R)-3-aminohexahydro-1-benzyl-2H-azepin-2-one obtained by de-protection of [(3S)-hexahydro-2-oxo-1-(phenylmethyl)-1H-azepin-3-yl]-carbamic acid, 1,1-dimethylethyl ester with TFA, p-nitrophenyl chloroformate, diisopropylethyl amine and 7-chloro-4-(1-piperazinyl)-2-quinolinamine are reacted to afford the product. LC-MS 506 (M$^+$+1). $^1$H NMR (CDCl$_3$) δ 7.70 (d, 1H), 7.58 (s, 1H), 7.30 (m, 5H), 7.15 (d, 1H), 6.35 (d, 1H), 6.12 (s, 1H), 4.90 (s, 2H), 4.64 (m, 1H), 4.50 (m, 2H), 3.65 (m, 4H), 3.50 (m, 1H), 3.22 (m, 1H), 3.10 (m, 4H), 2.10 (m, 1H), 1.70–2.00 (m, 3H), 1.50 (m, 1H), 1.20 (m, 1H).

Example 200

Preparation of 4-(2-Amino-7-chloro-4-quinolinyl)-N-[(3S)-1-[(2,6-dimethylphenyl)methyl]hexahydro-2-oxo-1H-azepin-3-yl]-1-piperazinecarboxamide

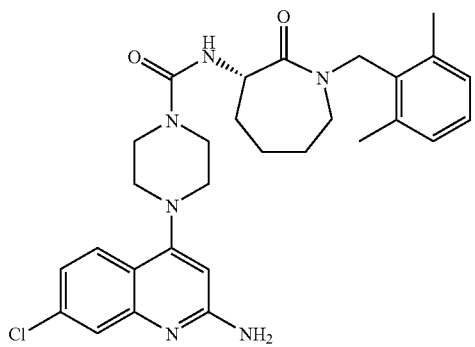

As described for example 78, (3R)-3-amino-1-[(2,6-dimethylphenyl)methyl]hexahydro-2H-azepin-2-one obtained by de-protection of [(3S)-1-[(2,6-dimethylphenyl)methyl]hexahydro-2-oxo-1H-azepin-3-yl]-carbamic acid, 1,1-dimethylethyl ester with TFA, p-nitrophenyl chloroformate, diisopropylethyl amine and 7-chloro-4-(1-piperazinyl)-2-quinolinamine are reacted to afford the product. LC-MS 535 ($M^+$+1).

Example 201

Preparation of 4-(2-Amino-7-chloro-4-quinolinyl)-N-[(3S)-hexahydro-2-oxo-1-(2-pyridinylmethyl)-1H-azepin-3-yl]-1-piperazinecarboxamide

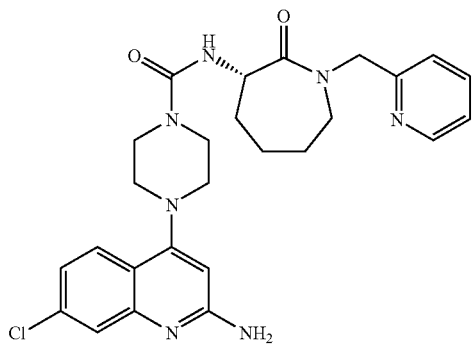

As described for example 78, (3R)-3-aminohexahydro-1-(2-pyridinylmethyl)-2H-azepin-2-one obtained by de-protection of [(3S)-hexahydro-2-oxo-1-(2-pyridinylmethyl)-1H-azepin-3-yl]-carbamic acid, 1,1-dimethylethyl ester with TFA, p-nitrophenyl chloroformate, diisopropylethyl amine and 7-chloro-4-(1-piperazinyl)-2-quinolinamine are reacted to afford the product. LC-MS 508 ($M^+$+1). $^1$H NMR (CDCl$_3$) δ 8.50 (m, 1H), 7.60 (m, 3H), 7.15 (m, 3H), 6.20 (m, 1H), 6.05 (s, 1H), 4.80 (s, 2H), 4.70 (m, 2H), 4.60 (m, 1H), 3.60 (m, 4H), 3.50 (m, 1H), 3.40 (m, 1H), 3.05 (m, 4H), 2.10 (m, 1H), 1.60–1.90 (m, 3H), 1.50 (m, 1H), 1.30 (m, 1H).

Example 202

Preparation of 4-(2-Amino-7-chloro-4-quinolinyl)-N-[(3S)-hexahydro-2-oxo-1-(3-pyridinylmethyl)-1H-azepin-3-yl]-1-piperazincarboxamide

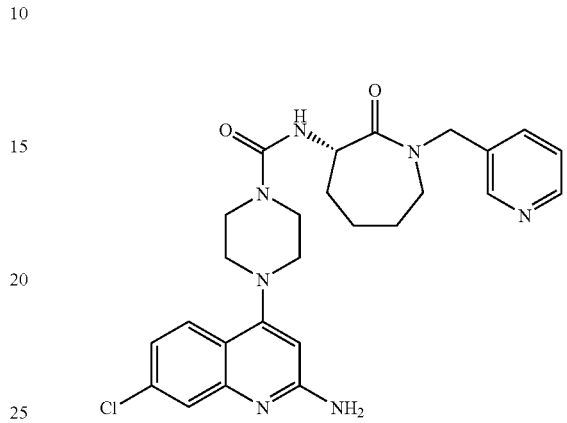

As described for example 78, (3R)-3-aminohexahydro-1-(3-pyridinylmethyl)-2H-azepin-2-one obtained by de-protection of [(3S)-hexahydro-2-oxo-1-(3-pyridinylmethyl)-1H-azepin-3-yl]-carbamic acid, 1,1-dimethylethyl ester with TFA, p-nitrophenyl chloroformate, diisopropylethyl amine and 7-chloro-4-(1-piperazinyl)-2-quinolinamine are reacted to afford the product. LC-MS 508 ($M^+$+1). $^1$H NMR (CDCl$_3$) δ 8.50 (m, 2H), 7.65 (d, 1H), 7.52 (m, 2H), 7.20 (m, 1H), 7.10 (d, 1H), 6.18 (d, 1H), 6.10 (s, 1H), 4.80 (s, 2H), 4.65 (m, 2H), 4.60 (m, 1H), 3.60 (m, 4H), 3.45 (m, 1H), 3.20 (m, 1H), 3.06 (m, 4H), 2.07 (m, 1H), 1.65–1.90 (m, 3H), 1.47 (m, 1H), 1.20 (m, 1H).

Example 203

Preparation of 4-(2-Amino-7-chloro-4-quinolinyl)-N-[(3S)-hexahydro-2-oxo-1-(4-pyridinylmethyl)-1H-azepin-3-yl]-1-piperazinecarboxamide

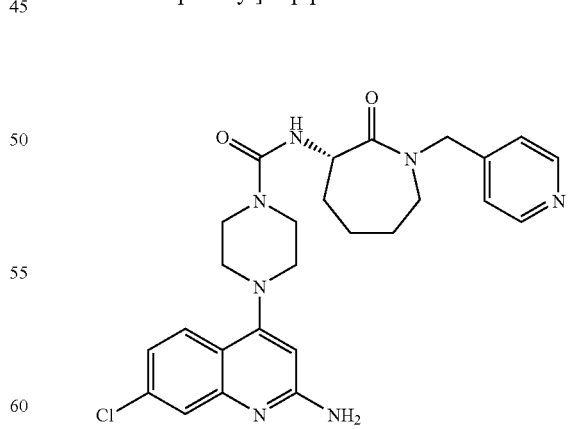

As described for example 78, (3R)-3-aminohexahydro-1-(4-pyridinylmethyl)-2H-azepin-2-one obtained by de-protection of [(3S)-hexahydro-2-oxo-1-(4-pyridinylmethyl)-1H-azepin-3-yl]-carbamic acid, 1,1-dimethylethyl ester with TFA, p-nitrophenyl chloroformate, diisopropylethyl amine

Exampl 204

Preparation of 4-(2-Amino-7-chloro-4-quinolinyl)-N-[(3S)-hexahydro-1-(2-hydroxy-3-phenoxypropyl)-2-oxo-1H-azepin-3-yl]-1-piperazinecarboxamide

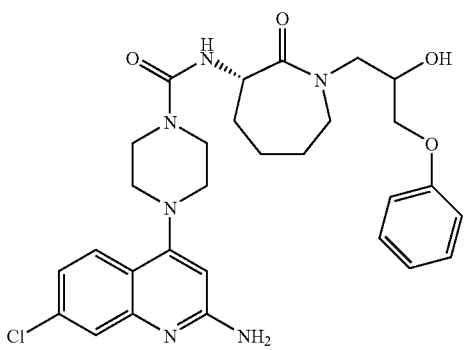

Preparation of [(3S)-hexahydro-1-(2-hydroxy-3-phenoxypropyl)-2-oxo-1H-azepin-3-yl]-carbamic acid, 1,1-dimethylethyl ester To a solution of [(3R)-hexahydro-2-oxo-1H-azepin-3-yl]-carbamic acid, 1,1-dimethylethyl ester (500 mg) in THF at –78° C. was added LiHMDS (4.4 mL, 1.0 M in THF). After addition, the reaction mixture was allowed to warm to rt. After 30 min at rt, the reaction mixture was re-cooled to –78° C., then 2-(phenoxymethyl)-oxirane (0.6 mL) was introduced. The reaction was kept at rt for additional 1 h, and was quenched with NH₄Cl (sat., 20 mL). The reaction mixture was extracted with EtOAc, washed with brine, and dried over Na₂SO₄. Concentration in vacuo afforded the crude product which was used directly for next step reaction without further purification.

In a similar manner, [(3S)-hexahydro-1-(2-hydroxypropyl)-2-oxo-1H-azepin-3-yl]-carbamic acid, 1,1-dimethylethyl ester was prepared.

Preparation of 4-(2-amino-7-chloro-4-quinolinyl)-N-[(3S)-hexahydro-1-(2-hydroxy-3-phenoxypropyl)-2-oxo-1H-azepin-3-yl]-1-piperazinecarboxamide: As described for example 78, (3R)-3-aminohexahydro-1-(2-hydroxy-3-phenoxypropyl)-2H-azepin-2-one obtained by de-protection of [(3S)-hexahydro-1-(2-hydroxy-3-phenoxypropyl)-2-oxo-1H-azepin-3-yl]-carbamic acid, 1,1-dimethylethyl ester with TFA, 4-nitrophenyl chloroformate, diisopropyl(ethyl)amine, and 7-chloro-4-(1-piperazinyl)-2-quinolinamine are reacted to afford the product as a light yellow solid. LC-MS: 566 (M⁺+1). ¹H NMR (CDCl₃) δ 1.4–1.65 (m, 2H), 1.7–2.24 (m, 4H), 3.05–3.2 (m, 4H), 3.34–3.5 (m, 2H), 3.56–3.74 (m, 6H), 3.75–4.04 (m, 3H), 4.13–4.28 (m, 1H), 4.6–4.75 (m, 1H), 4.8–5.0 (s, 2H), 6.1–6.25 (m, 2H), 6.88–6.94 (m, 2H), 6.95–7.05 (m, 1H), 7.14–7.2 (m, 1H), 7.26–7.33 (m, 2H), 7.6–7.63 (d, 1H), 7.7–7.75 (d, 1H), 8.56–8.74 (m, 1H).

Example 205

Preparation of 4-(2-Amino-7-chloro-4-quinolinyl)-N-[(3S)-hexahydro-1-(2-hydroxypropyl)-2-oxo-1H-azepin-3-yl]-1-piperazinecarboxamide

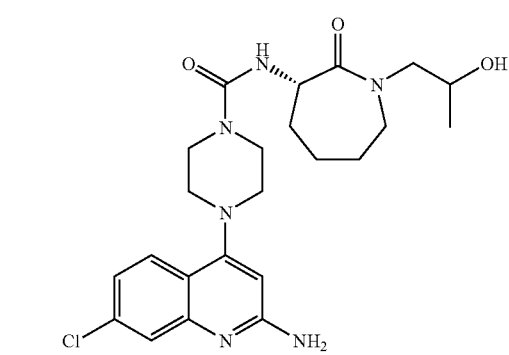

As described for example 78, (3R)-3-aminohexahydro-1-(2-hydroxypropyl)-2H-azepin-2-one obtained by de-protection of [(3S)-hexahydro-1-(2-hydroxypropyl)-2-oxo-1H-azepin-3-yl]-carbamic acid, 1,1-dimethylethyl ester with TFA, 4-nitrophenyl chloroformate, diisopropyl(ethyl)amine, and 7-chloro-4-(1-piperazinyl)-2-quinolinamine are reacted to afford the product as a light yellow solid. LC-MS: 474 (M⁺+1). ¹H NMR (CDCl₃) δ 0.75–1.0 (m, 1H), 1.18–1.3 (m, 3H), 1.3–1.6 (m, 2H), 1.7–2.4 (m, 4H), 3.05–3.2 (m, 4H), 3.2–3.36 (m, 3H), 3.6–3.8 (m, 4H), 3.9–4.1 (m, 1H), 4.45–4.7 (m, 1H), 4.96–5.1 (s, 2H), 6.1–6.3 (m, 3H), 7.1–7.2 (m, 1H), 7.6 (m, 1H), 7.7–7.8 (m, 1H).

Example 206

Preparation of (3S)-[[[4-(2-Amino-7-chloro-4-quinolinyl)-1-piperazinyl]carbonyl]amino]hexahydro-2-oxo-1H-azepine-1-acetic Acid, Methyl ester

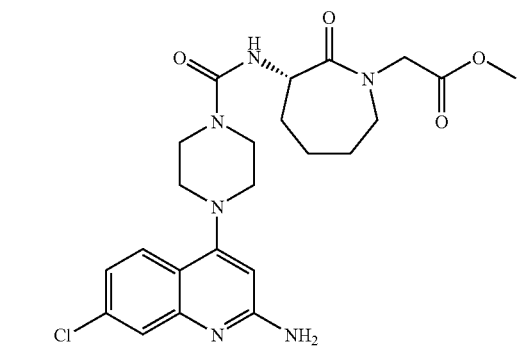

As described for example 78, (3S)-3-aminohexahydro-2-oxo-1H-azepine-1-acetic acid, methyl ester obtained by de-protection of (3S)-3-[[(1,1-dimethylethoxy)carbonyl]amino]hexahydro-2-oxo-1H-azepine-1-acetic acid, methyl ester with TFA, p-nitrophenyl chloroformate, diisopropylethyl amine and 7-chloro-4-(1-piperazinyl)-2-quinolinamine are reacted to afford the product. LC-MS 489 (M⁺+1). ¹H NMR (CDCl₃) δ 7.70 (d, 1H), 7.60 (s, 1H), 7.18 (d, 1H), 6.15 (m, 2H), 4.80 (s, 2H), 4.65 (m, 1H), 4.20 (s, 2H), 3.75 (m, 4H), 3.65 (m, 4H), 3.20 (m, 1H), 3.10 (m, 4H), 2.10 (m, 1H), 1.80–2.05 (m, 3H), 1.60 (m, 2H).

Example 207

Preparation of (3S)-[[[4-(2-Amino-7-chloro-4-quinolinyl)-1-piperazinyl]carbonyl]amino]hexahydro-2-oxo-1H-azepine-1-acetic Acid

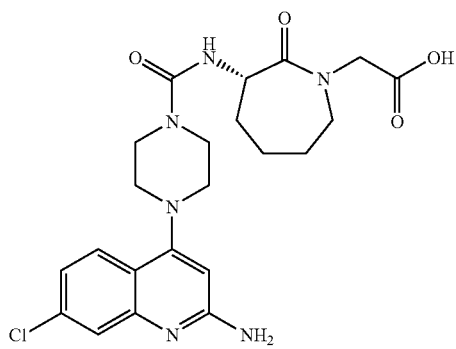

To a stirred solution of (3S)-[[[4-(2-amino-7-chloro-4-quinolinyl)-1-piperazinyl]carbonyl]amino]hexahydro-2-oxo-1H-azepine-1-acetic acid, methyl ester (300 mg, 0.613 mmol) in THF (3.0 mL) was added 2N NaOH solution (3 mL) at rt. After 30 min, THF was evaporated in vacuo, and the resulting residue was acidified to pH 4–5. The reaction mixture was extracted with ethyl acetate, washed with brine, and dried over $Na_2SO_4$. The product (15 mg) was obtained after concentration in vacuo. LC-MS: 475 ($M^+$+1). $^1$H NMR ($CD_3OD$) δ 7.82 (d, 1H), 7.50 (s, 1H), 7.38 (d, 1H), 6.25 (s, 1H), 4.58 (d, 1H), 4.10 (m, 2H), 3.80 (m, 1H), 3.65 (m, 4H), 3.30 (m, 5H), 1.60–1.96 (m, 6H).

Example 208

Preparation of (3S)-[[[4-(2-Amino-7-chloro-4-quinolinyl)-1-piperazinyl]carbonyl]amino]hexahydro-2-oxo-N-(phenylmethyl)-1H-azepine-1-acetamide

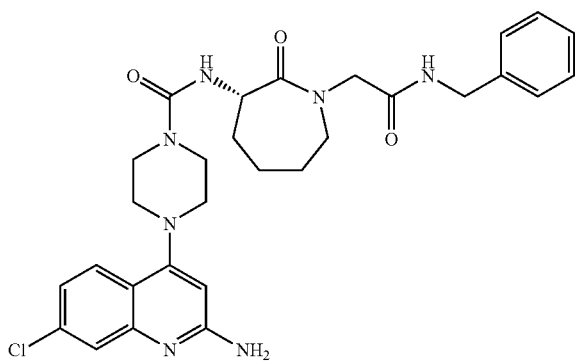

The mixtures of (3S)-[[[4-(2-amino-7-chloro-4-quinolinyl)-1-piperazinyl]carbonyl]amino]hexahydro-2-oxo-1H-azepine-1-acetic acid (50.0 mg, 0.1 mmol), benzyl amine (0.2 mL), HATU (50 mg), and diisopropylethyl amine (0.3 mL) in DMF (5 mL) was stirred at rt for 2 h. The reaction mixture was diluted with ethyl acetate (100 mL), washed with $NaHCO_3$ (sat.) and water, dried over $Na_2SO_4$. Concentration in vacuo followed by flash chromatography afforded the title product. LC-MS: 564 ($M^+$+1). $^1$H NMR ($CD_3OD$) δ 7.82 (d, 1H), 7.45 (s, 1H), 7.25 (m, 4H), 7.20 (m, 2H), 6.30 (s, 1H), 4.65 (d, 1H), 4.40 (s, 2H), 4.15 (m, 2H), 3.75 (m, 1H), 3.65 (m, 4H), 3.30 (m, 1H), 3.10 (m, 4H), 1.96 (m, 2H), 1.80 (m, 2H), 1.60 (m, 2H).

Example 209

Preparation of (3S)-[[[4-(2-Amino-7-chloro-4-quinolinyl)-1-piperazinyl]carbonyl]amino]hexahydro-N-methyl-2-oxo-1H-azepine-1-acetamid

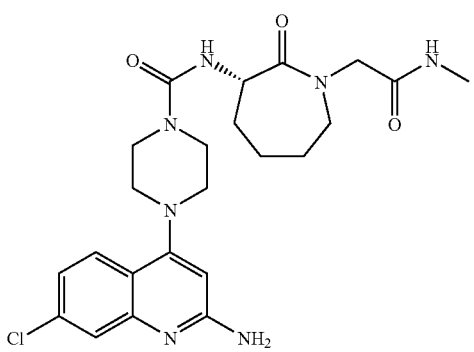

As described as example 208, (3S)-[[[4-(2-amino-7-chloro-4-quinolinyl)-1-piperazinyl]carbonyl]amino] hexahydro-2-oxo-1H-azepine-1-acetic acid, methyl amine, HATU, and diisopropylethylamine are reacted to afford the product. LC-MS 488 ($M^+$+1). $^1$H NMR ($CD_3OD$) δ 7.86 (d, 1H), 7.50 (s, 1H), 7.30 (d, 1H), 6.30 (s, 1H), 4.65 (m, 1H), 4.00 (m, 2H), 3.70 (m, 5H), 3.30 (m, 5H), 2.75 (s, 3H), 1.98 (m, 2H), 1.80 (m, 2H), 1.60 (m, 2H).

Example 210

Preparation of (3S)-[[[4-(2-Amino-7-chloro-4-quinolinyl)-1-piperazinyl]carbonyl]amino]hexahydro-2-oxo-N-(4-pyridinyl)-1H-azepine-1-acetamide

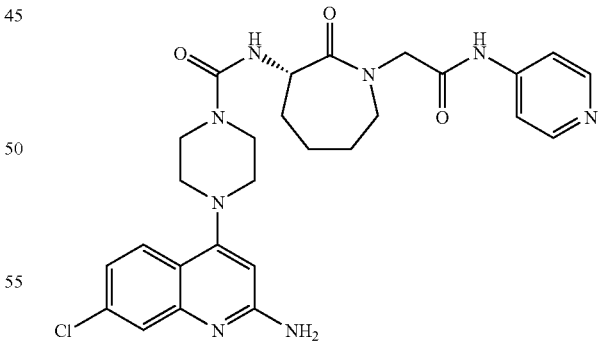

As described as example 208, (3S)-[[[4-(2-amino-7-chloro-4-quinolinyl)-1-piperazinyl]carbonyl]amino] hexahydro-2-oxo-1H-azepine-1-acetic acid, 4-aminopyridine, HATU, and diisopropylethylamine are reacted to afford the product. LC-MS: 551 ($M^+$+1). $^1$H NMR ($CD_3OD$) δ 1.60–1.80 (m, 4H), 1.90 (m, 2H), 3.10 (m, 4H), 3.30 (m, 1H), 3.60 (m, 4H), 4.20 (m, 2H), 4.60 (d, 1H), 6.24 (s, 1H), 7.08 (d, 1H), 7.39 (s, 1H), 7.55 (m, 2H), 7.75 (d, 2H), 8.30 (m, 2H).

Example 211

Preparation of 4-(2-Amino-7-chloro-4-quinolinyl)-N-[(3R)-1-(4-fluorophenyl)hexahydro-2-oxo-1H-azepin-3-yl]-1-piperazinecarboxamide

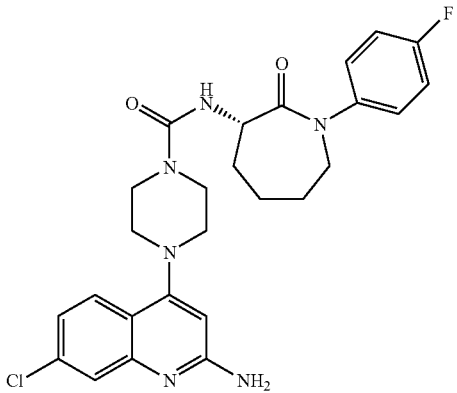

Preparation of [(3S)-1'-(4-fluorophenyl)hexahydro-2-oxo-1H-azepin-3-yl]-carbamic acid, 1,1-dimethylethyl ester (According to *Tetrahedron Lett.*, 1998, 39, 2933–2936): The mixture of [(3R)-hexahydro-2-oxo-1H-azepin-3-yl]-carbamic acid, 1,1-dimethylethyl ester 400 mg, 4-fluorophenylboronic acid (200 mg), Et$_3$N (0.3 mL), and CuI (150 mg) in CH$_2$Cl$_2$ (5 mL) are mixture at rt for 4 days. The reaction mixture was diluted with brine, extracted with EtOAc, and dried. Concentration followed by flash chromatograph afforded the product (180 mg).

Preparation of 4-(2-amino-7-chloro-4-quinolinyl)-N-[(3R)-1-(4-fluorophenyl)hexahydro-2-oxo-1H-azepin-3-yl]-1-piperazinecarboxamide: As described for example 78, (3S)-3-amino-1-(4-fluorophenyl)hexahydro-2H-azepin-2-one obtained by the de-protection of [(3S)-1-(4-fluorophenyl)hexahydro-2-oxo-1H-azepin-3-yl]-carbamic acid, 1,1-dimethylethyl ester with TFA, 4-nitrophenyl chloroformate, diisopropyl(ethyl)amine, and 7-chloro-4-(1-piperazinyl)-2-quinolinamine are reacted to afford the product as a light yellow solid. LC-MS: 511 (M$^+$+1). $^1$H NMR (CDCl$_3$) δ 1.62 (m, 2H), 1.83~2.31 (m, 4H), 3.14 (m, 4H), 3.62 (m 4H), 3.95 (dd, 1H), 4.81 (m, 1H), 6.17 (s, 1H), 6.22 (d, 1H), 7.06 (m, 2H), 7.18 (m, 2H), 7.6 (s, 1H), 7.65 (d, 1H).

Example 212

Preparation of 4-[7-Chloro-2-(methylamino)-4-quinolinyl]-N-[(3S)-hexahydro-2-oxo-1H-azepin-3-yl]-1-piperazinecarboxamide

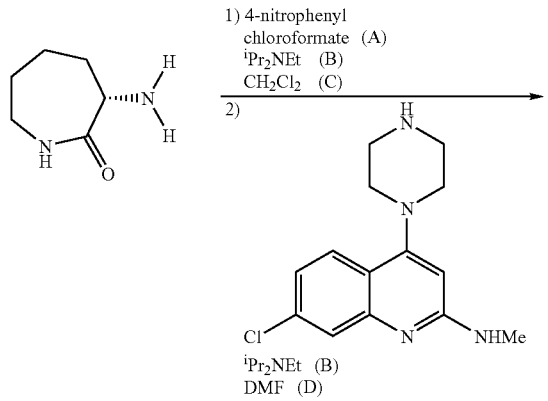

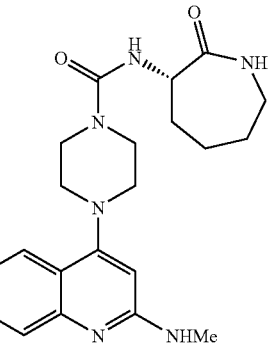

As described for example 78, (3S)-3-aminohexahydro-2H-azepin-2-one, 4-nitrophenyl chloroformate, diisopropyl (ethyl)amine, and 7-chloro-4-(1-piperazinyl)-2-quinolinamine are reacted to afford the product as a light yellow solid. LC-MS: 431 (M$^+$+1). $^1$H NMR (CDCl$_3$): δ 1.34~1.60 (m, 2H), 1.80~1.92 (m, 2H), 1.98~2.08 (m, 1H), 2.10~2.18 (m, 1H), 3.06 (d, 3H), 3.12 (br.s, 4H), 3.20~3.38 (m, 2H), 3.67 (br.s, 4H), 4.52 (br. dd, 1H), 5.98~6.06 (m, 2H), 6.12 (d, 1H), 7.12 (dd, 1H), 7.67 (d, 1H), 7.70 (d, 1H).

Example 213

Preparation of 4-(2-Amino-7-chloro-4-quinolinyl)-N-[(3S)-hexahydro-2-oxo-1-(2-phenoxyacetyl)-1H-azepin-3-yl]-1-piperazinecarboxamide

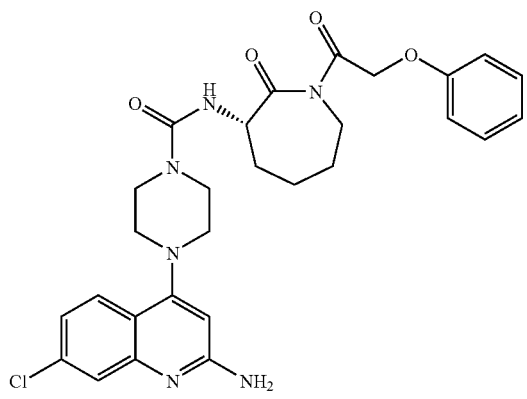

Preparation of [(3S)-hexahydro-2-oxo-1-(phenoxyacetyl)-1H-azepin-3-yl]-carbamic acid, 1,1-dimethylethyl ester (A. D. Borthwick, et al. *J. Med. Chem.*, 2000, 43, 4452-4464): To a stirred solution of [(3S)-hexahydro-2-oxo-1H-azepin-3-yl]-carbamic acid-1,1-dimethylethyl ester (500 mg, 2.2 mmol) in THF (10 mL) at −78° C. was added LiHDMS (3 mL, 3 mmol, 1.0 M in THF). After addition, dry-ice bath was removed, and the reaction was stirred at room temperature for about 30 min. The reaction was re-cooled to −78° C., and phenoxyacetyl chloride (0.91 mL, 6.58 mmol.) was added. The reaction was allowed to warm to rt over 2 h, and was quenched with NH$_4$Cl (sat., 10 mL). The reaction mixture was extracted with EtOAc (3×30 mL), washed with brine (15 mL), and dried over Na$_2$SO$_4$. Concentration in vacuo followed by flash chromatography (hexane: EtOAc/5:1) afforded the title product. $^1$H NMR (CDCl$_3$) δ 1.38 (m, 1H), 1.42 (s, 9H), 1.63 (m, 1H), 1.77–1.98 (m, 3H), 2.18 (m, 1H), 3.21 (m, 1H), 4.67 (m, 1H), 4.83 (m, 1H), 5.2 (m, 1H), 5.61 (m, 1H), 6.9 (m, 3H), 7.28 (m, 2H).

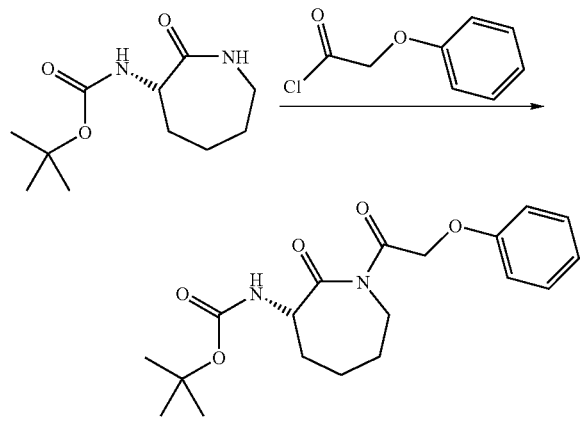

The following intermediates were prepared in a similar manner:
[(3S)-1-acetylhexahydro-2-oxo-1H-azepin-3-yl]-carbamic acid, 1,1-dimethylethyl ester
[(3S)-1-(cyclopropylcarbonyl)hexahydro-2-oxo-1H-azepin-3-yl]-carbamic acid, 1,1-dimethylethyl ester
[(3S)-1-benzoylhexahydro-2-oxo-1H-azepin-3-yl]-carbamic acid, 1,1-dimethylethyl ester
[(3S)-1-(ethylsulfonyl)hexahydro-2-oxo-1H-azepin-3-yl]-carbamic acid, 1,1-dimethylethyl ester
[(3S)-hexahydro-2-oxo-1-(phenylsulfonyl)-1H-azepin-3-yl]-carbamic acid, 1,1-dimethylethyl ester
[(3S)-1-(cyclohexylcarbonyl)hexahydro-2-oxo-1H-azepin-3-yl]-carbamic acid, 1,1-dimethylethyl ester
[(3S)-hexahydro-2-oxo-1-[[(phenylsulfonyl)amino]carbonyl]-1H-azepin-3-yl]-carbamic acid, 1,1-dimethylethyl ester
[(3S)-hexahydro-2-oxo-1-(phenylacetyl)-1H-azepin-3-yl]-carbamic acid, 1,1-dimethylethyl ester
[(3R)-1-formylhexahydro-2-oxo-1H-azepin-3-yl]-carbamic acid-1,1-dimethylethyl ester
[(3R)-1-(2,2-dimethyl-1-oxopropyl)hexahydro-2-oxo-1H-azepin-3-yl]-carbamic acid-1,1-dimethylethyl ester
[(3R)-hexahydro-1-(methylsulfonyl)-2-oxo-1H-azepin-3-yl]-carbamic acid-1,1-dimethylethyl ester
3R)-3-[[(1,1-dimethylethoxy)carbonyl]amino]hexahydro-2-oxo-1H-azepine-1-carboxylic acid, methyl ester
(3R)-3-[[(1,1-dimethylethoxy)carbonyl]amino]hexahydro-2-oxo-1H-azepine-1-carboxylic acid-ethyl ester
(3R)-3-[[(1,1-dimethylethoxy)carbonyl]amino]hexahydro-2-oxo-1H-azepine-1-carboxylic acid, 2,2,2-trifluoroethyl ester
(3S)-3-[[(1,1-dimethylethoxy)carbonyl]amino]hexahydro-1H-azepine-1-carboxylic acid 2-oxo-, 2-propenyl ester
(3R)-3-[[(1,1-dimethylethoxy)carbonyl]amino]hexahydro-2-oxo-1H-azepine-1-carboxylic acid, phenyl ester
(3R)-3-[[(1,1-dimethylethoxy)carbonyl]amino]hexahydro-2-oxo-1H-azepine-1-carboxylic acid-4-fluorophenyl ester
(3S)-3-[[(1,1-dimethylethoxy)carbonyl]amino]hexahydro-2-oxo-1H-azepine-1-carboxylic acid, phenylmethyl ester
[(3S)-1-cyanohexahydro-2-oxo-1H-azepin-3-yl]-carbamic-acid-1,1-dimethylethyl ester:

Preparation of 4-(2-amino-7-chloro-4-quinolinyl)-N-[(3S)-hexahydro-2-oxo-1-(2-phenoxyacetyl)-1H-azepin-3-yl]-1-piperazinecarboxamide: To a mixture of 3-amino-hexahydro-1-(phenoxyacetyl)-2H-azepin-2-one (~0.43 mmol) [obtained by the de-protection of de-protection of [(3S)-hexahydro-2-oxo-1-(phenoxyacetyl)-1H-azepin-3-yl]-carbamic acid, 1,1-dimethylethyl ester with TFA] in $CH_2Cl_2$ (2 mL) and $NaHCO_3$ (sat., 2 mL) was added triphosgene (42 mg, 0.14 mmol) in at 0° C. After 15 min, the mixture was diluted with water and extracted with minimum $CH_2Cl_2$, then dried over $Na_2SO_4$, which was used directly in the next step. To this solution was added a hot DMSO (3 mL) solution of 7-chloro-4-(1-piperazinyl)-2-quinolinamine followed by $^iPr_2NEt$ (0.1 mL, 0.57 mmol,). After 1.5 h at rt, the mixture was poured into ice-water. The reaction mixture was extracted with EtOAc, washed with brine, and dried over $Na_2SO_4$. Concentration in vacuo followed by preparative TLC ($CH_2Cl_2$-MeOH-$Et_3N$, 9:1:1%) afforded the title product as a light yellow solid. LC-MS: 551 ($M^+$+1). $^1H$ NMR ($CDCl_3$): δ 1.32~2.24 (m, 6H), 3.14~3.30 (m, 5H), 3.70 (m, 4H), 4.76~4.86 (m, 3H), 4.94 (m, 1H), 5.16 (s, 2H), 5.78 (br.d, 1H), 6.16 (s, 1H), 6.92 (m, 2H), 6.99 (m, 1H), 7.18 (dd, 1H), 7.26~7.32 (m, 3H), 7.62 (d, 1H), 7.73 (d, 1H).

Example 214

Preparation of 4-(7-Chloro-4-quinolinyl)-N-[(3S)-1-acetylhexahydro-2-oxo-1H-azepin-3-yl]-1-piperazinecarboxamide:

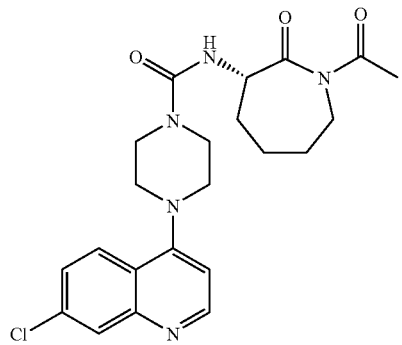

As described for example 78, (3R)-1-acetyl-3-aminohexahydro-2H-azepin-2-one obtained by de-protection of [(3S)-1-acetylhexahydro-2-oxo-1H-azepin-3-yl]-carbamic acid, 1,1-dimethylethyl ester with TFA, diisopropyl(ethyl)amine, diisopropyl(ethyl)amine, and 7-chloro-4-(piperazin-1-yl)quinoline are reacted to give the product. LC-MS: 444 ($M^+$+1). $^1H$ NMR ($CDCl_3$) δ 8.68 (d, 1H), 8.00 (s, 1H), 7.90 (d, 1H), 7.40 (d, 1H), 6.80 (d, 1H), 5.80 (d, 1H), 4.83 (m, 1H), 4.70 (m, 1H), 3.65 (m, 4H), 3.18 (m, 5H), 2.50 (s, 3H), 2.10 (m, 1H), 1.90 (m, 3H), 1.50 (m, 1H), 1.30 (m, 1H).

Example 215

Preparation of 4-(2-Amino-7-chloro-4-quinolinyl)-N-[(3S)-1-acetylhexahydro-2-oxo-1H-azepin-3-yl]-1-piperazinecarboxamide

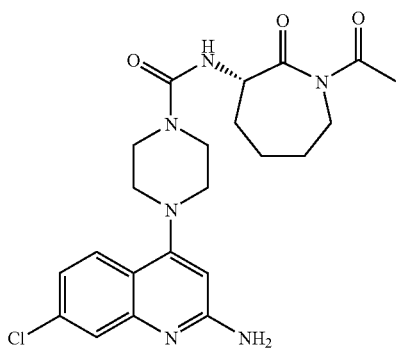

As described for example 78, (3R)-1-acetyl-3-amino-hexahydro-2H-azepin-2-one obtained by de-protection of [(3S)-1-acetylhexahydro-2-oxo-1H-azepin-3-yl]-carbamic acid, 1,1-dimethylethyl ester with TFA, diisopropyl(ethyl)amine, and 7-chloro-4-(1-piperazinyl)-2-quinolinamine are reacted to give the product. LC-MS: 459 (M$^+$+1). $^1$H NMR (CDCl$_3$) δ 7.65 (d, 1H), 7.55 (s, 1H), 7.10 (d, 1H), 6.10 (s, 1H), 5.80 (m, 1H), 5.15 (s, 2H), 4.85 (m, 1H), 4.70 (m, 1H), 3.60 (m, 4H), 3.10 (m, 5H), 2.45 (s, 3H), 2.10 (m, 1H), 1.85 (m, 3H), 1.50 (m, 1H), 1.30 (m, 1H).

Example 216

Preparation of 4-(2-Amino-7-chloro-4-quinolinyl)-N-[(3S)-1-(cyclopropylcarbonyl)hexahydro-2-oxo-1H-azepin-3-yl]-1-piperazinecarboxamide:

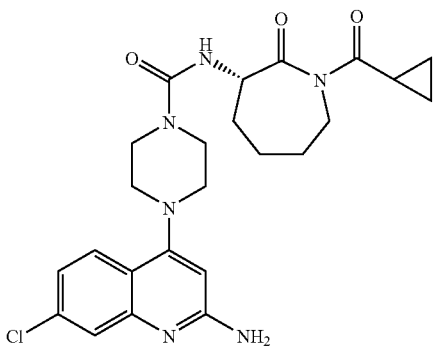

As described for example 78, (3R)-3-amino-1-(cyclopropylcarbonyl)hexahydro-2H-azepin-2-one obtained by de-protection of [(3S)-1 (cyclopropylcarbonyl)hexahydro-2-oxo-1H-azepin-3-yl]-carbamic acid, 1,1-dimethylethyl ester with TFA, diisopropyl(ethyl)amine, and 7-chloro-4-(1-piperazinyl)-2-quinolinamine are reacted to give the product. LC-MS: 485 (M$^+$+1). $^1$H NMR (CDCl$_3$) δ 7.65 (d, 1H), 7.58 (s, 1H), 7.12 (d, 1H), 6.06 (s, 1H), 5.86 (d, 1H), 4.95 (s, 2H), 4.80 (m, 1H), 4.58 (m, 1H), 3.60 (m, 4H), 3.10 (m, 5H), 2.70 (m, 1H), 2.10 (m, 1H), 1.70–1.90 (m, 3H), 1.60 (m, 1H), 1.30 (m, 1H), 1.10 (m, 2H), 0.90 (m, 2H).

Example 217

Preparation of 4-(2-Amino-7-chloro-4-quinolinyl)-N-[(3S)-1-benzoylhexahydro-2-oxo-1H-azepin-3-yl]-1-piperazinecarboxamide

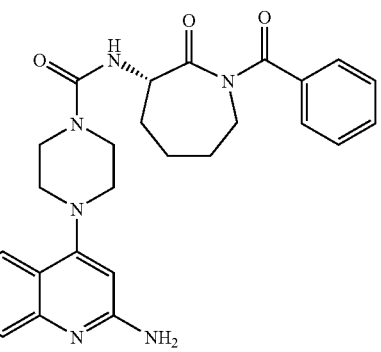

As described for 78, (3R)-3-amino-1-benzoylhexahydro-2H-azepin-2-one obtained from de-protection of [(3S)-1-benzoylhexahydro-2-oxo-1H-azepin-3-yl]-carbamic acid, 1,1-dimethylethyl ester with TFA, 4-nitrophenyl chloroformate, diisopropyl(ethyl)amine, and 7-chloro-4-(1-piperazinyl)-2-quinolinamine are reacted to afford the product. LC-MS: 521 (M$^+$+1). $^1$H NMR (CDCl$_3$) δ 7.75 (d, 1H), 7.60 (m, 3H), 7.50 (m, 1H), 7.43 (m, 2H), 7.20 (d, 1H), 6.10 (s, 1H), 5.75 (d, 1H), 4.85 (m, 1H), 4.75 (s, 2H), 4.55 (m, 1H), 3.60 (m, 4H), 3.50 (m, 1H), 3.10 (m, 4H), 2.25 (m, 1H), 2.10 (m, 3H), 1.70 (m, 2H).

Example 218

Preparation of 4-(2-Amino-7-chloro-4-quinolinyl)-N-[(3S)-1-(ethylsulfonyl)hexahydro-2-oxo-1H-azepin-3-yl]-1-piperazinecarboxamide

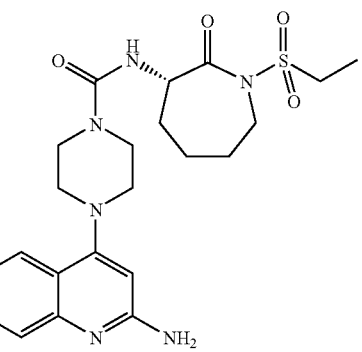

As described for 78, (3R)-3-amino-1-(ethylsulfonyl)hexahydro-2H-azepin-2-one obtained from the de-protection of [(3S)-1-(ethylsulfonyl)hexahydro-2-oxo-1H-azepin-3-yl]-carbamic acid, 1,1-dimethylethyl ester with TFA, 4-nitrophenyl chloroformate, diisopropyl(ethyl)amine, and 7-chloro-4-(1-piperazinyl)-2-quinolinamine are reacted to afford the product. LC-MS: 509 (M$^+$+1). $^1$H NMR (CDCl$_3$) δ 7.75 (d, 1H), 7.60 (s, 1H), 7.20 (d, 1H), 6.15 (s, 1H), 5.80

(d, 1H), 4.80 (m, 3H), 4.40 (m, 1H), 3.65 (m, 4H), 3.45–3.60 (m, 2H), 3.16 (m, 4H), 2.18 (m, 1H), 2.00 (m, 2H), 1.70 (m, 4H), 1.35 (t, 3H).

Example 219

Preparation of 4-(2-Amino-7-chloro-4-quinolinyl)-N-[(3S)-hexahydro-2-oxo-1-(phenylsulfonyl)-1H-azepin-3-yl]-1-piperazinecarboxamide

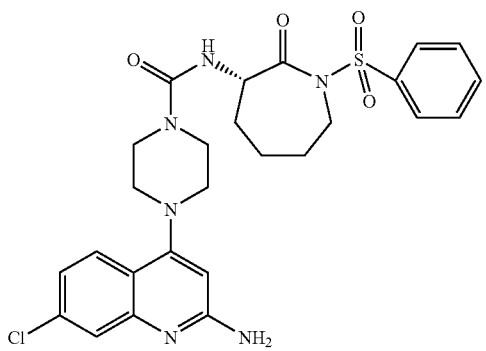

As described for 78, (3R)-3-aminohexahydro-1-(phenylsulfonyl)-2H-azepin-2-one obtained from de-protection of [(3S)-hexahydro-2-oxo-1-(phenylsulfonyl)-1H-azepin-3-yl]-carbamic acid, 1,1-dimethylethyl ester with TFA, 4-nitrophenyl chloroformate, diisopropyl(ethyl)amine, and 7-chloro-4-(1-piperazinyl)-2-quinolinamine are reacted to afford the product. LC-MS: 557 (M$^+$+1).

Example 220

Preparation of 4-(2-Amino-7-chloro-4-quin linyl)-N-[(3S)-1-(cyclohexylcarbonyl)hexahydro-2-oxo-1H-azepin-3-yl]-1-piperazinecarboxamide

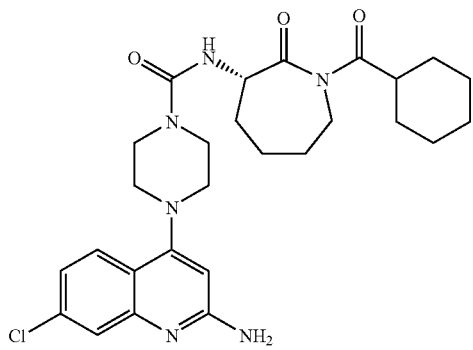

As described for 78, (3R)-3-amino-1-(cyclohexylcarbonyl)hexahydro-2H-azepin-2-one obtained from de-protection of [(3S)-1-(cyclohexylcarbonyl)hexahydro-2-oxo-1H-azepin-3-yl]-carbamic acid, 1,1-dimethylethyl ester with TFA, 4-nitrophenyl chloroformate, diisopropyl(ethyl)amine, and 7-chloro-4-(1-piperazinyl)-2-quinolinamine are reacted to afford the product. LC-MS: 527 (M$^+$+1). $^1$H NMR (CDCl$_3$) δ 7.75 (d, 1H), 7.60 (s, 1H), 7.18 (d, 1H), 6.15 (s, 1H), 5.98 (d, 1H), 4.90 (m, 3H), 4.65 (m, 1H), 3.70 (m, 4H), 3.75 (m, 1H), 3.12 (m, 3H), 2.20 (m, 1H), 1.60–1.95 (m, 10H), 1.20–1.40 (m, 6H).

Example 221

Preparation of 4-(2-Amino-7-chloro-4-quinolinyl)-N-[(3S)-hexahydro-2-oxo-1-[[(phenylsulfonyl)amino]carbonyl]-1H-azepin-3-yl]-1-piperazinecarboxamide As described for 78, N-[[(3R)-3-aminohexahydro-2-oxo-1H-azepin-1-yl]carbonyl]-benzenesulfonamide obtained from de-protection of [(3S)-hexahydro-2-oxo-1-[[(phenylsulfonyl)amino]carbonyl]-1H-azepin-3-yl]-carbamic acid, 1,1-dimethylethyl ester with TFA, 4-nitrophenyl chloroformate, diisopropyl(ethyl)amine, and 7-chloro-4-(1-piperazinyl)-2-quinolinamine are reacted to afford the product. LC-MS: 600 (M$^+$+1).
$^1$H NMR (CDCl$_3$) δ 8.10 (m, 2H), 7.80 (m, 2H), 7.50 (m, 4H), 7.40 (m, 1H), 6.15 (s, 1H), 5.25 (m, 1H), 4.60 (m, 1H), 3.60–3.80 (m, 5H), 3.30 (m, 5H), 2.10 (m, 1H), 2.00 (m, 1H), 1.80 (m, 2H), 1.60 (m, 2H).

Example 222

Preparation of 4-(2-Amino-7-chloro-4-quinolinyl)-N-[(3S)-hexahydro-2-oxo-1-(2-phenylacetyl)-1H-azepin-3-yl]-1-piperazinecarboxamide

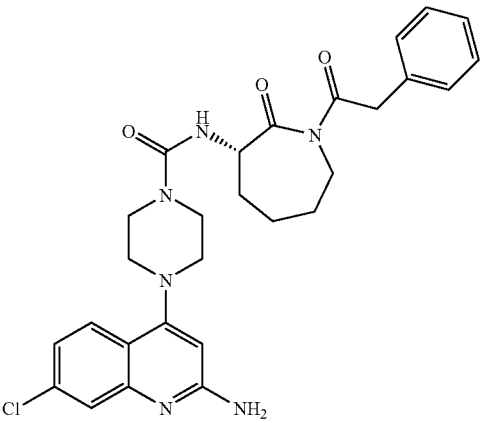

As described for example 213, [(3S)-hexahydro-2-oxo-1-(phenylacetyl)-1H-azepin-3-yl]-carbamic acid, 1,1-dimethylethyl ester, TFA, triphosgene, NaHCO₃ (sat.), and 7-chloro-4-(1-piperazinyl)-2-quinolinamine are reacted to afford the product as a light yellow solid. LC-MS: 535 (M⁺+1). ¹H NMR (CDCl₃, 400 MHz): δ 1.20~1.50 (m, 2H), 1.80~2.20 (m, 4H), 3.10~3.20 (m, 5H), 3.60~3.70 (m, 4H), 4.28 (AB, 2H), 4.75 (dd, 1H), 4.80~4.95 (m, 3H), 5.85 (d, 1H), 6.16 (s, 1H), 7.18 (dd, 1H), 7.22~7.36 (m, 5H), 7.62 (d, 1H), 7.72 (d, 1H).

4-[4-[[4-(2-Amino-7-chloro-4-quinolinyl)-1-piperazinyl]carbonyl]-1-piperazinyl]-chloro-2-quinolinamine

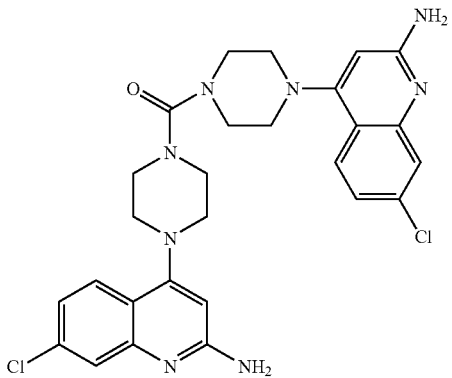

The title compound was obtained as a product in example 222. LC-MS: 551 (M⁺+1). ¹H NMR (DMSO-d₆-TFA): δ 2.95 (br.s, 8H), 3.13 (br.s, 8H), 5.98 (s, 2H), 7.06 (dd, 2H), 7.29 (d, 2H), 7.54 (d, 2H), 8.92 (br.s, 4H).

Example 223

Preparation of 4-(2-Amino-7-chloro-4-quinolinyl)-N-[(3S)-1-formylhexahydro-2-oxo-1H-azepin-3-yl]-1-piperazinecarboxamide

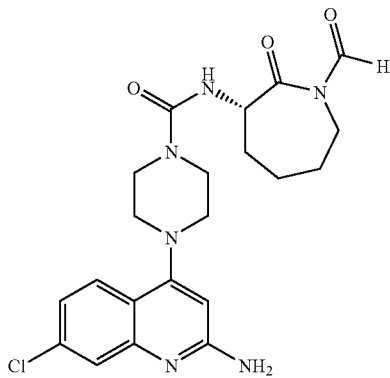

As described for example 213, [(3R)-1-formylhexahydro-2-oxo-1H-azepin-3-yl]-carbamic acid-1,1-dimethylethyl ester, TFA, triphosgene, NaHCO₃ (sat.), and 7-chloro-4-(1-piperazinyl)-2-quinolinamine are reacted to afford the product as a light yellow solid. LC-MS: 445 (M⁺+1). ¹H NMR (CDCl₃): δ 1.30 (m, 1H), 1.65 (m, 1H), 1.80~2.30 (m, 4H), 3.09 (dd, 1H), 3.14 (m, 4H), 3.68 (m, 4H), 4.62 (br.dd, 1H), 4.82 (ddd, 1H), 4.90 (br.s, 2H), 5.84 (d, 1H), 6.16 (s, 1H), 7.18 (dd, 1H), 7.62 (d, 1H), 7.72 (d, 1H), 9.47 (s, 1H).

Example 224

Preparation of 4-(2-Amino-7-chloro-4-quinolinyl)-N-[(3S)-1-(2,2-dimethyl-1-oxopropyl)hexahydro-2-oxo-1H-azepin-3-yl]-1-piperazinecarboxamide

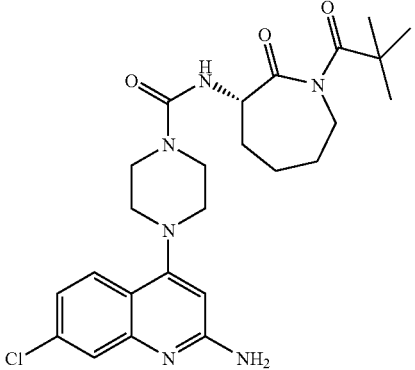

As described for example 213, [(3R)-1-(2,2-dimethyl-1-oxopropyl)hexahydro-2-oxo-1H-azepin-3-yl]-carbamic acid-1,1-dimethylethyl ester, TFA, triphosgene, NaHCO₃ (sat.), and 7-chloro-4-(1-piperazinyl)-2-quinolinamine are reacted to afford the product as a light yellow solid. LC-MS: 501 (M⁺+1). ¹H NMR (CDCl₃) δ 1.30 (s, 9H), 1.50~1.70 (m, 1H), 1.80~2.08 (m, 3H), 2.10–2.20 (m, 1H), 3.05~3.20 (m, 4H), 3.45 (dd, 1H), 3.60–3.74 (m, 4H), 3.80 (br.dd, 1H), 4.66 (m, 1H), 4.94 (br.s, 2H), 5.96 (d, 1H), 6.15 (s, 1H), 7.16 (dd, 1H), 7.60 (d, 1H), 7.71 (d, 1H).

4-[7-Chloro-2-[[[[(3R)-1-(2,2-dimethyl-1-oxopropyl)hexahydro-2-oxo-1H-azepin-3-yl]amino]carbonyl]amino]-4-quinolinyl]-N-[(3S)-1-(2,2-dimethyl-1-oxopropyl)hexahydro-2-oxo-1H-azepin-3-yl]-1-piperazinecarboxamide

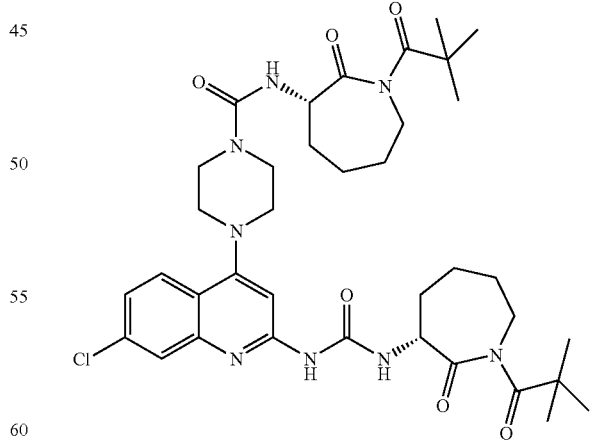

The title compound was obtained as a product in example 224. LC-MS: 739 (M⁺+1). ¹H NMR (DMSO-d₆-TFA) δ 1.10–2.35 (m, 30H), 3.10–3.90 (m, 12H), 4.65 (m, 1H), 4.70 (m, 1H), 5.95 (d, 1H), 6.30 (s, 1H), 7.30 (dd, 1H), 7.60 (br.s, 1H), 7.80 (d, 1H), 7.95 (s, 1H).

Example 225

Preparation of 4-(2-Amino-7-chloro-4-quinolinyl)-N-[(3S)-hexahydro-1-(methylsulfonyl)-2-oxo-1H-azepin-3-yl]-1-piperazinecarboxamide

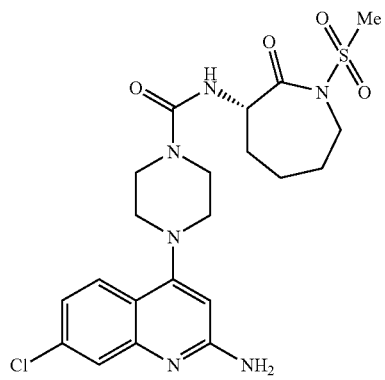

As described for example 213, [(3R)-hexahydro-1-(methylsulfonyl)-2-oxo-1H-azepin-3-yl]-carbamic acid-1,1-dimethylethyl ester, TFA, triphosgene, NaHCO$_3$ (sat.), and 7-chloro-4-(1-piperazinyl)-2-quinolinamine are reacted to afford the product as a light yellow solid. LC-MS: 495 (M$^+$+1). $^1$H NMR (CDCl$_3$) δ 1.52 (m, 1H), 1.70 (m, 1H), 1.86 (m, 1H), 1.95~2.05 (m, 2H), 2.15 (m, 1H), 3.09 (m, 4H), 3.45 (s, 3H), 3.48 (m, 1H), 3.65 (m, 4H), 4.45 (m, 1H), 4.81 (m, 1H), 5.17 (br.s, 2H), 5.95 (d, 1H), 6.15 (s, 1H), 7.15 (dd, 1H), 7.60 (d, 1H), 7.69 (d, 1H).

Example 226

Preparation of (3S)-3-[[[4-(2-Amino-7-chloro-4-quinolinyl)-1-piperazinyl]carbonyl]amino]hexahydro-2-oxo-1H-azepine-1-carboxylic Acid, Methyl Ester

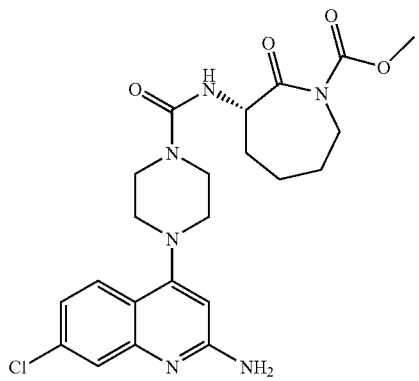

As described for example 213, (3R)-3-[[(1,1-dimethylethoxy)carbonyl]amino]hexahydro-2-oxo-1H-azepine-1-carboxylic acid-methyl ester, TFA, triphosgene, NaHCO$_3$ (sat.), and 7-chloro-4-(1-piperazinyl)-2-quinolinamine are reacted to afford the title product as a light yellow solid. LC-MS: 475 (M$^+$+1). $^1$H NMR (CDCl$_3$): δ 1.45–2.05 (m, 5H), 2.15 (m, 1H), 3.12 (m, 4H), 3.42 (dd, 1H), 3.66 (m, 4H), 3.90 (s, 3H), 4.45 (m, 1H), 4.75~4.85 (m, 3H), 5.95 (d, 1H), 6.15 (s, 1H), 7.19 (dd, 1H), 7.62 (d, 1H), 7.74 (d, 1H).

Example 227

Preparation of (3S)-3-[[[4-(2-Amino-7-chloro-4-quinolinyl)-1-piperazinyl]carbonyl]amino]hexahydro-2-oxo-1H-azepine-1-carboxylic Acid-ethyl Ester

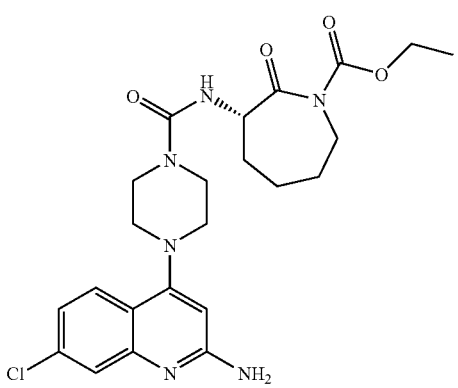

As described for example 213, (3R)-3-[[(1,1-dimethylethoxy)carbonyl]amino]hexahydro-2-oxo-1H-azepine-1-carboxylic acid, ethyl ester, TFA, triphosgene, NaHCO$_3$ (sat.), and 7-chloro-4-(1-piperazinyl)-2-quinolinamine are reacted to afford the title product as a light yellow solid. LC-MS: 489 (M$^+$+1). $^1$H NMR (CDCl$_3$): δ 1.37 (t, 3H), 1.44~2.02 (m, 5H), 2.12~2.20 (m, 1H), 3.13 (m, 4H), 3.41 (dd, 1H), 3.67 (m, 4H), 4.35 (m, 2H), 4.42 (m, 1H), 4.74~4.86 (m, 3H), 6.00 (d, 1H), 6.16 (s, 1H), 7.18 (dd, 1H), 7.62 (d, 1H), 7.73 (d, 1H).

Example 228

Preparation of (3S)-3-[[[4-(2-Amino-7-chloro-4-quinolinyl)-1-piperazinyl]carbonyl]amino]hexahydro-2-oxo-1H-azepine-1-carboxylic acid, 2,2,2-trifluoroethyl Ester

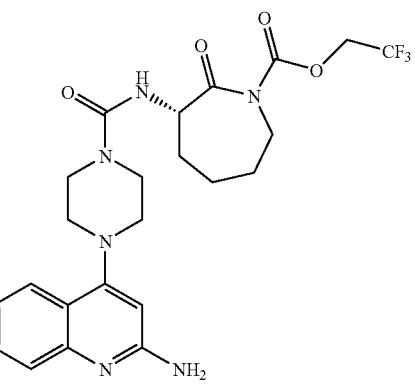

As described for example 213, (3R)-3-[[(1,1-dimethylethoxy)carbonyl]amino]hexahydro-2-oxo-1H-azepine-1-carboxylic acid, 2,2,2-trifluoroethyl ester, TFA, triphosgene, NaHCO$_3$ (sat.), and 7-chloro-4-(1-piperazinyl)-2-quinolinamine are reacted to afford the product as a white solid.

LC-MS: 543 (M++1). ¹H NMR (DMSO+TFA): δ 1.32–1.45 (m, 1H), 1.56~1.90 (m, 5H), 3.26 (m, 4H), 3.54–3.66 (m, 5H), 4.15 (m, 1H), 4.68 (br.d, 1H), 4.83 (m, 2H), 6.32 (s, 1H), 7.42 (dd, 1H), 7.60 (d, 1H), 7.90 (d, 1H).

Example 229

Preparation of (3S)-[[[4-(2-Amino-7-chloro-4-quinolinyl)-1-piperazinyl]carbonyl]amino]hexahydro-2-oxo-1H-azepine-1-carboxylic acid, 2-propenyl ester

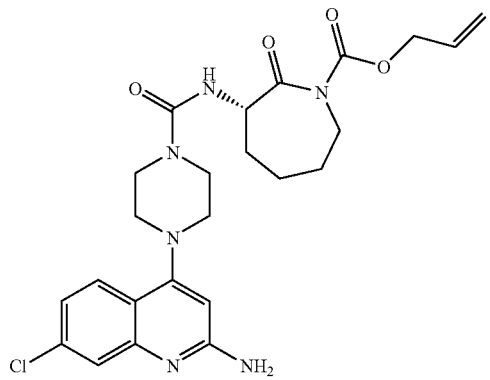

As described for example 213, (3S)-3-[[(1,1-dimethylethoxy)carbonyl]amino]hexahydro-1H-azepine-1-carboxylic acid 2-oxo-, 2-propenyl ester, TFA, triphosgene, NaHCO₃ (sat.), and 7-chloro-4-(1-piperazinyl)-2-quinolinamine are reacted to afford the product as a white solid. LC-MS: 501 (M++1). ¹H NMR (CDCl₃) δ 7.70 (d, 1H), 7.60 (s, 1H), 7.15 (d, 1H), 6.0 (s, 2H), 5.40 (d, 1H), 5.30 (m, 2H), 4.80 (m, 5H), 4.40 (m, 1H), 3.65 (m, 4H), 3.40 (m, 1H), 3.10 (m, 4H), 2.10 (m, 1H), 1.95 (m, 3H), 1.60 (m, 1H), 1.50 (m, 1H).

Example 230

Preparation of (3S)-3-[[[4-(2-Amino-7-chloro-4-quinolinyl)-1-piperazinyl]carbonyl]amino]hexahydro-2-oxo-1H-azepine-1-carboxylic Acid Phenyl Ester

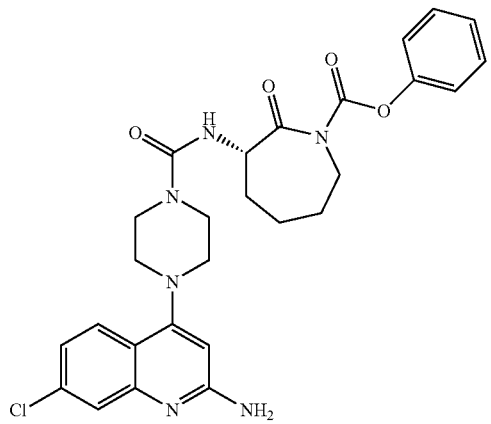

As described for example 213, (3R)-3-[[(1,1-dimethylethoxy)carbonyl]amino]hexahydro-2-oxo-1H-azepine-1-carboxylic acid, phenyl ester, TFA, triphosgene, NaHCO₃ (sat.), and 7-chloro-4-(1-piperazinyl)-2-quinolinamine are reacted to afford the product as a light yellow solid. LC-MS: 537 (M++1). ¹H NMR (CDCl₃,) δ 1.56~2.08 (m, 5H), 2.16–2.24 (m, 1H), 3.14 (m, 4H), 3.54 (dd, 1H), 3.68 (m, 4H), 4.54 (br.dd, 1H), 4.84 (br.s, 2H), 4.90 (ddd, 1H), 5.80 (d, 1H), 6.15 (s, 1H), 7.16~7.22 (m, 3H), 7.27 (m, 1H), 7.41 (m, 2H), 7.62 (d, 1H), 7.72 (d, 1H).

Example 231

Preparation of (3S)-3-[[[4-(2-Amino-7-chloro-4-quinolinyl)-1-piperazinyl]carbonyl]amino]hexahydro-2-oxo-1H-azepine-1-carboxylic acid-4-fluorophenyl Ester

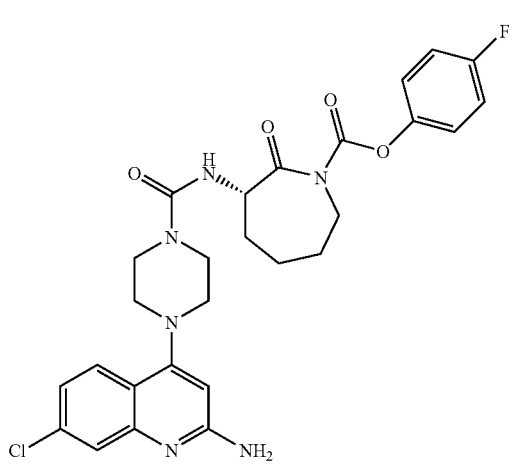

As described for example 213, (3R)-3-[[(1,1-dimethylethoxy)carbonyl]amino]hexahydro-2-oxo-1H-azepine-1-carboxylic acid-4-fluorophenyl ester, TFA, triphosgene, NaHCO₃ (sat.), and 7-chloro-4-(1-piperazinyl)-2-quinolinamine are reacted to afford the product as a light yellow solid. LC-MS: 555 (M++1). ¹H NMR (CDCl₃): δ 1.54~2.10 (m, 5H), 2.16–2.24 (m, 1H), 3.14 (m, 4H), 3.54 (dd, 1H), 3.68 (m, 4H), 4.52 (dd, 1H), 4.84 (br.s, 2H), 4.90 (ddd, 1H), 5.94 (d, 1H), 6.15 (s, 1H), 7.06–7.13 (m, 2H), 7.13–7.20 (m, 3H), 7.62 (d, 1H), 7.72 (d, 1H).

Example 232

Preparation of (3S)-[[[4-(2-Amino-7-chloro-4-quinolinyl)-1-piperazinyl]carbonyl]amino]hexahydro-2-oxo-1H-azepine-1-carboxylic Acid, Phenylmethyl Ester

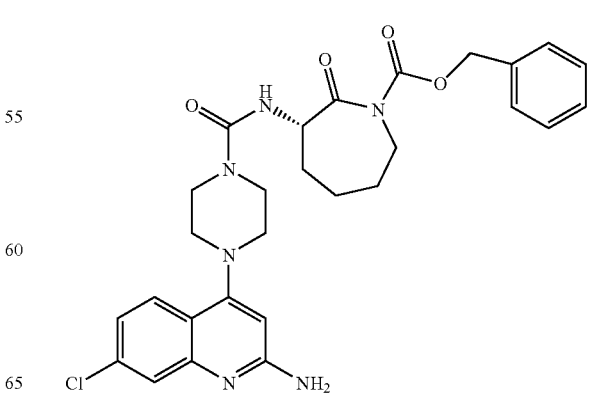

As described example 78, (3R)-3-aminohexahydro-2-oxo-, phenylmethyl ester-1H-azepine-1-carboxylic acid obtained by de-protection of (3S)-3-[[(1,1-dimethylethoxy)carbonyl]amino]hexahydro-2-oxo-1H-azepine-1-carboxylic acid, phenylmethyl ester with TFA, p-nitrophenyl chloroformate, diisopropyl(ethyl)amine, and 7-chloro-4-(1-piperazinyl)-2-quinolinamine are reacted to afford the product as a white solid. LC-MS: 551 (M$^+$+1). $^1$H NMR (CDCl$_3$) δ 1.50 (m, 1H), 1.65 (m, 1H), 1.92 (m, 3H), 2.13 (d, 1H), 3.10 (m, 4H), 3.40 (m, 1H), 3.65 (m, 4H), 4.45 (m, 1H), 4.85 (m, 3H), 5.30 (s, 2H), 6.00 (d, 1H), 6.15 (s, 1H), 7.20 (d, 1H), 7.40 (m, 5H), 7.60 (s, 1H), 7.70 (d, 1H).

Example 233

Preparation of 4-(2-Amino-7-chloro-4-quinolinyl)-N-[(3S)-1-cyanohexahydro-2-oxo-1H-azepin-3-yl]-1-piperazinecarboxamide

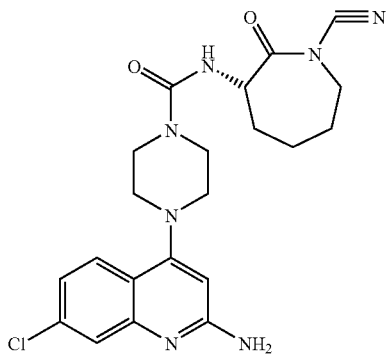

As described example 78, (3R)-3-amino-1-cyanohexahydro-2H-azepin-2-one obtained by de-protection of [(3S)-1-cyanohexahydro-2-oxo-1H-azepin-3-yl]-carbamic acid-1,1-dimethylethyl ester with TFA, p-nitrophenyl chloroformate, diisopropyl(ethyl)amine, and 7-chloro-4-(1-piperazinyl)-2-quinolinamine are reacted to afford the product as a white solid. LC-MS: 551 (M$^+$+1). $^1$H NMR (DMSO-d$_6$): 61.6 (m, 2H), 1.92 (m, 3H), 3.23 (br. s, 4H), 3.61 (br. s, 4H), 3.77 (m, 1H), 3.95 (dd, 1H), 4.58 (t, 1H), 6.38 (s, 1H), 7.0 (d, 1H), 7.43 (d, 1H), 7.62 (s, 1H), 7.9 (d, 1H), 8.41 (br., s, 1H).

Example 234

Preparation of (3S)-3-[[[4-(2-Amino-7-chloro-4-quinolinyl)-1-piperazinyl]carbonyl]amino]-N-cyclohexylhexahydro-2-oxo-1H-azepine-1-carboxamide

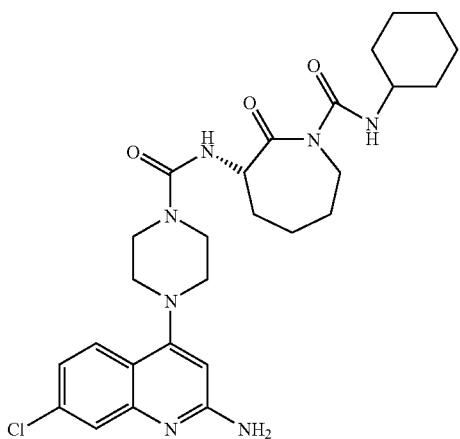

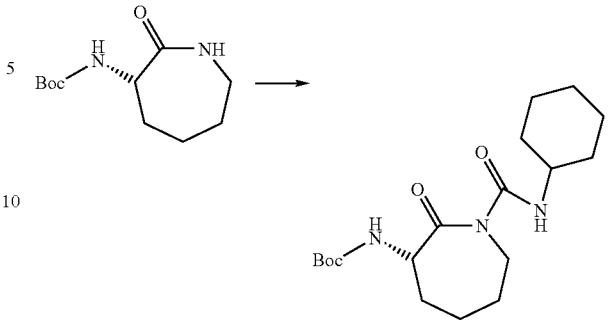

Preparation of [(3S)-1-[(cyclohexylamino)carbonyl]hexahydro-2-oxo-1H-azepin-3-yl]-carbamic acid-1,1-dimethylethyl ester (A. D. Borthwick, et al. *J. Med. Chem.*, 2000, 43, 4452–4464): To a stirred solution of [(3S)-hexahydro-2-oxo-1H-azepin-3-yl]-carbamic acid-1,1-dimethylethyl ester (500 mg, 2.2 mmol) in THF (10 mL) at −78° C. was added LiHDMS (4.4 ml, 4.4 mmol, 1.0 M in THF). After addition, dry-ice bath was removed, and the reaction was stirred at room temperature for about 30 min. The reaction was re-cooled to −78° C., and cyclohexyl isocyanate (554 mg, 4.4 mmol) was added. The reaction was allowed to warm to rt over 2 h, and was quenched with NH$_4$Cl (sat., 10 mL). The reaction mixture was extracted with EtOAc (3×30 mL), washed with brine (15 mL), and dried over Na$_2$SO$_4$. Concentration in vacuo followed by purification through flash chromatography (hexane:EtOAc/5:1) afforded the title product. $^1$H NMR (CDCl$_3$) δ 1.1–1.4 (m, 6H), 1.45 (s, 9H), 1.5–1.7 (m, 3H), 1.75 (m, 1H), 1.96 (m, 2H), 2.28 (dq, 1H), 3.46 (br. s, 1H), 4.41 (br. s, 1H), 4.51 (tt, 1H).

In a similar manner following intermediates were prepared:

[(3R)-1-(aminocarbonyl)hexahydro-2-oxo-1H-azepin-3-yl]-carbamic acid, 1,1-dimethylethyl ester

[(3R)-hexahydro-2-oxo-1-[[(2,2,2-trifluoroethyl)amino]carbonyl]-1H-azepin-3-yl]-carbamic acid, 1,1-dimethylethyl ester

[(3R)-1-[(cyclopropylamino)carbonyl]hexahydro-2-oxo-1H-azepin-3-yl]-carbamic acid-1,1-dimethylethyl ester

[(3R)-hexahydro-2-oxo-1-[(propylamino)carbonyl]-1H-azepin-3-yl]-carbamic acid, 1,1-dimethylethyl ester (3S)-hexahydro-2-oxo-1-(1-pyrrolidinylcarbonyl)-1H-azepin-3-yl]-carbamic acid, 1,1-dimethylethyl ester

[(3S)-1-[(cyclopentylamino)carbonyl]hexahydro-2-oxo-1H-azepin-3-yl]-carbamic acid-1,1-dimethylethyl ester. $^1$H NMR (CDCl$_3$) δ 1.36 (m, 2H), 1.41 (s, 9H), 1.5–1.7 (m, 5H), 1.87 (m, 4H), 2.12 (m, 2H), 3.86 (m, 1H), 4.44 (br. s, 1H), 5.17 (m, 1H).

[(3S)-1-[(cyclobutylamino)carbonyl]hexahydro-2-oxo-1H-azepin-3-yl]carbamic acid-1,1-dimethylethyl ester. $^1$H NMR (CDCl$_3$) δ 1.4 (m, 1H), 1.43 (s, 9H), 1.5–1.98 (m, 6H), 2.1 (m, 1H), 2.38 (m, 2H), 3.17 (m, 1H), 4.33 (m, 1H), 4.64 (m, 1H), 4.81 (m, 1H), 5.61 (br. s, 1H), 9.25 (br. s, 1H).

[(3S)-1-[[(4-fluorophenyl)amino]carbonyl]hexahydro-2-oxo-1H-azepin-3-yl]-carbamic acid, 1,1-dimethylethyl ester

[(3S)-1-[(ethylamino)carbonyl]hexahydro-2-oxo-1H-azepin-3-yl]-carbamic acid, 1,1-dimethylethyl ester

[(3S)-hexahydro-2-oxo-1-[(phenylamino)carbonyl]-1H-azepin-3-yl]-carbamic acid, 1,1-dimethylethyl ester

[(3S)-hexahydro-1-[[(1-methylethyl)amino]carbonyl]-2-oxo-1H-azepin-3-yl]-carbamic acid, 1,1-dimethylethyl ester

[(3S)-1-[(butylamino)carbonyl]hexahydro-2-oxo-1H-azepin-3-yl]-carbamic acid, 1,1-dimethylethyl ester

[(3S)-hexahydro-1-[[(2-methylpropyl)amino]carbonyl]-2-oxo-1H-azepin-3-yl]-carbamic acid, 1,1-dimethylethyl ester

[(3S)-1-[[(1,1-dimethylethyl)amino]carbonyl]hexahydro-2-oxo-1H-azepin-3-yl]-carbamic acid, 1,1-dimethylethyl ester

[(3S)-1-[(dimethylamino)carbonyl]hexahydro-2-oxo-1H-azepin-3-yl]-carbamic acid-1,1-dimethylethyl ester (3S)-hexahydro-2-oxo-1-[[[4-(trifluoromethyl)phenyl]amino]carbonyl]-1H-azepin-3-yl]-carbamic acid, 1,1-dimethylethyl ester

[(3S)-1-[[(3-fluorophenyl)amino]carbonyl]hexahydro-2-oxo-1H-azepin-3-yl]-carbamic acid, 1,1-dimethylethyl ester

[(3S)-hexahydro-1-[[(4-methylphenyl)amino]carbonyl]-2-oxo-1H-azepin-3-yl]-carbamic acid 1,1-dimethylethyl ester

[(3S)-1-[[(2-fluorophenyl)amino]carbonyl]hexahydro-2-oxo-1H-azepin-3-yl]-carbamic acid, 1,1-dimethylethyl ester

[(3S)-1-[[(2,6-diethylphenyl)amino]carbonyl]hexahydro-2-oxo-1H-azepin-3-yl]-carbamic acid, 1,1-dimethylethyl ester

[(3S)-hexahydro-1-[(methylamino)carbonothioyl]-2-oxo-1H-azepin-3-yl]-carbamic acid, 1,1-dimethylethyl ester

[(3S)-1-[(ethylamino)carbonothioyl]hexahydro-2-oxo-1H-azepin-3-yl]-carbamic acid, 1,1-dimethylethyl ester

[(3S)-hexahydro-1-[[(1-methylethyl)amino]carbonothioyl]-2-oxo-1H-azepin-3-yl]-carbamic acid, 1,1-dimethylethyl ester

[(3S)-hexahydro-2-oxo-1-[(2-propenylamino)carbonothioyl]-1H-azepin-3-yl]-carbamic acid, 1,1-dimethylethyl ester Preparation of (3S)-3-[[[4-(2-amino-7-chloro-4-quinolinyl)-1-piperazinyl]carbonyl]amino]-N-cyclohexylhexahydro-2-oxo-1H-azepine-1-carboxamide: As described example 78, (3R)-3-amino-N-cyclohexylhexahydro-2-oxo-1H-azepine-1-carboxamide obtained by de-protection of [(3S)-1-[(cyclohexylamino)carbonyl]hexahydro-2-oxo-1H-azepin-3-yl]-carbamic acid-1,1-dimethylethyl ester with TFA, p-nitrophenyl chloroformate, diisopropyl(ethyl)amine, and 7-chloro-4-(1-piperazinyl)-2-quinolinamine are reacted to afford the product as a white solid. $^1$H NMR (DMSO-d$_6$): δ 1.2 (m, 4H), 1.5 (m, 1H), 1.6–1.8 (m, 4H), 2.97 (m, 4H), 3.4 (m, 1H), 3.48 (m, 4H), 6.21 (s, 1H), 6.27 (d, 1H), 6.43 (m, 1H), 7.11 (d, 1H), 7.37 (s, 1H), 7.73 (d, 1H).

Example 235

Preparation of (3S)-3-[[[4-(2-Amino-7-chloro-4-quinolinyl)-1-piperazinyl]carbonyl]amino]hexahydro-2-oxo-1H-azepine-1-carboxamide

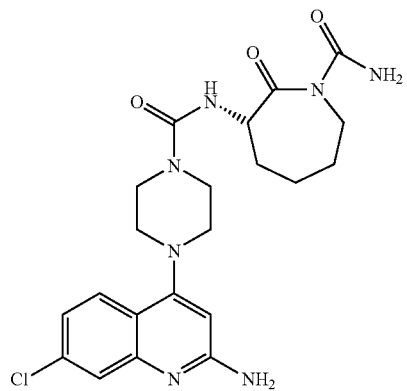

Preparation of (3S)-3-[[[4-(2-amino-7-chloro-4-quinolinyl)-1-piperazinyl]carbonyl]amino]hexahydro-2-oxo-1H-azepine-1-carboxamide: As described for example 213, [(3S)-1-(aminocarbonyl)hexahydro-2-oxo-1H-azepin-3-yl]-carbamic acid-1,1-dimethylethyl ester, TFA, triphosgene, NaHCO$_3$ (sat.), and 7-chloro-4-(1-piperazinyl)-2-quinolinamine are reacted to afford the product as a white solid. LC-MS: 460 (M$^+$+1). $^1$H NMR (DMSO-d$_6$+TFA): 1.16~1.30 (m, 1H), 1.54~1.88 (m, 5H), 3.26 (m, 4H), 3.60 (m, 4H), 4.56 (ddd, 1H), 4.70 (br.dd, 1H), 6.32 (s, 1H), 7.38–7.46 (m, 2H), 7.62 (d, 1H), 7.88 (d, 1H), 8.20–8.50 (m, 3H).

(2S)-2-[[[4-(2-Amino-7-chloro-4-quinolinyl)-1-piperazinyl]carbonyl]amino]-6-[[[(trichloroacetyl)amino]carbonyl]amino]-hexanoic Acid, Methyl Ester

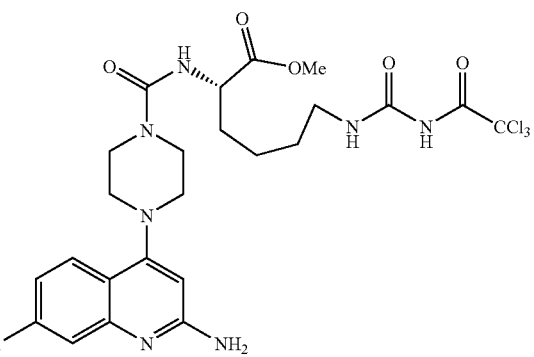

The title product was obtained as a product in example 235. LC-MS: 636 (M$^+$+1). $^1$HNMR (CDCl$_3$): δ 1.38~1.98 (m, 6H), 3.14 (m, 4H), 3.37 (dd, 2H), 3.68 (m, 4H), 3.78 (s, 3H), 4.56 (m, 1H), 4.98 (br.s, 1H), 5.14 (d, 1H), 6.16 (s, 1H), 7.18 (dd, 1H), 7.26 (s, 1H), 7.64 (d, 1H), 7.72 (d, 1H), 7.84 (m, 1H).

Example 236

Preparation of (3S)-3-[[[4-(2-Amino-7-chloro-4-quinolinyl)-1-piperazinyl]carbonyl]amino]hexahydro-2-oxo-N-(2,2,2-trifluoroethyl)-1H-azepine-1-carboxamide

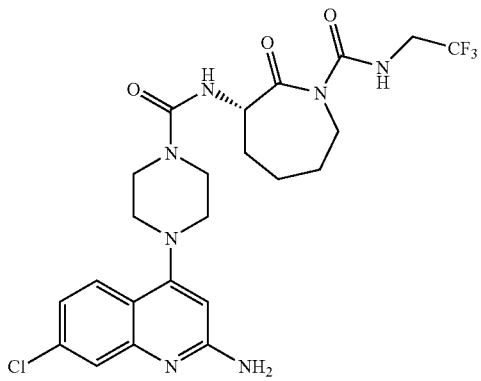

As described for example 213, [(3R)-hexahydro-2-oxo-1-[[(2,2,2-trifluoroethyl)amino]carbonyl]-1H-azepin-3-yl]-carbamic acid, 1,1-dimethylethyl ester, TFA, triphosgene, NaHCO$_3$ (sat.), and 7-chloro-4-(1-piperazinyl)-2-quinolinamine are reacted to afford the product as a light yellow solid. LC-MS: 542 (M$^+$+1). $^1$H NMR (CDCl$_3$,): δ 1.44 (m, 1H), 1.64 (m, 1H), 1.82~2.02 (m, 4H), 3.14 (m, 4H), 3.31 (dd, 1H), 3.68 (m, 4H), 3.98 (m, 2H), 4.84 (dd, 1H), 4.88–5.00 (m, 3H), 5.80 (d, 1H), 6.03 (s, 1H), 7.16 (dd, 1H), 7.60 (d, 1H), 7.71 (d, 1H), 9.54 (t, 1H).

Example 237

Preparation of (3S)-3-[[[4-(2-Amino-7-chloro-4-quinolinyl)-1-piperazinyl]carbonyl]amino]-N-cyclopropylhexahydro-2-oxo-1H-azepine-1-carboxamide

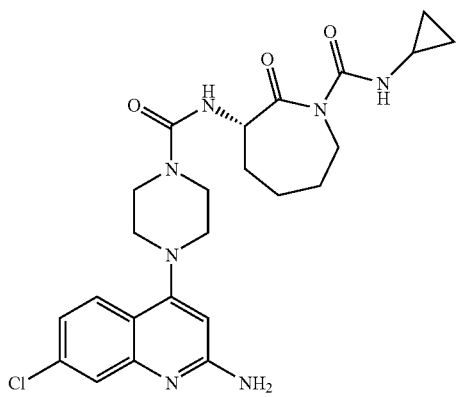

As described for example 213, [(3R)-1-[(cyclopropylamino)carbonyl]hexahydro-2-oxo-1H-azepin-3-yl]-carbamic acid-1,1-dimethylethyl ester, TFA, triphosgene, NaHCO$_3$ (sat.), and 7-chloro-4-(1-piperazinyl)-2-quinolinamine are reacted to afford the product as a white solid. LC-MS: 500 (M$^+$+1). $^1$H NMR (CDCl$_3$): δ 0.50~0.62 (m, 2H), 0.72–0.84 (m, 2H), 1.42 (m, 1H), 1.60 (m, 1H), 1.82~2.02 (m, 3H), 2.13 (m, 1H), 2.76 (ddd, 1H), 3.12 (br.dd, 4H), 3.24 (br.dd, 1H), 3.66 (m, 4H), 4.82~4.94 (m, 2H), 5.02 (br.s, 2H), 5.86 (d, 1H), 6.16 (s, 1H), 7.16 (dd, 1H), 7.60 (d, 1H), 7.72 (d, 1H), 9.10 (d, 1H).

Example 238

Preparation of (3S)-[[[4-(2-Amino-7-chloro-4-quinolinyl)-1-piperazinyl]carbonyl]amino]hexahydro-2-oxo-N-propyl-1H-azepine-1-carboxamide

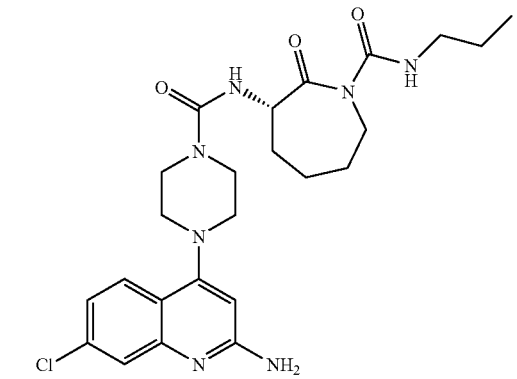

As described for example 213, [(3R)-hexahydro-2-oxo-1-[(propylamino)carbonyl]-1H-azepin-3-yl]-carbamic acid, 1,1-dimethylethyl ester, TFA, triphosgene, NaHCO$_3$ (sat.), and 7-chloro-4-(1-piperazinyl)-2-quinolinamine are reacted to afford the product as a white solid. LC-MS: 502 (M$^+$+1). $^1$H NMR (CD$_3$OD) δ 0.95 (t, 3H), 1.55 (m, 4H), 1.90 (m, 3H), 2.10 (d, 1H), 3.10 (m, 4H), 3.25 (m, 3H), 3.65 (m, 4H), 4.80–4.95 (m, 4H), 5.86 (d, 1H), 6.12 (s, 1H), 7.12 (d, 1H), 7.58 (s, 1H), 7.65 (d, 1H), 9.00 (m, 1H).

Example 239

Preparation of 4-(2-Amino-7-chloro-4-quinolinyl)-N-[(3S)-hexahydro-2-oxo-1-(1-pyrrolidinylcarbonyl)-1H-azepin-3-yl]-1-piperazinecarboxamide

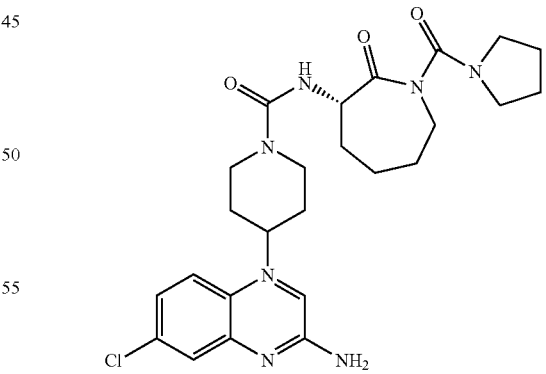

As described for example 78, (3R)-3-aminohexahydro-1-(1-pyrrolidinylcarbonyl)-2H-azepin-2-one obtained by deprotection of (3S)-hexahydro-2-oxo-1-(1-pyrrolidinylcarbonyl)-1H-azepin-3-yl]-carbamic acid, 1,1-dimethylethyl ester with TFA, diisopropyl(ethyl)amine, and 7-chloro-4-(piperazin-1-yl)quinoline are reacted to give the product. LC-MS: 514 (M$^+$+1). $^1$H NMR (CDCl$_3$) δ 7.70 (d, 1H), 7.62 (s, 1H), 7.18 (d, 1H), 6.15 (s, 1H), 6.00 (s, 1H), 5.00 (s, 2H), 4.60 (m, 1H), 3.75 (m, 1H), 3.65 (m, 4H), 3.50 (m, 3H), 3.35 (m, 2H), 3.15 (m, 4H), 1.80–2.20 (m, 7H), 1.60 (m, 2H), 1.30 (m, 1H).

Example 240

Preparation of (3S)-3-[[[4-(2-Amino-7-chloro-4-quinolinyl)-1-piperazinyl]carbonyl]amino]-N-cyclopentylhexahydro-2-oxo-1H-azepine-1-carboxamide

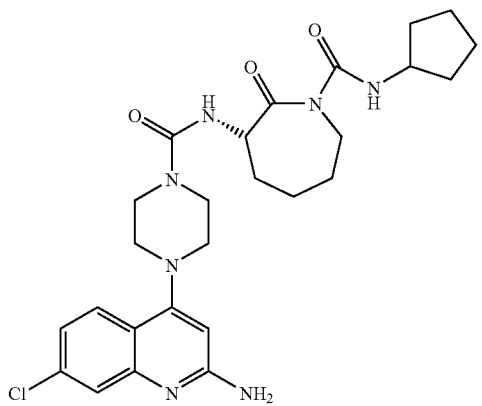

As described example 78, (3R)-3-amino-N-cyclopentyl-hexahydro-2-oxo-1H-azepine-1-carboxamide obtained by de-protection of [(3S)-1-[(cyclopentylamino)carbonyl]hexahydro-2-oxo-1H-azepin-3-yl]-carbamic acid-1,1-dimethylethyl ester with TFA, p-nitrophenyl chloroformate, diisopropyl(ethyl)amine, and 7-chloro-4-(1-piperazinyl)-2-quinolinamine are reacted to afford the product as a white solid. $^1$H NMR (DMSO-$d_6$): 61.38 (m, 2H), 1.63 (m, 5H), 2.06 (m, 2H), 3.15 (m, 4), 3.6 (m, 4H), 4.16 (m, 1H), 4.41 (d, 1H), 4.78 (br. s, 2H), 6.18 (s, 1H), 7.2 (d, 1H), 7.62 (s, 1H), 7.73 (d, 1H).

Example 241

Preparation of (3S)-3-[[[4-(2-Amino-7-chloro-4-quinolinyl)-1-piperazinyl]carbonyl]amino]-N-cyclobutylhexahydro-2-oxo-1H-azepine-1-carboxamide

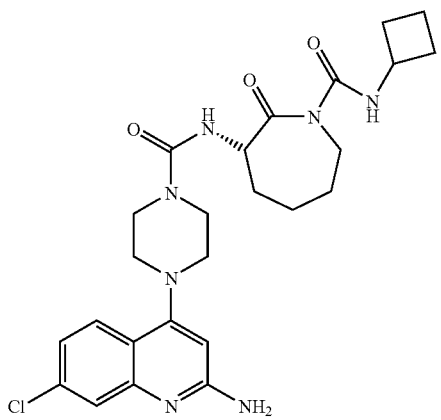

As described example 78, (3R)-3-amino-N-cyclobutyl-hexahydro-2-oxo-1H-azepine-1-carboxamide by de-protection of [(3S)-1-[(cyclobutylamino)carbonyl]hexahydro-2-oxo-1H-azepin-3-yl] carbamic acid-1,1-dimethylethyl ester with TFA, p-nitrophenyl chloroformate, diisopropyl(ethyl) amine, and 7-chloro-4-(1-piperazinyl)-2-quinolinamine are reacted to afford the product. $^1$HNMR (DMSO-$d_6$): δ 1.24 (br. s, 1H), 1.5–1.9 (m, 7H), 2.2 (m, 2H), 2.99 (m, 4H), 3.6 (m, 4H), 4.17 (m, 1H), 4.52 (m, 1H), 4.66 (t, 1H), 6.14 (s, 1H, 6.42 (br. s, 1H), 6.8 (d, 1H), 7.1 (d, 1H), 7.39 (s, 1H), 7.76 (d, 1H), 9.3 (d, 1H).

Example 242

Preparation of (3R)-3-[[[4-(2-Amino-7-chloro-4-quinolinyl)-1-piperazinyl]carbonyl]amino]-N-(4-fluorophenyl)hexahydro-2-oxo-1H-azepine-1-carboxamide

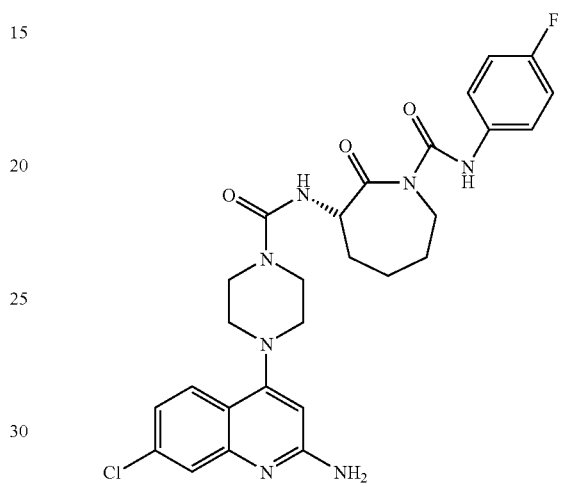

As described for example 78, (3R)-3-amino-N-(4-fluorophenyl)hexahydro-2-oxo-1H-azepine-1-carboxamide obtained by de-protection of [(3S)-1-[[(4-fluorophenyl)amino]carbonyl]hexahydro-2-oxo-1H-azepin-3-yl]-carbamic acid, 1,1-dimethylethyl ester with TFA, diisopropyl (ethyl)amine, and 7-chloro-4-(1-piperazinyl)-2-quinolinamine are reacted to give the product. LC-MS: 554 ($M^+$+1). $^1$H NMR (CDCl$_3$) δ 1.4–2.25 (m, 6H), 3.25–3.45 (m, 4H), 3.7–3.9 (m, 4H), 4.85–5.1 (m, 2H), 5.85–6.0 (s, 1H), 6.1–6.2 (m, 1H), 7.0–7.08 (m, 2H), 7.32–7.38 (m, 1H), 7.44–7.5 (m, 2H), 7.68–7.76 (m, 2H), 11.2 (s, 1H).

Example 243

Preparation of (3S)-3-[[[4-(2-Amino-7-chloro-4-quinolinyl)-1-piperazinyl]carbonyl]amino]-N-ethyl-hexahydro-2-oxo-1H-azepine-1-carboxamide

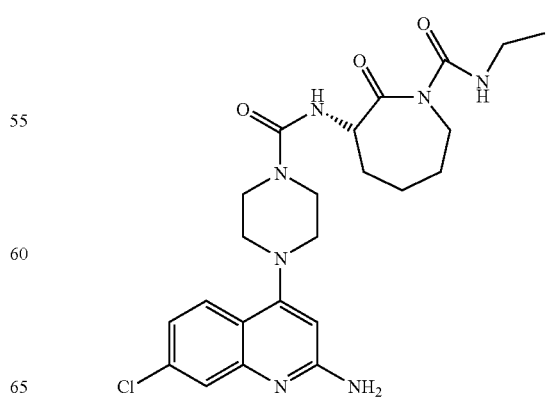

As described for example 78, (3R)-3-amino-N-ethyl-hexahydro-2-oxo-1H-azepine-1-carboxamide obtained by the de-protection of [(3S)-1-[(ethylamino)carbonyl]hexahydro-2-oxo-1H-azepin-3-yl]-carbamic acid, 1,1-dimethylethyl ester with TFA, diisopropyl(ethyl)amine, and 7-chloro-4-(1-piperazinyl)-2-quinolinamine are reacted to give the product. LC-MS: 487 (M$^+$+1). $^1$H NMR (CDCl$_3$) δ 1.2 (t, 3H), 1.3–1.7 (m, 2H), 1.7–2.2 (m, 4H), 3.15–3.45 (m, 7H), 3.6–3.8 (m, 4H), 4.8–5.0 (m, 2H), 5.8–6.0 (m, 1H), 6.0–6.2 (s, 1H), 7.34–7.4 (m, 1H), 7.7 (d, 1H), 7.8 (m, 1H), 8.9–9.0 (m, 1H).

Example 244

Preparation of (3S)-3-[[[4-(2-Amino-7-chloro-4-quinolinyl)-1-piperazinyl]carbonyl]amino]hexahydro-2-oxo-N-phenyl-1H-azepine-1-carboxamide

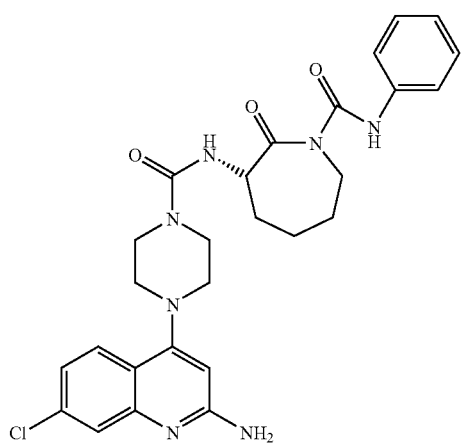

As described for example 78, (3R)-3-aminohexahydro-2-oxo-N-phenyl-1H-azepine-1-carboxamide obtained by de-protection of [(3S)-hexahydro-2-oxo-1-[(phenylamino)carbonyl]-1H-azepin-3-yl]-carbamic acid, 1,1-dimethylethyl ester with TFA, diisopropyl(ethyl)amine, and 7-chloro-4-(1-piperazinyl)-2-quinolinamine are reacted to give the product. LC-MS: 535 (M$^+$+1). $^1$H NMR (CDCl$_3$); δ 1.3–1.8 (m, 2H), 1.8–2.3 (m, 4H), 3.1–3.25 (m, 4H), 3.26–3.34 (m, 1H), 3.6–3.8 (m, 4H), 4.76–4.86 (s, 2H), 4.88–5.06 (m, 2H), 5.8–6.1 (m, 1H), 6.1–6.2 (s, 1H), 7.09–7.15 (m, 1H), 7.16–7.2 (m, 1H), 7.3–7.37 (m, 2H), 7.5–7.55 (m, 1H), 7.62–7.64 (d, 1H), 7.72–7.76 (d, 1H), 11.2–11.4 (s, 1H).

Example 245

Preparation of (3S)-3-[[[4-(2-Amino-7-chloro-4-quinolinyl)-1-piperazinyl]carbonyl]amino]hexahydro-N-(1-methylethyl)-2-oxo-1H-azepine-1-carboxamide

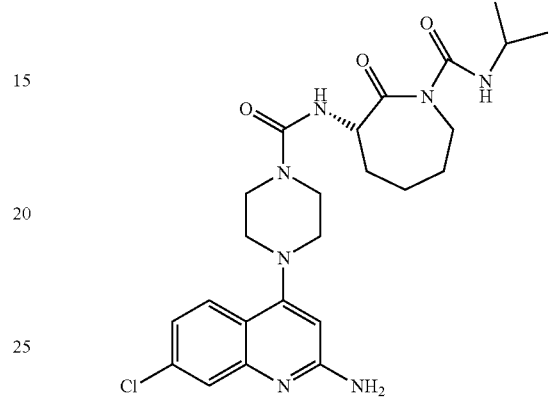

As described for example 78, (3R)-3-aminohexahydro-N-(1-methylethyl)-2-oxo-1H-azepine-1-carboxamide obtained by de-protection of [(3S)-hexahydro-1-[[(1-methylethyl)amino]carbonyl]-2-oxo-1H-azepin-3-yl]-carbamic acid, 1,1-dimethylethyl ester with TFA, diisopropyl(ethyl)amine, and 7-chloro-4-(1-piperazinyl)-2-quinolinamine are reacted to give the product. LC-MS: 501 (M$^+$+1). $^1$H NMR (CDCl$_3$); δ 1.2 (m, 6H), 1.3–1.5 (m, 1H), 1.5–1.7 (m, 1H), 1.8–2.2 (m, 4H), 3.1–3.3 (m, 5H), 3.6–3.8 (m, 4H), 3.9–4.1 (m, 1H), 4.78–5.0 (m, 4H), 5.8–5.9 (m, 1H), 6.1–6.2 (s, 1H), 7.1–7.2 (m, 1H), 7.6–7.64 (d, 1H), 7.7–7.76 (m, 1H), 8.9–8.96 (d, 1H).

Example 246

Preparation of (3S)-3-[[[4-(2-Amino-7-chloro-4-quinolinyl)-1-piperazinyl]carbonyl]amino]-N-butyl-hexahydro-2-oxo-1H-azepin-1-carboxamide

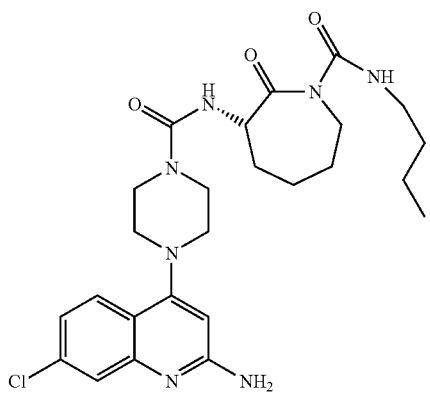

As described for example 78, (3R)-3-amino-N-butyl-hexahydro-2-oxo-1H-azepine-1-carboxamide obtained by de-protection of [(3S)-1-[(butylamino)carbonyl]hexahydro-2-oxo-1H-azepin-3-yl]-carbamic acid, 1,1-dimethylethyl ester with TFA, diisopropyl(ethyl)amine, and 7-chloro-4-(1-piperazinyl)-2-quinolinamine are reacted to give the product. $^1$H NMR (CDCl$_3$); δ 0.9–1.0 (t, 3H), 1.3–2.4 (m, 10H), 3.1–3.2 (m, 4H), 3.2–3.4 (m, 3H), 3.6–3.76 (m, 4H), 4.78–5.0 (m, 4H), 5.8–5.9 (m, 1H), 6.1–6.2 (s, 1H), 7.14–7.2 (m, 1H), 7.6–7.64 (d, 1H), 7.7–7.8 (d, 1H), 8.98–9.06 (m, 1H).

Example 247

Preparation of (3S)-3-[[[4-(2-Amino-7-chloro-4-quinolinyl)-1-piperazinyl]carbonyl]amino]hexahydro-N-(2-methylpropyl)-2-oxo-1H-azepine-1-carboxamide

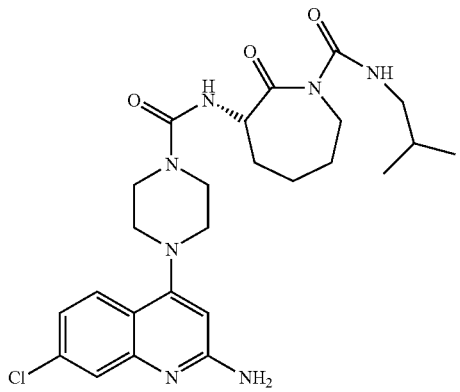

As described for example 78, (3R)-3-aminohexahydro-N-(2-methylpropyl)-2-oxo-1H-azepine-1-carboxamide obtained by de-protection of [(3S)-hexahydro-1-[[(2-methylpropyl)amino]carbonyl]-2-oxo-1H-azepin-3-yl]-carbamic acid, 1,1-dimethylethyl ester with TFA, diisopropyl(ethyl)amine, and 7-chloro-4-(1-piperazinyl)-2-quinolinamine are reacted to give the product. LC-MS: 515 (M$^+$+1). $^1$H NMR (CDCl$_3$); δ 0.9–1.1 (d, 6H), 1.3–2.3 (m, 7H), 3.1–3.3 (m, 3H), 3.3–3.4 (m, 4H), 3.64–3.8 (m, 4), 4.78–5.0 (m, 2H), 5.76–5.84 (m, 1H), 6.1–6.2 (s, 1H), 7.3–7.4 (m, 1H), 7.66–7.74 (d, 1H), 7.75–7.8 (d, 1H), 9.04–9.14 (m, 1H).

Example 248

Preparation of (3S)-3-[[[4-(2-Amino-7-chloro-4-quinolinyl)-1-piperazinyl]carbonyl]amino]-N-(1,1-dimethylethyl)hexahydro-2-oxo-1H-azepine-1-carboxamide

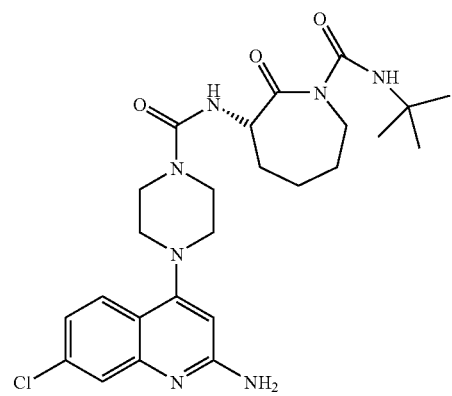

As described for example 78, (3R)-3-amino-N-(1,1-dimethylethyl)hexahydro-2-oxo-1H-azepine-1-carboxamide obtained by the de-protection of [(3S)-1-[[(1,1-dimethylethyl)amino]carbonyl]hexahydro-2-oxo-1H-azepin-3-yl]-carbamic acid, 1,1-dimethylethyl ester with TFA, diisopropyl(ethyl)amine, and 7-chloro-4-(1-piperazinyl)-2-quinolinamine are reacted to give the product. LC-MS: 515 (M$^+$+1). $^1$H NMR (CDCl$_3$); δ 1.3–1.5 (s, 9H), 1.5–2.3 (m, 6H), 3.1–3.29 (m, 5H), 3.6–3.75 (m, 4H), 4.76–5.0 (m, 4H), 5.8–6.0 (m, 1H), 6.1–6.2 (s, 1H), 7.15–7.2 (m, 1H), 7.6–7.64 (d, 1H), 7.70–7.75 (d, 1H), 9.0–9.2 (s, 1H).

Example 249

Preparation of (3S)-3-[[[4-(2-Amino-7-chloro-4-quinolinyl)-1-piperazinyl]carbonyl]amino]hexahydro-N,N-dimethyl-2-oxo-1H-azepine-1-carboxamide

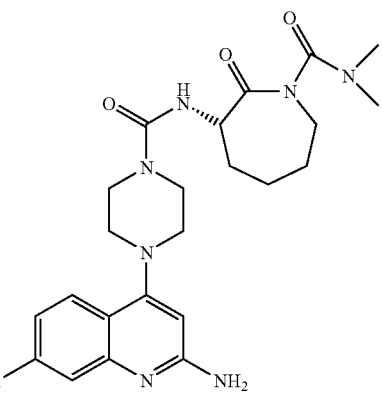

As described for example 78, (3R)-3-aminohexahydro-N,N-dimethyl-2-oxo-1H-azepine-1-carboxamide obtained by de-protection of [(3S)-1-[(dimethylamino)carbonyl]hexahydro-2-oxo-1H-azepin-3-yl]-carbamic acid, 1,1-dimethylethyl ester with TFA, diisopropyl(ethyl)amine, and 7-chloro-4-(1-piperazinyl)-2-quinolinamine are reacted to give the product. LC-MS: 587 (M$^+$+1). $^1$H NMR (CDCl$_3$); δ 1.36–2.2 (m, 5H), 2.6–3.2 (m, 8H), 3.22–3.4 (m, 4H), 3.4–3.9 (m, 4H), 4.4–4.8 (m, 2H), 5.9–6.2 (m, 2H), 6.4–6.6 (m, 1H), 7.3–7.4 (m, 1H), 7.65–7.73 (m, 1H), 7.74–7.8 (m, 1H).

Example 250

Preparation of (3S)-3-[[[4-(2-Amino-7-chloro-4-quinolinyl)-1-piperazinyl]carbonyl]amino]hexahydro-2-oxo-N-[4-(trifluoromethyl)phenyl]-1H-azepine-1-carboxamide

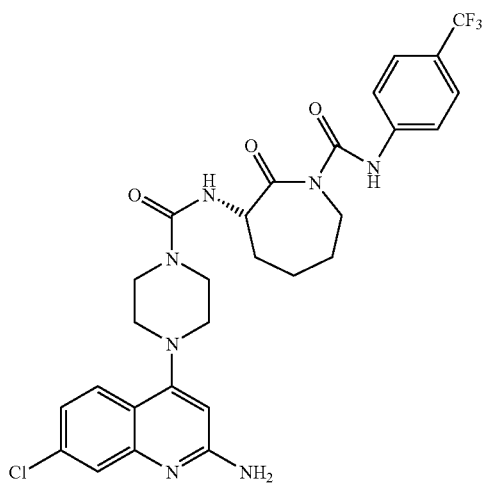

As described for example 78, (3R)-3-aminohexahydro-2-oxo-N-[4-(trifluoromethyl)phenyl]-1H-azepine-1-carboxamide obtained by de-protection of [(3S)-hexahydro-2-oxo-1-[[[4-(trifluoromethyl)phenyl]amino]carbonyl]-1H-azepin-3-yl]-carbamic acid, 1,1-dimethylethyl ester with TFA, diisopropyl(ethyl)amine, and 7-chloro-4-(1-piperazinyl)-2-quinolinamine are reacted to give the product. LC-MS: 603 (M$^+$+1). $^1$H NMR (CDCl$_3$); 61.3–1.8 (m, 2H), 1.8–2.3 (m, 4H), 3.1–3.25 (m, 4H), 3.26–3.4 (m, 1H), 3.6–3.8 (m, 4H), 4.76–5.1 (m, 4H), 5.7–5.9 (m, 1H), 6.1–6.2 (s, 1H), 7.16–7.2 (m, 1H), 7.56–7.68 (m, 5H), 7.7–7.76 (d, 1H), 11.4–11.6 (s, 1H).

Example 251

Preparation of (3S)-3-[[[4-(2-Amino-7-chloro-4-quinolinyl)-1-piperazinyl]carbonyl]amino]-N-(3-fluorophenyl)hexahydro-2-oxo-1H-azepine-1-carboxamide

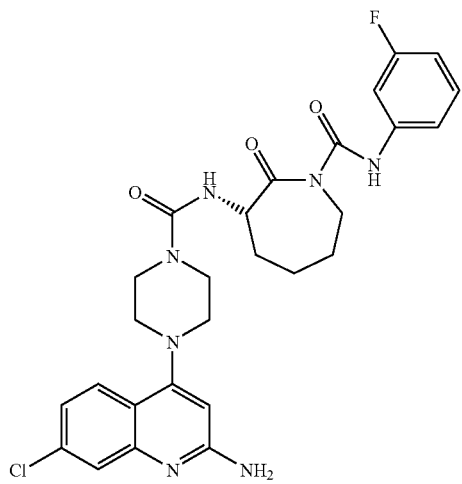

As described for example 78, (3R)-3-amino-N-(3-fluorophenyl)hexahydro-2-oxo-1H-azepine-1-carboxamide obtained by de-protection of [(3S)-1-[[(3-fluorophenyl)amino]carbonyl]hexahydro-2-oxo-1H-azepin-3-yl]-carbamic acid, 1,1-dimethylethyl ester with TFA, diisopropyl(ethyl)amine, and 7-chloro-4-(1-piperazinyl)-2-quinolinamine are reacted to give the product. LC-MS: 553 (M$^+$+1). $^1$H NMR (CDCl$_3$); δ 1.3–1.8 (m, 2H), 1.8–2.3 (m, 4H), 3.1–3.25 (m, 4H), 3.26–3.4 (m, 1H), 3.6–3.8 (m, 4H), 4.8–5.1 (m, 4H), 5.8–5.9 (m, 1H), 6.1–6.2 (s, 1H), 6.78–6.86 (m, 1H), 7.12–7.2 (m, 2H), 7.22–7.31 (m, 1H), 7.43–7.5 (m, 1H), 7.6–7.64 (d, 1H), 7.7–7.76 (d, 1H), 11.3–11.5 (s, 1H).

Example 252

Preparation of (3S)-3-[[[4-(2-Amino-7-chloro-4-quinolinyl)-1-piperazinyl]carbonyl]amino]hexahydro-N-(4-methylphenyl)-2-oxo-1H-azepine-1-carboxamide

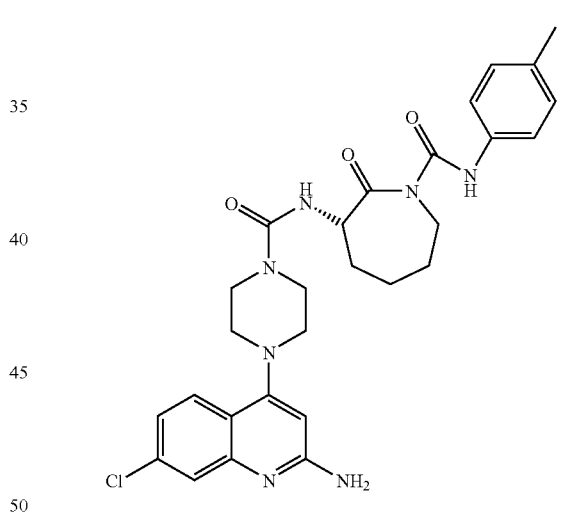

As described for example 78, (3R)-3-aminohexahydro-N-(4-methylphenyl)-2-oxo-1H-azepine-1-carboxamide obtained by de-protection of [(3S)-hexahydro-1-[[(4-methylphenyl)amino]carbonyl]-2-oxo-1H-azepin-3-yl]-carbamic acid 1,1-dimethylethyl ester with TFA, diisopropyl(ethyl)amine, diisopropyl(ethyl)amine, and 7-chloro-4-(1-piperazinyl)-2-quinolinamine are reacted to give the product. LC-MS: 549 (M$^+$+1). $^1$H NMR (CDCl$_3$); δ 1.3–2.23 (m, 6H), 2.31–2.4 (s, 3H), 3.1–3.22 (m, 4H), 3.28–3.4 (m, 1H), 3.6–3.8 (m, 4H), 4.8–5.1 (m, 4H), 5.8–5.9 (m, 1H), 6.1–6.2 (s, 1H), 7.1–7.2 (m, 3H), 7.37–7.43 (m, 2H), 7.61–7.64 (d, 1H), 7.7–7.76 (d, 1H), 11.1–11.3 (s, 1H).

Example 253

Preparation of (3S)-3-[[[4-(2-Amino-7-chloro-4-quinolinyl)-1-piperazinyl]carbonyl]amino]-N-(2-fluorophenyl)hexahydro-2-oxo-1H-azepine-1-carboxamide

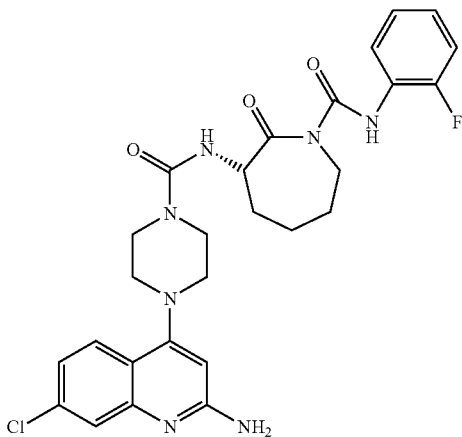

As described for example 78, (3R)-3-amino-N-(2-fluorophenyl)hexahydro-2-oxo-1H-azepine-1-carboxamide obtained by de-protection of [(3S)-1-[[(2-fluorophenyl)amino]carbonyl]hexahydro-2-oxo-1H-azepin-3-yl]-carbamic acid, 1,1-dimethylethyl ester with TFA, diisopropyl (ethyl)amine, and 7-chloro-4-(1-piperazinyl)-2-quinolinamine are reacted to give the product. LC-MS: 553 (M$^+$+1). $^1$H NMR (CDCl$_3$); δ 1.2–2.3 (m, 6H), 3.1–3.24 (m, 4H), 3.28–3.44 (m, 1H), 3.6–3.84 (m, 4H), 4.7–4.88 (s, 2H), 4.9–5.1 (m, 2H), 5.8–5.9 (m, 1H), 6.16–6.24 (s, 1H), 7.02–7.24 (m, 2H), 7.61–7.65 (d, 1H), 7.71–7.78 (d, 1H), 8.2–8.28 (m, 1H), 11.5–11.7 (s, 1H).

Example 254

Preparation of (3S)-3-[[[4-(2-Amino-7-chloro-4-quinolinyl)-1-piperazinyl]carbonyl]amino]-N-(2,6-diethylphenyl)hexahydro-2-oxo-1H-azepine-1-carboxamide

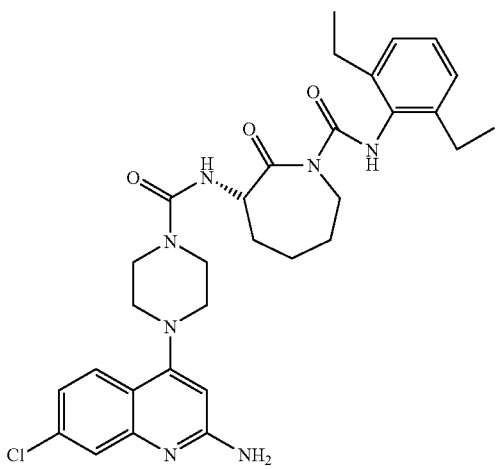

As described for example 78, (3R)-3-amino-N-(2,6-diethylphenyl)hexahydro-2-oxo-1H-azepine-1-carboxamide obtained by de-protection of [(3S)-1-[[(2,6-diethylphenyl)amino]carbonyl]hexahydro-2-oxo-1H-azepin-3-yl]-carbamic acid, 1,1-dimethylethyl ester with TFA, diisopropyl (ethyl)amine, and 7-chloro-4-(1-piperazinyl)-2-quinolinamine are reacted to give the product. LC-MS: 591 (M$^+$+1). $^1$H NMR (CDCl$_3$). δ 1.2 (t, 6H), 1.3–2.3 (m, 6H), 2.6 (q, 2H), 3.1–3.23 (m, 4H), 3.3–3.4 (m, 1H), 3.6–3.8 (m, 4H), 4.8–5.1 (m, 4H), 5.8–6.0 (m, 1H), 6.1–6.2 (s, 1H), 7.1–7.28 (m, 4H), 7.6–7.64 (d, 1H), 7.70–7.75 (d, 1H), 10.36–10.48 (s, 1H).

Example 255

Preparation of 4-(2-Amino-7-chloro-4-quinolinyl)-N-[(3S)-hexahydro-1-[(methylamino)carbonothioyl]-2-oxo-1H-azepin-3-yl]-1-piperazinecarboxamide:

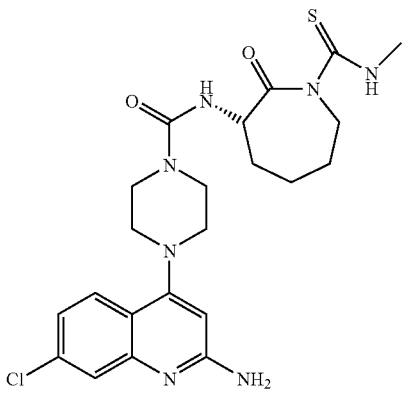

As described for example 78, obtained (3R)-3-amino-hexahydro-N-methyl-2-oxo-1H-azepine-1-carbothioamide by de-protection of [(3S)-hexahydro-1-[(methylamino)carbonothioyl]-2-oxo-1H-azepin-3-yl]-carbamic acid, 1,1-dimethylethyl ester with TFA, diisopropyl(ethyl)amine, and 7-chloro-4-(1-piperazinyl)-2-quinolinamine are reacted to give the product. LC-MS: 489 (M$^+$+1). $^1$H NMR (CDCl$_3$); δ 1.5–2.2 (m, 6H), 3.1–3.17 (m, 4H), 3.17–3.22 (d, 3H), 3.46–3.58 (m, 1H), 3.6–3.74 (m, 4), 4.8–4.9 (s, 2H), 5.0 (m, 1H), 5.6–5.8 (m, 2H), 6.1–6.2 (s, 1H), 7.14–7.2 (m, 1H), 7.6–7.63 (d, 1H), 7.7–7.74 (d, 1H), 11.2 (m, 1H).

Example 256

Preparation of 4-(2-Amino-7-chloro-4-quinolinyl)-N-[(3S)-1-[(ethylamino)carbonothioyl]hexahydro-2-oxo-1H-azepin-3-yl]-1-piperazinecarboxamide

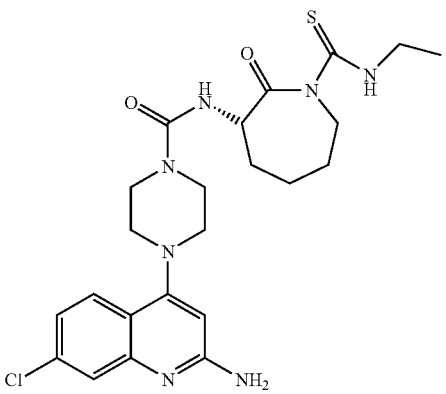

As described for example 78, (3R)-3-amino-N-ethyl-hexahydro-2-oxo-1H-azepine-1-carbothioamide obtained by de-protection of [(3S)-1-[(ethylamino)carbonothioyl]hexahydro-2-oxo-1H-azepin-3-yl]-carbamic acid, 1,1-dimethylethyl ester with TFA, diisopropyl(ethyl)amine, diisopropyl(ethyl)amine, and 7-chloro-4-(1-piperazinyl)-2-quinolinamine are reacted to give the product. LC-MS: 503 (M$^+$+1). $^1$H NMR (CDCl$_3$); δ 1.2–1.4 (t, 3H), 1.5–1.78 (m, 2H), 1.8–2.2 (m, 4H), 3.12–3.18 (m, 4H), 3.44–3.56 (m, 1H), 3.6–3.76 (m, 6H), 4.8–4.9 (s, 2H), 5.0 (m, 1H), 5.64–5.8 (m, 2H), 6.1–6.2 (s, 1H), 7.14–7.2 (m, 1H), 7.6–7.64 (d, 1H), 7.7–7.76 (d, 1H), 11.1–11.3 (m, 1H).

Example 257

Preparation of 4-(2-Amino-7-chloro-4-quinolinyl)-N-[(3S)-hexahydro-1-[[(1-methylethyl)amino]carbonothioyl]-2-oxo-1H-azepin-3-yl]-1-piperazinecarboxamide:

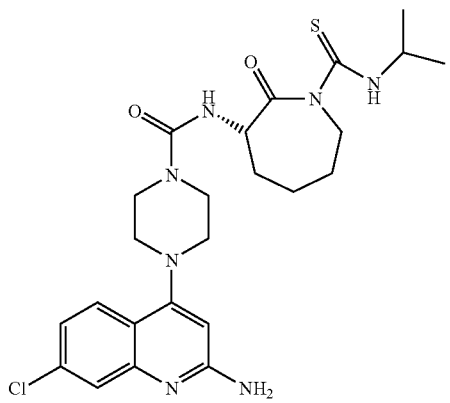

As described for example 78, (3R)-3-aminohexahydro-N-(1-methylethyl)-2-oxo-1H-azepine-1-carbothioamide obtained by de-protection of [(3S)-hexahydro-1-[[(1-methylethyl)amino]carbonothioyl]-2-oxo-1H-azepin-3-yl]-carbamic acid, 1,1-dimethylethyl ester with TFA, diisopropyl (ethyl)amine, and 7-chloro-4-(1-piperazinyl)-2-quinolinamine are reacted to give the product. LC-MS: 517 (M$^+$+1). $^1$H NMR (CDCl$_3$); δ 1.3 (t, 6H), 1.5–2.2 (m, 6H), 3.1–3.17 (m, 4H), 3.4–3.53 (m, 1H), 3.6–3.75 (m, 4H), 4.49–4.6 (m, 1H), 4.88–4.97 (s, 2H), 4.97–5.05 (m, 1H), 5.6–5.7 (m, 1H), 5.74–5.82 (d, 1H), 6.1–6.2 (s, 1H), 7.14–7.2 (m, 1H), 7.6–7.63 (d, 1H), 7.69–7.74 (d, 1H), 11.0–11.2 (m, 1H).

Example 258

Preparation of 4-(2-Amino-7-chloro-4-quinolinyl)-N-[(3S)-hexahydro-2-oxo-1-[(2-propenylamino)carbonothioyl]-1H-azepin-3-yl]-1-piperazinecarboxamide

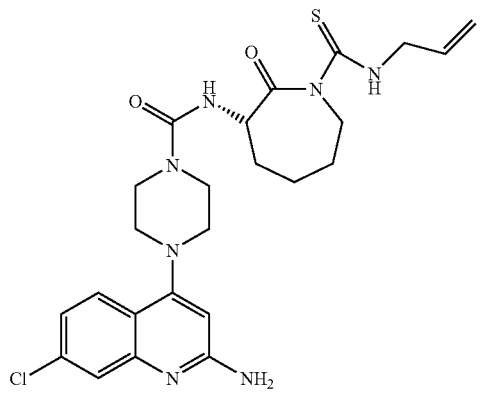

As described for example 78, (3R)-3-aminohexahydro-2-oxo-N-(2-propenyl)-1H-azepine-1-carbothioamide obtained by de-protection of [(3S)-hexahydro-2-oxo-1-[(2-propenylamino)carbonothioyl]-1H-azepin-3-yl]-carbamic acid, 1,1-dimethylethyl ester with TFA, diisopropyl(ethyl)amine, and 7-chloro-4-(1-piperazinyl)-2-quinolinamine are reacted to give the product. LC-MS: 515 (M$^+$+1). $^1$H NMR (CDCl$_3$); δ 1.5–2.3 (m, 6H), 3.1–3.19 (m, 4H), 3.48–3.58 (m, 1H), 3.6–3.75 (m, 4H), 4.26–4.34 (m, 2H), 4.8–4.9 (s, 2H), 4.99–5.08 (m, 1H), 5.2–5.34 (m, 2H), 5.65–5.78 (m, 2H), 5.9–6.02 (m, 1H), 6.1–6.2 (s, 1H), 7.14–7.2 (m, 1H), 7.6–7.64 (d, 1H), 7.70–7.75 (d, 1H), 11.2–11.4 (m, 1H).

Example 259

Preparation of (3S)-3-[[[4-(2-Amino-7-chloro-4-quinolinyl)-1-piperazinyl]carbonyl]amino]hexahydro-N-methyl-2-oxo-1H-azepine-1-carboxamide

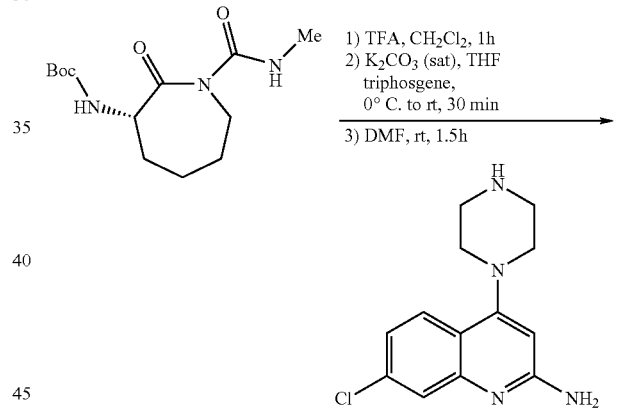

61%

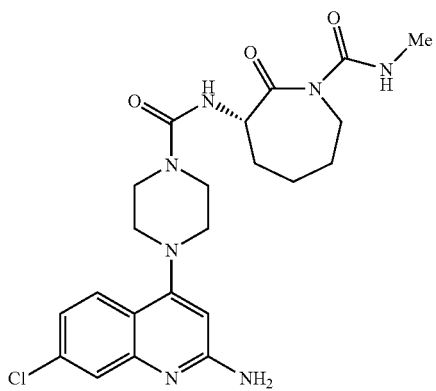

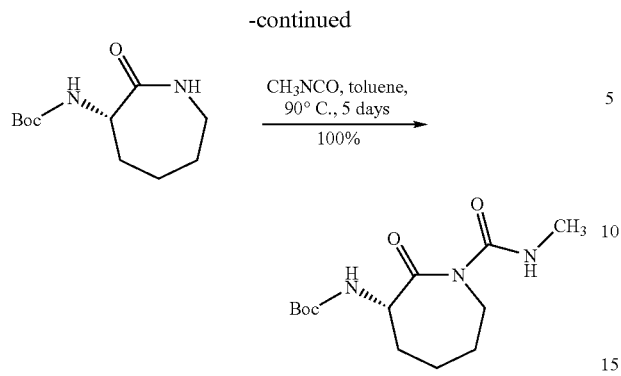

Preparation of [(3R)-Hexahydro-1-[(methylamino)carbonyl]-2-oxo-1H-azepin-3-yl]-carbamic acid-1,1-dimethylethyl ester A mixture of [(3R)-hexahydro-2-oxo-1H-azepin-3-yl]carbamic acid, 1,1-dimethylethyl ester (540 mg, 2.4 mmol) and methyl isocyanate (200 mg, 3.51 mmol) in toluene (20 mL) in a sealed tube was kept at 90° C. for 5 days, then cooled to rt. After the removal of solvents in vacuo, the crude product was purified by column chromatography with 1% MeOH in $CH_2Cl_2$ to afford 680 mg (100%) of the product as a colorless syrup. LC-MS: 285 ($M^+$+1). $^1H$ NMR ($CDCl_3$): δ 1.37 (m, 1H), 1.42 (s, 9H), 1.63 (m, 1H), 1.96 (m, 3H), 2.08 (m, 1H), 2.91 (d, 3H), 3.18 (d, 1H), 4.63 (m, 1H), 4.84 (m, 1H), 5.67 (d, 1H), 8.96 (s, 1H).

The following intermediates were prepared in a similar manner:

[(3S)-hexahydro-2-oxo-1-[(2-propenylamino)carbonyl]-1H-azepin-3-yl]-carbamic acid-1,1-dimethylethyl ester. $^1H$ NMR ($CDCl_3$) δ 1.39 (m, 1H), 1.42 (s, 9H), 1.6 (m, 1H), 1.9 (m, 2H), 2.11 (m, 1H), 3.23 (m, 1H), 3.97 (br. s, 2H), 4.67 (m, 1H), 4.82 (m, 1H), 5.2 (m, 2H), 5.62 (br. s, 1H), 5.89 (m, 1H), 9.23 (br. s 1H).

[(3S)-1-[[(2-chloroethyl)amino]carbonyl]hexahydro-2-oxo-1H-azepin-3-yl]carbamic acid-1,1-dimethylethyl ester. $^1H$ NMR ($CDCl_3$): δ 1.38 (m, 1H), 1.44 (s, 9H), 1.62 (m, 1H), 1.9 (m, 3H), 2.1 (m, 1H), 3.22 (m, 1H), 3.63 (m, 5H), 4.7 (m, 1H), 4.81 (m, 1H), 5.68 (br. s, 1H), 9.44 (br., s, 1H).

[(3R)-hexahydro-1-[(methylamino)carbonyl]-2-oxo-1H-azepin-3-yl]-carbamic acid-1,1-dimethylethyl ester. $^1H$ NMR ($CDCl_3$): δ 1.38 (m, 1H), 1.43 (s, 9H), 1.65 (m, 1H), 1.9 (m, 3H), 2.1 (m, 1H), 2.91 (s, 3H), 3.17 (m, 1H0, 4.68 (m, 1H0, 4.82 (m, 1H, 5.66 (br. s, 1H), 8.97 (br.s, 1H).

Preparation of (3S)-3-[[[4-(2-amino-7-chloro-4-quinolinyl)-1-piperazinyl]carbonyl]amino]hexahydro-N-methyl-2-oxo-1H-azepine-1-carboxamide: As described for example 213, [(3R)-Hexahydro-1-[(methylamino)carbonyl]-2-oxo-1H-azepin-3-yl]carbamic acid-1,1-dimethylethyl ester, TFA, triphosgene, $NaHCO_3$ (sat.), and 7-chloro-4-(1-piperazinyl)-2-quinolinamine are reacted to afford the product as a white powder. LC-MS, 473 ($M^+$). $^1H$ NMR (400 MHz, DMSO): 61.38 (m, 1H), 1.57 (m, 1H), 1.9 (m, 2H), 2.03 (br. d, 1H), 2.19 (s, 1H), 2.85 (d, 3H), 3.08 (m, 4H), 3.21 (m, 1H), 3.63 (m, 4H), 4.83 (m, 1H), 4.85 (m, 1H), 4.95 (s, 2H), 5.85 (d, 1H), 6.11 (s, 1H), 7.11 (dd, 1H), 7.56 (d, 1H), 7.67 (d, 1H), 8.91 (q, 1).

Example 260

Preparation of (3S)-3-[[[4-(2-Amino-7-chloro-4-quinolinyl)-1-piperazinyl]carbonyl]amino]hexahydro-2-oxo-N-(2-propenyl)-1H-azepine-1-carboxamide

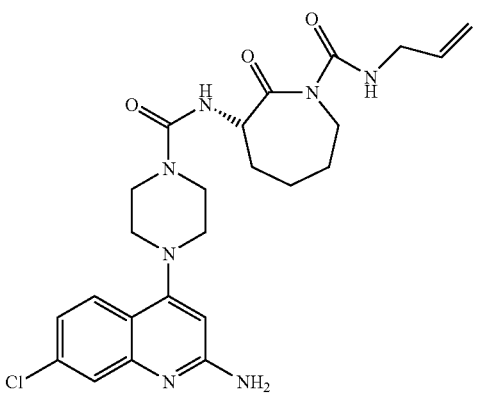

As described for example 78, (3R)-3-aminohexahydro-N-(2-propenyl)-2-oxo-1H-azepine-1-carboxamide obtained by de-protection of [(3S)-hexahydro-2-oxo-1-[(2-propenylamino)carbonyl]-1H-azepin-3-yl]-carbamic acid, 1,1-dimethylethyl ester with TFA, diisopropyl(ethyl)amine, and 7-chloro-4-(1-piperazinyl)-2-quinolinamine are reacted to give the product. $^1H$ NMR (DMSO-$d_6$): δ 1.4 (m, 1H), 1.62 (m, 1H), 1.93 (m, 2H), 2.16 (m, 1H), 3.17 (m, 4H), 3.29 (m, 1H), 3.62 (m, 4H), 3.98 (t, 2H), 4.78 (br., s, 2H), 4.91 (m, 2H), 5.2 (m, 2H), 5.91 (m, 2H), 6.18 (s, 1H), 7.18 (d, 1H), 7.61 (s, 1H), 7.76 (d, 1H), 9.12 (m, 1H).

Example 261

Preparation of (3S)-3-[[[4-(2-Amino-7-chloro-4-quinolinyl)-1-piperazinyl]carbonyl]amino]-N-(2-chloroethyl)hexahydro-2-oxo-1H-azepine-1-carboxamide

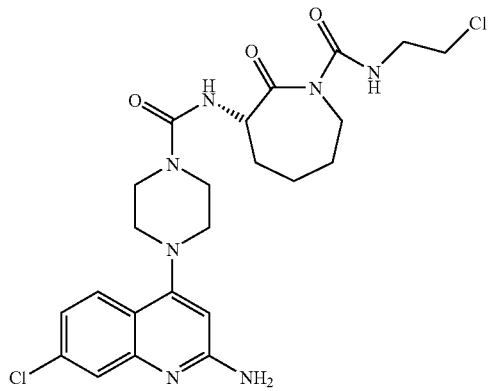

As described example 78, (3R)-3-amino-N-(2-chloroethyl)hexahydro-2-oxo-1H-azepine-1-carboxamide obtained by de-protection of [(3S)-1-[[(2-chloroethyl)amino]carbonyl]hexahydro-2-oxo-1H-azepin-3-yl]carbamic acid-1,1-dimethylethyl ester with TFA, p-nitrophenyl chloroformate, diisopropyl(ethyl)amine, and 7-chloro-4-(1-piperazinyl)-2-quinolinamine are reacted to afford the product as a white solid. $^1$H NMR (DMSO-$d_6$): δ 1.41 (m, 1H), 1.63 (m, 1H), 1.79 (m, 1H), 1.96 (m, 3H), 2.17 (m, 1H), 3.16 (m, 4H), 3.34 (dd, 1H), 3.68 (m, 8H), 4.8 (m, 2H), 4.91 (m, 1H), 5.82 (d, 1H), 6.2 (s, 1H), 7.18 (d, 1H), 7.61 (s, 1H), 7.73 (d, 1H), 9.44 (br.s, 1H).

Example 262

Preparation of (3R)-3-[[[4-(2-Amino-7-chloro-4-quinolinyl)-1-piperazinyl]carbonyl]amino]hexahydro-N-methyl-2-oxo-1H-azepine-1-carboxamide

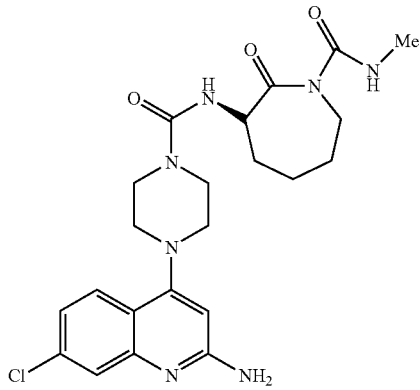

As described for example 213, [(3R)-hexahydro-1-[(methylamino)carbonyl]-2-oxo-1H-azepin-3-yl]-carbamic acid-1,1-dimethylethyl ester, TFA, $K_2CO_3$ (sat.) 7-chloro-4-(1-piperazinyl)-2-quinolinamine are reacted to afford the product. $^1$H NMR (DMSO-$d_6$): δ 1.2 (m, 1H), 1.6 (m, 1H), 1.71 (m, 2H), 1.84 (m, 2H), 2.73 (s, 3H), 2.98 (m, 4H), 3.31 (m, 2H), 3.58 (m, 4H), 4.57 (m, 1H), 4.64 (t, 1H), 6.22 (s, 1H), 6.45 (br. s, 1H), 6.78 (d, 1H), 7.11 (d, 1H), 7.37 (s, 1H), 7.76 (d, 1H), 8.84 (m, 1H).

Pyrrolidinylquinolines

Example 263

Preparation of 4-[3-(tert-Butoxycarbonylamino)pyrrolidin1-yl]-7-chloroquinolin

In a method similar to Example A 4,7-dichloroquinoline (0.49 g, 2.0 mmol), 3-(tert-butoxycarbonylamino)pyrrolidine (1.86 g, 10.0 mmol) and 1,4-diazabicyclo[2.2.2]octane (1.12 g, 10.0 mmol) are heated in EtOH for 15 h at reflux. The reaction mixture is concentrated, diluted with EtOAc, washed with water, dried ($MgSO_4$), and concentrated. The residue is purified by column chromatography with hexane-EtOAc yielding 245 mg of the product as a colorless solid. $^1$H NMR (CDCl$_3$) δ 1.42 (s, 9H), 2.03 (sext, 1H), 2.28 (sext, 1H), 3.50 (dd, 1H), 3.67 (td, 1H), 3.79 (dt, 1H), 3.92 (dd, 1H), 4.39 (br., 1H), 4.81 (br., 1H), 6.41 (d, 1H), 7.29 (dd, 1H), 7.93 (d, 1H), 8.05 (d, 1H), 8.47 (d, 1H).

Example 264

Preparation of 4-[3-(4-Fluorophenylaminocarbonylamino)pyrrolidin1-yl]-7-chloroquinoline A solution of 4-[3-(tert-butoxycarbonylamino)pyrrolidin1-yl]-7-chloroquinoline (214 mg, 0.62 mmol) in $CH_2Cl_2$ (5 mL) is treated with trifluoroacetic acid (1 mL). After 1 h the reaction mixture is concentrated. The residue is dissolved in $CH_2Cl_2$ (10 mL), and 4-fluorophenyl isocyanate (70 μL, 0.62 mmol) and triethylamine (1 mL) are added. The reaction mixture is concentrated, and the residue is purified by column chromatography and an aqueous work-up step yielding the title product.
$^1$H NMR ([D]$_6$-DMSO) δ 2.07 (sext, 1H), 2.28 (sext, 1H), 3.80 (dd, 1H), 3.97 (m, 2H), 4.20 (dd, 1H), 4.39 (m, 1H), 6.77 (d, 1H), 6.84 (d, 1H), 7.02 (t, 2H), 7.36 (dd, 2H), 7.59 (dd, 1H), 7.89 (d, 1H), 8.45 (d, 1H), 8.48 (d, 1H), 8.62 (s, 1H).

Example 265

Preparation of 4-[3-[tert-Butoxycarbonyl(methyl)amino]pyrrolidin1-yl]-7-chloroquinoline 4,7-Dichloroquinoline (0.49 g, 2.0 mmol), 3-[tert-butoxycarbonyl(methyl)amino]pyrrolidine (1.96 mL, 10.0 mmol) and 1,4-diazabicyclo[2.2.2]octane (1.12 g, 10.0 mmol) are heated in EtOH for 15 h at reflux. The reaction mixture is concentrated, diluted with EtOAc, washed with water, dried ($MgSO_4$), and concentrated. The residue is purified by column chromatography with hexane-EtOAc yielding the title product as a colorless solid.
$^1$H NMR (CDCl$_3$) δ 1.47 (s, 9H), 2.19 (m, 2H), 2.87 (s, 3H), 3.64 (q, 1H), 3.70 (m, 3H), 4.83 (br., 1H), 6.45 (d, 1H), 7.28 (dd, 1H), 7.94 (d, 1H), 8.07 (d, 1H), 8.48 (d, 1H)

Example 266

Preparation of 4-[3-[4-Fluorophenylaminocarbonyl(methyl)amino]pyrrolidin1-yl]-7-chloroquinoline A solution of 4-[3-[tert-butoxycarbonyl(methyl)amino]pyrrolidin1-yl]-7-chloroquinoline (285 mg, 0.79 mmol) in $CH_2Cl_2$ (5 mL) is treated with trifluoroacetic acid (1 mL). After 1 h the reaction mixture is concentrated. The residue is dissolved in $CH_2Cl_2$ (10 mL), and 4-fluorophenyl isocyanate (90 μL, 0.79 mmol) and triethylamine (1 mL) are added. The reaction mixture is concentrated, and the residue is purified by column chromatography and an aqueous work-up step yielding the title product.
$^1$H NMR ([D]$_6$-DMSO) δ 2.18 (m, 1H), 2.25 (m, 1H), 2.97 (s, 3H), 4.00 (m, 4H), 4.97 (m, 1H), 6.80 (d, 1H), 7.06 (t, 2H), 7.44 (dd, 2H), 7.60 (dd, 1H), 7.90 (d, 1H), 8.45 (s, 1H), 8.48 (d, 1H), 8.56 (d, 1H).

Modes of Preparation of Pharmaceutical Compositions

Example 267

This example illustrates the preparation of representative pharmaceutical compositions for oral administration containing a compound of the invention, or a pharmaceutically acceptable salt thereof:

| A. Ingredients | % wt./wt. |
|---|---|
| Compound of the invention | 20.0% |
| Lactose | 79.5% |
| Magnesium stearate | 0.5% |

The above ingredients are mixed and dispensed into hard-shell gelatin capsules containing 100 mg each, one capsule would approximate a total daily dosage.

| B. Ingredients | % wt./wt. |
|---|---|
| Compound of the invention | 20.0% |
| Magnesium stearate | 0.9% |
| Starch | 8.6% |
| Lactose | 69.6% |
| PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. Ingredients | |
|---|---|
| Compound of the invention | 0.1 g |
| Propylene glycol | 20.0 g |
| Polyethylene glycol 400 | 20.0 g |
| Polysorbate 80 | 1.0 g |
| Water | q.s. 100 mL |

The compound of the invention is dissolved in propylene glycol, polyethylene glycol 400 and polysorbate 80. A sufficient quantity of water is then added with stirring to provide 100 mL of the solution, which is filtered and bottled.

| D. Ingredients | % wt./wt. |
|---|---|
| Compound of the invention | 20.0% |
| Peanut Oil | 78.0% |
| Span 60 | 2.0% |

The above ingredients are melted, mixed and filled into soft elastic capsules.

| E. Ingredients | % wt./wt. |
|---|---|
| Compound of the invention | 1.0% |
| Methyl or carboxymethyl cellulose | 2.0% |
| 0.9% saline | q.s. 100 mL |

The compound of the invention is dissolved in the cellulose/saline solution, filtered and bottled for use.

Example 268

This example illustrates the preparation of a representative pharmaceutical formulation for parenteral administration containing a compound of the invention, or a pharmaceutically acceptable salt thereof:

| Ingredients | |
|---|---|
| Compound of the invention | 0.02 g |
| Propylene glycol | 20.0 g |
| Polyethylene glycol 400 | 20.0 g |

-continued

| Ingredients | |
|---|---|
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution, which is filtered through a 0.2 m membrane filter and packaged under sterile conditions.

Example 269

This example illustrates the preparation of a representative pharmaceutical composition in suppository form containing a compound of the invention, or a pharmaceutically acceptable salt thereof:

| Ingredients | % wt./wt. |
|---|---|
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 270

This example illustrates the preparation of a representative pharmaceutical formulation for insufflation containing a compound of the invention, or a pharmaceutically acceptable salt thereof:

| Ingredients | % wt./wt. |
|---|---|
| Micronized compound of the invention | 1.0% |
| Micronized lactose | 99.0% |

The ingredients are milled, mixed, and packaged in an insufflator equipped with a dosing pump.

Example 271

This example illustrates the preparation of a representative pharmaceutical formulation in nebulized form containing a compound of the invention, or a pharmaceutically acceptable salt thereof:

| Ingredients | % wt./wt. |
|---|---|
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

Example 272

This example illustrates the preparation of a representative pharmaceutical formulation in aerosol form containing a compound of the invention, or a pharmaceutically acceptable salt thereof:

| Ingredients | % wt./wt. |
|---|---|
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

Example 273

CCR5 R c ptor MIP-1a Scintillati n Proximity Binding Assay

A) Assay Buffer: 50 mM Hepes, 5 mM MgCl2, 1 mM CaCl2, 30 ug/ml bacitracin, 0.1% BSA, pH 7.4.

B) Ligand: MIP-1a labeled with I-125 at 20,000–25,000 cpm/well. Non specific binding (nsb) was defined as bound cpm in the presence of 100 nM unlabeled MIP-1b.

C) Cells: Human embryonic kidney, (HEK-293) expressing human CCR5 and CD4 pretreated overnight with 5 mM sodium butyrate. Harvest cells with calcium and magnesium free phosphate buffered saline. Cell number is counted with hemacytometer. Cell number per assay point was selected so the total counts per minute (cpm) bound was approximately 10% of the total cpms 1–125-MIP-1a added per assay point.

D) Beads: Use wheatgerm agglutinin coated scintillation proximity assay beads (sold by Amersham Pharmacia Biotech Inc.) hydrated with the assay buffer for at least an hour before use. Final bead concentration was 0.2 mg beads per well.

E) Scintillation Proximity Assay: 100 ul of assay volume: 60 ul of cell/beads mix (premixed for at least 30 minutes), 20 ul of I-125-MIP-1a, 20 ul of assay buffer for total binding value, or 20 ul of 0.5 uM MIP-1 b for nsb, or 20 ul of test compound. Shake the 96 well plates for 30 minutes on an orbital shaker, then let them settle for 30 minutes before reading with a scintillation counter.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of formula (3a):

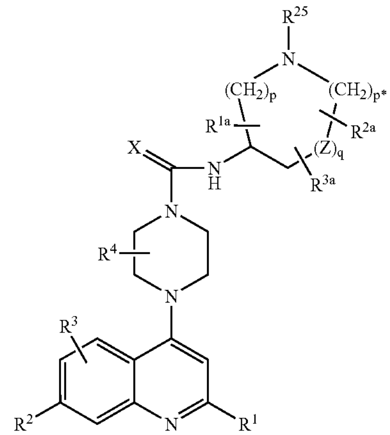

(3a)

or an enantiomer, a diastereomer, a salt or a solvate thereof, wherein:

$R^1$ is hydrogen or amino;

$R^2$ is halogen;

$R^3$ is hydrogen, alkyl, halogenated alkyl, halogen, substituted or unsubstituted amino, nitro, cyano, or alkoxy;

$R^4$ is hydrogen or one or more alkyl groups;

$R^{1a}$ is oxo or thioxo;

$R^{2a}$ and $R^{3a}$ are independently hydrogen, oxo, or thioxo;

or, when bonded to adjacent ring carbon atoms, $R^{2a}$ and $R^{3a}$ may combine to form a fused aryl or heterocyclyl ring;

$R^{25}$ is (i) hydrogen, or cyano;

(ii) alkyl, cycloalkyl, haloalkyl, hydroxyalkyl, alkoxyalkyl, aryloxyalkyl, alkenyl, cycloalkylalkyl, heterocyclylalkyl, aryl, or arylalkyl, any of which may be optionally independently substituted with one to three halogen, alkoxy, hydroxy, alkyl, or haloalkyl; or (iii) $—(CR^{20}R^{21})_m—C(═O)R^{15}$, $—(CR^{20}R^{21})_m—C(═O)OR^{15}$, $—(CR^{20}R^{21})_m—SO_2R^{15a}$, $—(CR^{20}R^{21})_m—C(═O)NR^{16}R^{17}$, $—(CR^{20}R^{21})_m—C(═S)NR^{16}R^{17}$; or $—(CR^{20}R^{21})_m—C(═O)NR^{16}—SO_2R^{15b}$;

$R^{15}$ is hydrogen, alkyl, haloalkyl, alkenyl, cycloalkyl, cycloalkylalkyl, aryl, arylalkyl, aryloxyalkyl;

$R^{15a}$ is hydrogen, alkyl, haloalkyl, alkenyl, cycloalkyl, cycloalkylalkyl, aryl, arylalkyl, aryloxyalkyl provided that when m is zero $R^{15a}$ is not hydrogen;

$R^{15b}$ is alkyl, haloalkyl, alkenyl, cycloalkyl, cycloalkylalkyl, aryl, arylalkyl, aryloxyalkyl;

$R^{16}$ and $R^{17}$ are independently hydrogen, alkyl, cycloalkyl, haloalkyl, hydroxyalkyl, alkoxyalkyl, aryloxyalkyl, alkenyl, cycloalkylalkyl, heterocyclylalkyl, aryl, or arylalkyl;

or $R^{16}$ and $R^{17}$ together with the nitrogen atom to which they are bonded may combine to form a heterocyclyl ring;

$R^{20}$ and $R^{21}$ at each occurrence are the same or different and are independently selected from hydrogen or alkyl;

X is O or X;

Z is —S—, —S(O)— or —S(O)$_2$—;
p is 1 or 2;
p* is 0, 1, 2, 3 or 4;
q is 0 or 1; and
m is 0, 1 or 2.

2. A compound according to claim 1 which is selected from the group consisting of:

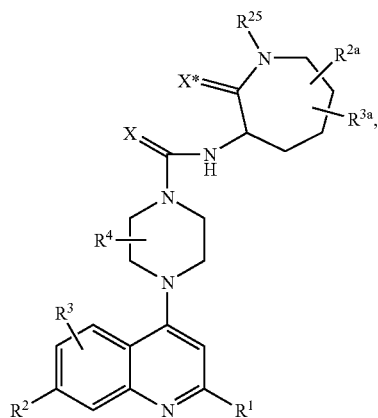

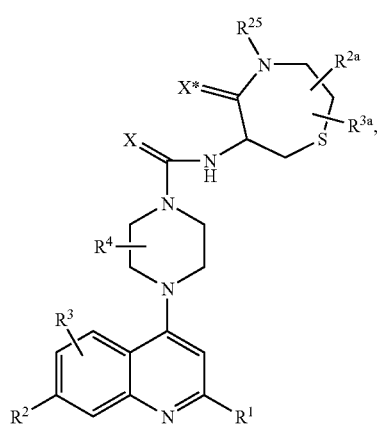

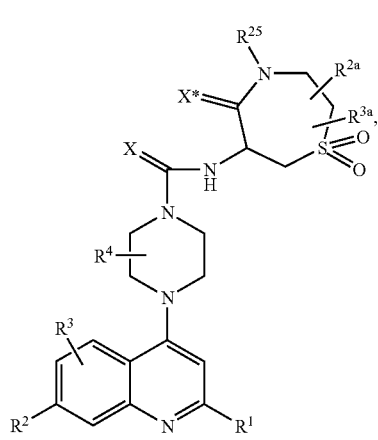

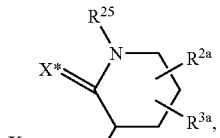

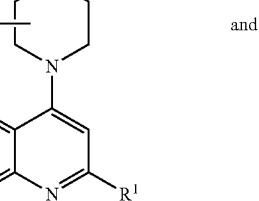

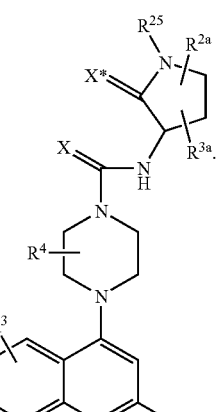

and where X and X* are independently O or S.

3. A compound according to claim 2 selected from the group consisting of:

4-[[[4-(7-Chloro-4-quinolinyl)-1-piperazinyl]carbonyl]amino]hexahydro-1H-azepine-1-carboxylic acid, 1,1-dimethylethyl ester;

4-[[[4-(7-Chloro-4-quinolinyl)-1-piperazinyl]carbonyl]amino]hexahydro-1H-azepine-1-carboxylic acid, methyl ester;

4-[[[4-(7-Chloro-4-quinolinyl)-1-piperazinyl]carbonyl]amino]hexahydro-1H-azepine-1-carboxylic acid, methyl ester;

4-[[[4-(7-Chloro-4-quinolinyl)-1-piperazinyl]carbonyl]amino]hexahydro-1H-azepine-1-carboxylic acid, phenylmethyl ester;

4-(7-Chloro-4-quinolinyl)-N-[(3R)-hexahydro-2-oxo-1H-azepin-3-yl]-1-piperazinecarboxamide;

4-(7-Chloro-4-quinolinyl)-N-[(3S)-hexahydro-2-oxo-1H-azepin-3-yl]-1-piperazinecarboxamide;

4-(7-Chloro-4-quinolinyl)-N-[(3S)-hexahydro-1-methyl-2-oxo-1H-azepin-3-yl]-1-piperazinecarboxamide;

4-(7-Chloro-4-quinolinyl)-N-[(3S)-hexahydro-2-oxo-1-(phenylmethyl)-1H-azepin-3-yl]-1-piperazinecarboxamide;

4-(7-Chloro-4-quinolinyl)-N-[(3S)-1-[(4-fluorophenyl)methyl]hexahydro-2-oxo-1H-azepin-3-yl]-1-piperazinecarboxamide;

4-(7-Chloro-4-quinolinyl)-N-[(3S)-1-ethylhexahydro-2-oxo-1H-azepin-3-yl]-1-piperazinecarboxamide;

(3S)-[[[4-(7-Chloro-4-quinolinyl)-1-piperazinyl]carbonyl]amino]hexahydro-2-oxo-1H-azepine-1-acetamide;

4-(7-Chloro-4-quinolinyl)-N-[(3S)-hexahydro-2-oxo-1-(3-pyridinylmethyl)-1H-azepin-3-yl]-1-piperazinecarboxamide;

4-(7-Chloro-4-quinolinyl)-N-[(3S)-hexahydro-2-oxo-1-(2-propenyl)-1H-azepin-3-yl]-1-piperazinecarboxamide;

4-(7-Chloro-4-quinolinyl)-N-[(3S)-1-(cyclopropylmethyl)hexahydro-2-oxo-1H-azepin-3-yl]-1-piperazinecarboxamide;

4-(7-Chloro-4-quinolinyl)-N-[(3S)-hexahydro-1-[(4-methoxyphenyl)methyl]-2-oxo-1H-azepin-3-yl]-1-piperazinecarboxamide;

(3S)-[[[4-(7-Chloro-4-quinolinyl)-1-piperazinyl]carbonyl]amino]hexahydro-2-oxo-1H-azepin-1-acetic acid, ethyl ester;

4-(7-Chloro-4-quinolinyl)-N-[(3S)-hexahydro-1-[3-(4-morpholinyl)propyl]-2-oxo-3-yl]-1-piperazinecarboxamide;

4-(2-Amino-7-chloro-4-quinolinyl)-N-[(6R)-hexahydro-5-oxo-1,4-thiazepin-6-yl]-1-piperazinecarbothioamide;

4-(2-Amino-7-chloro-4-quinolinyl)-N-[(6R)-hexahydro-5-oxo-1,4-thiazepin-6-yl]-1-piperazinecarboxamide;

4-(2-Amino-7-chloro-4-quinolinyl)-N-[(6R)-hexahydro-1,1-dioxido-5-oxo-1,4-thiazepin-6-yl]-1-piperazinecarboxamide;

4-(2-Amino-7-chloro-4-quinolinyl)-N-[(3S)-2-oxopyrrolidinyl]-1-piperazinecarboxamide;

4-(2-Amino-7-chloro-4-quinolinyl)-N-[(3S)-2,3,4,5-tetrahydro-2-oxo-1H-1-benzazepin-3-yl]-1-piperazinecarboxamide;

4-(2-Amino-7-chloro-4-quinolinyl)-N-[(3S)-2,3,4,5-tetrahydro-1-methyl-2-oxo-1H-1-benzazepin-3-yl]-1-piperazinecarboxamide;

4-(2-Amino-7-chloro-4-quinolinyl)-N-[(3S)-1,2,3,4-tetrahydro-2-oxoquinolinyl]-1-piperazinecarboxamide;

4-(2-Amino-7-chloro-4-quinolinyl)-N-[(3R)-hexahydro-2-thioxo-1H-azepin-3-yl]-1-piperazinecarboxamide;

4-(2-Amino-7-chloro-4-quinolinyl)-N-[(3S)-1-acetylhexahydro-1H-azepin-3-yl]-1-piperazinecarboxamide;

4-(2-Amino-7-chloro-4-quinolinyl)-N-[(3S)-hexahydro-2-oxo-1H-azepin-3-yl]-1-piperazinecarboxamide;

4-(2-Amino-7-chloro-4-quinolinyl)-N-[(3S)-hexahydro-1-methyl-2-oxo-1H-azepin-3-yl]-1-piperazinecarboxamide;

4-(2-Amino-7-chloro-4-quinolinyl)-N-[(3S)-1-(cyclopropylmethyl)hexahydro-2-oxo-1H-azepin-3-yl]-1-piperazinecarboxamide;

4-(2-Amino-7-chloro-4-quinolinyl)-N-[(3S)-hexahydro-2-oxo-1-(phenylmethyl)-1H-azepin-3-yl]-1-piperazinecarboxamide;

4-(2-Amino-7-chloro-4-quinolinyl)-N-[(3S)-1-[(2,6-dimethylphenyl)methyl]hexahydro-2-oxo-1H-azepin-3-yl]-1-piperazinecarboxamide;

4-(2-Amino-7-chloro-4-quinolinyl)-N-[(3S)-hexahydro-2-oxo-1-(2-pyridinylmethyl)-1H-azepin-3-yl]-1-piperazinecarboxamide;

4-(2-Amino-7-chloro-4-quinolinyl)-N-[(3S)-hexahydro-2-oxo-1-(3-pyridinylmethyl)-1H-azepin-3-yl]-1-piperazinecarboxamide;

4-(2-Amino-7-chloro-4-quinolinyl)-N-[(3S)-hexahydro-2-oxo-1-(4-pyridinylmethyl)-1H-azepin-3-yl]-1-piperazinecarboxamide;

4-(2-Amino-7-chloro-4-quinolinyl)-N-[(3S)-hexahydro-1-(2-hydroxy-3-phenoxypropyl)-2-oxo-1H-azepin-3-yl]-1-piperazinecarboxamide;

4-(2-Amino-7-chloro-4-quinolinyl)-N-[(3S)-hexahydro-1-(2-hydroxypropyl)-2-oxo-1H-azepin-3-yl]-1-piperazinecarboxamide;

(3S)-[[[4-(2-Amino-7-chloro-4-quinolinyl)-1-piperazinyl]carbonyl]amino]hexahydro-2-oxo-1H-azepine-1-acetic acid, methyl ester;

(3S)-[[[4-(2-Amino-7-chloro-4-quinolinyl)-1-piperazinyl]carbonyl]amino]hexahydro-2-oxo-1H-azepine-1-acetic acid;

(3S)-[[[4-(2-Amino-7-chloro-4-quinolinyl)-1-piperazinyl]carbonyl]amino]hexahydro-2-oxo-N-(phenylmethyl)-1H-azepine-1-acetamide;

(3S)-[[[4-(2-Amino-7-chloro-4-quinolinyl)-1-piperazinyl]carbonyl]amino]hexahydro-N-methyl-2-oxo-1H-azepine-1-acetamide;

(3S)-[[[4-(2-Amino-7-chloro-4-quinolinyl)-1-piperazinyl]carbonyl]amino]hexahydro-2-oxo-N-(4-pyridinyl)-1H-azepine-1-acetamide;

4-(2-Amino-7-chloro-4-quinolinyl)-N-[(3R)-1-(4-fluorophenyl)hexahydro-2-oxo-1H-azepin-3-yl]-1-piperazinecarboxamide;

4-[7-Chloro-2-(methylamino)-4-quinolinyl]-N-[(3S)-hexahydro-2-oxo-1H-azepin-3-yl]-1-piperazinecarboxamide;

4-(2-Amino-7-chloro-4-quinolinyl)-N-[(3S)-hexahydro-2-oxo-1-(2-phenoxyacetyl)-1H-azepin-3-yl]-1-piperazinecarboxamide;

4-(7-Chloro-4-quinolinyl)-N-[(3S)-1-acetylhexahydro-2-oxo-1H-azepin-3-yl]-1-piperazinecarboxamide;

4-(2-Amino-7-chloro-4-quinolinyl)-N-[(3S)-1-acetylhexahydro-2-oxo-1H-azepin-3-yl]-1-piperazinecarboxamide;

4-(2-Amino-7-chloro-4-quinolinyl)-N-[(3S)-1-(cyclopropylcarbonyl)hexahydro-2-oxo-1H-azepin-3-yl]-1-piperazinecarboxamide;

4-(2-Amino-7-chloro-4-quinolinyl)-N-[(3S)-1-benzoylhexahydro-2-oxo-1H-azepin-3-yl]-1-piperazinecarboxamide;

4-(2-Amino-7-chloro-4-quinolinyl)-N-[(3S)-1-(ethylsulfonyl)hexahydro-2-oxo-1H-azepin-3-yl]-1-piperazinecarboxamide;

4-(2-Amino-7-chloro-4-quinolinyl)-N-[(3S)-hexahydro-2-oxo-1-(phenylsulfonyl)-1H-azepin-3-yl]-1-piperazinecarboxamide;

4-(2-Amino-7-chloro-4-quinolinyl)-N-[(3S)-1-(cyclohexylcarbonyl)hexahydro-2-oxo-1H-azepin-3-yl]-1-piperazinecarboxamide;

4-(2-Amino-7-chloro-4-quinolinyl)-N-[(3S)-hexahydro-2-oxo-1-[[(phenylsulfonyl)amino]carbonyl]-1H-azepin-3-yl]-1-piperazinecarboxamide;

4-(2-Amino-7-chloro-4-quinolinyl)-N-[(3S)-hexahydro-2-oxo-1-(2-phenylacetyl)-1H-azepin-3-yl]-1-piperazinecarboxamide;

4-(2-Amino-7-chloro-4-quinolinyl)-N-[(3S)-1-formylhexahydro-2-oxo-1H-azepin-3-yl]-1-piperazinecarboxamide;

4-(2-Amino-7-chloro-4-quinolinyl)-N-[(3S)-1-(2,2-dimethyl-1-oxopropyl)hexahydro-2-oxo-1H-azepin-3-yl]-1-piperazinecarboxamide;

4-(2-Amino-7-chloro-4-quinolinyl)-N-[(3S)-hexahydro-1-(methylsulfonyl)-2-oxo-1H-azepin-3-yl]-1-piperazinecarboxamide;

(3S)-3-[[[4-(2-Amino-7-chloro-4-quinolinyl)-1-piperazinyl]carbonyl]amino]hexahydro-2-oxo-1H-azepine-1-carboxylic acid, methyl ester;

(3S)-3-[[[4-(2-Amino-7-chloro-4-quinolinyl)-1-piperazinyl]carbonyl]amino]hexahydro-2-oxo-1H-azepine-1-carboxylic acid-ethyl ester;

(3S)-3-[[[4-(2-Amino-7-chloro-4-quinolinyl)-1-piperazinyl]carbonyl]amino]hexahydro-2-oxo-1H-azepine-1-carboxylic acid, 2,2,2-trifluoroethyl ester;

(3S)-[[[4-(2-Amino-7-chloro-4-quinolinyl)-1-piperazinyl]carbonyl]amino]hexahydro-2-oxo-1H-azepine-1-carboxylic acid, 2-propenyl ester;

(3S)-3-[[[4-(2-Amino-7-chloro-4-quinolinyl)-1-piperazinyl]carbonyl]amino]hexahydro-2-oxo-1H-azepine-1-carboxylic acid phenyl ester;

(3S)-3-[[[4-(2-Amino-7-chloro-4-quinolinyl)-1-piperazinyl]carbonyl]amino]hexahydro-2-oxo-1H-azepine-1-carboxylic acid-4-fluorophenyl ester;

(3S)-[[[4-(2-Amino-7-chloro-4-quinolinyl)-1-piperazinyl]carbonyl]amino]hexahydro-2-oxo-1H-azepine-1-carboxylic acid, phenylmethyl ester;

4-(2-Amino-7-chloro-4-quinolinyl)-N-[(3S)-1-cyanohexahydro-2-oxo-1H-azepin-3-yl]-1-piperazinecarboxamide;

(3S)-3-[[[4-(2-Amino-7-chloro-4-quinolinyl)-1-piperazinyl]carbonyl]amino]-N-cyclohexylhexahydro-2-oxo-1H-azepine-1-carboxamide;

(3S)-3-[[[4-(2-Amino-7-chloro-4-quinolinyl)-1-piperazinyl]carbonyl]amino]hexahydro-2-oxo-1H-azepine-1-carboxamide;

(3S)-3-[[[4-(2-Amino-7-chloro-4-quinolinyl)-1-piperazinyl]carbonyl]amino]hexahydro-2-oxo-N-(2,2,2-trifluoroethyl)-1H-azepine-1-carboxamide;

(3S)-3-[[[4-(2-Amino-7-chloro-4-quinolinyl)-1-piperazinyl]carbonyl]amino]-N-cyclohexylhexahydro-2-oxo-1H-azepine-1-carboxamide;

(3S)-[[[4-(2-Amino-7-chloro-4-quinolinyl)-1-piperazinyl]carbonyl]amino]hexahydro-2-oxo-N-propyl-1H-azepine-1-carboxamide;

4-(2-Amino-7-chloro-4-quinolinyl)-N-[(3S)-hexahydro-2-oxo-1-(1-pyrrolidinylcarbonyl)-1H-azepin-3-yl]-1-piperazinecarboxamide;

(3S)-3-[[[4-(2-Amino-7-chloro-4-quinolinyl)-1-piperazinyl]carbonyl]amino]-N-cyclopentylhexahydro-2-oxo-1H-azepine-1-carboxamide;

(3S)-3-[[[4-(2-Amino-7-chloro-4-quinolinyl)-1-piperazinyl]carbonyl]amino]-N-cyclobutylhexahydro-2-oxo-1H-azepine-1-carboxamide;

(3R)-3-[[[4-(2-Amino-7-chloro-4-quinolinyl)-1-piperazinyl]carbonyl]amino]-N-(4-fluorophenyl)hexahydro-2-oxo-1H-azepine-1-carboxamide;

(3S)-3-[[[4-(2-Amino-7-chloro-4-quinolinyl)-1-piperazinyl]carbonyl]amino]-N-ethylhexahydro-2-oxo-1H-azepine-1-carboxamide;

(3S)-3-[[[4-(2-Amino-7-chloro-4-quinolinyl)-1-piperazinyl]carbonyl]amino]hexahydro-2-oxo-N-phenyl-1H-azepine-1-carboxamide;

(3S)-3-[[[4-(2-Amino-7-chloro-4-quinolinyl)-1-piperazinyl]carbonyl]amino]hexahydro-N-1-methylethyl)-2-oxo-1H-azepine-1-carboxamide;

(3S)-3-[[[4-(2-Amino-7-chloro-4-quinolinyl)-1-piperazinyl]carbonyl]amino]-N-butylhexahydro-2-oxo-1H-azepine-1-carboxamide;

(3S)-3-[[[4-(2-Amino-7-chloro-4-quinolinyl)-1-piperazinyl]carbonyl]amino]hexahydro-N-2-methylpropyl)-2-oxo-1H-azepine-1-carboxamide;

(3S)-3-[[[4-(2-Amino-7-chloro-4-quinolinyl)-1-piperazinyl]carbonyl]amino]-N-(1,1-dimethylethyl)hexahydro-2-oxo-1H-azepine-1-carboxamide;

(3S)-3-[[[4-(2-Amino-7-chloro-4-quinolinyl)-1-piperazinyl]carbonyl]amino]hexahydro-N, 2-oxo-1H-azepine-1-carboxamide;

(3S)-3-[[[4-(2-Amino-7-chloro-4-quinolinyl)-1-piperazinyl]carbonyl]amino]hexahydro-2-oxo-N-[4-(trifluoromethyl)phenyl]-1H-azepine-1-carboxamide;

(3S)-3-[[[4-(2-Amino-7-chloro-4-quinolinyl)-1-piperazinyl]carbonyl]amino]-N-(3-fluorophenyl)hexahydro-2-oxo-1H-azepine-1-carboxamide;

(3S)-3-[[[4-(2-Amino-7-chloro-4-quinolinyl)-1-piperazinyl]carbonyl]amino]hexahydro-N-4-methylphenyl)-2-oxo-1H-azepine-1-carboxamide;

(3S)-3-[[[4-(2-Amino-7-chloro-4-quinolinyl)-1-piperazinyl]carbonyl]amino]-N-(2-fluorophenyl)hexahydro-2-oxo-1H-azepine-1-carboxamide;

(3S)-3-[[[4-(2-Amino-7-chloro-4-quinolinyl)-1-piperazinyl]carbonyl]amino]-N-(2,6-diethylphenyl)hexahydro-2-oxo-1H-azepine-1-carboxamide;

4-(2-Amino-7-chloro-4-quinolinyl)-N-[(3S)-hexahydro-1-[(methylamino)carbonothioyl]-2-oxo-1H-azepin-3-yl]-1-piperazinecarboxamide;

4-(2-Amino-7-chloro-4-quinolinyl)-N-[(3S)-1-[(ethylamino)carbonothioyl]hexahydro-2-oxo-1H-azepin-3-yl]-1-piperazinecarboxamide;

4-(2-Amino-7-chloro-4-quinolinyl)-N-[(3S)-hexahydro-1-[[(1-methylethyl)amino]carbonothioyl]-2-oxo-1H-azepin-3-yl]-1-piperazinecarboxamide;

4-(2-Amino-7-chloro-4-quinolinyl)-N-[(3S)-hexahydro-2-oxo-1-[(2-propenylamino)carbonothioyl]-1H-azepin-3-yl]-1-piperazinecarboxamide;

(3S)-3-[[[4-(2-Amino-7-chloro-4-quinolinyl)-1-piperazinyl]carbonyl]amino]hexahydro-N-2-oxo-1H-azepine-1-carboxamide;

(3S)-3-[[[4-(2-Amino-7-chloro-4-quinolinyl)-1-piperazinyl]carbonyl]amino]hexahydro-2-oxo-N-(2-propenyl)-1H-azepine-1-carboxamide;

(3S)-3-[[[4-(2-Amino-7-chloro-4-quinolinyl)-1-piperazinyl]carbonyl]amino]-N-(2-chloroethyl)hexahydro-2-oxo-1H-azepine-1-carboxamide; and (3R)-3-[[[4-(2-Amino-7-chloro-4-quinolinyl)-1-piperazinyl]carbonyl]amino]hexahydro-N-2-oxo-1H-azepine-1-carboxamide.

4. A compound of claim 3 selected from the group consisting of:

4-(2-Amino-7-chloro-4-quinolinyl)-N-[(3S)-hexahydro-2-oxo-1H-azepin-3-yl]-1-piperazinecarboxamide;

4-(2-Amino-7-chloro-4-quinolinyl)-N-[(3S)-1-acetylhexahydro-2-oxo-1H-azepin-3-yl]-1-piperazinecarboxamide;

(3S)-3-[[[4-(2-Amino-7-chloro-4-quinolinyl)-1-piperazinyl]carbonyl]amino]hexahydro-2-oxo-1H-azepine-1-carboxamide;-

(3S)-3-[[[4-(2-Amino-7-chloro-4-quinolinyl)-1-piperazinyl]carbonyl]amino]hexahydro-2-oxo-1H-azepine-1-carboxylic acid, methyl ester;

(3S)-3-[[[4-(2-Amino-7-chloro-4-quinolinyl)-1-piperazinyl]carbonyl]amino]-N-ethylhexahydro-2-oxo-1H-azepine-1-carboxamide;

(3S)-3-[[[4-(2-Amino-7-chloro-4-quinolinyl)-1-piperazinyl]carbonyl]amino]hexahydro-N-2-oxo-1H-azepine-1-carboxamide;

(3S)-3-[[[4-(2-Amino-7-chloro-4-quinolinyl)-1-piperazinyl]carbonyl]amino]-N-cyclopropylhexahydro-2-oxo-1H-azepine-1-carboxamide;

(3S)-3-[[[4-(2-Amino-7-chloro-4-quinolinyl)-1-piperazinyl]carbonyl]amino]hexahydro-N-1-methylethyl)-2-oxo-1H-azepine-1-carboxamide;

(3S)-3-[[[4-(2-Amino-7-chloro-4-quinolinyl)-1-piperazinyl]carbonyl]amino]hexahydro-2-oxo-N-(2,2,2-trifluoroethyl)-1H-azepine-1-carboxamide; and (3S)-3-[[[4-(2-Amino-7-chloro-4-quinolinyl)-1-piperazinyl]carbonyl]amino]hexahydro-2-oxo-1H-azepine-1-carboxylic acid-ethyl ester.

5. A pharmaceutical composition comprising at least one compound of claim 1 and a pharmaceutically acceptable vehicle or carrier therefor.

6. A pharmaceutical composition according to claim 5 wherein the compound is selected from the group consisting of:

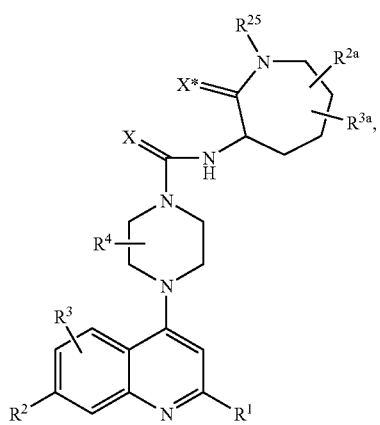

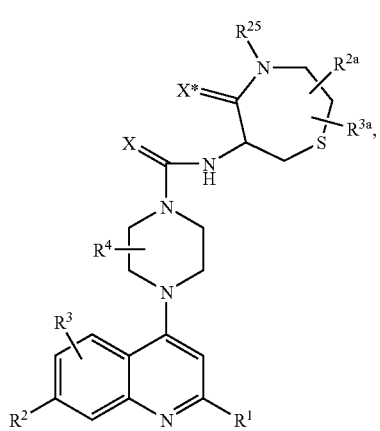

-continued

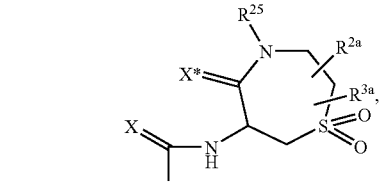

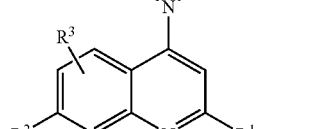

and

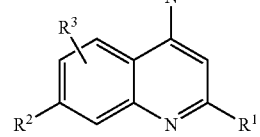

where X and X* are independently O or S.

7. A pharmaceutical composition according to claim 6 wherein the compound is selected from the group consisting of:

4-[[[4-(7-Chloro-4-quinolinyl)-1-piperazinyl]carbonyl]amino]hexahydro-1H-azepine-1-carboxylic acid, 1,1-dimethylethyl ester;

4-[[[4-(7-Chloro-4-quinolinyl)-1-piperazinyl]carbonyl]amino]hexahydro-1H-azepine-1-carboxylic acid, methyl ester;

4-[[[4-(7-Chloro-4-quinolinyl)-1-piperazinyl]carbonyl]amino]hexahydro-1H-azepine-1-carboxylic acid, methyl ester;

4-[[[4-(7-Chloro-4-quinolinyl)-1-piperazinyl]carbonyl]amino]hexahydro-1H-azepine-1-carboxylic acid, phenylmethyl ester;

4-(7-Chloro-4-quinolinyl)-N-[(3R)-hexahydro-2-oxo-1H-azepin-3-yl]-1-piperazinecarboxamide;

4-(7-Chloro-4-quinolinyl)-N-[(3S)-hexahydro-2-oxo-1H-azepin-3-yl]-1-piperazinecarboxamide;

4-(7-Chloro-4-quinolinyl)-N-[(3S)-hexahydro-1-methyl-2-oxo-1H-azepin-3-yl]-1-piperazinecarboxamide;

4-(7-Chloro-4-quinolinyl)-N-[(3S)-hexahydro-2-oxo-1-(phenylmethyl)-1H-azepin-3-yl]-1-piperazinecarboxamide;

4-(7-Chloro-4-quinolinyl)-N-[(3S)-1-[(4-fluorophenyl)methyl]hexahydro-2-oxo-1H-azepin-3-yl]-1-piperazinecarboxamide;

4-(7-Chloro-4-quinolinyl)-N-[(3S)-1-ethylhexahydro-2-oxo-1H-azepin-3-yl]-1-piperazinecarboxamide;

(3S)-[[[4-(7-Chloro-4-quinolinyl)-1-piperazinyl]carbonyl]amino]hexahydro-2-oxo-1H-azepin-1-acetamide;

4-(7-Chloro-4-quinolinyl)-N-[(3S)-hexahydro-2-oxo-1-(3-pyridinylmethyl)-1H-azepin-3-yl]-1-piperazinecarboxamide;

4-(7-Chloro-4-quinolinyl)-N-[(3S)-hexahydro-2-oxo-1-(2-propenyl)-1H-azepin-3-yl]-1-piperazinecarboxamide;

4-(7-Chloro-4-quinolinyl)-N-[(3S)-1-(cyclopropylmethyl)hexahydro-2-oxo-1H-azepin-3-yl]-1-piperazinecarboxamide;

4-(7-Chloro-4-quinolinyl)-N-[(3S)-hexahydro-1-[(4-methoxyphenyl)methyl]-2-oxo-1H-azepin-3-yl]-1-piperazinecarboxamide;

(3S)-[[[4-(7-Chloro-4-quinolinyl)-1-piperazinyl]carbonyl]amino]hexahydro-2-oxo-1H-azepin-1-acetic acid, ethyl ester;

4-(7-Chloro-4-quinolinyl)-N-[(3S)-hexahydro-1-[3-(4-morpholinyl)propyl]-2-oxo-1H-azepin-3-yl]-1-piperazinecarboxamide;

4-(2-Amino-7-chloro-4-quinolinyl)-N-[(6R)-hexahydro-5-oxo-1,4-thiazepin-6-yl]-1-piperazinecarbothioamide;

4-(2-Amino-7-chloro-4-quinolinyl)-N-[(6R)-hexahydro-5-oxo-1,4-thiazepin-6-yl]-1-piperazinecarboxamide;

4-(2-Amino-7-chloro-4-quinolinyl)-N-[(6R)-hexahydro-1,1-dioxido-5-oxo-1,4-thiazepin-6-yl]-1-piperazinecarboxamide;

4-(2-Amino-7-chloro-4-quinolinyl)-N-[(3S)-2-oxopyrrolidinyl]-1-piperazinecarboxamide;

4-(2-Amino-7-chloro-4-quinolinyl)-N-[(3S)-2,3,4,5-tetrahydro-2-oxo-1H-1-benzazepin-3-yl]-1-piperazinecarboxamide;

4-(2-Amino-7-chloro-4-quinolinyl)-N-[(3S)-2,3,4,5-tetrahydro-1-methyl-2-oxo-1H-1-benzazepin-3-yl]-1-piperazinecarboxamide;

4-(2-Amino-7-chloro-4-quinolinyl)-N-[(3S)-1,2,3,4-tetrahydro-2-oxoquinolinyl]-1-piperazinecarboxamide;

4-(2-Amino-7-chloro-4-quinolinyl)-N-[(3R)-hexahydro-2-thioxo-1H-azepin-3-yl]-1-piperazinecarboxamide;

4-(2-Amino-7-chloro-4-quinolinyl)-N-[(3S)-1-acetylhexahydro-1H-azepin-3-yl]-1-piperazinecarboxamide;

4-(2-Amino-7-chloro-4-quinolinyl)-N-[(3S)-hexahydro-2-oxo-1H-azepin-3-yl]-1-piperazinecarboxamide;

4-(2-Amino-7-chloro-4-quinolinyl)-N-[(3S)-hexahydro-1-methyl-2-oxo-1H-azepin-3-yl]-1-piperazinecarboxamide;

4-(2-Amino-7-chloro-4-quinolinyl)-N-[(3S)-1-(cyclopropylmethyl)hexahydro-2-oxo-1H-azepin-3-yl]-1-piperazinecarboxamide;

4-(2-Amino-7-chloro-4-quinolinyl)-N-[(3S)-hexahydro-2-oxo-1-(phenylmethyl)-1H-azepin-3-yl]-1-piperazinecarboxamide;

4-(2-Amino-7-chloro-4-quinolinyl)-N-[(3S)-1-[(2,6-dimethylphenyl)methyl]hexahydro-2-oxo-1H-azepin-3-yl]-1-piperazinecarboxamide;

4-(2-Amino-7-chloro-4-quinolinyl)-N-[(3S)-hexahydro-2-oxo-1-(2-pyridinylmethyl)-1H-azepin-3-yl]-1-piperazinecarboxamide;

4-(2-Amino-7-chloro-4-quinolinyl)-N-[(3S)-hexahydro-2-oxo-1-(3-pyridinylmethyl)-1H-azepin-3-yl]-1-piperazinecarboxamide;

4-(2-Amino-7-chloro-4-quinolinyl)-N-[(3S)-hexahydro-2-oxo-1-(4-pyridinylmethyl)-1H-azepin-3-yl]-1-piperazinecarboxamide;

4-(2-Amino-7-chloro-4-quinolinyl)-N-[(3S)-hexahydro-1-(2-hydroxy-3-phenoxypropyl)-2-oxo-1H-azepin-3-yl]-1-piperazinecarboxamide;

4-(2-Amino-7-chloro-4-quinolinyl)-N-[(3S)-hexahydro-1-(2-hydroxypropyl)-2-oxo-1H-azepin-3-yl]-1-piperazinecarboxamide;

(3S)-[[[4-(2-Amino-7-chloro-4-quinolinyl)-1-piperazinyl]carbonyl]amino]hexahydro-2-oxo-1H-azepine-1-acetic acid, methyl ester;

(3S)-[[[4-(2-Amino-7-chloro-4-quinolinyl)-1-piperazinyl]carbonyl]amino]hexahydro-2-oxo-1H-azepine-1-acetic acid;

(3S)-[[[4-(2-Amino-7-chloro-4-quinolinyl)-1-piperazinyl]carbonyl]amino]hexahydro-2-oxo-N-(phenylmethyl)-1H-azepine-1-acetamide;

(3S)-[[[4-(2-Amino-7-chloro-4-quinolinyl)-1-piperazinyl]carbonyl]amino]hexahydro-N-methyl-2-oxo-1H-azepine-1-acetamide;

(3S)-[[[4-(2-Amino-7-chloro-4-quinolinyl)-1-piperazinyl]carbonyl]amino]hexahydro-2-oxo-N-(4-pyridinyl)-1H-azepine-1-acetamide;

4-(2-Amino-7-chloro-4-quinolinyl)-N-[(3R)-1-(4-fluorophenyl)hexahydro-2-oxo-1H-azepin-3-yl]-1-piperazinecarboxamide;

4-[7-Chloro-2-(methylamino)-4-quinolinyl]-N-[(3S)-hexahydro-2-oxo-1H-azepin-3-yl]-1-piperazinecarboxamide;

4-(2-Amino-7-chloro-4-quinolinyl)-N-[(3S)-hexahydro-2-oxo-1-(2-phenoxyacetyl)-1H-azepin-3-yl]-1-piperazinecarboxamide;

4-(7-Chloro-4-quinolinyl)-N-[(3S)-1-acetylhexahydro-2-oxo-1H-azepin-3-yl]-1-piperazinecarboxamide;

4-(2-Amino-7-chloro-4-quinolinyl)-N-[(3S)-1-acetylhexahydro-2-oxo-1H-azepin-3-yl]-1-piperazinecarboxamide;

4-(2-Amino-7-chloro-4-quinolinyl)-N-[(3S)-1-(cyclopropylcarbonyl)hexahydro-2-oxo-1H-azepin-3-yl]-1-piperazinecarboxamide;

4-(2-Amino-7-chloro-4-quinolinyl)-N-[(3S)-1-benzoylhexahydro-2-oxo-1H-azepin-3-yl]-1-piperazinecarboxamide;

4-(2-Amino-7-chloro-4-quinolinyl)-N-[(3S)-1-(ethylsulfonyl)hexahydro-2-oxo-1H-azepin-3-yl]-1-piperazinecarboxamide;

4-(2-Amino-7-chloro-4-quinolinyl)-N-[(3S)-hexahydro-2-oxo-1-(phenylsulfonyl)-1H-azepin-3-yl]-1-piperazinecarboxamide;

4-(2-Amino-7-chloro-4-quinolinyl)-N-[(3S)-1-(cyclohexylcarbonyl)hexahydro-2-oxo-1H-azepin-3-yl]-1-piperazinecarboxamide;

4-(2-Amino-7-chloro-4-quinolinyl)-N-[(3S)-hexahydro-2-oxo-1-[[(phenylsulfonyl)amino]carbonyl]-1H-azepin-3-yl]-1-piperazinecarboxamide;
4-(2-Amino-7-chloro-4-quinolinyl)-N-[(3S)-hexahydro-2-oxo-1-(2-phenylacetyl)-1H-azepin-3-yl]-1-piperazinecarboxamide;
4-(2-Amino-7-chloro-4-quinolinyl)-N-[(3S)-1-formylhexahydro-2-oxo-1H-azepin-3-yl]-1-piperazinecarboxamide;
4-(2-Amino-7-chloro-4-quinolinyl)-N-[(3S)-1-(2,2-dimethyl-1-oxopropyl)hexahydro-2-oxo-1H-azepin-3-yl]-1-piperazinecarboxamide;
4-(2-Amino-7-chloro-4-quinolinyl)-N-[(3S)-hexahydro-1-(methylsulfonyl)-2-oxo-1H-azepin-3-yl]-1-piperazinecarboxamide;
(3S)-3-[[[4-(2-Amino-7-chloro-4-quinolinyl)-1-piperazinyl]carbonyl]amino]hexahydro-2-oxo-1H-azepine-1-carboxylic acid, methyl ester;
(3S)-3-[[[4-(2-Amino-7-chloro-4-quinolinyl)-1-piperazinyl]carbonyl]amino]hexahydro-2-oxo-1H-azepine-1-carboxylic acid-ethyl ester;
(3S)-3-[[[4-(2-Amino-7-chloro-4-quinolinyl)-1-piperazinyl]carbonyl]amino]hexahydro-2-oxo-1H-azepine-1-carboxylic acid, 2,2,2-trifluoroethyl ester;
(3S)-[[[4-(2-Amino-7-chloro-4-quinolinyl)-1-piperazinyl]carbonyl]amino]hexahydro-2-oxo-1H-azepine-1-carboxylic acid, 2-propenyl ester;
(3S)-3-[[[4-(2-Amino-7-chloro-4-quinolinyl)-1-piperazinyl]carbonyl]amino]hexahydro-2-oxo-1H-azepine-1-carboxylic acid phenyl ester;
(3S)-3-[[[4-(2-Amino-7-chloro-4-quinolinyl)-1-piperazinyl]carbonyl]amino]hexahydro-2-oxo-1H-azepine-1-carboxylic acid-4-fluorophenyl ester;
(3S)-[[[4-(2-Amino-7-chloro-4-quinolinyl)-1-piperazinyl]carbonyl]amino]hexahydro-2-oxo-1H-azepine-1-carboxylic acid, phenylmethyl ester;
4-(2-Amino-7-chloro-4-quinolinyl)-N-[(3S)-1-cyanohexahydro-2-oxo-1H-azepin-3-yl]-1-piperazinecarboxamide;
(3S)-3-[[[4-(2-Amino-7-chloro-4-quinolinyl)-1-piperazinyl]carbonyl]amino]-N-cyclohexylhexahydro-2-oxo-1H-azepine-1-carboxamide;
(3S)-3-[[[4-(2-Amino-7-chloro-4-quinolinyl)-1-piperazinyl]carbonyl]amino]hexahydro-2-oxo-1H-azepine-1-carboxamide;
(3S)-3-[[[4-(2-Amino-7-chloro-4-quinolinyl)-1-piperazinyl]carbonyl]amino]hexahydro-2-oxo-N-(2,2,2-trifluoroethyl)-1H-azepine-1-carboxamide;
(3S)-3-[[[4-(2-Amino-7-chloro-4-quinolinyl)-1-piperazinyl]carbonyl]amino]-N-cyclopropylhexahydro-2-oxo-1H-azepine-1-carboxamide;
(3S)-[[[4-(2-Amino-7-chloro-4-quinolinyl)-1-piperazinyl]carbonyl]amino]hexahydro-2-oxo-N-propyl-1H-azepine-1-carboxamide;
4-(2-Amino-7-chloro-4-quinolinyl)-N-[(3S)-hexahydro-2-oxo-1-(1-pyrrolidinylcarbonyl)-1H-azepin-3-yl]-1-piperazinecarboxamide;
(3S)-3-[[[4-(2-Amino-7-chloro-4-quinolinyl)-1-piperazinyl]carbonyl]amino]-N-cyclopentylhexahydro-2-oxo-1H-azepine-1-carboxamide;
(3S)-3-[[[4-(2-Amino-7-chloro-4-quinolinyl)-1-piperazinyl]carbonyl]amino]-N-cyclobutylhexahydro-2-oxo-1H-azepine-1-carboxamide;
(3R)-3-[[[4-(2-Amino-7-chloro-4-quinolinyl)-1-piperazinyl]carbonyl]amino]-N-(4-fluorophenyl)hexahydro-2-oxo-1H-azepine-1-carboxamide;
(3S)-3-[[[4-(2-Amino-7-chloro-4-quinolinyl)-1-piperazinyl]carbonyl]amino]-N-ethylhexahydro-2-oxo-1H-azepine-1-carboxamide;
(3S)-3-[[[4-(2-Amino-7-chloro-4-quinolinyl)-1-piperazinyl]carbonyl]amino]hexahydro-2-oxo-N-phenyl-1H-azepine-1-carboxamide;
(3S)-3-[[[4-(2-Amino-7-chloro-4-quinolinyl)-1-piperazinyl]carbonyl]amino]hexahydro-N-1-methylethyl)-2-oxo-1H-azepine-1-carboxamide;
(3S)-3-[[[4-(2-Amino-7-chloro-4-quinolinyl)-1-piperazinyl]carbonyl]amino]-N-butylhexahydro-2-oxo-1H-azepine-1-carboxamide;
(3S)-3-[[[4-(2-Amino-7-chloro-4-quinolinyl)-1-piperazinyl]carbonyl]amino]hexahydro-N-2-methylpropyl)-2-oxo-1H-azepine-1-carboxamide;
(3S)-3-[[[4-(2-Amino-7-chloro-4-quinolinyl)-1-piperazinyl]carbonyl]amino]-N-(1,1-dimethylethyl)hexahydro-2-oxo-1H-azepine-1-carboxamide;
(3S)-3-[[[4-(2-Amino-7-chloro-4-quinolinyl)-1-piperazinyl]carbonyl]amino]hexahydro-N-2-oxo-1H-azepine-1-carboxamide;
(3S)-3-[[[4-(2-Amino-7-chloro-4-quinolinyl)-1-piperazinyl]carbonyl]amino]hexahydro-2-oxo-N-[4-(trifluoromethyl)phenyl]-1H-azepine-1-carboxamide;
(3S)-3-[[[4-(2-Amino-7-chloro-4-quinolinyl)-1-piperazinyl]carbonyl]amino]-N-(3-fluorophenyl)hexahydro-2-oxo-1H-azepine-1-carboxamide;
(3S)-3-[[[4-(2-Amino-7-chloro-4-quinolinyl)-1-piperazinyl]carbonyl]amino]hexahydro-N-4-methylphenyl)-2-oxo-1H-azepine-1-carboxamide;
(3S)-3-[[[4-(2-Amino-7-chloro-4-quinolinyl)-1-piperazinyl]carbonyl]amino]-N-(2-fluorophenyl)hexahydro-2-oxo-1H-azepine-1-carboxamide;
(3S)-3-[[[4-(2-Amino-7-chloro-4-quinolinyl)-1-piperazinyl]carbonyl]amino]-N-(2,6-diethylphenyl)hexahydro-2-oxo-1H-azepine-1-carboxamide;
4-(2-Amino-7-chloro-4-quinolinyl)-N-[(3S)-hexahydro-1-[(methylamino)carbonothioyl]-2-oxo-1H-azepin-3-yl]-1-piperazinecarboxamide;
4-(2-Amino-7-chloro-4-quinolinyl)-N-[(3S)-1-[(ethylamino)carbonothioyl]hexahydro-2-oxo-1H-azepin-3-yl]-1-piperazinecarboxamide;
4-(2-Amino-7-chloro-4-quinolinyl)-N-[(3S)-hexahydro-1-[[(1-methylethyl)amino]carbonothioyl]-2-oxo-1H-azepin-3-yl]-1-piperazinecarboxamide;
4-(2-Amino-7-chloro-4-quinolinyl)-N-[(3S)-hexahydro-2-oxo-1-[(2-propenylamino)carbonothioyl]-1H-azepin-3-yl]-1-piperazinecarboxamide;
(3S)-3-[[[4-(2-Amino-7-chloro-4-quinolinyl)-1-piperazinyl]carbonyl]amino]hexahydro-N-2-oxo-1H-azepine-1-carboxamide;
(3S)-3-[[[4-(2-Amino-7-chloro-4-quinolinyl)-1-piperazinyl]carbonyl]amino]hexahydro-2-oxo-N-(2-propenyl)-1H-azepine-1-carboxamide;
(3S)-3-[[[4-(2-Amino-7-chloro-4-quinolinyl)-1-piperazinyl]carbonyl]amino]-N-(2-chloroethyl)hexahydro-2-oxo-1H-azepine-1-carboxamide; and
(3R)-3-[[[4-(2-Amino-7-chloro-4-quinolinyl)-1-piperazinyl]carbonyl]amino]hexahydro-N-2-oxo-1H-azepine-1-carboxamide.

8. A pharmaceutical composition according to claim 7 wherein the compound is selected from the group consisting of:
4-(2-Amino-7-chloro-4-quinolinyl)-N-[(3S)-hexahydro-2-oxo-1H-azepin-3-yl]-1-piperazinecarboxamide;

4-(2-Amino-7-chloro-4-quinolinyl)-N-[(3S)-1-acetyl-hexahydro-2-oxo-1H-azepin-3-yl]-1-piperazinecarboxamide;

(3S)-3-[[[4-(2-Amino-7-chloro-4-quinolinyl)-1-piperazinyl]carbonyl]amino]hexahydro-2-oxo-1H-azepine-1-carboxamide;

(3S)-3-[[[4-(2-Amino-7-chloro-4-quinolinyl)-1-piperazinyl]carbonyl]amino]hexahydro-2-oxo-1H-azepine-1-carboxylic acid, methyl ester;

(3S)-3-[[[4-(2-Amino-7-chloro-4-quinolinyl)-1-piperazinyl]carbonyl]amino]-N-ethylhexahydro-2-oxo-1H-azepine-1-carboxamide;

(3S)-3-[[[4-(2-Amino-7-chloro-4-quinolinyl)-1-piperazinyl]carbonyl]amino]hexahydro-N-2-oxo-1H-azepine-1-carboxamide;

(3S)-3-[[[4-(2-Amino-7-chloro-4-quinolinyl)-1-piperazinyl]carbonyl]amino]-N-cyclopropylhexahydro-2-oxo-1H-azepine-1-carboxamide;

(3S)-3-[[[4-(2-Amino-7-chloro-4-quinolinyl)-1-piperazinyl]carbonyl]amino]hexahydro-N-1-methylethyl)-2-oxo-1H-azepine-1-carboxamide;

(3S)-3-[[[4-(2-Amino-7-chloro-4-quinolinyl)-1-piperazinyl]carbonyl]amino]hexahydro-2-oxo-N-(2,2,2-trifluoroethyl)-1H-azepine-1-carboxamide; and (3S)-3-[[[4-(2-Amino-7-chloro-4-quinolinyl)-1-piperazinyl]carbonyl]amino]hexahydro-2-oxo-1H-azepine-1-carboxylic acid-ethyl ester.

* * * * *